US008999635B2

(12) United States Patent
McLean et al.

(10) Patent No.: US 8,999,635 B2
(45) Date of Patent: Apr. 7, 2015

(54) FILAGGRIN

(75) Inventors: William Henry Irwin McLean, Dundee (GB); Frances Jane Dorothy Smith, Dundee (GB)

(73) Assignee: University Court of The University of Dundee, Dundee (GB)

( * ) Notice: Subject to any disclaimer, the term of this patent is extended or adjusted under 35 U.S.C. 154(b) by 976 days.

(21) Appl. No.: 12/097,493

(22) PCT Filed: Dec. 15, 2006

(86) PCT No.: PCT/GB2006/004707
§ 371 (c)(1),
(2), (4) Date: Nov. 19, 2008

(87) PCT Pub. No.: WO2007/068946
PCT Pub. Date: Jun. 21, 2007

(65) Prior Publication Data
US 2010/0017896 A1 Jan. 21, 2010

(30) Foreign Application Priority Data
Dec. 15, 2005 (GB) .................................. 0525492.5

(51) Int. Cl.
*C12Q 1/68* (2006.01)
*C12P 19/34* (2006.01)
*C07H 21/04* (2006.01)
*G01N 33/68* (2006.01)

(52) U.S. Cl.
CPC .......... *C12Q 1/6883* (2013.01); *G01N 33/6881* (2013.01); *G01N 2800/122* (2013.01); *G01N 2800/202* (2013.01); *G01N 2800/205* (2013.01); *G01N 2800/24* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 6,143,502 A | 11/2000 | Grentzmann et al. |
| 2003/0124553 A1* | 7/2003 | Ginger .............................. 435/6 |
| 2005/0014835 A1 | 1/2005 | Arakawa et al. |
| 2010/0210578 A1 | 8/2010 | McLean et al. |

FOREIGN PATENT DOCUMENTS

| WO | WO 01/44516 | 6/2001 |
| WO | WO 2004/010106 | 1/2004 |
| WO | WO 2005/063261 | 7/2005 |

OTHER PUBLICATIONS

Ginger et al. Arch Dermatol Res, 2005, 297:235-241.*
Gan et al, Biochemistry, 1990, vol. 29, pp. 9432-9440.*
Rugg et al. Prenatal Diagnosis, 2000, vol. 20, pp. 371-377.*
Hirshhorn et al. (Genetics in Medicine, 2002, 4(2): 45-61).*
Erichsen et al. (Br J. Cancer, 2004, vol. 90, pp. 747-751).*
U.S. Appl. No. 12/161,534, Jan. 9, 2012 Non-Final Office Action.
Candi et al., 2005, "The Cornified Envelope: A Model of Cell Death in the Skin," *Nat Rev Mol Cell Biol*, vol. 6: p. 328-340.
Dale et al., 1985, "Filaggrin: A Keratin Filament Associated Protein," *Ann. NY Acad. Sci.*, vol. 455: p. 330-342.
Fleckman et al., 1987, "Keratinocytes Cultured From Subjects With Ichthyosis Vulgaris are Phenotypically Abnormal," *J. Invest Dermatol*, vol. 88: p. 640-645.
Hewett Duncan et al., 2005 "Lethal, Neonatal Ichthyosis With Increased Proteolytic Processing of Filaggrin in a Mouse Model of Netherton Syndrome," *Human Molecular Genetics*, vol. 14, No. 2: p. 335-346.
Ishida-Yamamoto et al., 1998, "Translocation of Profilaggrin N-Terminal Domain Into Keratinocyte Nuclei With Fragmented DNA in Normal Human Skin and Loricrin Keratoderma," *Lab Invest*, vol. 78: p. 1245-1253.
Judge et al., 2004, "Disorders of Keratinization," *Rook's Textbook of Dermatology*, vol. 2: p. 34.54-34.56.
Lane, P.W., 1972, "Two New Mutations in Linkage Group XVI of the House Mouse, Flaky Tail and Varitint-Waddler-J," *J Hered*, vol. 63: p. 135-140.
Listwan et al., 2004, "Keratin Bundling Proteins," *Methods Cell Biol*, vol. 78: p. 817-827.
Nirunsuksiri et al., 1995, "Decreased Profilaggrin Expression in Ichthyosis Vulgaris is a Result of Selectively Impaired Post-transcriptional Control," *The Journal of Biological Chemistry*, vol. 270, No. 2: p. 871-876.
Nirunsuksiri et al., 1998, "Reduced Stability and Biallelic, Coequal Expression of Profilaggrin mRNA in Keratinocytes Cultured From Subjects With Ichyosis Vulgaris," *J. Invest Dermatol*, vol. 110: p. 851-861.
Palmer et al., 2006, "Common loss-of-function variants of the epidermal barrier protein filaggrin are a major predisposing factor for atopic dermatitis," *Nature Genetics*, vol. 38, No. 4: p. 441-446.
Panchal et al., 1999, "Partial Functional Correction of Xeroderma Pigmentosum Group A Cells by Suppressor tRNA," *Human Gene Therapy*, vol. 10, No. 13: p. 2216-2217.
Pena Penabad et al., 1998, "Differential Patterns of Filaggrin Expression in Lamellar Ichthyosis," *Br J Dermatol*, vol. 139: p. 958-964.
Presland et al., 1997, "Evidence for Specific Proteolytic Clevage of the N-Terminal Domain of Human Profilaggrin During Epidermal Differentiation," *J Invest Dermatol*, vol. 108: p. 107-178.

(Continued)

*Primary Examiner* — Sarae Bausch
(74) *Attorney, Agent, or Firm* — Baker Botts LLP

(57) ABSTRACT

The present invention relates to the identification of loss-of-function mutations in the filaggrin gene and their use in diagnosing ichthyosis vulgaris and/or susceptibility to other diseases including atopic dermatitis (eczema), asthma, psoriasis and allergies (including food allergy).

10 Claims, 62 Drawing Sheets

(56) References Cited

OTHER PUBLICATIONS

Presland et al., 2000, "Loss of Normal Profilaggrin and Filaggrin in Flaky Tail (ft/ft) Mice: An Animal Model for the Filaggrin-Deficient Skin Disease Ichtyosis Vulgaris," *J Invest Dermatol*, vol. 115: p. 1072-1081.

Rothnagel et al., 1994, "Characterization of the Mouse Loricrin Gene: Linkage With Profilaggrin and the Flaky Tail and Soft Coat Mutant Loci on Chromosome 3," *Genomics*, vol. 23: p. 450-456.

Smith Frances et al., 2006, "Loss-of-Function Mutations in the Gene Encoding Filaggrin Cause Ichthyosis Vulgaris," *Nature Genetics*, vol. 38, No. 3: p. 337-342.

Steinert et al., 1981, "Characterization of a Class of Cationic Proteins That Specifically Interact With Intermediate Filaments," *Proc Natl Acad Sci*, vol. 78: p. 4097-4101.

Sybert et al., 1985, "Ichthyosis Vulgaris: Identification of a Defect in Synthesis of Filaggrin Correlated With an Absence of Keratohyaline Granules," *J Invest Dermatol*, vol. 84: p. 191-194.

Wells et al., 1966, "Clinical Features of Autosomal Dominant and Sex-linked Ichthyosis in an English Population," *Br Med*, vol. 1: p. 947-949.

Silverman, "The Organic Chamistry of drug Design and Drug Action", *Academic Press*, pp. 4-47 (published 1992).

STN Database Descriptions, published 2006 by Chemical Abstracts, p. 52.

Merriam-Webster's Collegiate Dictionary, Tenth Edition, published 1998 by Merriam-Webster, Incorporated, p. 924.

Hennies et al., "Genetic and immunohistochemical detection of mutations inactivating the keratinocyte transglutaminase in patients with lamellar ichthyosis", *Human Genetics*, 102:314-318 (1998).

U.S. Appl. No. 12/161,534, Aug. 21, 2012 Notice of Allowance

Nirunsuksiri, et al., "Reduced Stability and Bi-Allelic, coequal Expression of Profilaggrin mRNA in Keratinocytes Cultured from Subjects with Ichthyosis Vulgaris", *Investigative Dermatology*, 110(6):854-861 (1998).

* cited by examiner

Pedigrees and *FLG* genotypes of of IV families studied

*FLG* mutation detection and confirmation

Figure 3
Histological and ultrastructural features of ichthyosis vulgaris
a. Control H&E
b. R501X/R501X H&E
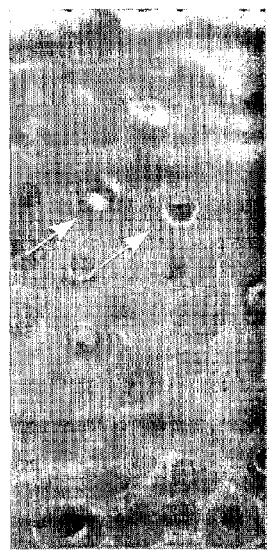
c. Control EM
d. R501X/R501X EM
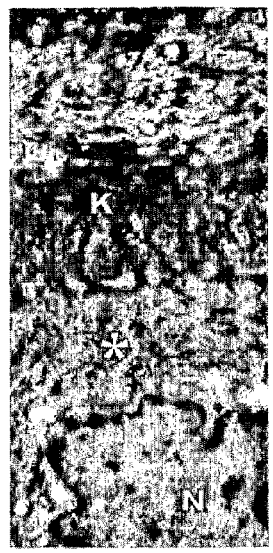
e. Control FLG
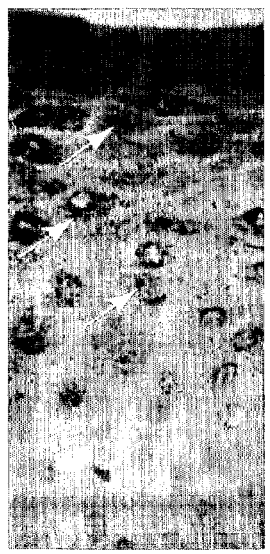
f. R501X/R501X FLG
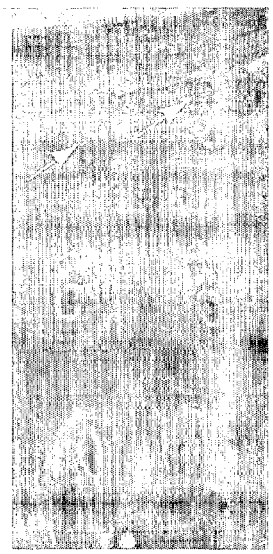
g. Control ProFLG B1
h. R501X/R501X B1

Figure 4

Profilaggrin CDS and translation

```
                 10        20        30        40        50
S-100     ATGTCTACTCTCCTGGAAAACATCTTTGCCATAATTAATCTTTTCAAGCA
domain    TACAGATGAGAGGACCTTTTGTAGAAACGGTATTAATTAGAAAAGTTCGT
           M  S  T  L  L  E  N  I  F  A  I  I  N  L  F  K  Q 60        70        80        90       100
          ATATTCAAAAAAAGATAAAAACACTGACACATTGAGTAAAAAAGAGCTGA
          TATAAGTTTTTTTCTATTTTTGTGACTGTGTAACTCATTTTTTCTCGACT
            Y  S  K  K  D  K  N  T  D  T  L  S  K  K  E  L 110       120       130       140       150
          AGGAACTTCTGGAAAAGGAATTTCGGCAAATCCTGAAGAATCCAGATGAC
          TCCTTGAAGACCTTTTCCTTAAAGCCGTTTAGGACTTCTTAGGTCTACTG
            K  E  L  L  E  K  E  F  R  Q  I  L  K  N  P  D  D 160       170       180       190       200
          CCAGATATGGTTGATGTCTTCATGGATCACTTGGATATAGACCACAACAA
          GGTCTATACCAACTACAGAAGTACCTAGTGAACCTATATCTGGTGTTGTT
            P  D  M  V  D  V  F  M  D  H  L  D  I  D  H  N  K 210       220       230       240       250
          GAAAATTGACTTCACTGAGTTTCTTCTGATGGTATTCAAGTTGGCTCAAG
          CTTTTAACTGAAGTGACTCAAAGAAGACTACCATAAGTTCAACCGAGTTC
            K  I  D  F  T  E  F  L  L  M  V  F  K  L  A  Q 260       270       280       290       300
          CATATTATGAGTCTACCAGAAAAGAGAATTTACCGATATCAGGACACAAG
          GTATAATACTCAGATGGTCTTTTCTCTTAAATGGCTATAGTCCTGTGTTC
            A  Y  Y  E  S  T  R  K  E  N  L  P  I  S  G  H  K 310       320       330       340       350
          CACAGAAAGCACAGTCATCATGATAAACATGAAGATAATAAACAGGAAGA
          GTGTCTTTCGTGTCAGTAGTACTATTTGTACTTCTATTATTTGTCCTTCT
            H  R  K  H  S  H  H  D  K  H  E  D  N  K  Q  E  E 360       370       380       390       400
          AAACAAAGAAAACAGAAAAAGACCCTCAAGTCTGGAAAGAAGAAACAATA
          TTTGTTTCTTTTGTCTTTTTCTGGGAGTTCAGACCTTTCTTCTTTGTTAT
            N  K  E  N  R  K  R  P  S  S  L  E  R  R  N  N 410       420       430       440       450
          GAAAAGGGAATAAGGGAAGATCCAAGAGCCCAAGAGAAACAGGGGGGAAA
          CTTTTCCCTTATTCCCTTCTAGGTTCTCGGGTTCTCTTTGTCCCCCCTTT
            R  K  G  N  K  G  R  S  K  S  P  R  E  T  G  G  K
```

Figure 4-continued

```
                    460        470        480        490        500
RPTO        AGGCATGAATCTAGTTCTGAAAAAAAGAAAGAAAAGGATATTCACCTAC
low         TCCGTACTTAGATCAAGACTTTTTTTCTTTCTTTTCCTATAAGTGGATG
homology     R  H  E  S  S  S  E  K  K  E  R  K  G  Y  S  P  T 510        520        530        540        550
            TCATAGAGAAGAAGAATATGGAAAAAACCATCATAACTCAAGTAAAAAAG
            AGTATCTCTTCTTCTTATACCTTTTTTGGTAGTATTGAGTTCATTTTTC
             A  R  E  E  E  Y  G  K  N  H  H  N  S  S  K  K 560        570        580        590        600
            AGAAAAACAAGACTGAAAATACTAGATTAGGAGACAATAGGAAGAGGCTA
            TCTTTTTGTTCTGACTTTTATGATCTAATCCTCTGTTATCCTTCTCCGAT
             E  K  N  K  T  E  N  T  R  L  G  D  N  R  K  R  L 610        620        630        640        650
            AGTGAAAGACTTGAAGAGAAAGAAGACAATGAAGAAGGAGTATATGATTA
            TCACTTTCTGAACTTCTCTTTCTTCTGTTACTTCTTCCTCATATACTAAT
             S  E  R  L  E  E  K  E  D  N  E  E  G  V  Y  D  Y 660        670        680        690        700
            TGAAAATACAGGAAGAATGACTCAAAAATGGATACAATCAGGCCATATTG
            ACTTTTATGTCCTTCTTACTGAGTTTTTACCTATGTTAGTCCGGTATAAC
             E  N  T  G  R  M  T  Q  K  W  I  Q  S  G  H  I 710        720        730        740        750
            CCACATATTACACAATCCAGGATGAAGCCTATGACACCACTGATAGTCTA
            GGTGTATAATGTGTTAGGTCCTACTTCGGATACTGTGGTGACTATCAGAT
             A  T  Y  Y  T  I  Q  D  E  A  Y  D  T  T  D  S  L 760        770        780        790        800
            TTAGAAGAAAACAAAATATATGAAAGATCAAGGTCATCTGATGGCAAATC
            AATCTTCTTTTGTTTTATATACTTTCTAGTTCCAGTAGACTACCGTTTAG
             L  E  E  N  K  I  Y  E  R  S  R  S  S  D  G  K  S 810        820        830        840        850
            ATCATCTCAAGTGAACAGGTCAAGACATGAAAATACAAGCCAGGTACCAT
            TAGTAGAGTTCACTTGTCCAGTTCTGTACTTTTATGTTCGGTCCATGGTA
             S  S  Q  V  N  R  S  R  H  E  N  T  S  Q  V  P 860        870        880        890        900
RPTO        TGCAGGAGTCCAGGACAAGAAAGCGTAGGGGATCCAGAGTTAGCCAGGAC
start       ACGTCCTCAGGTCCTGTTCTTTCGCATCCCCTAGGTCTCAATCGGTCCTG
high         L  Q  E  S  R  T  R  K  R  R  G  S  R  V  S  Q  D
homology 910        920        930        940        950
            AGGGACAGTGAGGGACACTCAGAAGACTCTGAGAGGCACTCTGGGTCGGC
            TCCCTGTCACTCCCTGTGAGTCTTCTGAGACTCTCCGTGAGACCCAGCCG
             R  D  S  E  G  H  S  E  D  S  E  R  H  S  G  S  A
```

Figure 4-continued

```
        960       970       980       990      1000
TTCCAGAAACCATCATGGATCTGCGTGGGAGCAGTCAAGAGATGGCTCCA
AAGGTCTTTGGTAGTACCTAGACGCACCCTCGTCAGTTCTCTACCGAGGT
   S  P  N  H  H  G  S  A  W  E  Q  S  P  D  G  S 1010      1020      1030      1040      1050
GACACCCCAGGTCCCATGATGAAGACAGAGCCAGTCATGGGCACTCTGCA
CTGTGGGGTCCAGGGTACTACTTCTGTCTCGGTCAGTACCCGTGAGACGT
 P  H  P  R  S  H  D  E  D  R  A  S  H  G  H  S  A 1060      1070      1080      1090      1100
GACAGCTCCAGACAATCAGGCACTCGTCACGCAGAGACTTCCTCTCGTGG
CTGTCGAGGTCTGTTAGTCCGTGAGCAGTGCGTCTCTGAAGGAGAGCACC
  D  S  S  R  Q  S  G  T  R  H  A  E  T  S  S  R  G 1110      1120      1130      1140      1150
ACAGACTGCATCATCCCATGAACAGGCAAGATCAAGTCCAGGAGAAAGAC
TGTCTGACGTAGTAGGGTACTTGTCCGTTCTAGTTCAGGTCCTCTTTCTG
  Q  T  A  S  S  H  E  Q  A  R  S  S  P  G  E  R 1160      1170      1180      1190      1200
ATGGATCCGGCCACCAGCAGTCAGCAGACAGCTCCAGACACTCAGCCACT
TACCTAGGCCGGTGGTCGTCAGTCGTCTGTCGAGGTCTGTGAGTCGGTGA
 H  G  S  G  H  Q  Q  S  A  D  S  S  R  H  S  A  T 1210      1220      1230      1240      1250
GGGCGCGGGCAAGCTTCATCTGCAGTCAGCGATCGTGGACACCGGGGGTC
CCCGCGCCCGTTCGAAGTAGACGTCAGTCGCTAGCACCTGTGGCCCCCAG
   G  R  G  Q  A  S  S  A  V  S  D  R  G  H  P  G  S 1260      1270      1280      1290      1300
TAGCGGTAGTCAGGCCAGTGACAGTGAGGGACATTCAGAA ACTCAGACA
ATCGCCATCAGTCCGGTCACTGTCACTCCCTGTAAGTCTT TGAGTCTGT
   S  G  S  Q  A  S  D  S  E  G  H  S  E  N  S  D 1310      1320      133       1340      1350
CACA TCAGTGTCAGGCCACGGAAAGGCT GGC     CAGCAGAGCCAC
GTGT AGTCACAGTCCGGTGCCTTTCCGA CCG     GTCGTCTCGGTG
 T  Q  S  V  S  G  H  G  K  A  G  L  P  Q  Q  S  H 136       1370      1380      1390      1400
CAAGAGTCC CACGTGGCCGGTCAGGGGAA  GGTCTGGACGTTCAGGGTC
GTTCTCAGG GTGCACCGGCCAGTCCCCTT  CCAGACCTGCAAGTCCCAG
  Q  E  S  T  P  G  R  S  G  E  R  S  G  R  S  G  S
```

Figure 4-continued

```
                  1410       1420       1430       1440       1450
End RPT0    TT CTCTACCAGGTGAGCACTCATGAACAG CTGA TCTGCCCAIGGAC
            AA GGAGATGGTCCACTCGTGAGTACTTGTC GACT AGACGGGTACCTG
             S  L  Y  Q  V  S  T  H  E  Q  P  D  S  A  H  G 1460       1470       1480       1490       1500
RPT1        GGACCGGGACCAGCACTGGAGGAAGACAAGGAT CACCACGA CAGGCA
            CCTGGCCCTGGTCGTGACCTCCTTCTGTTCCTAG GTGGTGCT GTCCGT
             R  T  G  T  S  T  G  G  P  Q  G  S  H  H  E  Q  A 1510       1520       1530       1540       1550
            AGACAGCTCCAGGCA TCAGCGTCCAAGAGGGTCAGGACACCATTCG
            TCTGTCGAGGTCCGT AGTCGCAGGTTCTCCCAGTCCTGTGGTAAGC
             P  D  S  S  R  H  S  A  S  Q  E  G  Q  D  T  I  P 1560       1570       1580       1590       1600
            TGGA ACCCGGGGTCAAGCAGAGGAGGAAGGCAGGGATCCCACCACGAGC
            ACCT TGGGCCCCAGTTCGTCTCCTCCTTCCGTCCCTAGGGTGGTGCTCG
             G  E  P  G  S  S  R  G  G  R  Q  G  S  H  H  E 1610       1620       1630       1640       1650
            AATCGGTA ATAGGTCTGGACACTCAGC TCCGATCACAGCCACACCACA
            TTAGCCAT TATCCAGACCTGTGAGTCG AGGCTAGTGTCGGTGTGGTGT
             Q  S  V  H  R  S  G  H  S  G  S  H  H  S  H  T  T 1660       1670       1680       1690       1700
            TCCCAGGGAAGGCTGAGGCCTCCCATGGGCAGTCAGGATCCAGAACTGC
            AGGGTCCCTTCCGACTACGGAGGGTACCCGTCAGTCCTAGGTCTTGACG
             S  Q  G  R  S  D  A  H  G  Q  S  G  S  R  S  A 4
                  1710       1720       1730       1740       1750
            AAGCAGACAAACACG AATGAGGAACAATCAGGAGACGGC CCAGGCACT
            TTCGTCTGTTTGTGC TTACTCCTTGTTAGTCCTCTGCCG GGTCCGTGA
             S  R  Q  T  P  N  E  Q  S  G  D  G  T  R  H 6
                  1760       1770       1780       1790       1800
            CAGGGTCACGTCA CATGAAGCTTCCTCTCAGGCTGACAGCTCTAGACAC
            GTCCCAGTGCAGT GTACTTCGAAGGAGAGTCCGACTGTCGAGATCTGTG
             S  G  S  P  H  R  E  A  S  S  Q  A  D  S  S  R 1810       1820       1830       1840       1850
            TCACAGGTGGGCCAGGGACAATCATCGGGGCCCAGGACAAG AGGAACCA
            AGTGTCCACCCGGTCCCTGTTAGTAGCCCCGGGTCCTGTTC TCCTTGGT
             S  Q  V  G  Q  G  Q  S  S  G  P  R  T  S  R  N  Q
```

Figure 4-continued

```
        1860       1870       1880       1890       1900
GGGATCCAGTGTTAGCCAGGACAGTGACAGTCAGGGACACTCAGAAGACT
CCCTAGGTCACAATCGGTCCTGTCACTGTCAGTCCCTGTGAGTCTTCTGA
  G  S  V  S  Q  D  S  D  S  Q  G  H  S  E  D 1910       1920       1930       1940       1950
CTGAGAGGTGGTCTGGGTCTGCTTCCAGAAACCATCATGGATCTGCTCAG
GACTCTCCACCAGACCCAGACGAAGGTCTTTGGTAGTACCTAGACGAGTC
  S  E  P  W  S  G  S  A  S  R  N  H  G  S  A  Q 1960       1970       1980       1990       2000
GAGCAGTCAAGAGATGGCTCCAGACACCCCAGGTCCCATCACGAAGACAG
CTCGTCAGTTCTCTACCGAGGTCTGTGGGGTCCAGGGTAGTGCTTCTGTC
  E  Q  S  K  D  G  S  R  H  P  S  H  R  E  D 2010       2020       2030       2040       2050
AGCTGGTCATGGGCACTCTGCAGACAGCTCCAGAXAATCAGGCACTCGTC
TCGACCAGTACCCGTGAGACGTCTGTCGAGGTCTXTTAGTCCGTGAGCAG
  A  G  R  H  S  A  D  S  S  R  X  S  G  T  R 2060       2070       2080       2090       2100
ACACACAGAATTCCTCTCAGTGGACAGGCTGCGTCATCCCATGAACAGGCA
TGTGTGTCTTAAGGAGATCACCTGTCCGACGCAGTAGGGTACTTGTCCGT
  R  T  Q  N  S  S  S  G  Q  A  A  S  S  H  E  Q  A 555
        2110       2120       2130       2140       2150
AGATCAAGTGCAGGAGAAAGACATGGATCCCGCCACCAGCTXXAGTCAGC
TCTAGTTCACGTCCTCTTTCTGTACCTAGGCGGTGGTCGXXTCAGTCG
  R  S  S  A  G  E  R  H  G  S  R  R  Q  L  Q  S  A 2160       2170       2180       2190       2200
AGACAGCTCCAGACACTCAGGCACTGGGCACGGACAAGCTTCATCTGCAG
TCTGTCGAGGTCTGTGAGTCCGTGACCCGTGCCTGTTCGAAGTAGACGTC
  D  S  S  R  H  S  G  T  G  H  G  Q  A  S  S  A 2210       2220       2230       2240       2250
TCAGAGACAGTGGACACCGAGGGTCCAGTGGTAGTCAGGCCACTGACAGT
AGTCTCTGTCACCTGTGGCTCCCAGGTCACCATCAGTCCGGTGACTGTCA
  V  P  D  S  G  H  P  G  S  S  G  S  Q  A  T  D  S 2260       2270       2280       2290       2300
GAGGGACATTCAGAAGACTCAGACACACAGTXXXGTCAGGCCATGGACA
CTCCCTGTAAGTCTTCTGAGTCTGTGTGTCAXXXCAGTCCGGTACCTGT
  E  G  H  S  E  D  S  D  T  Q  S  V  S  G  H  G  Q
```

Figure 4-continued

```
         2310      2320      2330      2340      2350
        GGCTGG  CCATCAGCAGAGCCACCAAGAGTCCGCACGTGACGGGTCAG
        CCGACC  GGTAGTCGTCTCGGTGGTTCTCAGGGCGTGCACTGGCCAGTC
          A  G  R  R  Q  S  H  Q  E  S  A  P  D  R  S 2360      2370      2380      2390      2400
        GGGAAAGGTCT GACGTTCAGGGTCTTTCTCTACCAGGTGAGCACTCAT
        CCCTTTCCAGA CTGCAAGTCCCAGAAAGGAGATGGTCCACTCGTGAGTA
          G  K  R  S  R  P  S  Q  S  F  L  T  Q  V  S  T  H 5
         2410      2420      2430      2440      2450
End RPT1 AACAGTCTGAGTCCTCCCATGGATGGAC GGGCCCAGTACTGGAG AAG
        TTGTCAGACTCAGGAGGGTACCTACCTG CCCGGGTCGTGACCTC TTC
         K  Q  S  E  S  S  H  G  W  T  G  P  S  T  G  V  R 2460      2470      2480      2490      2500
RPT2    ACAAGGATCCCACCATGAGCAGGCACGAGACA CTCCAGGCACTCAGCAT
        TGTTCCTAGGGTGGTACTCGTCCGTGCTCTGT GAGGTCCGTGAGTCGTA
          Q  G  S  H  H  E  Q  A  R  D  N  S  R  S  A 10
         2510      2520      2530      2540      2550
        CCCAAGA GGTCAGGACACCATTCGTGGACACCCGGGGTCAAGCAGA GA
        GGGTTCT CCAGTCCTGTGGTAAGCACCTGTGGGCCCCAGTTCGTCT CT
          S  Q  D  G  Q  D  T  I  R  G  R  P  G  S  S  R  R 2560      2570      2580      2590      2600
        GGAAGGCAGGGGTCCCACCACGAGCAATGGGTAGATAGGTCTGGACACTC
        CCTTCCGTCCCCAGGGTGGTGCTCGTTACCCATCTATCCAGACCTGTGAG
          G  P  Q  G  S  H  H  E  Q  S  V  D  P  S  G  H  S 2610      2620      2630      2640      2650
        AGGGTCCATCACAGCCACACCACATCCCAGGGAAGGTCTGATGCCTCCC
        TCCCAGGGTAGTGTCGGTGTGGTGTAGGGTCCCTTCCAGACTACGGAGGG
          G  S  H  H  S  R  T  T  S  Q  G  R  S  D  A  S 2660      2670      2680      2690      2700
        GTGGGCAGTCAGGATCCAGAAGTGCAAGCAGAACAACACGTAATGAGGAA
        CACCCGTCAGTCCTAGGTCTTCACGTTCGTCTTGTTGTGCATTACTCCTT
          R  G  Q  S  G  C  R  S  A  S  R  T  T  P  N  E  E 2710      2720      2730      2740      2750
        CAATCA GAGACGGCTCCAGGCACTCAGGGTCACGTCACCATGAAGCTTC
        GTTAGT CTCTGCCGAGGTCCGTGAGTCCCAGTGCAGTGGTACTTCGAAG
          Q  S  P  D  G  S  R  H  S  G  S  R  H  E  A  S 2760      2770      2780      2790      2800
        CTCTCATGCCGACATCTCTAGACACTCACAGGCAGGCCAGGGACAATCAG
        GAGAGTACGGCTGTAGAGATCTGTGAGTGTCCGTCCGGTCCCTGTTAGTC
          S  R  H  D  I  S  R  H  S  Q  A  G  Q  G  Q  S
```

Figure 4-continued

```
          2810      2820      2830      2840      2850
     AGGGGTCCAGGACAAGCAGGCGCCAGGGATCCAGTGTTAGCCAGGACAGT
     TCCCCAGGTCCTGTTCGTCCGCGGTCCCTAGGTCACAATCGGTCCTGTCA
      E  G  S  P  T  S  R  K  Q  G  S  S  V  S  Q  D  S 2860      2870      2880      2890      2900
     GACAGTGAGGGACATTCAGAAGACTCTGAGAGGTGGTCTGGGTCTGCTTC
     CTGTCACTCCCTGTAAGTCTTCTGAGACTCTCCACCAGACCCAGACGAAG
       D  S  E  G  R  S  E  D  S  E  R  W  G  S  A  S 2910      2920      2930      2940      2950
     CAGAAACCATCGTGGATCCGCTCAGGAGCAGTCAAGACATCGCTCCAGAC
     GTCTTTGGTAGCACCTAGACGAGTCCTCGTCAGTTCTGTACCGAGGTCTG
        P  N  H  R  G  S  A  Q  E  Q  S  R  Q  S  R 2960      2970      2980      2990      3000
     ACCCCAGGTCCCATCACGAAGACAGAGCCGGTCACGGGCACTCTGCAGAC
     TGGGGTCCAGGGTAGTGCTTCTGTCTCGGCCAGTGCCCGTGAGACGTCTG
        R  P  R  G  H  H  E  D  R  A  G  R  G  H  S  A  D 3010      3020      3030      3040      3050
     AGCTCCAGACAATCAGGGACTCCTCACGCAGAGACTTCCTCTGGTGGACA
     TCGAGGTCTGTTAGTCCCTGAGGAGTGCGTCTCTGAAGGAGACCACCTGT
        S  S  R  Q  S  G  T  P  H  A  E  T  S  S  G  G  Q 3060      3070      3080      3090      3100
     GGCTGCGTCATCCCATGAACAGGCAAGATCAAGTCCAGGAGAAAGACACG
     CCGACGCAGTAGGGTACTTGTCCGTTCTAGTTCAGGTCCTCTTTCTGTGC
         A  A  S  S  H  E  Q  A  R  S  S  P  G  E  R 3110      3120      3130      3140      3150
     GATCCCGCCACCAGCAGTCAGTCAGACAGCTCCAGACACTCAGGCATTCG
     CTAGGGCGGTGGTCGTCAGTCGTCTGTCGAGGTCTGTGAGTCCGTAAGC
        G  S  R  H  Q  Q  S  A  D  S  S  R  S  G  I  P 3160      3170      3180      3190      3200
     CGCAGACAAGCTTCATCTGCAGTCAGAGACAGTGGACACTGGGGGTCCAG
     GCGTCTGTTCGAAGTAGACGTCAGTCTCTGTCACCTGTGACCCCAGGTC
        R  R  Q  A  S  S  A  V  P  D  S  G  W  G  S  S 3210      3220      3230      3240      3250
     TGGTAGTCAGGCCAGTGATAGTGAGGGACATTCAGACAGTCAGACACAC
     ACCATCAGTCCGGTCACTATCACTCCCTGTAAGTCTGTCAGTCTGTGTG
         G  S  Q  A  S  D  S  E  G  R  S  E  E  S  D  T 3260      3270      3280      3290      3300
     AGTCAGTGTCAGGCCATGGACAGGTGGGCCCCATCAGCAGAGCCACCAA
     TCAGTCACAGTCCGGTACCTGTCCACCCGGGGTAGTCGTCTCGGTGGTT
         Q  S  V  S  G  H  G  Q  D  G  P  H  Q  Q  S  H  Q
```

Figure 4-continued

```
             3310       3320       3330       3340       3350
            GAGTCCGCACGTGAC GGTCAGGGGGAAGGTCTGGACGTTCAGGGTCTTT
            CTCAGGCGTGCACTG CCAGTCCCCTTCCAGACCTGCAAGTCCCAGAAA
             E  S  A  P  D  W  S  G  G  P  S  G  K  S  G  S  F 10
             3360       3370       3380       3390       3400
End RPT2    C TCTACCAGGTGAGCACTCATGAACAGTCTGAGTCTGCCCATGG CGGA
            G AGATGGTCCACTCGTGAGTACTTGTCAGACTCAGACGGGTACC GCCT
             I  Y  Q  V  S  T  H  E  Q  S  E  S  A  H  G  R 10          10
             3410       3420       3430       3440       3450
RPT3        CC GGACCAGCACTGGA GAAGACAAGGATCCCACCACGAGCAGGCACGA
            GG CCTGGTCGTGACCT CTTCTGTTCCTAGGGTGGTGCTCGTCCGTGCT
             T  P  T  S  G  R  R  Q  G  S  H  H  E  Q  A  R 3460       3470       3480       3490       3500
            GACAGCTCCAGGCACTCAGCGTCCCAAGAGGGTCAGGACACCATTCGTG
            CTGTCGAGGTCCGTGAGTCGCAGGGTTCTCCCAGTCCTGTGGTAAGCAC
             D  S  S  R  H  S  A  S  Q  E  G  Q  D  T  I  P  A 11                        5
             3510       3520       3530       3540       3550
            ACACCCGGGGTCAAG AGAGGAGGAAGGCAGGGATCCCACCA GAGCAAT
            TGTGGGCCCCAGTTC TCTCCTCCTTCCGTCCCTAGGGTGGT CTCGTTA
             H  P  G  S  R  R  G  G  R  Q  G  S  H  R  E  Q 7
             3560       3570       3580       3590       3600
            CGGTAGATAC TCTGGACACTCAGGGTCCCATCACAGCCACA CCACATCC
            GCCATCTATG AGACCTGTGAGTCCCAGGGTAGTGTCGGTGT GGTGTAGG
             S  V  D  R  S  G  H  S  G  S  H  H  S  H  T  T  S 3610       3620       3630       3640       3650
            CAGGGAAGGTCTGATGCCTCCCATGGGCAGTCAGGATCCAGAAGTGCAAG
            GTCCCTTCCAGACTACGGAGGGTACCCGTCAGTCCTAGGTCTTCACGTTC
             Q  G  R  S  D  A  S  H  G  Q  S  G  S  R  S  A  S 105
             3660       3670       3680       3690       3700
            CAGACAAACTCGTAA GA AAACAATCAGGAGACGGCTCCAGGCACTCAG
            GTCTGTTTGAGCATT CT TTTGTTAGTCCTCTGCCGAGGTCCGTGAGTC
             R  Q  T  P  K  D  Q  S  G  D  G  S  R  S 6
             3710       3720       3730       3740       3750
            G TCACGTCACCATGAAGCT CCTCT GGGCTGACAGCTCTAGACACTCA
            C AGTGCAGTGGTACTTCGA GGAGA CCCGACTGTCGAGATCTGTGAGT
             G  S  R  H  E  A  A  S  W  A  D  S  S  R  H
```

Figure 4-continued

```
        3760      3770      3780      3790      3800
CAGGTGGG CAGC ACAATCATCGGGGTCCAGGACAAGCAGGCACCAGGG
GTCCACCC GTCC TGTTAGTAGCCCCAGGTCCTGTTCGTCCGTGGTCCC
    Q  V  G  Q  E  Q  S  S  G  S  R  T  S  P  Q  G 3810      3820      3830      3840      3850
ATCCAGTGTTAGCCAGGACAGTGACAGTGAG GACACTCAGA GACTC G
TAGGTCACAATCGGTCCTGTCACTGTCACTC CTGTGAGTCT CTGAG C
    S  S  V  S  Q  D  S  D  S  E  P  R  S  D  D  S 3860      3870      3880      3890      3900
AGAGGT GTCTCGGGTCTGCTTCCAGAAACCATCATGGATCT CTCGGGAG
TCTCCA CAGACCCAGACGAAGGTCTTTGGTAGTACCTAGA GAGCCCTC
    E  R  L  S  G  S  A  S  R  N  H  G  S  S  R  E 55
        3910      3920      3930      3940      3950
CAGTCAAGAGATGGCTCCAGACACCC GGT CATCAAGAAGACAGAGC
GTCAGTTCTCTACCGAGGTCTGTGGG CCA GTAGTTCTTCTGTCTCG
    Q  S  P  D  G  S  R  H  P  G  F  H  Q  E  D  R  A 3960      3970      3980      3990      4000
CAGTCACGGGCACTCTGCAGACAGTCCAGACAATCAGGCACTCATCACA
GTCAGTGCCCGTGAGACGTCTGTCAGGTCTGTTAGTCCGTGAGTAGTGT
    S  H  G  H  S  A  D  S  S  R  Q  S  G  T  H  H 5
        4010      4020      4030      4040      4050
CAGAG CTTCCTCTC TGGACAGGCT GTCATCCCATGAACAGGCAAGA
GTCTC GAAGGAGAG ACCTGTCCGAC CAGTAGGGTACTTGTCCGTTCT
    T  E  S  S  H  G  Q  A  V  S  S  H  E  Q  A  R 4060      4070      4080      4090      4100
TCAAGTCCAGGAGAAAGACATGGATCCCGCCACCAGCAGTCAGCAGACAG
AGTTCAGGTCCTCTTTCTGTACCTAGGGCGGTGGTCGTCAGTCGTCTGTC
    S  S  P  G  E  P  R  G  S  R  H  Q  S  A  D  S 4110      4120      4130      4140      4150
CTCCAGACACTCAGGCATTGGGCACAGACAAGCTTCATCTGCAGTCAGAG
GAGGTCTGTGAGTCCGTAACCCGTGTCTGTTCGAAGTAGACGTCAGTCTC
    S  R  H  S  G  I  G  H  P  Q  A  S  S  A  V  R 1
        4160      4170      4180      4190      4200
ACAGTGGACACCGAGGGTCCAGTGGTAGTCAGG UAC T ACAGTGAGGGA
TGTCACCTGTGGCTCCCAGGTCACCATCAGTCC TA TGTCACTCCCT
    D  S  G  R  R  G  S  S  G  S  Q  V  F  H  S  E  G 5
        4210      4220      4230      4240      4250
CATTCAGAAGACTCAGACACACAGTCAGTGTCAGCCCACGGACA GCTGG
GTAAGTCTTCTGAGTCTGTGTGTCAGTCACAGTCGGGTGCCTGT CGACC
    H  S  E  D  S  D  T  Q  S  V  S  A  R  G  Q  A  G
```

Figure 4-continued

```
             4260      4270      4280      4290      4300
        GCCCCATCAGCAGAGCCACAAAGAGTCGGCACGTGGCCAGTCAGGGGAAA
        CGGGGTAGTCGTCTCGGTGTTTCTCAGGCGTGCACCGGTCAGTCCCCTTT
         P  H  Q  Q  S  H  K  E  S  A  R  G  Q  S  G  E 4310      4320      4330      4340      4350
End RPT3 GGTCTGGACGTTCAGGGTCTTTCCTCTACCAGGTGAGCTCTCATGAACAG
         CCAGACCTGCAAGTCCCAGAAAGGAGATGGTCCACTCGGAGTACTTGTC
         S  S  G  R  S  P  S  F  L  Y  Q  V  S  S  H  Q 4360      4370      4380      4390      4400
RPT4     TCTGAGTCCACTCAGGACCGACTGGTCCAGCACTGGAGGAAGACAAGG
         AGACTCAGGTGAGTCCTGGCTGACCAGGTCGTGACCTCCTTCTGTTCC
          S  E  S  T  R  G  Q  T  A  P  S  T  G  G  P  Q  G 4410      4420      4430      4440      4450
        ATCCCGCCATGAGCAGGCACGACACAGGTCGAGGCACTCAGCATCCCAAG
        TAGGGCGGTACTCGTCCGTGCTGTGTCGAGCTCCGTGAGTCGTAGGGTTC
         S  P  H  E  Q  A  R  N  S  S  R  H  S  A  S  Q 4460      4470      4480      4490      4500
        ACGGTCAGGACACCATTCGTGGACACCCGGGGTCAAGCAGAGGAGGAAGG
        TGCCAGTCCTGTGGTAAGCACCTGTGGGCCCCAGTTCGTCTCCTCCTTCC
         D  G  Q  D  T  I  P  G  R  P  G  S  S  R  G  R 4510      4520      4530      4540      4550
        CAGGGATCCTACCACGAGCAATCGTAGATAGGTCTGGACACTCAGGGT
        GTCCCTAGGATGGTGCTCGTTAGCATCTATCCAGACCTGTGAGTCCCA
         Q  G  S  Y  H  E  Q  S  V  D  R  S  G  H  S  G 4560      4570      4580      4590      4600
        CCATCACAGCCACACCACACCCAGGGAAGGTCTGATGCCTCCCATGGGC
        GGTAGTGTCGGTGTGGTGTGGGTCCCTTCCAGACTACGGAGGGTACCCG
         H  H  S  R  T  T  P  Q  G  R  S  D  A  S  H  G 4610      4620      4630      4640      4650
        AGTCAGGACCAGAAGTGCAAGCAGCCAAACAGGAAATGAGGAACAATCA
        TCAGTCCTGGTCTTCACGTTCGTCGGTTTGTCCTTTACTCCTTGTTAGT
         Q  S  G  P  R  S  A  S  R  Q  T  R  N  E  Q  S 4660      4670      4680      4690      4700
        GGAGACGGCTCCAGGCACTCAGGGTCACGTCACCATGAACTTCCACTCG
        CCTCTGCCGAGGTCCGTGAGTCCCAGTGCAGTGGTACTTGAAGGTGAGC
         G  D  G  S  R  G  S  F  R  R  P  S  T  R 4710      4720      4730      4740      4750
        GGCCGCCAGCTCTAGACAACTCACAGGTGGGCCAGGGAGAATCAGCGGGGT
        CCGGCGGTCGAGATCTGTGAGTGTCCACCCGGTCCCTCTTAGTCGCCCCA
         A  G  S  S  R  H  S  Q  V  G  Q  G  E  S  A  G
```

Figure 4-continued

```
       4760       4770       4780       4790       4800
     CCA GACAAGCAGGCGCCAGGGATCCAGTGTTAG CAGGACAG GACAGT
     GGT CTGTTCGTCCGCGGGTCCCTAGGTCACAATC GTCCTGTC CTGTCA
      S   K   T   S   R   R   G   S   S   V   G   Q   D   R   D   S 4810       4820       4830       4840       4850
     GAGGGACAACTCAGAAGACTCTGAGAGGCGGTCTG GTC GGTTCCAGAA
     CTCCCTGTGAGTCTTCTGAGACTCTCCGCCAGAC CAG CCAAGGTCTTT
      E   G   H   S   E   D   S   E   K   R   S   E   S   A   S   F   N 4860       4870       4880       4890       4900
     CCAT ATGGATCTGCTGGGAGCAGTCAAGACATGGCTCCAG ACCCCA
     GGTA TACCTAGACGAGCCCTCGTCAGTTCTGTACCGAGGTC TGGGGT
      H   Y   G   S   A   R   E   Q   S   F   R   G   S   P   N   P 11
       4910       4920       4930       4940       4950
     GGTCCCATCAAGAAGA AGAGCCAGTCAT GGCACTCTGCAGAGAGCTCC
     CCAGGGTAGTTCTTCT TCTCGGTCAGTA CCCGTGAGACGTCTCTCGAGG
      R   S   H   Q   E   D   R   A   S   H   G   N   S   A   R   S   S 4960       4970       4980       4990       5000
     AGACAATCAGGCACTCGTCATGCAGAGACTTCCTCTGGTGGACAGGCTGC
     TCTGTTAGTCCGTGAGCAGTACGTCTCTGAAGGAGACCACCTGTCCGACG
      P   Q   S   G   T   R   H   A   E   T   S   S   G   G   Q   A   A 5010       5020       5030       5040       5050
     ATCATCCCA GAACAGGCAAG TCAAGTCCAGGAGAAAGACATGGATCCC
     TAGTAGGGT CTTGTCCGTTC AGTTCAGGTCCTCTTTCTGTACCTAGGG
      S   S   Q   E   Q   A   P   S   S   F   G   E   R   G   G 5060       5070       5080       5090       5100
     GCCACCAGCAGTCAGCAGACAGCTCCA A ACTCAGGCACTGGGCGCAGA
     CGGTGGTCGTCAGTCGTCTGTCGAGGT T TGAGTCCGTGACCCGCGTCT
      R   R   Q   Q   S   A   D   S   T   D   S   G   T   G   P   P 5110       5120       5130       5140       5150
     CAAG TTCATCTG AGTT GAGACAGTGGA ACCGAGGGGTCCAGTGGTAG
     GTTC AAGTAGAC TCAG CTCTGTCACCT TGGCTCCCAGGTCACCATC
      Q   D   S   S   V   V   G   D   S   G   N   R   G   S   S   G 5160       5170       5180       5190       5200
     CAGGCCAGTGACAG CAGGGACA TCAGAACAGTCAGACACAGTCAG
     GTCCGGTCACTGTC GTCCCTGT AGTCTTCTCAGTCTGTGTCAGTC
      Q   A   S   D   S   E   G   R   S   E   E   S   D   T   Q   S 5210       5220       5230       5240       5250
     TGTCAGCCCACGGACAGGCTGGGGCCCATCAGCAGAGCCACCAAGAGTCC
     ACAGTCGGGTGCCTGTCCGACCCCGGGTAGTCGTCTCGGTGGTTCTCAGG
      V   S   A   H   G   Q   A   G   P   H   Q   Q   S   H   Q   E   S
```

Figure 4-continued

```
          5260      5270      5280      5290      5300
     ACAGGTGGCCAGTCAGGGGAAAGGTCTGGACGTTCAGGGTCTTTCCTCTA
     TGTCCACCGGTCAGTCCCCTTTTCCAGACCTGCAAGTCCCAGAAAGGAGAT
        T  K  G  Q  S  G  E  K  S  G  R  S  G  S  F  L  Y 5310      5320      5330      5340      5350
End RPT4     CCAGGTGAGCACTCATGAACAGTCTGAGTCCGCCCATGGACCAC GGGC
             GGTCCACTCGTGAGTACTTGTCAGACTCAGGCGGGTACCTGGTG CCCG
                Q  V  S  T  E  Q  S  E  S  A  H  G  P  T  G 5360      5370      5380      5390      5400
RPT5         CCAGCACTGGAGGAAGACAA GATCCCGGCCACGAGCAGGCACGAGACAGC
             GGTCGTGACCTCCTTCTGTT CTAGGGCGGTGCTCGTCCGTGCTCTGTCG
                P  S  T  G  G  R  Q  P  S  R  E  E  Q  A  R  D  S 5410      5420      5430      5440      5450
             TCCAGGCACTCAGCGTCCCAAGAGGGTCAGGACACCATTCGTGGACACCC
             AGGTCCGTGAGTCGCAGGGTTCTCCCAGTCCTGTGGTAAGCACCTGTGGG
                S  R  E  S  A  S  Q  E  G  Q  D  T  I  R  G  H  P (3)
                  5460      5470      5480      5490      5500
             GGGTCAAGCAGAGGAGGAAGGCAGGGATCCCACTA GAGCAATCGGTAG
             CCCAGTTCGTCTCCTCCTTCCGTCCCTAGGGTGAT CTCGTTAGCCATC
                G  S  P  G  G  K  Q  G  S  H  Y  E  Q  S  V (0)
                  5510      5520      5530      5540      5550
             ATAG TCTGGACACTCAGGGTCTCATCACAGCCAGACCAC TCCCAGG A
             TATC AGACCTGTGAGTCCCAGAGTAGTGTCGGTCTGGTG AGGGTCC T
                D  S  S  G  H  S  G  S  R  H  S  H  T  T  S  Q  E 5560      5570      5580      5590      5600
             AGGTCTGATG CTCCCGTGGGCAGTCAGGATCCAGAAGTG AGCAGACA
             TCCAGACTAC GAGGGCACCCGTCAGTCCTAGGTCTTCAC TCGTCTGT
                P  S  D  V  S  P  G  Q  S  G  P  E  V  S  P  Q

3(+0)
                  5610      5620      5630      5640      5650
             AACACGTAATGAG AACAATCAGGAGACGGCTCCAGGCACTCAGGGTCGC
             TTGTGCATTACTC TTGTTAGTCCTCTGCCGAGGTCCGTGAGTCCCAGCG
                T  R  N  E  K  Q  S  G  D  G  S  R  H  S  G 7
                  5660      5670      5680      5690      5700
             GTCACCATGAAGCTTCCTCTCGGGCCGACAGCTCTAGACACTC CAGGTG
             CAGTGGTACTTCGAAGGAGAGCCCGGCTGTCGAGATCTGTGAG GTCCAC
                R  H  H  E  A  S  S  P  A  D  S  S  R  H  S  Q  V 6
                  5710      5720      5730      5740      5750
             GGCCAGGGACAATCATC GGGCCAGGACAAGCAGGAACCAGGGATCCAG
             CCGGTCCCTGTTAGTAG CCCGGTCCTGTTCGTCCTTGGTCCCTAGGTC
                G  Q  G  Q  S  S  G  P  R  T  S  P  N  G  S  S
```

Figure 4-continued

```
       5760      5770      5780      5790      5800
TGTTAGCCAGGACAGTGACAGTCAGGGACACTCAGAAGACTCTGAGAGGT
ACAATCGGTCCTGTCACTGTCAGTCCCTGTGAGTCTTCTGAGACTCTCCA
  V  S  Q  D  S  Q  G  H  S  E  D  S  E  R 0
       5810      5820      5830      5840      5850
GGTCTGGGTCTGCTTCCAGAAACCATCTTGGATCTGCTTGGGAGCAGTCA
CCAGACCCAGACGAAGGTCTTTGGTAGAACCTAGACGACCCTCGTCAGT
  W  S  G  S  A  S  R  N  H  L  G  S  A  W  E  Q  S 33
       5860      5870      5880      5890      5900
AGAGATGGCTCCAGACACCCTGGTCCCATCACGAAGACAGAGCCGGTCA
TCTCTACCGAGGTCTGTGGGACCAGGGTAGTGCTTCTGTCTCGGCCAGT
  R  D  G  S  R  H  P  G  S  H  H  E  D  R  A  G  H 3
       5910      5920      5930      5940      5950
CGGGCACTCTGCAGACAGCTCCAGACAATCAGGCACTCGTCACACAGAC
GCCCGTGAGACGTCTGTCGAGGTCTGTTAGTCCGTGAGCAGTGTGTCTC
  G  H  S  A  D  S  S  R  Q  S  G  T  R  H  T  E 5960      5970      5980      5990      6000
CTTCCTCTCGTGGACAGGCTGCGTCATCCCATGAACAGGCAAGATCAAGT
GAAGGAGAGCACCTGTCCGACGCAGTAGGGTACTTGTCCGTTCTAGTTCA
  S  S  S  P  G  Q  A  A  S  S  R  E  Q  A  P  S  S 111
       6010      6020      6030      6040      6050
GCAGGACAAAGACATGGATCCCACCACCAGCTTAGTCAGCAGACACTTC
CGTCCTGTTTCTGTACCTAGGGTGGTGGTCGAATCAGTCGTCTGTGAAG
  A  G  E  R  H  G  S  H  Q  L  Q  S  A  D  S  S 9
       6060      6070      6080      6090      6100
CAGACACTCAGGCATTGGGCATGGACAAGCTTCATCTCCAGTCAGGACA
GTCTGTGAGTCCGTAACCCGTACCTGTTCGAAGTAGACGTCAGTCCTGT
  R  H  S  G  I  G  R  Q  A  S  S  A  V  R  D 6110      6120      6130      6140      6150
GTGGACACCGAGGGTACAGTGGTAGTCAGGCCAGTGACAGTGAGGGACAT
CACCTGTGGCTCCCATGTCACCATCAGTCCGGTCACTGTCACTCCCTGTA
  S  G  H  P  G  Y  S  G  S  Q  A  S  D  S  E  G  H 3
       6160      6170      6180      6190      6200
TCAGAAGACTCAGACACACAGTCAGTGTCAGCCCATGGAAAGCTGGCC
AGTCTTCTGAGTCTGTGTGTCAGTCACAGTCGGTACCTTTCGACCCGG
  S  E  D  S  D  T  Q  S  V  S  A  Q  G  K  A  G  P 3                                 3
       6210      6220      6230      6240      6250
CCATCAGCAGAGCCACAAGAGTCGGCACGTGGCCAGTCAGGGGAAAGCT
GGTAGTCGTCTCGGTGTTCTCAGCCGTGCACCGGTCAGTCCCCTTTCGA
  H  Q  Q  S  H  K  E  S  A  R  G  Q  S  G  E  S
```

Figure 4-continued

```
                6260       6270       6280       6290       6300
End RPT5   CTGGACGTTCAGGGTCTTTCCTCTACCAGGTGAGCACTCATGAACAGTCT
           GACCTGCAAGTCCCAGAAAGGAGATGGTCCACTCGTGAGTACTTGTCAGA
            S  G  P  S  G  S  F  L  Y  Q  V  S  T  H  E  Q  S 4         4  4
                6310       6320       6330       6340       6350
RPT6       GAGTCCACCCATGGACTGCCTGGGCCTCAGCACTGGAGGAAGACAAGGATC
           CTCAGGTGGGTACCTGACGGACCCGGAGTCGTGACCTCCTTCTGTTCCTAG
            E  S  T  H  G  Q  S  A  P  S  T  G  G  R  Q  G  S 6360       6370       6380       6390       6400
           CCAGATGACCAGGCACAAGACAGCTCCAGGCACTCAGCATCCCAAGAGG
           GGTCTACTGGTCCGTGTTCTGTCGAGGTCCGTGAGTCGTAGGGTTCTCC
            H  Y  D  Q  A  Q  D  S  S  R  A  S  Q  E
                                                             11
                6410       6420       6430       6440       6450
           GTCAGGACACCATTCGTGGACACCCCGGGCCAAGCAGAGGAGGAAGGCAG
           CAGTCCTGTGGTAAGCACCTGTGGGCCCGGTTCGTCTCCTCCTTCCGTC
            G  Q  D  T  I  R  G  H  P  G  P  S  R  G  G  R  Q 6460       6470       6480       6490       6500
           GGGTCCCACCAGAGCAATCGGTAGATAGGTCTGGACACTCAGGGTCTCA
           CCCAGGGTGGTCTCGTTAGCCATCTATCCAGACCTGTGAGTCCCAGAGT
            G  S  R  Q  E  Q  S  V  D  R  S  G  R  S  G  S  H 6510       6520       6530       6540       6550
           TCACAGCCACACCACATCCCAGGGAAGGTCTGATGCCTCCCGTGGGCAGT
           AGTGTCGGTGTGGTGTAGGGTCCCTTCCAGACTACGGAGGGCACCCGTCA
            H  S  R  T  T  S  Q  G  R  S  D  A  S  R  G  Q
                                                  7
                6560       6570       6580       6590       6600
           CAGGATCCAGAAGTGCAAGCAGAAAAACAGTTACAGGAACAATCAGGA
           GTCCTAGGTCTTCACGTTCGTCTTTTTGTCAATGTCCTTGTTAGTCCT
            S  G  S  R  S  A  S  R  K  T  Y  D  K  E  Q  S  G 10             10  1                         3
                6610       6620       6630       6640       6650
           GATGGCTCAGGCACTCAGGGTGGATCATCATGAAGCTCCCCTGGGC
           CTACCGAGTCCGTGAGTCCCAGCCTAGTAGTACTTCGAGGGGACCCG
            D  G  S  R  G  S  R  R  E  A  S  W  A
                                              5
                6660       6670       6680       6690       6700
           CGACAGCTCTAGACACTCACGGTGGGCAGGACAATCATCGGGCCCA
           GCTGTCGAGATCTGTGAGTGCCACCCGTCCCTGTTAGTAGCCCGGGT
            D  S  S  R  H  S  L  V  G  Q  G  Q  S  S  G
                    7
                6710       6720       6730       6740       6750
           GGACAAGCAGGCCCCGGGATCCAGTGTTAGCCAGGACAGTGACAGTGAG
           CCTGTTCGTCCGGGGCCCTAGGTCACAATCGGTCCTGTCACTGTCACTC
            P  T  S  R  P  G  S  S  V  S  Q  D  S  D  S  E
```

Figure 4-continued

```
       6760      6770      6780      6790      6800
GGACACTCAGAAGATTCTGAGAGGCGGTCTGGGTCTGCTCCAGAAACCA
CCTGTGAGTCTTCTAAGACTCTCCGCCAGACCCAGACGAGGTCTTTGGT
  G  H  S  E  D  S  P  R  S  G  G  A  S  R  N  H 6810      6820      6830      6840      6850
TCATGGATCTGCTCAGGAGCAGTCAAGAGATGGCTCCAGACACCCCAGGT
AGTACCTAGACGAGTCCTCGTCAGTTCTCTACCGAGGTCTGTGGGGTCCA
  R  G  S  A  Q  E  Q  S  R  D  G  S  R  H  P 6860      6870      6880      6890      6900
CCCATCACGAAGACAGAGCCGGTCATGGGCACTCTGCAGAGAGCTCCAGA
GGGTAGTGCTTCTGTCTCGGCCAGTACCCGTGAGACGTCTCTCGAGGTCT
  S  H  H  E  D  R  A  G  H  G  H  S  A  E  S  S 6910      6920      6930      6940      6950
CAATCAGGCACTCATCATGCAGAGAATTCCTCTGGTGGACAGGCTGCATC
GTTAGTCCGTGAGTAGTACGTCTCTTAAGGAGACCACCTGTCCGACGTAG
  Q  S  G  T  H  H  A  E  N  S  S  G  G  Q  A  A  S 6960      6970      6980      6990      7000
ATCCCATGAACAGGCAAGATCAAGTGCAGGAGAGAGACACGGATCCCACC
TAGGGTACTTGTCCGTTCTAGTTCACGTCCTCTCTCTGTGCCTAGGGTGG
  S  H  E  Q  A  P  S  S  A  G  E  P  R  G  H 7010      7020      7030      7040      7050
ACCAGCAGTCAGCAGACAGCTCCAGACACTCAGGCATTGGGCACGGACAA
TGGTCGTCAGTCGTCTGTCGAGGTCTGTGAGTCCGTAACCCGTGCCTGTT
  H  Q  Q  S  A  D  S  S  R  H  S  G  I  G  R  G  Q 7060      7070      7080      7090      7100
GCTTCATCTGCAGTCAGAGACAGTGGACACCGAGGGTCAGTGGTAGTCA
CGAAGTAGACGTCAGTCTCTGTCACCTGTGGCTCCCAGTCACCATCAGT
  A  S  S  A  V  R  D  S  G  H  P  G  S  S  G  S  Q 7110      7120      7130      7140      7150
GGCCAGTGACAGTGAGGGACATTCAGAAGACTCAGACACACAGTCAGTGT
CCGGTCACTGTCACTCCCTGTAAGTCTTCTGAGTCTGTGTGTCAGTCACA
  A  S  D  S  E  G  H  S  E  D  S  D  T  Q  S  V 7160      7170      7180      7190      7200
CAGCCCACGGACAGGCTGGGCCCATCAGCAGAGCCACCAAGAGTCCACA
GTCGGGTGCCTGTCCGACCCGGGTAGTCGTCTCGGTGGTTCTCAGGTGT
  S  A  R  Q  A  G  P  R  Q  Q  S  H  Q  E  S  T 7210      7220      7230      7240      7250
CGTGGCCGGTCAGGGGAAGGTCTGACGTTCAGGGTCTTTCCTCTACCA
GCACCGGCCAGTCCCCTTCCAGACCTGCAAGTCCCAGAAAGGAGATGGT
  P  G  R  S  A  G  P  S  G  K  S  G  S  F  L  Y  Q
```

Figure 4-continued

```
              7260      7270      7280      7290      7300
End RPT6   GGTGAGCACTCATGAACAGTCTGAGTCCGCCCATGGACGGACCGGGACCA
           CCACTCGTGAGTACTTGTCAGACTCAGGCGGGTACTTGCCTGGCCCTGGT
            V  S  T  E  Q  S  E  S  A  H  G  P  T  G  T 7310      7320      7330      7340      7350
RPT7       GCACTGGAGGAAGACAAGGATCCCACCACAAGCAGGCACGAGACAGCTCC
           CGTGACCTCCTTCTGTTCCTAGGGTGGTGTTCGTCCGTGCTCTGTCGAGG
            S  T  G  G  R  Q  G  S  H  H  K  Q  A  R  D  S  S 7360      7370      7380      7390      7400
           AGGCACTCAAGTCCCAAGAGGGTCAGGACACCATTCATGGACACCCGGG
           TCCGTGAGTTCAGGGTTCTCCCAGTCCTGTGGTAACACCTGTGGGCCC
            R  H  S  T  S  Q  E  G  Q  D  T  I  H  G  H  P  G 7410      7420      7430      7440      7450
           GTCAAGCAGGGAGGAAGGCAGGGATCCCACTACGAGCAATGGTAGATA
           CAGTTCGTCCCTCCTTCCGTCCCTAGGGTGATGCTCGTTACCATCTAT
            S  S  S  G  G  R  Q  G  S  R  Y  E  Q  L  V  D 3
              7460      7470      7480      7490      7500
           GCTCTGGACACTCAGGGTCATCACAGCCACACCACATCCCAGGGAAGG
           CGAGACCTGTGAGTCCCAGAGTAGTGTCGGTGTGGTGTAGGGTCCCTTCC
            P  S  G  H  S  G  R  R  S  K  T  T  Q  G  P 7510      7520      7530      7540      7550
           TCTGATGCCTCCCATGGGCATCAGGATCCAGAAGTGCAAGCAGACAAAC
           AGACTACGGAGGGTACCCGTAGTCCTAGGTCTTCACGTTCGTCTGTTTG
            S  D  A  S  H  G  H  S  G  S  R  S  A  S  R  Q  T 6
              7560      7570      7580      7590      7600
           TCGTAAGGAGAACAATCAGGAGACGGCTCCAGGCACTCAGGGTCGCGTC
           AGCATTCCTCTTGTTAGTCCTCTGCCGAGGTCCGTGAGTCCCAGCGCAG
            R  N  D  E  Q  S  G  D  G  S  P  R  S  G  P 5
              7610      7620      7630      7640      7650
           ACCATGAAGCTTCCTCTGGGCGACAGCTCTGACACTCCAGGTGGGC
           TGGTACTTCGAAGGAGAGCCCGCTGTCGAGACTGTGAGGTCCACCCG
            H  H  E  A  S  S  R  A  D  S  S  G  H  S  Q  V  G 6
              7660      7670      7680      7690      7700
           CAGGGACAATCAGAGGGGCCCAGGACAAGCAGGAACGGGATCCAGTT
           GTCCCTGTTAGTCTCCCCGGGTCCTGTTCGTCCTTGCCCTAGGTCAA
            Q  G  Q  S  E  G  P  T  S  K  N  G  S  F 7710      7720      7730      7740      7750
           TAGCCAGGACAGTCACAGTCAGGGACACTCAGAAGACTCTGACAGGTCGT
           ATCGGTCCTGTCAGTGTCAGTCCCTGTGAGTCTTCTGAGACTCTCCAGCA
            S  Q  D  S  D  S  Q  G  H  S  E  D  S  E  R  W
```

Figure 4-continued

```
         7760      7770      7780      7790      7800
    CTGGGTCTGCTTCCAGAAACCATCATGGATCTGCTCAGGAGCAGTAAGA
    GACCCAGACGAAGGTCTTTGGTAGTACCTAGACGAGTCCTCGTCATTCT
     G  G  S  A  S  K  N  H  H  G  S  A  Q  E  Q  L  R 7810      7820      7830      7840      7850
    GATGGCTCCAGACACCCCAGGTCCCATCAAGAAGACAGAGCTGCTCATGG
    CTACCGAGGTCTGTGGGGTCCAGGGTAGTTCTTCTGTCTCGACGAGTACC
      D  G  S  R  H  P  R  S  H  Q  E  D  R  A  G  H  G 7860      7870      7880      7890      7900
    GCACTCTGCAGACAGCTCCAGACAATCAGGCACTCGTCACACACAGACTT
    CGTGAGACGTCTGTCGAGGTCTGTTAGTCCGTGAGCAGTGTGTGTCTGAA
       H  S  A  D  S  S  R  Q  S  G  T  R  H  T  Q  T 7910      7920      7930      7940      7950
    CCTCTGGTGGACAGGCTGCATCATCCCATGAACAGGCAAGATCAAGTGCA
    GGAGACCACCTGTCCGACGTAGTAGGGTACTTGTCCGTTCTAGTTCACGT
     S  S  G  G  Q  A  A  S  S  H  E  Q  A  P  S  S  A 7960      7970      7980      7990      8000
    GGAGAAAGACATGGATCCCACCACCAGCAGTCAGCAGACAGCTCCAGACA
    CCTCTTTCTGTACCTAGGGTGGTGGTCGTCAGTCGTCTGTCGAGGTCTGT
       G  E  R  H  G  S  H  H  Q  S  A  D  S  S  R  H 8010      8020      8030      8040      8050
    CTCAGGCATTGGGCACGGACAAGCTTCATCTGCAGTCAGAGACAGTGGAC
    GAGTCCGTAACCCGTGCCTGTTCGAAGTAGACGTCAGTCTCTGTCACCTG
      S  G  I  G  H  G  Q  A  S  S  A  V  R  D  S  G 8060      8070      8080      8090      8100
    ACGGAGGGTACAGTGGTAGTCAGGCAGTGACATGAGGGACATTCAGAA
    TGCCTCCCATGTCACCATCAGTCCGTCACTGTACTCCCTGTAAGTCTT
       R  R  G  Y  S  G  S  Q  A  S  D  N  E  G  H  E 8110      8120      8130      8140      8150
    GACTCAGACACACAGTCAGTGTCAGCCCACGGACAGGCTGGGTCCCATCA
    CTGAGTCTGTGTGTCAGTCACAGTCGGGTGCCTGTCCGACCCAGGGTAGT
      D  S  D  T  Q  S  V  S  A  H  G  Q  A  G  S  R  Q 8160      8170      8180      8190      8200
    GCAGAGCCACCAAGAGTCCGGCACGTGGGCGGTCAGGGGAAACGTCTGGAC
    CGTCTCGGTGGTTCTCAGGCCGTGCACCCGCCAGTCCCCTTTGCAGACCTG
      Q  S  R  E  S  A  P  G  R  S  G  E  T  S  G 8210      8220      8230      8240      8250
End RPT7  GTTCAGGCTCTTTCCTCTACCAGGTGAGCACTCATGAACAGTCTGAGTCC
    CAAGTCCAGAAAGGAGATGGTCCACTCGTGAGTACTTGTCAGACTCAGG
       H  S  G  S  F  L  Y  Q  V  S  T  H  E  Q  S  E
```

Figure 4-continued

```
              9          9
      8260       8270       8280       8290       8300
RPT8  TCCCATGGATGGACGGGCCCAGCACTGGAGGAAGACAAGGATCCCGGCCA
      AGGGTACCTACCTGCCCGGGTCGTGACCTCCTTCTGTTCCTAGGGCCGGT
       S  H  G  W  T  G  P  S  T  R  G  K  Q  G  S  R  M 8310       8320       8330       8340       8350
      TGACCAGGCACAAGACAGCTCCAGGCACTCAGCATCCAAGACGGTCAGG
      ACTGGTCCGTGTTCTGTCGAGGTCCGTGAGTCGTAGGGTTCTGCCAGTCC
       E  Q  A  Q  D  S  S  R  H  S  A  S  Q  D  G  Q 9
      8360       8370       8380       8390       8400
      ACACCATTCGTGGACACCCGGGGTCAAGCAGAGGAGGAAGGCAGGGGTGC
      TGTGGTAAGCACCTGTGGGCCCCAGTTCGTCTCCTCCTTCCGTCCCCACG
       D  T  I  R  G  H  P  G  S  S  R  G  G  R  Q  G  Y 9          9
      8410       8420       8430       8440       8450
      CACCACGAGCATTCGGTAGATAGGTCTGGACACTCCAGGGTCCCATCACAG
      GTGGTGCTCGTAAGCCATCTATCAGACCTGTGAGGTCCCAGGGTAGTGTC
       H  H  E  H  S  V  D  S  S  G  H  S  G  S  H  H  S 8460       8470       8480       8490       8500
      CCACACCACATCCCAGGGAAGGTCTGATGCCTCCTGTGGGCAGTCAGGAT
      GGTGTGGTGTAGGGTCCCTTCCAGACTACGGAGGGCACCCGTCAGTCCTA
       H  T  T  S  Q  G  R  S  D  A  S  R  G  Q  S  G 8510       8520       8530       8540       8550
      CCAGAAGTGCAAGCAGAACAACACGTAATGAGGAACAATCAGGAGACGGC
      GGTCTTCACGTTCGTCTTGTTGTGCATTACTCCTTGTTAGTCCTCTGCCG
       S  R  S  A  S  P  T  T  R  N  E  Q  S  G  D  G 8560       8570       8580       8590       8600
      TCCAGGCACTCAGGGTCGCGTCACCATGAAGCTTCCACTCATGCCGACAT
      AGGTCCGTGAGTCCCAGCGCAGTGGTACTTCGAAGGTGAGTACGGCTGTA
       S  P  H  S  G  S  R  H  H  S  A  S  T  H  A  D  I 9
      8610       8620       8630       8640       8650
      CTCTAGACACTCACAGGCAGTCCAGGGACAATCAGAGGGGTCAGGACAA
      GAGATCTGTGAGTGTCCGTCAGGTCCCTGTTAGTCTCCCCAGTCCTGTT
       S  R  S  Q  A  V  Q  G  Q  S  E  G  S  R  K 9
      8660       8670       8680       8690       8700
      GCAGGCCGCAGGGATCCAGTGTGAGCCAGGACAGTGACAGTCACGGACAT
      CGTCCGGCGTCCCTAGGTCACACTCGGTCCTGTCACTGTCAGTGCCTGTA
       S  R  K  Q  G  S  S  V  S  Q  D  S  D  S  E  G  H 8710       8720       8730       8740       8750
      TCAGAAGACTCTGAGAGGTGGTCTGGGTCTGCTTCAGAAACCATCATGG
      AGTCTTCTGAGACTCTCCACCAGACCCAGACGAAGGTCTTTGGTAGTACC
       S  E  D  S  E  R  W  S  G  S  A  S  R  N  H  H  G
```

Figure 4-continued

```
              77
     8760      8770      8780      8790      8800
ATCTGCTCAGGAGCAGCAAGAGATGGCTCCAGACACCCAGGTCCCATC
TAGACGAGTCCTCGTCGATTCTCTACCGAGGTCTGTGGGGTCCAGGGTAG
  S  A  Q  E  Q  L  R  D  G  S  R  H  P  S  H 8810      8820      8830      8840      8850
AAGAAGACAGAGCTGGTCATGGGCACTCTGCAGACAGCTCCAGACAATCA
TTCTTCTGTCTCGACCAGTACCCGTGAGACGTCTGTCGAGGTCTGTTAGT
  Q  E  D  R  A  G  H  G  H  S  A  D  S  R  Q  S 8860      8870      8880      8890      8900
GGCACTCGTCACACAGACTCCTCTGGTGGACAGGCTGCATCATCCCA
CCGTGAGCAGTGTGTCTGAAGGAGACCACCTGTCCGACGTAGTAGGGT
  G  T  R  H  T  Q  T  S  S  G  G  Q  A  A  S  H 8910      8920      8930      8940      8950
TGAACAGGCAAGAACAAGTGCAGGAGAAAGACATGGATCCACCACCAGC
ACTTGTCCGTTCTAGTTCACGTCCTCTTTCTGTACCTAGGGTGGTGGTCG
  E  Q  A  R  S  S  A  G  E  P  H  G  S  H  H  Q 8960      8970      8980      8990      9000
AGTCAGCAGACAGCTCCAGACACTCAGGCATTGGCTACGGACAAGCTTCA
TCAGTCGTCTGTCGAGGTCTGTGAGTCCGTAACCGATGCCTGTTCGAAGT
  Q  S  A  D  S  S  R  H  S  G  I  G  H  G  Q  A  S 9010      9020      9030      9040      9050
TCTGCAGTCAGAGACAGTGGACACCGAGGGTACAGTGGTAGTCAGGCCAG
AGACGTCAGTCTCTGTCACCTGTGGCTCCCATGTCACCATCAGTCCGGTC
  S  A  V  R  D  S  G  H  P  G  Y  S  G  S  Q  A  S 9
     9060      9070      9080      9090      9100
TGACATGAGGGACATTCAGAAGACTCAGACACACAGTCAGTGTCAGCCC
ACTGTACTCCCTGTAAGTCTTCTGAGTCTGTGTGTCAGTCACAGTCGGG
  D  H  E  G  H  S  E  D  S  D  T  Q  S  V  S  A 9
     9110      9120      9130      9140      9150
ACGGACAGGGCTGGGCCCATCAGCAGAGCCACCAAGAGTGCGCACGTGGC
TGCCTGTCCGACCCGGGTAGTCGTCTCGGTGGTTCTCAGGCGTGCACCG
  H  G  Q  A  G  S  H  Q  S  H  Q  E  S  A  R  G 7    7    7
     9160      9170      9180      9190      9200
CGGTCAGGGGAAAGGTCTGGACATTCAGGTCTTTCCTCTACCAGCTGAC
GCCAGTCCCCTTTCCAGACCTGTAAGTCCAGAAAGGAGATGGTCGACTC
  R  S  G  E  T  S  G  R  S  G  S  F  L  Y  Q  V  S
```

Figure 4-continued

```
              9210       9220       9230       9240       9250
End RPT8  CACTCATGAACAGTCTGAGTCCTCCCATGGATGGACGGGGCCCAGCACTG
          GTGAGTACTTGTCAGACTCAGGAGGGTACCTACCTGCCCCGGGTCGTGAC
           T  H  E  Q  S  E  S  S  R  G  W  T  G  P  S  T 9260       9270       9280       9290       9300
RPT9      GAGGAAGACAAGGATCCCGCCATGAGCAGGCACAGACAGCTCCAGGCAC
          CTCCTTCTGTTCCTAGGGCGGTACTCGTCCGTGTCTGTCGAGGTCCGTG
           R  R  Q  G  S  P  R  E  Q  A  D  S  S  P 9310       9320       9330       9340       9350
          TCAGCATCCCAAACGGTCAGGACACCATTCGTGGACACCCGGGGTCAAG
          AGTCGTAGGGTTTGCCAGTCCTGTGGTAAGCACCTGTGGGCCCCAGTTC
           S  A  S  Q  Y  G  Q  D  T  I  R  G  H  P  G  S  S 9360       9370       9380       9390       9400
          CAGAGGAGGAAGGCAGGGGTCCACCACGAGCATCGGTAGATACCTCTG
          GTCTCCTCCTTCCGTCCCCAGGTGGTGCTCGTAGCCATCTATGGAGAC
           R  G  G  R  Q  G  Y  H  R  E  H  S  V  D  S  S 9410       9420       9430       9440       9450
          GACACTCAGGGTCCCATCACAGCCACACCACATCCCAGGGAAGGTCTGAT
          CTGTGAGTCCCAGGGTAGTGTCGGTGTGGTGTAGGGTCCCTTCCAGACTA
           G  H  S  G  H  H  S  R  T  T  S  Q  G  R  S  D 9460       9470       9480       9490       9500
          GCCTCCCGTGGGCAGTCAGGATCCAGAAGTGCAAGCAGAACAACACGTAA
          CGGAGGGCACCCGTCAGTCCTAGGTCTTCACGTTCGTCTTGTTGTGCATT
           A  S  R  G  Q  S  G  S  R  S  A  S  R  T  T  P  R 9510       9520       9530       9540       9550
          TGAGGAACAATCAGGAGACGGTCCAGGCACTCAGGGTCACGTCACCATG
          ACTCCTTGTTAGTCCTCTGCCAGGTCCGTGAGTCCCAGTGCAGTGGTAC
           E  E  Q  S  G  D  S  S  R  H  S  V  S  R  H 9560       9570       9580       9590       9600
          AAGCTTCCACTCATGCCGACATCTCTAGACACTCACAGGCCGCCAGTCA
          TTCGAAGGTGAGTACGGCTGTAGAGATCTGTGAGTGTCCGGCGGTCAGT
           E  A  S  T  H  A  D  I  S  P  R  S  Q  A  V  Q  G 9610       9620       9630       9640       9650
          CAATCAGAGGGGTCCAGGAGAAGCAGGCGCCAGGGATCCAGTGTTAGCCA
          GTTAGTCTCCCCAGGTCCTCTTCGTCCGCGGTCCCTAGGTCACATCGGT
           Q  S  E  G  S  R  P  S  R  R  Q  G  S  S  V  S  Q 9660       9670       9680       9690       9700
          GGACAGTGACAGTGAGGGACATTCAGAAGACTCTGAGAGGTGGTCTGGGT
          CCTGTCACTGTCACTCCCTGTAAGTCTTCTGAGACTCTCCACCAGACCCA
           D  S  D  S  E  G  H  S  E  D  S  E  R  W  S  G
```

Figure 4-continued

```
         9710      9720      9730      9740      9750
    CTGCTTCCAGAAACCATCGTGGATCTGTTCAGGAGCAGTCAAGGCACGGC
    GACGAAGGTCTTTGGTAGCACCTAGACAAGTCCTCGTCAGTTCCGTGCCG
     G  A  S  R  N  H  K  G  S  V  Q  E  Q  S  R  H  G 9760      9770      9780      9790      9800
    TCCAGACACCCCAGGTCCCATCACGAAGACAGAGGCGGGTCACCGGCACTC
    AGGTCTGTGGGGTCCAGGGTAGTGCTTCTGTCTCGGCCAGTGGCCGTGAG
        S  R  H  P  S  R  R  E  D  P  A  G  H  G  H  S 9810      9820      9830      9840      9850
    TGCAGACTGCTCCAGACAATCAGGCACTCGTCAGGCAGAGACTTCCTCTG
    ACGTCTGACGAGGTCTGTTAGTCCGTGAGCAGTCCGTCTCTGAAGGAGAC
      A  D  R  S  P  Q  S  G  H  R  A  E  H  S  S 9860      9870      9880      9890      9900
    GTGGACAGGCTGCATCATCCCATGAACAGGCAAGATCAAGTCCAGGAGAG
    CACCTGTCCGACGTAGTAGGGTACTTGTCCGTTCTAGTTCAGGTCCTCTC
     G  G  Q  A  A  S  S  H  E  Q  A  R  S  S  P  G  E 9910      9920      9930      9940      9950
    AGACACGGATCCCGCCACCAGCAGTCAGCAGACAGCTCCAGACACTCAGG
    TCTGTGCCTAGGGCGGTGGTCGTCAGTCGTCTGTCGAGGTCTGTGAGTCC
      P  R  G  S  R  H  Q  Q  S  A  D  S  G  R  H  S  G 9960      9970      9980      9990     10000
    CATTCGCGTGGACAAGTTCATCTGCAGTCAGAGACAGTTGACACTGGG
    GTAAGCGCACCTGTTCGAAGTAGACGTCAGTCTCTGTCAACTGTGACCC
      I  F  R  G  Q  A  S  S  A  V  R  D  S  R  H  W 2
        10010     10020     10030     10040     10050
    GGTCCAGTGGTAGTCAGGCCAGTGATAGTGAGGGACATTCAGAAGAGTCA
    CCAGGTCACCATCAGTCCGGTCACTATCACTCCCTGTAAGTCTTCTCAGT
      G  S  S  G  S  Q  A  S  D  S  G  R  S  E  E  S 10060     10070     10080     10090     10100
    GACACACAGTCAGTGTCAGGCCATGGACAGGCTGGGCCCCATCAGCAGAG
    CTGTGTGTCAGTCACAGTCCGGTACCTGTCCGACCCGGGGTAGTCGTCTC
      D  T  Q  S  V  S  G  H  G  Q  A  G  P  H  Q  Q  S 10110     10120     10130     10140     10150
    CCACCAAGAGTCCGCACGTGACCGGTCAGGGGAAGGTCTGGACGTTCAG
    GGTGGTTCTCAGGCGTGCACTGGCCAGTCCCCCTTCCAGACCTGCAAGTC
      H  Q  E  S  A  R  D  R  S  G  P  S  G  R  S 10160     10170     10180     10190     10200
End RPT9  GGTCTTTCCTCTACCAGGTGAGCACTCATGAACAGCTGAGTCTGCCCAT
    CCAGAAAGGAGATGGTCCACTCGTGAGTACTTGTCAGACTCAGACGGGTA
      G  S  F  L  Y  Q  V  S  T  H  E  Q  S  E  S  A  H
```

Figure 4-continued

RPT10

```
       3        3          3
       10210    10220      10230    10240    10250
    GGTCGGACCAGGACCAGCACTGGAGGAAGACAAGGATCCCACCACGAGCA
    CCAGCCTGGTCCTGGTCGTGACCTCCTTCTGTTCCTAGGGTGGTGCTCGT
      G  R  T  P  T  S  G  P  P  Q  C  S  H  H  E  Q 10260    10270    10280    10290    10300
    GGCAGGAGACAGCTCCAGGCACTCAGCGTCCCAAGAGGGTCAGGACACCA
    CCGTCCTCTGTCGAGGTCCGTGAGTCGCAGGGTTCTCCCAGTCCTGTGGT
      A  R  D  S  S  R  A  S  Q  E  G  Q  D  T 2
       10310    10320    10330    10340    10350
    TTCGTGGACACCCGGGGTCAAGCAGAGGAGGAAGGCAGGGATCCCACTAC
    AAGCACCTGTGGGCCCCAGTTCGTCTCCTCCTTCCGTCCCTAGGGTGATG
      I  R  G  H  P  G  S  S  R  P  G  R  Q  G  S  H  Y 10360    10370    10380    10390    10400
    GAGCAATCGGTAGATAGGTCTGGACACTCAGGGTCCCATCACAGCTACAC
    CTCGTTAGCCATCTATCCAGACCTGTGAGTCCCAGGGTAGTGTCGGTGTG
      E  Q  S  V  D  R  S  G  H  S  G  S  H  H  S  T 10410    10420    10430    10440    10450
    CACATCCCAGGGAAGGTCTGATGCCTCCCGTGGGCAGTCAGGATCCAGAA
    GTGTAGGGTCCCTTCCAGACTACGGAGGGCACCCGTCAGTCCTAGGTCTT
      T  S  Q  G  R  S  D  A  S  R  G  Q  S  G  S  R 5          3          6
       10460    10470    10480    10490    10500
    GTGCAGCAGACAAACTGGTAATGAGGAACAATCAGGAGATGGCTCCAGG
    CACGTCGTCTGTTTGAGCATTACTCCTTGTTAGTCCTCTACCGAGGTCC
      S  A  S  R  Q  T  R  N  D  E  Q  S  G  D  G  S  R 6                    (0)
       10510    10520    10530    10540    10550
    CACTCAGGTCGCGTCACCATGAAGCTTCCACTCAGGGCGACAGCTCTAG
    GTGAGTCCAGCGCAGTGGTACTTCGAAGGTGAGTCCCGCTGTCGAGATC
      H  S  W  S  H  H  E  A  S  T  Q  A  D  S  S  R 11
       10560    10570    10580    10590    10600
    ACACTCACAGTCCGGCCAGGGACAATCAGCGGGGGCCAGGACAAGCAGGA
    TGTGAGTGTCAGGCCGGTCCCTGTTAGTCGCCCCGGTCCTGTTCGTCCT
      H  S  Q  S  G  Q  G  Q  S  A  G  P  R  T  S  R 10610    10620    10630    10640    10650
    ACCAGGGATCCAGTGTTAGCCAGGACAGTGACAGTCAGGGACACTCAGAA
    TGGTCCCTAGGTCACAATCGGTCCTGTCACTGTCAGTCCCTGTGAGTCTT
      N  Q  G  S  S  V  S  Q  D  S  D  S  Q  G  R  S  E 10660    10670    10680    10690    10700
    GACTCTGAGAGGTGGTCTGGGTCTGCTTCCAGAAACCATCGTGGATCTGC
    CTGAGACTCTCCACCAGACCCAGACGAAGGTCTTTGGTAGCACCTAGACG
      D  S  E  R  W  S  G  S  A  S  P  H  R  G  S  A
```

Figure 4-continued

```
       10710     10720     10730     10740     10750
TCAGGAGCAGTCAAGAGATGGCTCCAGACACCCA GTCCCATCACGAAG
AGTCCTCGTCAGTTCTCTACCGAGGTCTGTGGGG CAGGGTAGTGCTTC
   Q  E  Q  S  P  D  G  S  R  H  P  T  S  H  E 10760     10770     10780     10790     10800
ACAGAGCCGGTCACGGGCACTCTGCAGAGAGTTCCAGACAATCAGGCACT
TGTCTCGGCCAGTGCCCGTGAGACGTCTCTCAAGGTCTGTTAGTCCGTGA
    D  R  A  G  R  G  H  S  A  E  S  S  R  Q  S  G  T 10810     10820     10830     10840     10850
CATCATGCAGAGAATTCCTCTGGTGGACAGGCTGCATCATCCCATGAACA
GTAGTACGTCTCTTAAGGAGACCACCTGTCCGACGTAGTAGGGTACTTGT
    H  H  A  E  N  S  S  G  G  Q  A  A  S  H  E  Q 10860     10870     10880     10890     10900
GGCAAGATCAAGTGCAGGAGAGAGACATGGATCCCACTACCAGCAGTCAG
CCGTTCTAGTTCACGTCCTCTCTCTGTACCTAGGGTGGTCGTCGTCAGTC
    A  R  S  S  A  G  E  R  H  G  S  H  Q  Q  S 10910     10920     10930     10940     10950
CAGACAGCTCCAGACATCAGGCATTGGGCACGGACAAGCTTCATCTGCA
GTCTGTCGAGGTCTGTGAGTCCGTAACCCGTGCCTGTTCGAAGTAGACGT
    A  D  S  S  R  H  S  G  L  G  R  G  Q  A  S  S  A 10960     10970     10980     10990     11000
GTCAGAGACAGTGGACACCGAGGGTCCAGTGGAGTCAGGCCAGTGACAG
CAGTCTCTGTCACCTGTGGCTCCCAGGTCACCTCAGTCCGGTCACTGTC
    V  R  D  S  G  H  P  G  S  S  G  S  Q  A  S  D  G 11010     11020     11030     11040     11050
TGAGGGACATTCAGAAGACTCAGACACACAGTCAGTGTCAGCCCACGGAC
ACTCCCTGTAAGTCTTCTGAGTCTGTGTGTCAGTCACAGTCGGGTGCCTG
    E  G  H  S  E  D  S  D  T  Q  S  V  S  A  H  G 11060     11070     11080     11090     11100
AGGCTGGGCCCCATCAGCAGAGCCACCAAGAGTCCACACGTGGCCGGTCA
TCCGACCCGGGGTAGTCGTCTCGGTGGTTCTCAGGTGTGCACCGGCCAGT
    Q  A  G  P  H  Q  Q  S  H  Q  E  S  T  P  G  R  S 11110     11120     11130     11140     11150
GCAGGAAGGTCTGGACGTTCAGGGTCTTTCCTCTACCAGGTGAGCACTCA
CGTCCTTCCAGACCTGCAAGTCCCAGAAAGGAGATGGTCCACTCGTGAGT
    A  G  P  S  G  K  S  G  S  F  L  Y  Q  V  S  T  H 11160     11170     11180     11190     11200
TGAACAGTCTGAGTCTGCCCATGGACGGGCTGGGCCCAG ACTGGAGGAA
ACTTGTCAGACTCAGACGGGTACCTGCCCGACCCGGGTC TGACCTCCTT
    E  Q  S  E  S  A  H  G  K  A  G  P  S  T  G  G
```
End RPT10

Figure 4-continued

```
              11210       11220       11230       11240       11250
RPT11         GACAAGGATCCCGCCACGAGCAGGCACGAGACAGCTCCAGGCACTCAGCG
high          CTGTTCCTAGGGCGGTGCTCGTCCGTGCTCTGTCGAGGTCCGTGAGTCGC
homology       R  Q  G  S  R  H  E  Q  A  R  D  S  S  R  H  S  A 11260       11270       11280       11290       11300
              TCCCAAGAGGGTCAGGACACCATTCGTGGACACCCGGGGGTCAAGGAGAGG
              AGGGTTCTCCCAGTCCTGTGGTAAGCACCTGTGGGCCCCAGTTCCTCTCC
               S  Q  E  G  Q  D  T  I  R  G  H  P  G  S  R  R  G 11310       11320       11330       11340       11350
              AGGAAGACAGGGATCCTACCACGAGCAATCGGTAGATAGGTCTGGACACT
              TCCTTCTGTCCCTAGGATGGTGCTCGTTAGCCATCTATCCAGACCTGTGA
                G  R  Q  G  S  Y  H  E  Q  S  V  D  R  S  G  H 11360       11370       11380       11390       11400
              CAGGGTCCCATCACAGCCACACCACATCCCAGGGAAGGTCTGATGCCTCC
              GTCCCAGGGTAGTGTCGGTGTGGTGTAGGGTCCCTTCCAGACTACGGAGG
               S  G  S  H  H  S  H  T  T  S  Q  G  R  S  D  A  S 11410       11420       11430       11440       11450
              CATGGGCAGTCAGGATCCAGAAGTGCAAGCAGAGAAACACGTAATGAGGA
              GTACCCGTCAGTCCTAGGTCTTCACGTTCGTCTCTTTGTGCATTACTCCT
                H  G  Q  S  G  S  R  S  A  S  R  E  T  R  N  E  E 11460       11470       11480       11490       11500
              ACAGTCAGGAGACGGCTCCAGGCACTCAGGGTCGCGTCACCATGAAGCTT
              TGTCAGTCCTCTGCCGAGGTCCGTGAGTCCCAGCGCAGTGGTACTTCGAA
                 Q  S  G  D  G  S  R  H  S  G  R  H  H  E  A 11510       11520       11530       11540       11550
              CCACTCAGGCTGACAGCTCTAGACACTCACAGTCCGGCCAGGGTGAATCA
              GGTGAGTCCGACTGTCGAGATCTGTGAGTGTCAGGCCGGTCCCACTTAGT
               S  T  Q  A  D  S  S  R  H  S  Q  S  G  Q  G  E  S 11560       11570       11580       11590       11600
              GCGGGGTCCAGGAGAAGCAGGCGCCAGGGATCCAGTGTTAGCCAGGACAG
              CGCCCCAGGTCCTCTTCGTCCGCGGTCCCTAGGTCACAATCGGTCCTGTC
                A  G  S  R  R  S  R  R  Q  G  S  S  V  S  Q  D  S 11610       11620       11630       11640       11650
              TGACAGTGAGGCATACCCAGAGGACTCTGAGAGGCGATCTGAGTCTGCTT
              ACTGTCACTCCGTATGGGTCTCCTGAGACTCTCCGCTAGACTCAGACGAA
                  D  S  E  A  Y  P  E  D  S  E  R  R  S  E  S  A 11660       11670       11680       11690       11700
              CCAGAAACCATCATGGATCTTCTCGGGAGCAGTCAAGAGATGGCTCCAGA
              GGTCTTTGGTAGTACCTAGAAGAGCCCTCGTCAGTTCTCTACCGAGGTCT
                 S  R  N  H  H  G  S  S  R  E  Q  S  R  D  G  S  P
```

Figure 4-continued

```
RPT11                11710     11720     11730     11740     11750
end         CACCCCGGATCCTCTCACCGCGATACAGCCAGTCATGTACAGTCTTCACC
high        GTGGGGCCTAGGAGAGTGGCGCTATGTCGGTCAGTACATGTCAGAAGTGG
homology      H  P  G  S  S  R  D  T  A  S  H  V  Q  S  S  P 11760     11770     11780     11790     11800
            TGTACAGTCAGACTCTAGTACCGCTAAGGAACATGGTCACTTTAGTAGTC
            ACATGTCAGTCTGAGATCATGGCGATTCCTTGTACCAGTGAAATCATCAG
              V  Q  S  D  S  S  T  A  K  E  H  G  H  F  S  S 11810     11820     11830     11840     11850
            TTTCACAAGATTCTGCGTATCACTCAGGAATACAGTCACGTGGCAGTCCT
            AAAGTGTTCTAAGACGCATAGTGAGTCCTTATGTCAGTGCACCGTCAGGA
              L  S  Q  D  S  A  Y  H  S  G  I  Q  S  R  G  S  P 11860     11870     11880     11890     11900
            CACAGTTCTAGTTCTTATCATTATCAATCTGAGGGCACTGAAAGGCAAAA
            GTGTCAAGATCAAGAATAGTAATAGTTAGACTCCCGTGACTTTCCGTTTT
              H  S  S  S  Y  H  Y  Q  S  E  G  T  E  R  Q  K 11910     11920     11930     11940     11950
            AGGTCAATCAGGTTTAGTTTGGAGACATGGCAGCTATGGTAGTGCAGATT
            TCCAGTTAGTCCAAATCAAACCTCTGTACCGTCGATACCATCACGTCTAA
              G  Q  S  G  L  V  W  R  H  G  S  Y  G  S  A  D 11960     11970     11980     11990     12000
            ATGATTATGGTGAATCCGGGTTTAGACACTCTCAGCACGGAAGTGTTAGT
            TACTAATACCACTTAGGCCCAAATCTGTGAGAGTCGTGCCTTCACAATCA
              Y  D  Y  G  E  S  G  F  R  H  S  Q  H  G  S  V  S 12010     12020     12030     12040     12050
            TACAATTCCAATCCTGTTGTTTTCAAGGAAAGATCTGATATCTGTAAAGC
            ATGTTAAGGTTAGGACAACAAAAGTTCCTTTCTAGACTATAGACATTTCG
              Y  N  S  N  P  V  V  F  K  E  R  S  D  I  C  K  A 12060     12070     12080     12090     12100
            AAGTGCGTTTGGTAAAGATCATCCAAGGTATTATGCAACGTATATTAATA
            TTCACGCAAACCATTTCTAGTAGGTTCCATAATACGTTGCATATAATTAT
              S  A  F  G  K  D  H  P  R  Y  Y  A  T  Y  I  N End RPT11            12110     12120     12130     12140     12150
low         AGGACCCAGGTTTATGTGGCCATTCTAGTGATATATCGAAACAACTGGGA
homology    TCCTGGGTCCAAATACACCGGTAAGATCACTATATAGCTTTGTTGACCCT
              K  D  P  G  L  C  G  H  S  S  D  I  S  K  Q  L  G 12160     12170     12180
Tail        TTTAGTCAGTCACAGAGATACTATTACTATGAGTAA
            AAATCAGTCAGTGTCTCTATGATAATGATACTCATT
              F  S  Q  S  Q  R  Y  Y  Y  Y  E  *
```

Figure 5.
Atopy transmitted as a dominant trait with reduced penetrance in an IV family.
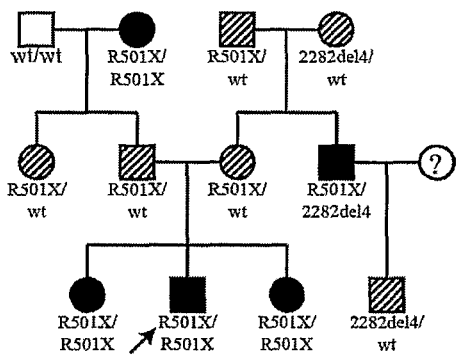
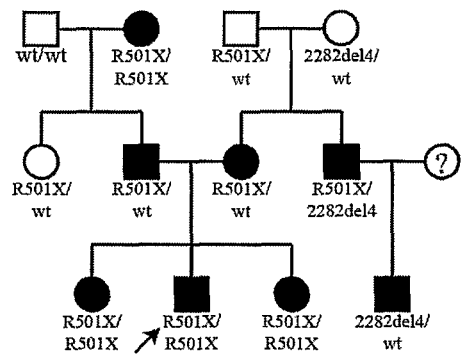

Figure 6. Filaggrin variants are associated with increased atopy

Increased number of positive allergens in carriers of filaggrin mutations.

Figure 9
Biochemical consequences of more 3' *FLG* mutations
(A) Immunohistochemistry
(B) Immunoblotting
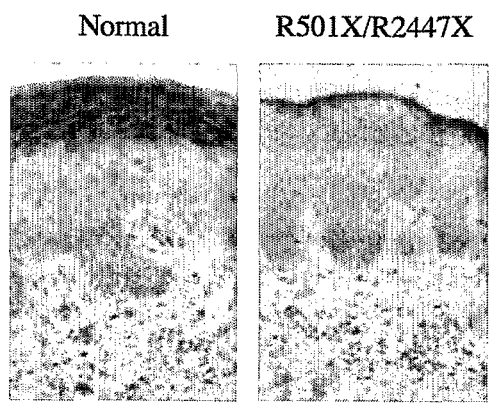
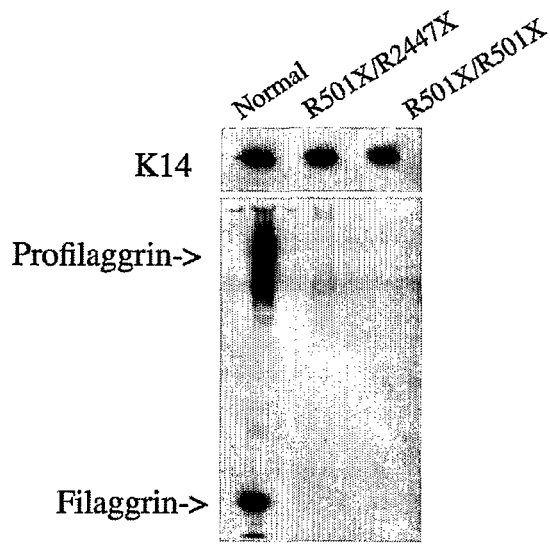
*Figure 10*
*Schematic diagram of profilaggrin proteins encoded by size variant alleles of FLG.*
Profilaggrin protein encoded by Human Genome Sequence
Population size variants encoded by larger alleles
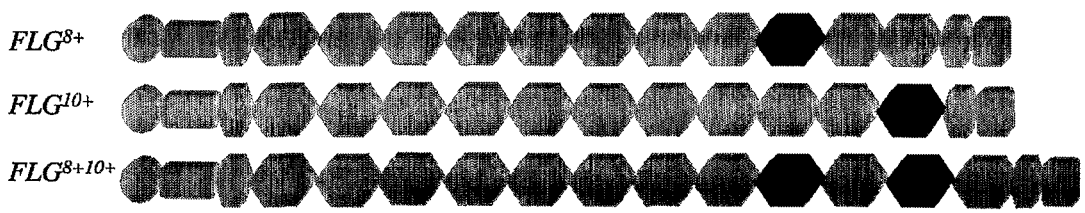

Figure 11
DNA sequence of *FLG* size variant allele *FLG*$^{8+}$

Both strands shown with amino acid translation.
Sequence Range: 1 to 5251

```
            10        20        30        40        50
      AGGACAAGCAGGAACCGGGGATCCAGTTTTAGCCAGGACAGTGACAGTCA
      TCCTGTTCGTCCTTGGCCCCTAGGTCAAAATCGGTCCTGTCACTGTCAGT
        R  T  S  R  N  R  G  S  S  F  S  Q  D  S  D  S  Q 60        70        80        90       100
      GGGACACTCAGAAGACTCTGAGAGGTGGTCTGGGTCTGCTTCCAGAAACC
      CCCTGTGAGTCTTCTGAGACTCTCCACCAGACCCAGACGAAGGTCTTTGG
        G  H  S  E  D  S  E  R  W  S  G  S  A  S  R  N 110       120       130       140       150
      ATCATGGATCTGCTCAGGAGCAGCTAAGAGATGGCTCCAGACACCCCAGG
      TAGTACCTAGACGAGTCCTCGTCGATTCTCTACCGAGGTCTGTGGGGTCC
        H  H  G  S  A  Q  E  Q  L  R  D  G  S  R  H  P  R 160       170       180       190       200
      TCCCATCAAGAAGACAGAGCTGGTCATGGGCACTCTGCAGACAGCTCCAG
      AGGGTAGTTCTTCTGTCTCGACCAGTACCCGTGAGACGTCTGTCGAGGTC
        S  H  Q  E  D  R  A  G  H  G  H  S  A  D  S  S  R 210       220       230       240       250
      ACAATCAGGCACTCGTCACACACAGACTTCCTCTGGTGGACAGGCTGCAT
      TGTTAGTCCGTGAGCAGTGTGTGTCTGAAGGAGACCACCTGTCCGACGTA
        Q  S  G  T  R  H  T  Q  T  S  S  G  G  Q  A  A 260       270       280       290       300
      CATCCCATGAACAGGCAAGATCAAGTGCAGGAGAAAGACATGGATCCCAC
      GTAGGGTACTTGTCCGTTCTAGTTCACGTCCTCTTTCTGTACCTAGGGTG
        S  S  H  E  Q  A  R  S  S  A  G  E  R  H  G  S  H 310       320       330       340       350
      CACCAGCAGTCAGCAGACAGCTCCAGACACTCAGGCATTGGGCACGGACA
      GTGGTCGTCAGTCGTCTGTCGAGGTCTGTGAGTCCGTAACCCGTGCCTGT
        H  Q  Q  S  A  D  S  S  R  H  S  G  I  G  H  G  Q 360       370       380       390       400
      AGCTTCATCTGCAGTCAGAGACAGTGGACACCGAGGGTACAGTGGTAGTC
      TCGAAGTAGACGTCAGTCTCTGTCACCTGTGGCTCCCATGTCACCATCAG
        A  S  S  A  V  R  D  S  G  H  R  G  Y  S  G  S 410       420       430       440       450
      AGGCCAGTGACAATGAGGGACATTCAGAAGACTCAGACACACAGTCAGTG
      TCCGGTCACTGTTACTCCCTGTAAGTCTTCTGAGTCTGTGTGTCAGTCAC
        Q  A  S  D  N  E  G  H  S  E  D  S  D  T  Q  S  V 460       470       480       490       500
      TCAGCCCACGGACAGGCTGGGTCCCATCAGCAGAGCCACCAAGAGTCCGC
      AGTCGGGTGCCTGTCCGACCCAGGGTAGTCGTCTCGGTGGTTCTCAGGCG
        S  A  H  G  Q  A  G  S  H  Q  Q  S  H  Q  E  S  A 510       520       530       540       550
      ACGTGGCCGGTCAGGGGAAACGTCTGGACATTCAGGGTCTTTCCTCTACC
      TGCACCGGCCAGTCCCCTTTTGCAGACCTGTAAGTCCCAGAAAGGAGATGG
        R  G  R  S  G  E  T  S  G  H  S  G  S  F  L  Y
```

Figure 11- continued

```
         560        570        580        590        600
AGGTGAGCACTCATGAACAGTCTGAGTCCTCCCATGGATGGACGGGGCCC
TCCACTCGTGAGTACTTGTCAGACTCAGGAGGGTACCTACCTGCCCCGGG
  Q  V  S  T  H  E  Q  S  E  S  S  H  G  W  T  G  P 610        620        630        640        650
AGCACTAGAGGAAGACAAGGATCCCGCCATGAGCAGGCACAAGACAGCTC
TCGTGATCTCCTTCTGTTCCTAGGGCGGTACTCGTCCGTGTTCTGTCGAG
   S  T  R  G  R  Q  G  S  R  H  E  Q  A  Q  D  S  S 660        670        680        690        700
CAGGCACTCAGCATCCCAAGACGGTCAGGACACCATTCGTGGACACCCGG
GTCCGTGAGTCGTAGGGTTCTGCCAGTCCTGTGGTAAGCACCTGTGGGCC
   R  H  S  A  S  Q  D  G  Q  D  T  I  R  G  H  P 710        720        730        740        750
GGTCAAGCAGAGGAGGAAGGCAGGGGTACCACCACGAGCATTCGGTAGAT
CCAGTTCGTCTCCTCCTTCCGTCCCCATGGTGGTGCTCGTAAGCCATCTA
  G  S  S  R  G  G  R  Q  G  Y  H  H  E  H  S  V  D 760        770        780        790        800
AGCTCTGGACACTCAGGGTCCCATCACAGCCACACCACATCCCAGGGAAG
TCGAGACCTGTGAGTCCCAGGGTAGTGTCGGTGTGGTGTAGGGTCCCTTC
  S  S  G  H  S  G  S  H  H  S  H  T  T  S  Q  G  R 810        820        830        840        850
GTCTGATGCCTCCCGTGGGCAGTCAGGATCCAGACGTGCAAGCAGAACAA
CAGACTACGGAGGGCACCCGTCAGTCCTAGGTCTGCACGTTCGTCTTGTT
      S  D  A  S  R  G  Q  S  G  S  R  R  A  S  R  T 860        870        880        890        900
CACGTAATGAGGAACAATCAGGAGACGGCTCCAGGCACTCAGGGTCGCGT
GTGCATTACTCCTTGTTAGTCCTCTGCCGAGGTCCGTGAGTCCCAGCGCA
   T  R  N  E  E  Q  S  G  D  G  S  R  H  S  G  S  R 910        920        930        940        950
CACCATGAAGCTTCCACTCATGCCGACATCTCTAGACACTCACAGGCAGT
GTGGTACTTCGAAGGTGAGTACGGCTGTAGAGATCTGTGAGTGTCCGTCA
  H  H  E  A  S  T  H  A  D  I  S  R  H  S  Q  A  V 960        970        980        990       1000
CCAGGGACAATCAGAGGGGTCCAGGAGAAGCAGGCGCCAGGGATCCAGTG
GGTCCCTGTTAGTCTCCCCAGGTCCTCTTCGTCCGCGGTCCCTAGGTCAC
   Q  G  Q  S  E  G  S  R  R  S  R  R  Q  G  S  S 1010       1020       1030       1040       1050
TTAGCCAGGACAGTGACAGTGAGGGACATTCAGAAGACTCTGAGAGGTGG
AATCGGTCCTGTCACTGTCACTCCCTGTAAGTCTTCTGAGACTCTCCACC
   V  S  Q  D  S  D  S  E  G  H  S  E  D  S  E  R  W 1060       1070       1080       1090       1100
TCTGGGTCTGCTTCCAGAAACCATCATGGATCTGCTCAGGAGCAGCTAAG
AGACCCAGACGAAGGTCTTTGGTAGTACCTAGACGAGTCCTCGTCGATTC
   S  G  S  A  S  R  N  H  H  G  S  A  Q  E  Q  L  R 1110       1120       1130       1140       1150
AGATGGCTCCAGACACCCCAGGTCCCATCAAGAAGGCAGAGCTGGTCATG
TCTACCGAGGTCTGTGGGGTCCAGGGTAGTTCTTCCGTCTCGACCAGTAC
   D  G  S  R  H  P  R  S  H  Q  E  G  R  A  G  H
```

Figure 11- continued

```
              1160      1170      1180      1190      1200
         GGCACTCTGCAGACAGCTCCAGACAATCAGGCACTCGTCACACACAGACT
         CCGTGAGACGTCTGTCGAGGTCTGTTAGTCCGTGAGCAGTGTGTGTCTGA
          G  H  S  A  D  S  S  R  Q  S  G  T  R  H  T  Q  T 1210      1220      1230      1240      1250
         TCCTCTGGTGGACAGGCTGCATCATCYCATGAACAGGCAAGATCAAGTGC
         AGGAGACCACCTGTCCGACGTAGTAGRGTACTTGTCCGTTCTAGTTCACG
           S  S  G  G  Q  A  A  S  S  H  E  Q  A  R  S  S  A 1260      1270      1280      1290      1300
         AGGAGAAAGACATGGATCCCACCACCAGCAGTCAGCAGACAGCTCCAGAC
         TCCTCTTTCTGTACCTAGGGTGGTGGTCGTCAGTCGTCTGTCGAGGTCTG
            G  E  R  H  G  S  H  H  Q  Q  S  A  D  S  S  R 1310      1320      1330      1340      1350
         ACTCAGGCATTGGGCACGGACAAGCTTCATCTGCAGTCAGAGACAGTGGA
         TGAGTCCGTAACCCGTGCCTGTTCGAAGTAGACGTCAGTCTCTGTCACCT
          H  S  G  I  G  H  G  Q  A  S  S  A  V  R  D  S  G 1360      1370      1380      1390      1400
         CACCGAGGGTACAGTGGTAGTCAGGCCAGTGACAATGAGGGACATTCAGA
         GTGGCTCCCATGTCACCATCAGTCCGGTCACTGTTACTCCCTGTAAGTCT
           H  R  G  Y  S  G  S  Q  A  S  D  N  E  G  H  S  E 1410      1420      1430      1440      1450
         AGACTCAGACACACAGTCAGTGTCAGCCCACGGACAGGCTGGGTCCCATC
         TCTGAGTCTGTGTGTCAGTCACAGTCGGGTGCCTGTCCGACCCAGGGTAG
           D  S  D  T  Q  S  V  S  A  H  G  Q  A  G  S  H 1460      1470      1480      1490      1500
         AGCAGAGCCACCAAGAGTCCGCACGTGGCCGGTCAGGGGAAACGTCTGGA
         TCGTCTCGGTGGTTCTCAGGCGTGCACCGGCCAGTCCCCTTTGCAGACCT
          Q  Q  S  H  Q  E  S  A  R  G  R  S  G  E  T  S  G 1510      1520      1530      1540      1550
         CATTCAGGATCTTTCCTCTACCAGGTGAGCACTCATGAACAGTCTGAGTC
         GTAAGTCCTAGAAAGGAGATGGTCCACTCGTGAGTACTTGTCAGACTCAG
           H  S  G  S  F  L  Y  Q  V  S  T  H  E  Q  S  E  S 1560      1570      1580      1590      1600
         CTCCCATGGATGGACGGGGCCCAGCACTAGAGGAAGACAAGGATCCCGCC
         GAGGGTACCTACCTGCCCCGGGTCGTGATCTCCTTCTGTTCCTAGGGCGG
            S  H  G  W  T  G  P  S  T  R  G  R  Q  G  S  R 1610      1620      1630      1640      1650
         ATGAGCAGGCACAAGACAGCTCCAGGCACTCAGCATCCCAAGATGGTCAG
         TACTCGTCCGTGTTCTGTCGAGGTCCGTGAGTCGTAGGGTTCTACCAGTC
           H  E  Q  A  Q  D  S  S  R  H  S  A  S  Q  D  G  Q 1660      1670      1680      1690      1700
         GACACCATTCGTGGACACCCGGGGTCAAGCAGAGGAGGAAGGCAGGGGTA
         CTGTGGTAAGCACCTGTGGGCCCCAGTTCGTCTCCTCCTTCCGTCCCCAT
            D  T  I  R  G  H  P  G  S  S  R  G  G  R  Q  G  Y 1710      1720      1730      1740      1750
         CCACCACGAGCATTCGGTAGATAGCTCTGGACACTCAGGGTCCCATCACA
         GGTGGTGCTCGTAAGCCATCTATCGAGACCTGTGAGTCCCAGGGTAGTGT
            H  H  E  H  S  V  D  S  S  G  H  S  G  S  H  H
```

Figure 11- continued

```
        1760       1770       1780       1790       1800
GCCACACCACATCCCAGGGAAGGTCTGATGCCTCCCGTGGGCAGTCAGGA
CGGTGTGGTGTAGGGTCCCTTCCAGACTACGGAGGGCACCCGTCAGTCCT
 S  H  T  T  S  Q  G  R  S  D  A  S  R  G  Q  S  G 1810       1820       1830       1840       1850
TCCAGAAGTGCAAGCAGAACAACACGTAATGAGGAACAATCAGGAGACGG
AGGTCTTCACGTTCGTCTTGTTGTGCATTACTCCTTGTTAGTCCTCTGCC
   S  R  S  A  S  R  T  T  R  N  E  E  Q  S  G  D  G 1860       1870       1880       1890       1900
CTCCAGGCACTCAGGGTCGCGTCACCATGAAGCTTCCACTCATGCCGACA
GAGGTCCGTGAGTCCCAGCGCAGTGGTACTTCGAAGGTGAGTACGGCTGT
   S  R  H  S  G  S  R  H  H  E  A  S  T  H  A  D 1910       1920       1930       1940       1950
TCTCTAGACACTCACAGGCAGTCCAGGGACAATCAGAGGGGTCCAGGAGA
AGAGATCTGTGAGTGTCCGTCAGGTCCCTGTTAGTCTCCCCAGGTCCTCT
 I  S  R  H  S  Q  A  V  Q  G  Q  S  E  G  S  R  R 1960       1970       1980       1990       2000
AGCAGGCGCCAGGGATCCAGTGTTAGCCAGGACAGTGACAGTGAGGGACA
TCGTCCGCGGTCCCTAGGTCACAATCGGTCCTGTCACTGTCACTCCCTGT
  S  R  R  Q  G  S  S  V  S  Q  D  S  D  S  E  G  H 2010       2020       2030       2040       2050
TTCAGAAGACTCTGAGAGGTGGTCTGGGTCTGCTTCCAGAAACCATCATG
AAGTCTTCTGAGACTCTCCACCAGACCCAGACGAAGGTCTTTGGTAGTAC
  S  E  D  S  E  R  W  S  G  S  A  S  R  N  H  H 2060       2070       2080       2090       2100
GATCTGCTCAGGAGCAGCTAAGAGATGGCTCCAGACACCCCAGGTCCCAT
CTAGACGAGTCCTCGTCGATTCTCTACCGAGGTCTGTGGGGTCCAGGGTA
  G  S  A  Q  E  Q  L  R  D  G  S  R  H  P  R  S  H 2110       2120       2130       2140       2150
CAAGAAGACAGAGCTGGTCATGGGCACTCTGCAGACAGCTCCAGACAATC
GTTCTTCTGTCTCGACCAGTACCCGTGAGACGTCTGTCGAGGTCTGTTAG
   Q  E  D  R  A  G  H  G  H  S  A  D  S  S  R  Q  S 2160       2170       2180       2190       2200
AGGCACTCGTCACACACAGGCTTCCTCTGGTGGACAGGCTGCATCATCCC
TCCGTGAGCAGTGTGTGTCCGAAGGAGACCACCTGTCCGACGTAGTAGGG
    G  T  R  H  T  Q  A  S  S  G  G  Q  A  A  S  S 2210       2220       2230       2240       2250
ATGAACAGGCAAGATCAAGTGCAGGAGAAAGACATGGATCCCACCACCAG
TACTTGTCCGTTCTAGTTCACGTCCTCTTTCTGTACCTAGGGTGGTGGTC
  H  E  Q  A  R  S  S  A  G  E  R  H  G  S  H  H  Q 2260       2270       2280       2290       2300
CAGTCAGCAGACAGCTCCAGACACTCAGGCATTGGGCACGGACAAGCTTC
GTCAGTCGTCTGTCGAGGTCTGTGAGTCCGTAACCCGTGCCTGTTCGAAG
   Q  S  A  D  S  S  R  H  S  G  I  G  H  G  Q  A  S 2310       2320       2330       2340       2350
ATCTGCAGTCAGAGACAGTGGACACCGAGGGTACAGTGGTAGTCAGGCCA
TAGACGTCAGTCTCTGTCACCTGTGGCTCCCATGTCACCATCAGTCCGGT
   S  A  V  R  D  S  G  H  R  G  Y  S  G  S  Q  A
```

Figure 11- continued

```
         2360       2370       2380       2390       2400
GTGACAATGAGGGACATTCAGAAGACTCAGACACACAGTCAGTGTCAGCC
CACTGTTACTCCCTGTAAGTCTTCTGAGTCTGTGTGTCAGTCACAGTCGG
 S  D  N  E  G  H  S  E  D  S  D  T  Q  S  V  S  A 2410       2420       2430       2440       2450
CACGGACAGGCTGGGTCCCATCAGCAGAGCCACCAAGAGTCCGCACGTGG
GTGCCTGTCCGACCCAGGGTAGTCGTCTCGGTGGTTCTCAGGCGTGCACC
    H  G  Q  A  G  S  H  Q  Q  S  H  Q  E  S  A  R  G 2460       2470       2480       2490       2500
CCGGTCAGGGGAAACGTCTGGACATTCAGGATCTTTCCTCTACCAGGTGA
GGCCAGTCCCCTTTGCAGACCTGTAAGTCCTAGAAAGGAGATGGTCCACT
 R  S  G  E  T  S  G  H  S  G  S  F  L  Y  Q  V 2510       2520       2530       2540       2550
GCACTCATGAACAGTCTGAGTCCTCCCATGGATGGACGGGGCCCAGCACT
CGTGAGTACTTGTCAGACTCAGGAGGGTACCTACCTGCCCCGGGTCGTGA
 S  T  H  E  Q  S  E  S  S  H  G  W  T  G  P  S  T 2560       2570       2580       2590       2600
AGAGGAAGACAAGGATCCCGCCATGAGCAGGCACAAGACAGCTCCAGGCA
TCTCCTTCTGTTCCTAGGGCGGTACTCGTCCGTGTTCTGTCGAGGTCCGT
  R  G  R  Q  G  S  R  H  E  Q  A  Q  D  S  S  R  H 2610       2620       2630       2640       2650
CTCAGCATCCCAAGACGGTCAGGACACCATTCGTGGACACCCGGGGTCAA
GAGTCGTAGGGTTCTGCCAGTCCTGTGGTAAGCACCTGTGGGCCCAGTT
  S  A  S  Q  D  G  Q  D  T  I  R  G  H  P  G  S 2660       2670       2680       2690       2700
GCAGAGGAGGAAGGCAGGGGTACCACCACGAGCATTCGGTAGATAGCTCT
CGTCTCCTCCTTCCGTCCCCATGGTGGTGCTCGTAAGCCATCTATCGAGA
  S  R  G  G  R  Q  G  Y  H  H  E  H  S  V  D  S  S 2710       2720       2730       2740       2750
GGACACTCAGGGTCCCATCACAGCCACACCCACATCCCAGGGAAGGTCTGA
CCTGTGAGTCCCAGGGTAGTGTCGGTGTGGTGTAGGGTCCCTTCCAGACT
  G  H  S  G  S  H  H  S  H  T  T  S  Q  G  R  S  D 2760       2770       2780       2790       2800
TGCCTCCCGTGGGCAGTCAGGATCCAGAAGTGCAAGCAGAACAACACGTA
ACGGAGGGCACCCGTCAGTCCTAGGTCTTCACGTTCGTCTTGTTGTGCAT
  A  S  R  G  Q  S  G  S  R  S  A  S  R  T  T  R 2810       2820       2830       2840       2850
ATGAGGAACAATCAGGAGACAGCTCCAGGCACTCAGGGTCGCGTCACCAT
TACTCCTTGTTAGTCCTCTGTCGAGGTCCGTGAGTCCCAGCGCAGTGGTA
  N  E  E  Q  S  G  D  S  S  R  H  S  G  S  R  H  H 2860       2870       2880       2890       2900
GAAGCTTCCACTCATGCCGACATCTCTAGACACTCACAGGCAGTCCAGGG
CTTCGAAGGTGAGTACGGCTGTAGAGATCTGTGAGTGTCCGTCAGGTCCC
  E  A  S  T  H  A  D  I  S  R  H  S  Q  A  V  Q  G 2910       2920       2930       2940       2950
ACAATCAGAGGGGTCCAGGAGAAGCAGGCGCCAGGGATCCAGTGTTAGCC
TGTTAGTCTCCCCAGGTCCTCTTCGTCCGCGGTCCCTAGGTCACAATCGG
  Q  S  E  G  S  R  R  S  R  R  Q  G  S  S  V  S
```

Figure 11- continued

```
          2960       2970       2980       2990       3000
AGGACAGTGACAGTGAGGGACATTCAGAAGACTCTGAGAGGTGGTCTGGG
TCCTGTCACTGTCACTCCCTGTAAGTCTTCTGAGACTCTCCACCAGACCC
  Q  D  S  D  S  E  G  H  S  E  D  S  E  R  W  S  G 3010       3020       3030       3040       3050
TCTGCTTCCAGAAACCATCGTGGATCTGTTCAGGAGCAGTCAAGGCACGG
AGACGAAGGTCTTTGGTAGCACCTAGACAAGTCCTCGTCAGTTCCGTGCC
   S  A  S  R  N  H  R  G  S  V  Q  E  Q  S  R  H  G 3060       3070       3080       3090       3100
CTCCAGACACCCCAGGTCCCATCACGAAGACAGAGCCGGTCACGGGCACT
GAGGTCTGTGGGGTCCAGGGTAGTGCTTCTGTCTCGGCCAGTGCCCGTGA
   S  R  H  P  R  S  H  H  E  D  R  A  G  H  G  H 3110       3120       3130       3140       3150
CTGCAGACCGCTCCAGACAATCAGGCACTCGTCACGCAGAGACTTCCTCT
GACGTCTGGCGAGGTCTGTTAGTCCGTGAGCAGTGCGTCTCTGAAGGAGA
   S  A  D  R  S  R  Q  S  G  T  R  H  A  E  T  S  S 3160       3170       3180       3190       3200
GGTGGACAGGCTGCATCATCCCATGAACAGGCAAGATCAAGTCCAGGAGA
CCACCTGTCCGACGTAGTAGGGTACTTGTCCGTTCTAGTTCAGGTCCTCT
   G  G  Q  A  A  S  H  E  Q  A  R  S  S  P  G  E 3210       3220       3230       3240       3250
GAGACACGGATCCCGCCACCAGCAGTCAGCAGACAGCTCCAGACACTCAG
CTCTGTGCCTAGGGCGGTGGTCGTCAGTCGTCTGTCGAGGTCTGTGAGTC
   R  H  G  S  R  H  Q  S  A  D  S  S  R  H  S 3260       3270       3280       3290       3300
GCATTCCGCGTGGACAGGCTTCATCTGCAGTCAGACACAGTAGACACTGG
CGTAAGGCGCACCTGTCCGAAGTAGACGTCAGTCTCTGTCATCTGTGACC
   G  I  P  R  G  Q  A  S  S  A  V  R  D  S  R  H  W 3310       3320       3330       3340       3350
GGGTCCAGTGGTAGTCAAGCCAGTGATAGTGAGGGACATTCAGAAGAGTC
CCCAGGTCACCATCAGTTCGGTCACTATCACTCCCTGTAAGTCTTCTCAG
   G  S  S  G  S  Q  A  S  D  S  E  G  H  S  E  E  S 3360       3370       3380       3390       3400
AGACACACAGTCAGTGTCAGGCCATGGACAGGCTGGGCCCCATCAGCAGA
TCTGTGTGTCAGTCACAGTCCGGTACCTGTCCGACCCGGGGTAGTCGTCT
   D  T  Q  S  V  S  G  H  G  Q  A  G  P  H  Q  Q 3410       3420       3430       3440       3450
GCCACCAAGAGTCCGCACGTGACCGGTCAGGGGGAAGGTCTGGACGTTCA
CGGTGGTTCTCAGGCGTGCACTGGCCAGTCCCCCTTCCAGACCTGCAAGT
   S  H  Q  E  S  A  R  D  R  S  G  G  R  S  G  R  S 3460       3470       3480       3490       3500
GGGTCTTTCCTCTACCAGGTGAGCACTCATGAACAGTCTGAGTCCGCCCA
CCCAGAAAGGAGATGGTCCACTCGTGAGTACTTGTCAGACTCAGGCGGGT
   G  S  F  L  Y  Q  V  S  T  H  E  Q  S  E  S  A  H 3510       3520       3530       3540       3550
TGGGCGGACCAGGACCAGCACTCGACGAAGACAAGGATCCCACCACGAGC
ACCCGCCTGGTCCTGGTCGTGACCTGCTTCTGTTCCTAGGGTGGTGCTCG
   G  R  T  R  T  S  T  G  R  R  Q  G  S  H  H  E
```

Figure 11- continued

```
            3560       3570       3580       3590       3600
      AGGCACGAGACAGCTCCAGGCACTCAGCGTCCCAAGAGGGTCAGGACACC
      TCCGTGCTCTGTCGAGGTCCGTGAGTCGCAGGGTTCTCCCAGTCCTGTGG
       Q  A  R  D  S  S  R  H  S  A  S  Q  E  G  Q  D  T 3610       3620       3630       3640       3650
      ATTCGTGCACACCCGGGGTCAAGCAGAAGAGGAAGGCAGGGATCCCACTA
      TAAGCACGTGTGGGCCCCAGTTCGTCTTCTCCTTCCGTCCCTAGGGTGAT
       I  R  A  H  P  G  S  S  R  R  G  R  Q  G  S  H  Y 3660       3670       3680       3690       3700
      CGAGCAATCGGTAGATAGGTCTGGACACTCAGGGTCCCATCACAGCCACA
      GCTCGTTAGCCATCTATCCAGACCTGTGAGTCCCAGGGTAGTGTCGGTGT
       E  Q  S  V  D  R  S  G  H  S  G  S  H  H  S  H 3710       3720       3730       3740       3750
      CCACATCCCAGGGAAGGTCTGATGCCTCCCGTGGGCAGTCAGGATCCAGA
      GGTGTAGGGTCCCTTCCAGACTACGGAGGGCACCCGTCAGTCCTAGGTCT
       T  T  S  Q  G  R  S  D  A  S  R  G  Q  S  G  S  R 3760       3770       3780       3790       3800
      AGTGCCAGCAGACAAACTCGTAACGACGAACAATCAGGAGACGGCTCCAG
      TCACGGTCGTCTGTTTGAGCATTGCTGCTTGTTAGTCCTCTGCCGAGGTC
       S  A  S  R  Q  T  R  N  D  E  Q  S  G  D  G  S  R 3810       3820       3830       3840       3850
      GCACTCATGGTCGCATCACCATGAAGCTTCCACTCAGGCGGACAGCTCTA
      CGTGAGTACCAGCGTAGTGGTACTTCGAAGGTGAGTCCGCCTGTCGAGAT
       H  S  W  S  H  H  H  E  A  S  T  Q  A  D  S  S 3860       3870       3880       3890       3900
      GACACTCACAGTCCGGCCAGGGACAATCAGCGGGGCCCAGTACAAGCAGG
      CTGTGAGTGTCAGGCCGGTCCCTGTTAGTCGCCCCGGGTCATGTTCGTCC
       R  H  S  Q  S  G  Q  G  Q  S  A  G  P  S  T  S  R 3910       3920       3930       3940       3950
      AACCAGGGATCCAGTGTTAGCCAGGACAGTGACAGTCAGGGACACTCAGA
      TTGGTCCCTAGGTCACAATCGGTCCTGTCACTGTCAGTCCCTGTGAGTCT
       N  Q  G  S  S  V  S  Q  D  S  D  S  Q  G  H  S  E 3960       3970       3980       3990       4000
      AGACTCTGAGAGGTGGTCTGGGTCTGCTTCCAGAAACCATCATGGATCTG
      TCTGAGACTCTCCACCAGACCCAGACGAAGGTCTTTGGTAGTACCTAGAC
       D  S  E  R  W  S  G  S  A  S  R  N  H  G  S 4010       4020       4030       4040       4050
      CTGGGGAGCAGTCAAGAGATGGCTCCAGACACCCTGGGTCCCATCAAGAA
      GACCCCTCGTCAGTTCTCTACCGAGGTCTGTGGGACCCAGGGTAGTTCTT
       A  G  E  Q  S  R  D  G  S  R  H  P  G  S  H  Q  E 4060       4070       4080       4090       4100
      GACAGAGCCGGTCACGGGCACTCTGCAGACAGCCCCAGACAATCAGGCAC
      CTGTCTCGGCCAGTGCCCGTGAGACGTCTGTCGGGGTCTGTTAGTCCGTG
       D  R  A  G  H  G  H  S  A  D  S  P  R  Q  S  G  T 4110       4120       4130       4140       4150
      TCGTCACACAGAGTCTTCCTCTCGTGGACAGGCTGCGTCATCCCATGAAC
      AGCAGTGTGTCTCAGAAGGAGAGCACCTGTCCGACGCAGTAGGGTACTTG
       R  H  T  E  S  S  S  R  G  Q  A  A  S  S  H  E
```

Figure 11- continued

```
         4160       4170       4180       4190       4200
    AGGCAAGATCAAGTGCAGGAGAAAGACATGGATCCCACCACCAGCTCCAG
    TCCGTTCTAGTTCACGTCCTCTTTCTGTACCTAGGGTGGTGGTCGAGGTC
     Q   A   R   S   S   A   G   E   R   H   G   S   H   H   Q   L   Q 4210       4220       4230       4240       4250
    TCAGCAGACAGCTCCAGACACGCAGGCATTGGGCACGGACAAGCTTCATC
    AGTCGTCTGTCGAGGTCTGTGCGTCCGTAACCCGTGCCTGTTCGAAGTAG
     S   A   D   S   S   R   H   A   G   I   G   H   G   Q   A   S   S 4260       4270       4280       4290       4300
    TGCAGTCAGAGACAGTGGACACCGAGGGTACAGTGGTAGTCAGGCCACTG
    ACGTCAGTCTCTGTCACCTGTGGCTCCCATGTCACCATCAGTCCGGTGAC
     A   V   R   D   S   G   H   R   G   Y   S   G   S   Q   A   T 4310       4320       4330       4340       4350
    ACAGTGAGGGACATTCAGAAGACTCAGACACACAGTCAGTGTCAGCACAG
    TGTCACTCCCTGTAAGTCTTCTGAGTCTGTGTGTCAGTCACAGTCGTGTC
     D   S   E   G   H   S   E   D   S   D   T   Q   S   V   S   A   Q 4360       4370       4380       4390       4400
    GGAAAAGCTGGGCCCCATCAGCAGAGCCACAAAGAGTCCGCACGTGGCCA
    CCTTTTCGACCCGGGGTAGTCGTCTCGGTGTTTCTCAGGCGTGCACCGGT
     G   K   A   G   P   H   Q   Q   S   H   K   E   S   A   R   G   Q 4410       4420       4430       4440       4450
    GTCAGGGGAAAGCTCTAGACGTTCAGGGTCTTTCCTCTACCAGGTGAGCA
    CAGTCCCCTTTCGAGATCTGCAAGTCCCAGAAAGGAGATGGTCCACTCGT
     S   G   E   S   S   R   R   S   G   S   F   L   Y   Q   V   S 4460       4470       4480       4490       4500
    CTCATGAACAGTCTGAGTCTGCCCATGGACGGGCTGGGCCCAGTACTGGA
    GAGTACTTGTCAGACTCAGACGGGTACCTGCCCGACCCGGGTCATGACCT
     T   H   E   Q   S   E   S   A   H   G   R   A   G   P   S   T   G 4510       4520       4530       4540       4550
    GGAAGACAAGGATCCCACCACGAGCAGGCACGAGACAGCTCCAGGCACTC
    CCTTCTGTTCCTAGGGTGGTGCTCGTCCGTGCTCTGTCGAGGTCCGTGAG
     G   R   Q   G   S   H   H   E   Q   A   R   D   S   S   R   H   S 4560       4570       4580       4590       4600
    AGCGTCCCAAGAGGGTCAGGACACCATTCGTGGACACCCGGGGTCAAGGA
    TCGCAGGGTTCTCCCAGTCCTGTGGTAAGCACCTGTGGGCCCCAGTTCCT
     A   S   Q   E   G   Q   D   T   I   R   G   H   P   G   S   R 4610       4620       4630       4640       4650
    GAGGAGGAAGACAGGGATCCTACCACGAGCAATCGGTAGATAGGTCTGGA
    CTCCTCCTTCTGTCCCTAGGATGGTGCTCGTTAGCCATCTATCCAGACCT
     R   G   G   R   Q   G   S   Y   H   E   Q   S   V   D   R   S   G 4660       4670       4680       4690       4700
    CACTCAGGGTCCCATCACAGCCACACCACATCCCAGGGAAGGTCTGATGC
    GTGAGTCCCAGGGTAGTGTCGGTGTGGTGTAGGGTCCCTTCCAGACTACG
     H   S   G   S   H   H   S   H   T   T   S   Q   G   R   S   D   A 4710       4720       4730       4740       4750
    CTCCCATGGGCAGTCAGGATCCAGAAGTGCAAGCAGAGAAACACGTAATG
    GAGGGTACCCGTCAGTCCTAGGTCTTCACGTTCGTCTCTTTGTGCATTAC
     S   H   G   Q   S   G   S   R   S   A   S   R   E   T   R   N
```

Figure 11- continued

```
          4760       4770       4780       4790       4800
     AGGAACAGTCAGGAGACGGCTCCAGGCACTCAGGGTCGCGTCACCATGAA
     TCCTTGTCAGTCCTCTGCCGAGGTCCGTGAGTCCCAGCGCAGTGGTACTT
      E  E  Q  S  G  D  G  S  R  H  S  G  R  H  H  E 4810       4820       4830       4840       4850
     GCTTCCACTCAGGCTGACAGCTCTAGACACTCACAGTCCGGCCAGGGTGA
     CGAAGGTGAGTCCGACTGTCGAGATCTGTGAGTGTCAGGCCGGTCCCACT
       A  S  T  Q  A  D  S  S  R  H  S  Q  S  G  Q  G  E 4860       4870       4880       4890       4900
     ATCAGCGGGGTCCAGGAGAAGCAGGCGCCAGGGATCCAGTGTTAGCCAGG
     TAGTCGCCCCAGGTCCTCTTCGTCCGCGGTCCCTAGGTCACAATCGGTCC
        S  A  G  S  R  R  S  R  R  Q  G  S  S  V  S  Q 4910       4920       4930       4940       4950
     ACAGTGACAGTGAGGCATACCCAGAGGACTCTGAGAGGCGATCTGAGTCT
     TGTCACTGTCACTCCGTATGGGTCTCCTGAGACTCTCCGCTAGACTCAGA
      D  S  D  S  E  A  Y  P  E  D  S  E  R  R  S  E  S 4960       4970       4980       4990       5000
     GCTTCCAGAAACCATCATGGATCTTCTCGGGAGCAGTCAAGAGATGGCTC
     CGAAGGTCTTTGGTAGTACCTAGAAGAGCCCTCGTCAGTTCTCTACCGAG
       A  S  R  N  H  H  G  S  S  R  E  Q  S  R  D  G  S 5010       5020       5030       5040       5050
     CAGACACCCCGGATCCTCTCACCGCGATACAGCCAGTCATGTACAGTCTT
     GTCTGTGGGGCCTAGGAGAGTGGCGCTATGTCGGTCAGTACATGTCAGAA
        R  H  P  G  S  S  H  R  D  T  A  S  H  V  Q  S 5060       5070       5080       5090       5100
     CACCTGTACAGTCAGACTCTAGTACCGCTAAGGAACATGGTCACTTTAGT
     GTGGACATGTCAGTCTGAGATCATGGCGATTCCTTGTACCAGTGAAATCA
      S  P  V  Q  S  D  S  S  T  A  K  E  H  G  H  F  S 5110       5120       5130       5140       5150
     AGTCTTTCACAAGATTCTGCGTATCACTCAGGAATACAGTCACGTGGCAG
     TCAGAAAGTGTTCTAAGACGCATAGTGAGTCCTTATGTCAGTGCACCGTC
       S  L  S  Q  D  S  A  Y  H  S  G  I  Q  S  R  G  S 5160       5170       5180       5190       5200
     TCCTCACAGTTCTAGTTCTTATCATTATCAATCTGAGGGCACTGAAAGGC
     AGGAGTGTCAAGATCAAGAATAGTAATAGTTAGACTCCCGTGACTTTCCG
        P  H  S  S  S  S  Y  H  Y  Q  S  E  G  T  E  R 5210       5220       5230       5240       5250
     AAAAAGGTCAATCAGGTTTAGTTTGGAGACATGGCAGCTATGGTAGTGCA G
     TTTTTCCAGTTAGTCCAAATCAAACCTCTGTACCGTCGATACCATCACGT C
      Q  K  G  Q  S  G  L  V  W  R  H  G  S  Y  G  S  A
```

Figure 12
DNA sequence of *FLG* size variant allele *FLG*$^{10+}$

```
Both strands shown with amino acid translation.
Sequence Range: 1 to 5251

10        20        30        40        50
AGGACAAGCAGGAACCGGGGATCCAGTTTTAGCCAGGACAGTGACAGTCA
TCCTGTTCGTCCTTGGCCCCTAGGTCAAAATCGGTCCTGTCACTGTCAGT
  R  T  S  R  N  R  G  S  S  F  S  Q  D  S  D  S  Q 60        70        80        90       100
GGGACACTCAGAAGACTCTGAGAGGTGGTCTGGGTCTGCTTCCAGAAACC
CCCTGTGAGTCTTCTGAGACTCTCCACCAGACCCAGACGAAGGTCTTTGG
   G  H  S  E  D  S  E  R  W  S  G  S  A  S  R  N 110       120       130       140       150
ATCATGGATCTGCTCAGGAGCAGCTAAGAGATGGCTCCAGACACCCCAGG
TAGTACCTAGACGAGTCCTCGTCGATTCTCTACCGAGGTCTGTGGGGTCC
   H  H  G  S  A  Q  E  Q  L  R  D  G  S  R  H  P  R 160       170       180       190       200
TCCCATCAAGAAGACAGAGCTGGTCATGGGCACTCTGCAGACAGCTCCAG
AGGGTAGTTCTTCTGTCTCGACCAGTACCCGTGAGACGTCTGTCGAGGTC
   S  H  Q  E  D  R  A  G  H  G  H  S  A  D  S  S  R 210       220       230       240       250
ACAATCAGGCACTCGTCACACACAGACTTCCTCTGGTGGACAGGCTGCAT
TGTTAGTCCGTGAGCAGTGTGTGTCTGAAGGAGACCACCTGTCCGACGTA
   Q  S  G  T  R  H  T  Q  T  S  S  G  G  Q  A  A 260       270       280       290       300
CATCCCATGAACAGGCAAGATCAAGTGCAGGAGAAAGACATGGATCCCAC
GTAGGGTACTTGTCCGTTCTAGTTCACGTCCTCTTTCTGTACCTAGGGTG
   S  S  H  E  Q  A  R  S  S  A  G  E  R  H  G  S  H 310       320       330       340       350
CACCAGCAGTCAGCAGACAGCTCCAGACACTCAGGCATTGGGCACGGACA
GTGGTCGTCAGTCGTCTGTCGAGGTCTGTGAGTCCGTAACCCGTGCCTGT
   H  Q  Q  S  A  D  S  S  R  H  S  G  I  G  H  G  Q 360       370       380       390       400
AGCTTCATCTGCAGTCAGAGACAGTGGACACCGAGGGTACAGTGGTAGTC
TCGAAGTAGACGTCAGTCTCTGTCACCTGTGGCTCCCATGTCACCATCAG
   A  S  S  A  V  R  D  S  G  H  R  G  Y  S  G  S 410       420       430       440       450
AGGCCAGTGACAATGAGGGACATTCAGAAGACTCAGACACACAGTCAGTG
TCCGGTCACTGTTACTCCCTGTAAGTCTTCTGAGTCTGTGTGTCAGTCAC
   Q  A  S  D  N  E  G  H  S  E  D  S  D  T  Q  S  V 460       470       480       490       500
TCAGCCCACGGACAGGCTGGGTCCCATCAGCAGAGCCACCAAGAGTCCGC
AGTCGGGTGCCTGTCCGACCCAGGGTAGTCGTCTCGGTGGTTCTCAGGCG
   S  A  H  G  Q  A  G  S  H  Q  Q  S  H  Q  E  S  A 510       520       530       540       550
ACGTGGCCGGTCAGGGGAAACGTCTGGACATTCAGGGTCTTTCCTCTACC
TGCACCGGCCAGTCCCCTTTGCAGACCTGTAAGTCCCAGAAAGGAGATGG
   R  G  R  S  G  E  T  S  G  H  S  G  S  F  L  Y
```

Figure 12- continued

```
            560        570        580        590        600
    AGGTGAGCACTCATGAACAGTCTGAGTCCTCCCATGGATGGACGGGGCCC
    TCCACTCGTGAGTACTTGTCAGACTCAGGAGGGTACCTACCTGCCCCGGG
      Q  V  S  T  H  E  Q  S  E  S  S  H  G  W  T  G  P 610        620        630        640        650
    AGCACTAGAGGAAGACAAGGATCCCGCCATGAGCAGGCACAAGACAGCTC
    TCGTGATCTCCTTCTGTTCCTAGGGCGGTACTCGTCCGTGTTCTGTCGAG
       S  T  R  G  R  Q  G  S  R  H  E  Q  A  Q  D  S  S 660        670        680        690        700
    CAGGCACTCAGCATCCCAAGACGGTCAGGACACCATTCGTGGACACCCGG
    GTCCGTGAGTCGTAGGGTTCTGCCAGTCCTGTGGTAAGCACCTGTGGGCC
        R  H  S  A  S  Q  D  G  Q  D  T  I  R  G  H  P 710        720        730        740        750
    GGTCAAGCAGAGGAGGAAGGCAGGGGTACCACCACGAGCATTCGGTAGAT
    CCAGTTCGTCTCCTCCTTCCGTCCCCATGGTGGTGCTCGTAAGCCATCTA
       G  S  S  R  G  G  R  Q  G  Y  H  H  E  H  S  V  D 760        770        780        790        800
    AGCTCTGGACACTCAGGGTCCCATCACAGCCACACCACATCCCAGGGAAG
    TCGAGACCTGTGAGTCCCAGGGTAGTGTCGGTGTGGTGTAGGGTCCCTTC
       S  S  G  H  S  G  S  H  H  S  H  T  T  S  Q  G  R 810        820        830        840        850
    GTCTGATGCCTCCCGTGGGCAGTCAGGATCCAGACGTGCAAGCAGAACAA
    CAGACTACGGAGGGCACCCGTCAGTCCTAGGTCTGCACGTTCGTCTTGTT
       S  D  A  S  R  G  Q  S  G  S  R  R  A  S  R  T 860        870        880        890        900
    CACGTAATGAGGAACAATCAGGAGACGGCTCCAGGCACTCAGGGTCGCGT
    GTGCATTACTCCTTGTTAGTCCTCTGCCGAGGTCCGTGAGTCCCAGCGCA
       T  R  N  E  E  Q  S  G  D  G  S  R  H  S  G  S  R 910        920        930        940        950
    CACCATGAAGCTTCCACTCATGCCGACATCTCTAGACACTCACAGGCAGT
    GTGGTACTTCGAAGGTGAGTACGGCTGTAGAGATCTGTGAGTGTCCGTCA
       H  H  E  A  S  T  H  A  D  I  S  R  H  S  Q  A  V 960        970        980        990        1000
    CCAGGGACAATCAGAGGGGTCCAGGAGAAGCAGGCGCCAGGGATCCAGTG
    GGTCCCTGTTAGTCTCCCCAGGTCCTCTTCGTCCGCGGTCCCTAGGTCAC
        Q  G  Q  S  E  G  S  R  R  S  R  R  Q  G  S  S 1010       1020       1030       1040       1050
    TTAGCCAGGACAGTGACAGTGAGGGACATTCAGAAGACTCTGAGAGGTGG
    AATCGGTCCTGTCACTGTCACTCCCTGTAAGTCTTCTGAGACTCTCCACC
      V  S  Q  D  S  D  S  E  G  H  S  E  D  S  E  R  W 1060       1070       1080       1090       1100
    TCTGGGTCTGCTTCCAGAAACCATCATGGATCTGCTCAGGAGCAGCTAAG
    AGACCCAGACGAAGGTCTTTGGTAGTACCTAGACGAGTCCTCGTCGATTC
       S  G  S  A  S  R  N  H  H  G  S  A  Q  E  Q  L  R 1110       1120       1130       1140       1150
    AGATGGCTCCAGACACCCCAGGTCCCATCAAGAAGGCAGAGCTGGTCATG
    TCTACCGAGGTCTGTGGGGTCCAGGGTAGTTCTTCCGTCTCGACCAGTAC
       D  G  S  R  H  P  R  S  H  Q  E  G  R  A  G  H
```

Figure 12- continued

```
       1160      1170      1180      1190      1200
GGCACTCTGCAGACAGCTCCAGACAATCAGGCACTCGTCACACACAGACT
CCGTGAGACGTCTGTCGAGGTCTGTTAGTCCGTGAGCAGTGTGTGTCTGA
 G  H  S  A  D  S  S  R  Q  S  G  T  R  H  T  Q  T 1210      1220      1230      1240      1250
TCCTCTGGTGGACAGGCTGCATCATCYCATGAACAGGCAAGATCAAGTGC
AGGAGACCACCTGTCCGACGTAGTAGRGTACTTGTCCGTTCTAGTTCACG
    S  S  G  G  Q  A  A  S  S  H  E  Q  A  R  S  S  A 1260      1270      1280      1290      1300
AGGAGAAAGACATGGATCCCACCACCAGCAGTCAGCAGACAGCTCCAGAC
TCCTCTTTCTGTACCTAGGGTGGTGGTCGTCAGTCGTCTGTCGAGGTCTG
  G  E  R  H  G  S  H  H  Q  Q  S  A  D  S  S  R 1310      1320      1330      1340      1350
ACTCAGGCATTGGGCACGGACAAGCTTCATCTGCAGTCAGAGACAGTGGA
TGAGTCCGTAACCCGTGCCTGTTCGAAGTAGACGTCAGTCTCTGTCACCT
 H  S  G  I  G  H  G  Q  A  S  S  A  V  R  D  S  G 1360      1370      1380      1390      1400
CACCGAGGGTACAGTGGTAGTCAGGCCAGTGACAATGAGGGACATTCAGA
GTGGCTCCCATGTCACCATCAGTCCGGTCACTGTTACTCCCTGTAAGTCT
 H  R  G  Y  S  G  S  Q  A  S  D  N  E  G  H  S  E 1410      1420      1430      1440      1450
AGACTCAGACACACAGTCAGTGTCAGCCCACGGACAGGCTGGGTCCCATC
TCTGAGTCTGTGTGTCAGTCACAGTCGGGTGCCTGTCCGACCCAGGGTAG
 D  S  D  T  Q  S  V  S  A  H  G  Q  A  G  S  H 1460      1470      1480      1490      1500
AGCAGAGCCACCAAGAGTCCGCACGTGGCCGGTCAGGGGAAACGTCTGGA
TCGTCTCGGTGGTTCTCAGGCGTGCACCGGCCAGTCCCCTTTGCAGACCT
 Q  Q  S  H  Q  E  S  A  R  G  R  S  G  E  T  S  G 1510      1520      1530      1540      1550
CATTCAGGATCTTTCCTCTACCAGGTGAGCACTCATGAACAGTCTGAGTC
GTAAGTCCTAGAAAGGAGATGGTCCACTCGTGAGTACTTGTCAGACTCAG
 H  S  G  S  F  L  Y  Q  V  S  T  H  E  Q  S  E  S 1560      1570      1580      1590      1600
CTCCCATGGATGGACGGGGCCCAGCACTAGAGGAAGACAAGGATCCCGCC
GAGGGTACCTACCTGCCCCGGGTCGTGATCTCCTTCTGTTCCTAGGGCGG
    S  H  G  W  T  G  P  S  T  R  G  R  Q  G  S  R 1610      1620      1630      1640      1650
ATGAGCAGGCACAAGACAGCTCCAGGCACTCAGCATCCCAAGACGGTCAG
TACTCGTCCGTGTTCTGTCGAGGTCCGTGAGTCGTAGGGTTCTGCCAGTC
 H  E  Q  A  Q  D  S  S  R  H  S  A  S  Q  D  G  Q 1660      1670      1680      1690      1700
GACACCATTCGTGGACACCCGGGGTCAAGCAGAGGAGGAAGGCAGGGGTA
CTGTGGTAAGCACCTGTGGGCCCCAGTTCGTCTCCTCCTTCCGTCCCCAT
  D  T  I  R  G  H  P  G  S  S  R  G  G  R  Q  G  Y 1710      1720      1730      1740      1750
CCACCACGAGCATTCGGTAGATAGCTCTGGACACTCAGGGTCCCATCACA
GGTGGTGCTCGTAAGCCATCTATCGAGACCTGTGAGTCCCAGGGTAGTGT
  H  H  E  H  S  V  D  S  S  G  H  S  G  S  H  H
```

Figure 12- continued

```
          1760       1770       1780       1790       1800
       GCCACACCACATCCCAGGGAAGGTCTGATGCCTCCCGTGGGCAGTCAGGA
       CGGTGTGGTGTAGGGTCCCTTCCAGACTACGGAGGGCACCCGTCAGTCCT
        S  H  T  T  S  Q  G  R  S  D  A  S  R  G  Q  S  G 1810       1820       1830       1840       1850
       TCCAGAAGTGCAAGCAGAACAACACGTAATGAGGAACAATCAGGAGACAG
       AGGTCTTCACGTTCGTCTTGTTGTGCATTACTCCTTGTTAGTCCTCTGTC
        S  R  S  A  S  R  T  T  R  N  E  E  Q  S  G  D  S 1860       1870       1880       1890       1900
       CTCCAGGCACTCAGGGTCGCGTCACCATGAAGCTTCCACTCATGCCGACA
       GAGGTCCGTGAGTCCCAGCGCAGTGGTACTTCGAAGGTGAGTACGGCTGT
        S  R  H  S  G  S  R  H  H  E  A  S  T  H  A  D 1910       1920       1930       1940       1950
       TCTCTAGACACTCACAGGCAGTCCAGGGACAATCAGAGGGGTCCAGGAGA
       AGAGATCTGTGAGTGTCCGTCAGGTCCCTGTTAGTCTCCCCAGGTCCTCT
        I  S  R  H  S  Q  A  V  Q  G  Q  S  E  G  S  R  R 1960       1970       1980       1990       2000
       AGCAGGCGCCAGGGATCCAGTGTTAGCCAGGACAGTGACAGTGAGGGACA
       TCGTCCGCGGTCCCTAGGTCACAATCGGTCCTGTCACTGTCACTCCCTGT
        S  R  R  Q  G  S  S  V  S  Q  D  S  D  S  E  G  H 2010       2020       2030       2040       2050
       TTCAGAAGACTCTGAGAGGTGGTCTGGGTCTGCTTCCAGAAACCATCGTG
       AAGTCTTCTGAGACTCTCCACCAGACCCAGACGAAGGTCTTTGGTAGCAC
        S  E  D  S  E  R  W  S  G  S  A  S  R  N  H  R 2060       2070       2080       2090       2100
       GATCTGTTCAGGAGCAGTCAAGGCACGGCTCCAGACACCCCAGGTCCCAT
       CTAGACAAGTCCTCGTCAGTTCCGTGCCGAGGTCTGTGGGGTCCAGGGTA
        G  S  V  Q  E  Q  S  R  H  G  S  R  H  P  R  S  H 2110       2120       2130       2140       2150
       CACGAAGACAGAGCCGGTCACGGGCACTCTGCAGACCGGCTCCAGACAATC
       GTGCTTCTGTCTCGGCCAGTGCCCGTGAGACGTCTGGCGAGGTCTGTTAG
        H  E  D  R  A  G  H  G  H  S  A  D  R  S  R  Q  S 2160       2170       2180       2190       2200
       AGGCACTCGTCACGCAGAGACTTCCTCTGGTGGACAGGCTGCATCATCCC
       TCCGTGAGCAGTGCGTCTCTGAAGGAGACCACCTGTCCGACGTAGTAGGG
           G  T  R  H  A  E  T  S  S  G  G  Q  A  A  S  S 2210       2220       2230       2240       2250
       ATGAACAGGCAAGATCAAGTCCAGGAGAGAGACACGGATCCCGCCACCAG
       TACTTGTCCGTTCTAGTTCAGGTCCTCTCTCTGTGCCTAGGGCGGTGGTC
        H  E  Q  A  R  S  S  P  G  E  R  H  G  S  R  H  Q 2260       2270       2280       2290       2300
       CAGTCAGCAGACAGCTCCAGACACTCAGGCATTCCGCGTGGACAGGCTTC
       GTCAGTCGTCTGTCGAGGTCTGTGAGTCCGTAAGGCGCACCTGTCCGAAG
        Q  S  A  D  S  S  R  H  S  G  I  P  R  G  Q  A  S 2310       2320       2330       2340       2350
       ATCTGCAGTCAGAGACAGTAGACACTGGGGGTCCAGTGGTAGTCAAGCCA
       TAGACGTCAGTCTCTGTCATCTGTGACCCCCAGGTCACCATCAGTTCGGT
        S  A  V  R  D  S  R  H  W  G  S  S  G  S  Q  A
```

Figure 12- continued

```
        2360       2370       2380       2390       2400
GTGATAGTGAGGGACATTCAGAAGAGTCAGACACACAGTCAGTGTCAGGC
CACTATCACTCCCTGTAAGTCTTCTCAGTCTGTGTGTCAGTCACAGTCCG
 S  D  S  E  G  H  S  E  E  S  D  T  Q  S  V  S  G 2410       2420       2430       2440       2450
CATGGACAGGCTGGGCCCCATCAGCAGAGCCACCAAGAGTCCGCACGTGA
GTACCTGTCCGACCCGGGGTAGTCGTCTCGGTGGTTCTCAGGCGTGCACT
  H  G  Q  A  G  P  H  Q  Q  S  H  Q  E  S  A  R  D 2460       2470       2480       2490       2500
CCGGTCAGGGGGAAGGTCTGGACGTTCAGGGTCTTTCCTCTACCAGGTGA
GGCCAGTCCCCCTTCCAGACCTGCAAGTCCCAGAAAGGAGATGGTCCACT
  R  S  G  G  R  S  G  R  S  G  S  F  L  Y  Q  V 2510       2520       2530       2540       2550
GCACTCATGAACAGTCTGAGTCCGCCCATGGGCGGACCAGGACCAGCACT
CGTGAGTACTTGTCAGACTCAGGCGGGTACCCGCCTGGTCCTGGTCGTGA
 S  T  H  E  Q  S  E  S  A  H  G  R  T  R  T  S  T 2560       2570       2580       2590       2600
GGACGAAGACAAGGATCCCACCACGAGCAGGCACGAGACAGCTCCAGGCA
CCTGCTTCTGTTCCTAGGGTGGTGCTCGTCCGTGCTCTGTCGAGGTCCGT
  G  R  R  Q  G  S  H  H  E  Q  A  R  D  S  S  R  H 2610       2620       2630       2640       2650
CTCAGCGTCCCAAGAGGGTCAGGACACCATTCGTGCACACCCGGGGTCAA
GAGTCGCAGGGTTCTCCCAGTCCTGTGGTAAGCACGTGTGGGCCCCAGTT
  S  A  S  Q  E  G  Q  D  T  I  R  A  H  P  G  S 2660       2670       2680       2690       2700
GCAGAAGAGGAAGGCAGGGATCCCACTACGAGCAATCGGTAGATAGGTCT
CGTCTTCTCCTTCCGTCCCTAGGGTGATGCTCGTTAGCCATCTATCCAGA
 S  R  R  G  R  Q  G  S  H  Y  E  Q  S  V  D  R  S 2710       2720       2730       2740       2750
GGACACTCAGGGTCCCATCACAGCCACACCACATCCCAGGGAAGGTCTGA
CCTGTGAGTCCCAGGGTAGTGTCGGTGTGGTGTAGGGTCCCTTCCAGACT
  G  H  S  G  S  H  H  S  H  T  T  S  Q  G  R  S  D 2760       2770       2780       2790       2800
TGCCTCCCGTGGGCAGTCAGGATCCAGAAGTGCCAGCAGACAAACTCGTA
ACGGAGGGCACCCGTCAGTCCTAGGTCTTCACGGTCGTCTGTTTGAGCAT
  A  S  R  G  Q  S  G  S  R  S  A  S  R  Q  T  R 2810       2820       2830       2840       2850
ACGACGAACAATCAGGAGACGGCTCCAGGCACTCATGGTCGCATCACCAT
TGCTGCTTGTTAGTCCTCTGCCGAGGTCCGTGAGTACCAGCGTAGTGGTA
  N  D  E  Q  S  G  D  G  S  R  H  S  W  S  H  H  H 2860       2870       2880       2890       2900
GAAGCTTCCACTCAGGCGGACAGCTCTAGACACTCACAGTCCGGCCAGGG
CTTCGAAGGTGAGTCCGCCTGTCGAGATCTGTGAGTGTCAGGCCGGTCCC
  E  A  S  T  Q  A  D  S  S  R  H  S  Q  S  G  Q  G 2910       2920       2930       2940       2950
ACAATCAGCGGGGCCCAGTACAAGCAGGAACCAGGGATCCAGTGTTAGCC
TGTTAGTCGCCCCGGGTCATGTTCGTCCTTGGTCCCTAGGTCACAATCGG
   Q  S  A  G  P  S  T  S  R  N  Q  G  S  S  V  S
```

Figure 12- continued

```
       2960       2970       2980       2990       3000
AGGACAGTGACAGTCAGGGACACTCAGAAGACTCTGAGAGGTGGTCTGGG
TCCTGTCACTGTCAGTCCCTGTGAGTCTTCTGAGACTCTCCACCAGACCC
 Q  D  S  D  S  Q  G  H  S  E  D  S  E  R  W  S  G 3010       3020       3030       3040       3050
TCTGCTTCCAGAAACCATCATGGATCTGCTGGGGAGCAGTCAAGAGATGG
AGACGAAGGTCTTTGGTAGTACCTAGACGACCCCTCGTCAGTTCTCTACC
  S  A  S  R  N  H  H  G  S  A  G  E  Q  S  R  D  G 3060       3070       3080       3090       3100
CTCCAGACACCCTGGGTCCCATCAAGAAGACAGAGCCGGTCACGGGCACT
GAGGTCTGTGGGACCCAGGGTAGTTCTTCTGTCTCGGCCAGTGCCCGTGA
  S  R  H  P  G  S  H  Q  E  D  R  A  G  H  G  H 3110       3120       3130       3140       3150
CTGCAGACAGCCCCAGACAATCAGGCACTCGTCACACAGAGTCTTCCTCT
GACGTCTGTCGGGGTCTGTTAGTCCGTGAGCAGTGTGTCTCAGAAGGAGA
  S  A  D  S  P  R  Q  S  G  T  R  H  T  E  S  S  S 3160       3170       3180       3190       3200
CGTGGACAGGCTGCGTCATCCCATGAACAGGCAAGATCAAGTGCAGGAGA
GCACCTGTCCGACGCAGTAGGGTACTTGTCCGTTCTAGTTCACGTCCTCT
  R  G  Q  A  A  S  S  H  E  Q  A  R  S  S  A  G  E 3210       3220       3230       3240       3250
AAGACATGGATCCCACCACCAGCTCCAGTCAGCAGACAGCTCCAGACACG
TTCTGTACCTAGGGTGGTGGTCGAGGTCAGTCGTCTGTCGAGGTCTGTGC
  R  H  G  S  H  H  Q  L  Q  S  A  D  S  S  R  H 3260       3270       3280       3290       3300
CAGGCATTGGGCACGGACAAGCTTCATCTGCAGTCAGAGACAGTGGACAC
GTCCGTAACCCGTGCCTGTTCGAAGTAGACGTCAGTCTCTGTCACCTGTG
  A  G  I  G  H  G  Q  A  S  S  A  V  R  D  S  G  H 3310       3320       3330       3340       3350
CGAGGGTACAGTGGTAGTCAGGCCACTGACAGTGAGGGACATTCAGAAGA
GCTCCCATGTCACCATCAGTCCGGTGACTGTCACTCCCTGTAAGTCTTCT
  R  G  Y  S  G  S  Q  A  T  D  S  E  G  H  S  E  D 3360       3370       3380       3390       3400
CTCAGACACACAGTCAGTGTCAGCACAGGGAAAAGCTGGGCCCCATCAGC
GAGTCTGTGTGTCAGTCACAGTCGTGTCCCTTTTCGACCCGGGGTAGTCG
  S  D  T  Q  S  V  S  A  Q  G  K  A  G  P  H  Q 3410       3420       3430       3440       3450
AGAGCCACAAAGAGTCCGACACGTGGCCAGTCAGGGGAAAGCTCTAGACGT
TCTCGGTGTTTCTCAGGCGTGCACCGGTCAGTCCCCTTTCGAGATCTGCA
  Q  S  H  K  E  S  A  R  G  Q  S  G  E  S  S  R  R 3460       3470       3480       3490       3500
TCAGGGTCTTTCCTCTACCAGGTGAGCACTCATGAACAGTCTGAGTCCAC
AGTCCCAGAAAGGAGATGGTCCACTCGTGAGTACTTGTCAGACTCAGGTG
  S  G  S  F  L  Y  Q  V  S  T  H  E  Q  S  E  S  T 3510       3520       3530       3540       3550
CCATGGACAGTCTGTGCCCAGCACTGGAGGAAGACAAGGATCCCACCATG
GGTACCTGTCAGACACGGGTCGTGACCTCCTTCTGTTCCTAGGGTGGTAC
   H  G  Q  S  V  P  S  T  G  G  R  Q  G  S  H  H
```

Figure 12- continued

```
         3560       3570       3580       3590       3600
ATCAGGCACAAGACAGCTCCAGGCACTCAGCATCCCAAGAGGGTCAGGAC
TAGTCCGTGTTCTGTCGAGGTCCGTGAGTCGTAGGGTTCTCCCAGTCCTG
 D  Q  A  Q  D  S  S  R  H  S  A  S  Q  E  G  Q  D 3610       3620       3630       3640       3650
ACCATTCGTGGACACCCGGGGCCAAGCAGAGGAGGAAGACAGGGGTCCCA
TGGTAAGCACCTGTGGGCCCCGGTTCGTCTCCTCCTTCTGTCCCCAGGGT
  T  I  R  G  H  P  G  P  S  R  G  G  R  Q  G  S  H 3660       3670       3680       3690       3700
CCACGAGCAATCGGTAGATAGGTCTGGACACTCAGGGTCCCATCACAGCC
GGTGCTCGTTAGCCATCTATCCAGACCTGTGAGTCCCAGGGTAGTGTCGG
  H  E  Q  S  V  D  R  S  G  H  S  G  S  H  H  S 3710       3720       3730       3740       3750
ACACCACATCCCAGGGAAGGTCTGATGCCTCCCGTGGGCAGTCAGGACCC
TGTGGTGTAGGGTCCCTTCCAGACTACGGAGGGCACCCGTCAGTCCTGGG
  H  T  T  S  Q  G  R  S  D  A  S  R  G  Q  S  G  P 3760       3770       3780       3790       3800
AGAAGTGCAAGCAGACAAACACATGACAAGGAACAATCAGGAGACGGCTC
TCTTCACGTTCGTCTGTTTGTGTACTGTTCCTTGTTAGTCCTCTGCCGAG
  R  S  A  S  R  Q  T  H  D  K  E  Q  S  G  D  G  S 3810       3820       3830       3840       3850
TAGGCACTCAGGGTCGCGTCATCATGAAGCTTCCTCTTGGGCCGACAGCT
ATCCGTGAGTCCCAGCGCAGTAGTACTTCGAAGGAGAACCCGGCTGTCGA
   R  H  S  G  S  R  H  H  E  A  S  S  W  A  D  S 3860       3870       3880       3890       3900
CTAGACACTCACAGGCAGTCCAGGGACAATCAGAGGGGTCCAGGAGAAGC
GATCTGTGAGTGTCCGTCAGGTCCCTGTTAGTCTCCCCAGGTCCTCTTCG
  S  R  H  S  Q  A  V  Q  G  Q  S  E  G  S  R  R  S 3910       3920       3930       3940       3950
AGGCGCCAGGGATCCAGTGTTAGCCAGGACAGTGACAGTCAGGGACACTC
TCCGCGGTCCCTAGGTCACAATCGGTCCTGTCACTGTCAGTCCCTGTGAG
   R  R  Q  G  S  S  V  S  Q  D  S  D  S  Q  G  H  S 3960       3970       3980       3990       4000
AGAAGACTCTGAGAGGCGGTCTGGGTCTGCTTCCAGAAACCATCGTGGAT
TCTTCTGAGACTCTCCGCCAGACCCAGACGAAGGTCTTTGGTAGCACCTA
   E  D  S  E  R  R  S  G  S  A  S  R  N  H  R  G 4010       4020       4030       4040       4050
CTGCTCAGGAGCAGTCAAGAGATGGCTCCAGACACCCCAGGTCCCATCAC
GACGAGTCCTCGTCAGTTCTCTACCGAGGTCTGTGGGGTCCAGGGTAGTG
   S  A  Q  E  Q  S  R  D  G  S  R  H  P  R  S  H  H 4060       4070       4080       4090       4100
GAAGACAGAGCCGGTCATGGGCACTCTGCAGACAGCTCCAGACAATCAGG
CTTCTGTCTCGGCCAGTACCCGTGAGACGTCTGTCGAGGTCTGTTAGTCC
   E  D  R  A  G  H  G  H  S  A  D  S  S  R  Q  S  G 4110       4120       4130       4140       4150
CACTCATCATGCAGAGAATTCCTCTGGTGGACAGCCTGCATCATCCCATG
GTGAGTAGTACGTCTCTTAAGGAGACCACCTGTCGGACGTAGTAGGGTAC
   T  H  H  A  E  N  S  S  G  G  Q  P  A  S  S  H
```

Figure 12- continued

```
       4160      4170      4180      4190      4200
AACAGGCAAGATCAAGTGCAGGAGAGAGACATGGATCCCACCACCAGCAG
TTGTCCGTTCTAGTTCACGTCCTCTCTCTGTACCTAGGGTGGTGGTCGTC
 E  Q  A  R  S  S  A  G  E  R  H  G  S  H  H  Q  Q 4210      4220      4230      4240      4250
TCAGCAGACAGCTCCAGACACTCAGGCATTGGGCACGGACAAGCTTCATC
AGTCGTCTGTCGAGGTCTGTGAGTCCGTAACCCGTGCCTGTTCGAAGTAG
  S  A  D  S  S  R  H  S  G  I  H  G  Q  A  S  S 4260      4270      4280      4290      4300
TGCAGTCAGAGACAGTGGACACCGAGGGTCCAGTGGTAGTCAGGCCAGTG
ACGTCAGTCTCTGTCACCTGTGGCTCCCAGGTCACCATCAGTCCGGTCAC
  A  V  R  D  S  G  H  R  G  S  S  G  S  Q  A  S 4310      4320      4330      4340      4350
ACAGTGAGGGACATTCAGAAGACTCAGACACACAGTCAGTGTCAGCCCAC
TGTCACTCCCTGTAAGTCTTCTGAGTCTGTGTGTCAGTCACAGTCGGGTG
  D  S  E  G  H  S  E  D  S  D  T  Q  S  V  S  A  H 4360      4370      4380      4390      4400
GGACAGGCTGGGCCCCATCAGCAGAGCCACCAAGAGTCCACACGTGGCCG
CCTGTCCGACCCGGGGTAGTCGTCTCGGTGGTTCTCAGGTGTGCACCGGC
  G  Q  A  G  P  H  Q  Q  S  H  Q  E  S  T  R  G  R 4410      4420      4430      4440      4450
GTCAGCAGGAAGGTCTGGACGTTCAGGGTCTTTCCTCTACCAGGTGAGCA
CAGTCGTCCTTCCAGACCTGCAAGTCCCAGAAAGGAGATGGTCCACTCGT
  S  A  G  R  S  G  R  S  G  S  F  L  Y  Q  V  S 4460      4470      4480      4490      4500
CTCATGAACAGTCTGAGTCTGCCCATGGACGGGCTGGGCCCAGTACTGGA
GAGTACTTGTCAGACTCAGACGGGTACCTGCCCGACCCGGGTCATGACCT
  T  H  E  Q  S  E  S  A  H  G  R  A  G  P  S  T  G 4510      4520      4530      4540      4550
GGAAGACAAGGATCCCACCACGAGCAGGCACGAGACAGCTCCAGGCACTC
CCTTCTGTTCCTAGGGTGGTGCTCGTCCGTGCTCTGTCGAGGTCCGTGAG
  G  R  Q  G  S  H  H  E  Q  A  R  D  S  S  R  H  S 4560      4570      4580      4590      4600
AGCGTCCCAAGAGGGTCAGGACACCATTCGTGGACACCCGGGGTCAAGGA
TCGCAGGGTTCTCCCAGTCCTGTGGTAAGCACCTGTGGGCCCCAGTTCCT
  A  S  Q  E  G  Q  D  T  I  R  G  H  P  G  S  R 4610      4620      4630      4640      4650
GAGGAGGAAGACAGGGATCCTACCACGAGCAATCGGTAGATAGGTCTGGA
CTCCTCCTTCTGTCCCTAGGATGGTGCTCGTTAGCCATCTATCCAGACCT
  R  G  G  R  Q  G  S  Y  H  E  Q  S  V  D  R  S  G 4660      4670      4680      4690      4700
CACTCAGGGTCCCATCACAGCCACACCACATCCCAGGGAAGGTCTGATGC
GTGAGTCCCAGGGTAGTGTCGGTGTGGTGTAGGGTCCCTTCCAGACTACG
  H  S  G  S  H  H  S  H  T  T  S  Q  G  R  S  D  A 4710      4720      4730      4740      4750
CTCCCATGGGCAGTCAGGATCCAGAAGTGCAAGCAGAGAAACACGTAATG
GAGGGTACCCGTCAGTCCTAGGTCTTCACGTTCGTCTCTTTGTGCATTAC
  S  H  G  Q  S  G  S  R  S  A  S  R  E  T  R  N
```

Figure 12- continued

```
        4760       4770       4780       4790       4800
AGGAACAGTCAGGAGACGGCTCCAGGCACTCAGGGTCGCGTCACCATGAA
TCCTTGTCAGTCCTCTGCCGAGGTCCGTGAGTCCCAGCGCAGTGGTACTT
 E  E  Q  S  G  D  G  S  R  H  S  G  S  R  H  H  E 4810       4820       4830       4840       4850
GCTTCCACTCAGGCTGACAGCTCTAGACACTCACAGTCCGGCCAGGGTGA
CGAAGGTGAGTCCGACTGTCGAGATCTGTGAGTGTCAGGCCGGTCCCACT
  A  S  T  Q  A  D  S  S  R  H  S  Q  S  G  Q  G  E 4860       4870       4880       4890       4900
ATCAGCGGGGTCCAGGAGAAGCAGGCGCCAGGGATCCAGTGTTAGCCAGG
TAGTCGCCCCAGGTCCTCTTCGTCCGCGGTCCCTAGGTCACAATCGGTCC
  S  A  G  S  R  R  S  R  R  Q  G  S  S  V  S  Q 4910       4920       4930       4940       4950
ACAGTGACAGTGAGGCATACCCAGAGGACTCTGAGAGGCGATCTGAGTCT
TGTCACTGTCACTCCGTATGGGTCTCCTGAGACTCTCCGCTAGACTCAGA
  D  S  D  S  E  A  Y  P  E  D  S  E  R  R  S  E  S 4960       4970       4980       4990       5000
GCTTCCAGAAACCATCATGGATCTTCTCGGGAGCAGTCAAGAGATGGCTC
CGAAGGTCTTTGGTAGTACCTAGAAGAGCCCTCGTCAGTTCTCTACCGAG
  A  S  R  N  H  H  G  S  S  R  E  Q  S  R  D  G  S 5010       5020       5030       5040       5050
CAGACACCCCGGATCCTCTCACCGCGATACAGCCAGTCATGTACAGTCTT
GTCTGTGGGGCCTAGGAGAGTGGCGCTATGTCGGTCAGTACATGTCAGAA
   R  H  P  G  S  S  H  R  D  T  A  S  H  V  Q  S 5060       5070       5080       5090       5100
CACCTGTACAGTCAGACTCTAGTACCGCTAAGGAACATGGTCACTTTAGT
GTGGACATGTCAGTCTGAGATCATGGCGATTCCTTGTACCAGTGAAATCA
 S  P  V  Q  S  D  S  S  T  A  K  E  H  G  H  F  S 5110       5120       5130       5140       5150
AGTCTTTCACAAGATTCTGCGTATCACTCAGGAATACAGTCACGTGGCAG
TCAGAAAGTGTTCTAAGACGCATAGTGAGTCCTTATGTCAGTGCACCGTC
  S  L  S  Q  D  S  A  Y  H  S  G  I  Q  S  R  G  S 5160       5170       5180       5190       5200
TCCTCACAGTTCTAGTTCTTATCATTATCAATCTGAGGGCACTGAAAGGC
AGGAGTGTCAAGATCAAGAATAGTAATAGTTAGACTCCCGTGACTTTCCG
  P  H  S  S  S  Y  H  Y  Q  S  E  G  T  E  R 5210       5220       5230       5240       5250
AAAAAGGTCAATCAGGTTTAGTTTGGAGACATGGCAGCTATGGTAGTGCA G
TTTTTCCAGTTAGTCCAAATCAAACCTCTGTACCGTCGATACCATCACGT C
  Q  K  G  Q  S  G  L  V  W  R  H  G  S  Y  G  S  A
```

Figure 13
**Specific fragment from *FLG* size variant allele "*FLG*$^{8+16+}$"**

Sequence Range: 1 to 6223

```
Repeat 7 (partial)
                                                                        50
          AGGACAAGCA  GGAACCGGGG  ATCCAGTTTT  AGCCAGGACA  GTGACAGTCA
          TCCTGTTCGT  CCTTGGCCCC  TAGGTCAAAA  TCGGTCCTGT  CACTGTCAGT
           R  T  S   R  N  R  G   S  S  F    S  Q  D     S  D  S  Q 100
          GGGACACTCA  GAAGACTCTG  AGAGGTGGTC  TGGGTCTGCT  TCCAGAAACC
          CCCTGTGAGT  CTTCTGAGAC  TCTCCACCAG  ACCCAGACGA  AGGTCTTTGG
           G  H  S   E  D  S     E  R  W  S   G  S  A   S  R  N 150
          ATCATGGATC  TGCTCAGGAG  CAGCTAAGAG  ATGGCTCCAG  ACACCCCAGG
          TAGTACCTAG  ACGAGTCCTC  GTCGATTCTC  TACCGAGGTC  TGTGGGGTCC
           H  H  G  S   A  Q  E    Q  L  R    D  G  S  R   H  P  R 200
          TCCCATCAAG  AAGACAGAGC  TGGTCATGGG  CACTCTGCAG  ACAGCTCCAG
          AGGGTAGTTC  TTCTGTCTCG  ACCAGTACCC  GTGAGACGTC  TGTCGAGGTC
           S  H  Q   E  D  R  A    G  H  G    H  S  A    D  S  S  R 250
          ACAATCAGGC  ACTCGTCACA  CACAGACTTC  CTCTGGTGGA  CAGGCTGCAT
          TGTTAGTCCG  TGAGCAGTGT  GTGTCTGAAG  GAGACCACCT  GTCCGACGTA
           Q  S  G   T  R  H     T  Q  T  S   G  G  Q   A  A 300
          CATCCCATGA  ACAGGCAAGA  TCAAGTGCAG  GAGAAAGACA  TGGATCCCAC
          GTAGGGTACT  TGTCCGTTCT  AGTTCACGTC  CTCTTTCTGT  ACCTAGGGTG
           S  S  H  E   Q  A  R   S  S  A     G  E  R  H   G  S  H 350
          CACCAGCAGT  CAGCAGACAG  CTCCAGACAC  TCAGGCATTG  GGCACGGACA
          GTGGTCGTCA  GTCGTCTGTC  GAGGTCTGTG  AGTCCGTAAC  CCGTGCCTGT
           H  Q  Q   S  A  D  S    S  R  H    S  G  I    G  H  G  Q 400
          AGCTTCATCT  GCAGTCAGAG  ACAGTGGACA  CCGAGGGTAC  AGTGGTAGTC
          TCGAAGTAGA  CGTCAGTCTC  TGTCACCTGT  GGCTCCCATG  TCACCATCAG
           A  S  S   A  V  R     D  S  G  H   R  G  Y   S  G  S 450
          AGGCCAGTGA  CAATGAGGGA  CATTCAGAAG  ACTCAGACAC  ACAGTCAGTG
          TCCGGTCACT  GTTACTCCCT  GTAAGTCTTC  TGAGTCTGTG  TGTCAGTCAC
           Q  A  S  D   N  E  G   H  S  E     D  S  D  T   Q  S  V 500
          TCAGCCCACG  GACAGGCTGG  GTCCCATCAG  CAGAGCCACC  AAGAGTCCGC
          AGTCGGGTGC  CTGTCCGACC  CAGGGTAGTC  GTCTCGGTGG  TTCTCAGGCG
           S  A  H   G  Q  A  G    S  H  Q    S  H  Q    E  S  A
```

Figure 13- continued

```
                                                                            550
         ACGTGGCCGG TCAGGGGAAA CGTCTGGACA TTCAGGGTCT TTCCTCTACC
         TGCACCGGCC AGTCCCCTTT GCAGACCTGT AAGTCCCAGA AAGGAGATGG
           R  G  R    S  G  E    T  S  G  H    S  G  S    F  L  Y

Repeat 8.1                          600
         AGGTGAGCAC TCATGAACAG TCTGAGTCCT CCCATGGATG GACGGGGCCC
         TCCACTCGTG AGTACTTGTC AGACTCAGGA GGGTACCTAC CTGCCCCGGG
           Q  V  S  T    H  E  Q    S  E  S    S  H  G  W    T  G  P
Repeat 8.1
                                                                      650
         AGCACTAGAG GAAGACAAGG ATCCCGCCAT GAGCAGGCAC AAGACAGCTC
         TCGTGATCTC CTTCTGTTCC TAGGGCGGTA CTCGTCCGTG TTCTGTCGAG
           S  T  R    G  R  Q  G    S  R  H    E  Q  A    Q  D  S  S 700
         CAGGCACTCA GCATCCCAAG ACGGTCAGGA CACCATTCGT GGACACCCGG
         GTCCGTGAGT CGTAGGGTTC TGCCAGTCCT GTGGTAAGCA CCTGTGGGCC
           R  H  S    A  S  Q    D  G  Q  D    T  I  R    G  H  P 750
         GGTCAAGCAG AGGAGGAAGG CAGGGGTACC ACCACGAGCA TTCGGTAGAT
         CCAGTTCGTC TCCTCCTTCC GTCCCCATGG TGGTGCTCGT AAGCCATCTA
           G  S  S  R    G  G  R    Q  G  Y    H  H  E  H    S  V  D 800
         AGCTCTGGAC ACTCAGGGTC CCATCACAGC CACACCACAT CCCAGGGAAG
         TCGAGACCTG TGAGTCCCAG GGTAGTGTCG GTGTGGTGTA GGGTCCCTTC
           S  S  G    H  S  G  S    H  H  S    H  T  T    S  Q  G  R

*            850
         GTCTGATGCC TCCCGTGGGC AGTCAGGATC CAGACGTGCA AGCAGAACAA
         CAGACTACGG AGGGCACCCG TCAGTCCTAG GTCTGCACGT TCGTCTTGTT
           S  D  A    S  R  G    Q  S  G  S    R  R  A    S  R  T

900
         CACGTAATGA GGAACAATCA GGAGACGGCT CCAGGCACTC AGGGTCGCGT
         GTGCATTACT CCTTGTTAGT CCTCTGCCGA GGTCCGTGAG TCCCAGCGCA
           T  R  N  E    E  Q  S    G  D  G    S  R  H  S    G  S  R

950
         CACCATGAAG CTTCCACTCA TGCCGACATC TCTAGACACT CACAGGCAGT
         GTGGTACTTC GAAGGTGAGT ACGGCTGTAG AGATCTGTGA GTGTCCGTCA
           H  H  E    A  S  T  H    A  D  I    S  R  H    S  Q  A  V

1000
         CCAGGGACAA TCAGAGGGGT CCAGGAGAAG CAGGCGCCAG GGATCCAGTG
         GGTCCCTGTT AGTCTCCCCA GGTCCTCTTC GTCCGCGGTC CCTAGGTCAC
           Q  G  Q    S  E  G    S  R  R  S    R  R  Q    G  S  S

1050
         TTAGCCAGGA CAGTGACAGT GAGGGACATT CAGAAGACTC TGAGAGGTGG
         AATCGGTCCT GTCACTGTCA CTCCCTGTAA GTCTTCTGAG ACTCTCCACC
           V  S  Q  D    S  D  S    E  G  H    S  E  D  S    E  R  W

1100
         TCTGGGTCTG CTTCCAGAAA CCATCATGGA TCTGCTCAGG AGCAGCTAAG
         AGACCCAGAC GAAGGTCTTT GGTAGTACCT AGACGAGTCC TCGTCGATTC
           S  G  S    A  S  R  N    H  H  G    S  A  Q    E  Q  L  R
```

Figure 13- continued

```
                                                                1150
        AGATGGCTCC AGACACCCCA GGTCCCATCA AGAAGGCAGA GCTGGTCATG
        TCTACCGAGG TCTGTGGGGT CCAGGGTAGT TCTTCCGTCT CGACCAGTAC
          D  G  S   R  H  P   R  S  H  Q   E  G  R   A  G  H

1200
        GGCACTCTGC AGACAGCTCC AGACAATCAG GCACTCGTCA CACACAGACT
        CCGTGAGACG TCTGTCGAGG TCTGTTAGTC CGTGAGCAGT GTGTGTCTGA
          G  H  S   A  D  S   S  R  Q  S   G  T  R   H  T  Q  T

1250
        TCCTCTGGTG GACAGGCTGC ATCATCCCAT GAACAGGCAA GATCAAGTGC
        AGGAGACCAC CTGTCCGACG TAGTAGGGTA CTTGTCCGTT CTAGTTCACG
          S  S  G   G  Q  A  A   S  S  H   E  Q  A   R  S  S  A

1300
        AGGAGAAAGA CATGGATCCC ACCACCAGCA GTCAGCAGAC AGCTCCAGAC
        TCCTCTTTCT GTACCTAGGG TGGTGGTCGT CAGTCGTCTG TCGAGGTCTG
          G  E  R   H  G  S   H  H  Q  Q   S  A  D   S  S  R

1350
        ACTCAGGCAT TGGGCACGGA CAAGCTTCAT CTGCAGTCAG AGACAGTGGA
        TGAGTCCGTA ACCCGTGCCT GTTCGAAGTA GACGTCAGTC TCTGTCACCT
          H  S  G   I   G  H  G   Q  A  S   S  A  V  R   D  S  G

1400
        CACCGAGGGT ACAGTGGTAG TCAGGCCAGT GACAATGAGG GACATTCAGA
        GTGGCTCCCA TGTCACCATC AGTCCGGTCA CTGTTACTCC CTGTAAGTCT
          H  R  G   Y  S  G  S   Q  A  S   D  N  E   G  H  S  E

1450
        AGACTCAGAC ACACAGTCAG TGTCAGCCCA CGGACAGGCT GGGTCCCATC
        TCTGAGTCTG TGTGTCAGTC ACAGTCGGGT GCCTGTCCGA CCCAGGGTAG
          D  S  D   T  Q  S   V  S  A  H   G  Q  A   G  S  H

1500
        AGCAGAGCCA CCAAGAGTCC GCACGTGGCC GGTCAGGGGA AACGTCTGGA
        TCGTCTCGGT GGTTCTCAGG CGTGCACCGG CCAGTCCCCT TTGCAGACCT
          Q  Q  S  H   Q  E  S   A  R  G   R  S  G   E  T  S  G

Repeat 8.2  1550
        CATTCAGGAT CTTTCCTCTA CCAGGTGAGC ACTCATGAAC AGTCTGAGTC
        GTAAGTCCTA GAAAGGAGAT GGTCCACTCG TGAGTACTTG TCAGACTCAG
          H  S  G   S  F  L  Y   Q  V  S   T  H  E   Q  S  E  S
Repeat 8.2
                                                                1600
        CTCCCATGGA TGGACGGGGC CCAGCACTAG AGGAAGACAA GGATCCCGC
        GAGGGTACCT ACCTGCCCCG GGTCGTGATC TCCTTCTGTT CCTAGGGCGG
          S  H  G   W  T  G   P  S  T  R   G  R  Q   G  S  R 1650
        ATGAGCAGGC ACAAGACAGC TCCAGGCACT CAGCATCCCA AGAGGGTCAG
        TACTCGTCCG TGTTCTGTCG AGGTCCGTGA GTCGTAGGGT TCTCCCAGTC
          H  E  Q  A   D  S   S  R  H   S  A  S  Q   D  G  Q 1700
        GACACCATTC GTGGACACCC GGGGTCAAGC AGAGGAGGAA GGCAGGGGTA
        CTGTGGTAAG CACCTGTGGG CCCCAGTTCG TCTCCTCCTT CCGTCCCCAT
          D  T  I   R  G  H  P   G  S  S   R  G  G   R  Q  G  Y
```

Figure 13- continued

```
                                                                    1750
          CCACCACGAG CATTCGGTAG ATAGCTCTGG ACACTCAGGG TCCCATCACA
          GGTGGTGCTC GTAAGCCATC TATCGAGACC TGTGAGTCCC AGGGTAGTGT
           H  H  E   H  S  V    D  S  S  G   H  S  G    S  H  H

1800
          GCCACACCAC ATCCCAGGGA AGGTCTGATG CCTCCCGTGG GCAGTCAGGA
          CGGTGTGGTG TAGGGTCCCT TCCAGACTAC GGAGGGCACC CGTCAGTCCT
           S  H  T  T    S  Q  G    R  S  D    A  S  R  G    Q  S  G

1850
          TCCAGAAGTG CAAGCAGAAC AACACGTAAT GAGGAACAAT CAGGAGACGG
          AGGTCTTCAC GTTCGTCTTG TTGTGCATTA CTCCTTGTTA GTCCTCTGCC
           S  R  S    A  S  R  T    T  R  N    E  E  Q    S  G  D  G

1900
          CTCCAGGCAC TCAGGGTCGC GTCACCATGA AGCTTCCACT CATGCCGACA
          GAGGTCCGTG AGTCCCAGCG CAGTGGTACT TCGAAGGTGA GTACGGCTGT
            S  R  H    S  G  S    R  H  H  E    A  S  T    H  A  D

1950
          TCTCTAGACA CTCACAGGCA GTCCAGGGAC AATCAGAGGG GTCCAGGAGA
          AGAGATCTGT GAGTGTCCGT CAGGTCCCTG TTAGTCTCCC CAGGTCCTCT
           I  S  R  H    S  Q  A    V  Q  G    Q  S  E  G    S  R  R

2000
          AGCAGGCGCC AGGGATCCAG TGTTAGCCAG GACAGTGACA GTGAGGGACA
          TCGTCCGCGG TCCCTAGGTC ACAATCGGTC CTGTCACTGT CACTCCCTGT
           S  R  R    Q  G  S  S    V  S  Q    D  S  D    S  E  G  H

2050
          TTCAGAAGAC TCTGAGAGGT GGTCTGGGTC TGCTTCCAGA AACCATCATG
          AAGTCTTCTG AGACTCTCCA CCAGACCCAG ACGAAGGTCT TTGGTAGTAC
            S  E  D    S  E  R    W  S  G  S    A  S  R    N  H  H

2100
          GATCTGCTCA GGAGCAGCTA AGAGATGGCT CCAGACACCC CAGGTCCCAT
          CTAGACGAGT CCTCGTCGAT TCTCTACCGA GGTCTGTGGG GTCCAGGGTA
           G  S  A  Q    E  Q  L    R  D  G    S  R  H  P    R  S  H

2150
          CAAGAAGACA GAGCTGGTCA TGGGCACTCT GCAGACAGCT CCAGACAATC
          GTTCTTCTGT CTCGACCAGT ACCCGTGAGA CGTCTGTCGA GGTCTGTTAG
           Q  E  D    R  A  G  H    G  H  S    A  D  S    S  R  Q  S

2200
          AGGCACTCGT CACACACAGS CTTCCTCTGG TGGACAGGCT GCATCATCCC
          TCCGTGAGCA GTGTGTGTCS GAAGGAGACC ACCTGTCCGA CGTAGTAGGG
            G  T  R    H  T  Q    A  S  S  G    G  Q  A    A  S  S

2250
          ATGAACAGGC AAGATCAAGT GCAGGAGAAA GACATGGATC CCACCACCAG
          TACTTGTCCG TTCTAGTTCA CGTCCTCTTT CTGTACCTAG GGTGGTGGTC
           H  E  Q  A    R  S  S    A  G  E    R  H  G  S    H  H  Q

2300
          CAGTCAGCAG ACAGCTCCAG ACACTCAGGC ATTGGGCACG GACAAGCTTC
          GTCAGTCGTC TGTCGAGGTC TGTGAGTCCG TAACCCGTGC CTGTTCGAAG
            Q  S  A    D  S  S  R    H  S  G    I  G  H    G  Q  A  S
```

Figure 13- continued

```
                                                              2350
ATCTGCAGTC AGAGACAGTG GACACCGAGG GTACAGTGGT AGTCAGGCCA
TAGACGTCAG TCTCTGTCAC CTGTGGCTCC CATGTCACCA TCAGTCCGGT
   S  A  V   R  D  S    G  H  R  G   Y  S  G    S  Q  A

2400
GTGACAATGA GGGACATTCA GAAGACTCAG ACACACAGTC AGTGTCAGCC
CACTGTTACT CCCTGTAAGT CTTCTGAGTC TGTGTGTCAG TCACAGTCGG
   S  D  N  E    G  H  S   E  D  S    D  T  Q  S    V  S  A

2450
CACGGACAGG CTGGGTCCCA TCAGCAGAGC CACCAAGAGT CCGCACGTGG
GTGCCTGTCC GACCCAGGGT AGTCGTCTCG GTGGTTCTCA GGCGTGCACC
   H  G  Q    A  G  S  H    Q  Q  S    H  Q  E    S  A  R  G

2500
CCGGTCAGGG GAAACGTCTG GACATTCAGG ATCTTTCCTC TACCAGGTGA
GGCCAGTCCC CTTTGCAGAC CTGTAAGTCC TAGAAAGGAG ATGGTCCACT
   R  S  G    E  T  S    G  H  S  G    S  F  L    Y  Q  V

Repeat 9                                2550
             GCACTCATGA ACAGTCTGAG TCCTCCCATG GATGGACGGG GCCCAGCACT
             CGTGAGTACT TGTCAGACTC AGGAGGGTAC CTACCTGCCC CGGGTCGTGA
               S  T  H  E    Q  S  E    S  S  H    G  W  T  G    P  S  T
Repeat 9

2600
AGAGGAAGAC AAGGATCCCG CCATGAGCAG GCACAAGACA GCTCCAGGCA
TCTCCTTCTG TTCCTAGGGC GGTACTCGTC CGTGTTCTGT CGAGGTCCGT
   R  G  R    Q  G  S  R    H  E  Q    A  Q  D    S  S  R  H

2650
CTCAGCATCC CAAGACGGTC AGGACACCAT TCGTGGACAC CCGGGGTCAA
GAGTCGTAGG GTTCTGCCAG TCCTGTGGTA AGCACCTGTG GGCCCCAGTT
   S  A  S    Q  D  G    Q  D  T  I    R  G  H    P  G  S

2700
GCAGAGGAGG AAAGGCAGGGG TACCACCACG AGCATTCGGT AGATAGCTCT
CGTCTCCTCC TTTCCGTCCCC ATGGTGGTGC TCGTAAGCCA TCTATCGAGA
   S  R  G  G    R  Q  G    Y  H  H    E  H  S  V    D  S  S

2750
GGACACTCAG GGTCCCATCA CAGCCACACC ACATCCCAGG GAAGGTCTGA
CCTGTGAGTC CCAGGGTAGT GTCGGTGTGG TGTAGGGTCC CTTCCAGACT
   G  H  S    G  S  H  H    S  H  T    T  S  Q    G  R  S  D

2800
TGCCTCCCGT GGGCAGTCAG GATCCAGAAG TGCAAGCAGA ACAACACGTA
ACGGAGGGCA CCCGTCAGTC CTAGGTCTTC ACGTTCGTCT TGTTGTGCAT
   A  S  R    G  Q  S    G  S  R  S    A  S  R    T  T  R

2850
ATGAGGAACA ATCAGGAGAC AGCTCCAGGC ACTCAGGGTC GCGTCACCAT
TACTCCTTGT TAGTCCTCTG TCGAGGTCCG TGAGTCCCAG CGCAGTGGTA
   N  E  E  Q    S  G  D    S  S  R    H  S  G    S  R  H  H

2900
GAAGCTTCCA CTCATGCCGA CATCTCTAGA CACTCACAGG CAGTCCAGGG
CTTCGAAGGT GAGTACGGCT GTAGAGATCT GTGAGTGTCC GTCAGGTCCC
   E  A  S    T  H  A  D    I  S  R    H  S  Q    A  V  Q  G
```

Figure 13- continued

```
                                                                2950
ACAATCAGAG GGGTCCAGGA GAAGCAGGCG CCAGGGATCC AGTGTTAGCC
TGTTAGTCTC CCCAGGTCCT CTTCGTCCGC GGTCCCTAGG TCACAATCGG
  Q  S  E   G  S  R    R  S  R  R   Q  G  S    S  V  S

3000
AGGACAGTGA CAGTGAGGGA CATTCAGAAG ACTCTGAGAG GTGGTCTGGG
TCCTGTCACT GTCACTCCCT GTAAGTCTTC TGAGACTCTC CACCAGACCC
  Q  D  S  D    S  E  G   H  S  E   D  S  E  R    W  S  G

3050
TCTGCTTCCA GAAACCATCG TGGATCTGTT CAGGAGCAGT CAAGGCACGG
AGACGAAGGT CTTTGGTAGC ACCTAGACAA GTCCTCGTCA GTTCCGTGCC
  S  A  S   R  N  H  R   G  S  V   Q  E  Q    S  R  H  G

3100
CTCCAGACAC CCCAGGTCCC ATCACGAAGA CAGAGCCGGT CACGGGCACT
GAGGTCTGTG GGGTCCAGGG TAGTGCTTCT GTCTCGGCCA GTGCCCGTGA
  S  R  H    P  R  S   H  H  E  D   R  A  G    H  G  H

3150
CTGCAGACCG CTCCAGACAA TCAGGCACTC GTCACGCAGA GACTTCCTCT
GACGTCTGGC GAGGTCTGTT AGTCCGTGAG CAGTGCGTCT CTGAAGGAGA
  S  A  D  R    S  R  Q   S  G  T   R  H  A  E    T  S  S

3200
GGTGGACAGG CTGCATCATC CCATGAACAG GCAAGATCAA GTCCAGGAGA
CCACCTGTCC GACGTAGTAG GGTACTTGTC CGTTCTAGTT CAGGTCCTCT
  G  G  Q    A  A  S  S    H  E  Q   A  R  S    S  P  G  E

3250
GAGACACGGA TCCCGCCACC AGCAGTCAGC AGACAGCTCC AGACACTCAG
CTCTGTGCCT AGGGCGGTGG TCGTCAGTCG TCTGTCGAGG TCTGTGAGTC
  R  H  G    S  R  H    Q  Q  S  A   D  S  S    R  H  S

3300
GCATTCCGCG TGGACAGGCT TCATCTGCAG TCAGAGACAG TAGACACTGG
CGTAAGGCGC ACCTGTCCGA AGTAGACGTC AGTCTCTGTC ATCTGTGACC
  G  I  P  R    G  Q  A   S  S  A   V  R  D  S   R  H  W

3350
GGGTCCAGTG GTAGTCAAGC CAGTGATAGT GAGGGACATT CAGAAGAGTC
CCCAGGTCAC CATCAGTTCG GTCACTATCA CTCCCTGTAA GTCTTCTCAG
  G  S  S    G  S  Q   A   S  D  S   E  G  H    S  E  E  S

3400
AGACACACAG TCAGTGTCAG GCCATGGACA GGCTGGGCCC CATCAGCAGA
TCTGTGTGTC AGTCACAGTC CGGTACCTGT CCGACCCGGG GTAGTCGTCT
  D  T  Q    S  V  S   G  H  G  Q    A  G  P    H  Q  Q

3450
GCCACCAAGA GTCCGCACGT GACCGGTCAG GGGGAAGGTC TGGACGTTCA
CGGTGGTTCT CAGGCGTGCA CTGGCCAGTC CCCCTTCCAG ACCTGCAAGT
  S  H  Q  E    S  A  R   D  R  S    G  G  R  S    G  R  S

3500
GGGTCTTTCC TCTACCAGGT GAGCACTCAT GAACAGTCTG AGTCCGCCCA
CCCAGAAAGG AGATGGTCCA CTCGTGAGTA CTTGTCAGAC TCAGGCGGGT
  G  S  F    L  Y  Q  V   S  T  H    E  Q  S   E  S  A  H
```

Figure 13- continued

```
Repeat 10.1                                                             3550
        TGGGCGGACC AGGACCAGCA CTGGACGAAG ACAAGGATCC CACCACGAGC
        ACCCGCCTGG TCCTGGTCGT GACCTGCTTC TGTTCCTAGG GTGGTGCTCG
          G   R   T   R   T   S   T   G   R   R   Q   G   S   H   H   E 3600
        AGGCACGAGA CAGCTCCAGG CACTCAGCGT CCCAAGAGGG TCAGGACACC
        TCCGTGCTCT GTCGAGGTCC GTGAGTCGCA GGGTTCTCCC AGTCCTGTGG
          Q   A   R   D   S   S   R   H   S   A   S   Q   E   G   Q   D   T 3650
        ATTCGTGCAC ACCCGGGGTC AAGCAGAAGA GGAAGGCAGG GATCCCACTA
        TAAGCACGTG TGGGCCCCAG TTCGTCTTCT CCTTCCGTCC CTAGGGTGAT
          I   R   A   H   P   G   S   S   R   R   G   R   Q   G   S   H   Y 3700
        CGAGCAATCG GTAGATAGGT CTGGACACTC AGGGTCCCAT CACAGCCACA
        GCTCGTTAGC CATCTATCCA GACCTGTGAG TCCCAGGGTA GTGTCGGTGT
          E   Q   S   V   D   R   S   G   H   S   G   S   H   H   S   H 3750
        CCACATCCCA GGGAAGGTCT GATGCCTCCC GTGGGCAGTC AGGATCCAGA
        GGTGTAGGGT CCCTTCCAGA CTACGGAGGG CACCCGTCAG TCCTAGGTCT
          T   T   S   Q   G   R   S   D   A   S   R   G   Q   S   G   S   R 3800
        AGTGCCAGCA GACAAACTCG TAACGACGAA CAATCAGGAG ACGGCTCCAG
        TCACGGTCGT CTGTTTGAGC ATTGCTGCTT GTTAGTCCTC TGCCGAGGTC
          S   A   S   R   Q   T   R   N   D   E   Q   S   G   D   G   S   R 3850
        GCACTCATGG TCGCATCACC ATGAAGCTTC CACTCAGGCG GACAGCTCTA
        CGTGAGTACC AGCGTAGTGG TACTTCGAAG GTGAGTCCGC CTGTCGAGAT
          H   S   W   S   H   H   H   E   A   S   T   Q   A   D   S   S 3900
        GACACTCACA GTCCGGCCAG GGACAATCAG CGGGGCCCAG TACAAGCAGG
        CTGTGAGTGT CAGGCCGGTC CCTGTTAGTC GCCCCGGGTC ATGTTCGTCC
          R   H   S   Q   S   G   Q   G   Q   S   A   G   P   S   T   S   R 3950
        AACCAGGGAT CCAGTGTTAG CCAGGACAGT GACAGTCAGG GACACTCAGA
        TTGGTCCCTA GGTCACAATC GGTCCTGTCA CTGTCAGTCC CTGTGAGTCT
          N   Q   G   S   S   V   S   Q   D   S   D   S   Q   G   H   S   E 4000
        AGACTCTGAG AGGTGGTCTG GGTCTGCTTC CAGAAACCAT CATGGATCTG
        TCTGAGACTC TCCACCAGAC CCAGACGAAG GTCTTTGGTA GTACCTAGAC
          D   S   E   R   W   S   G   S   A   S   R   N   H   G   S 4050
        CTGGGGAGCA GTCAAGAGAT GGCTCCAGAC ACCCTGGGTC CCATCAAGAA
        GACCCCTCGT CAGTTCTCTA CCGAGGTCTG TGGGACCCAG GGTAGTTCTT
          A   G   E   Q   S   R   D   G   S   R   H   P   G   S   H   Q   E 4100
        GACAGAGCCG GTCACGGGCA CTCTGCAGAC AGCCCCAGAC AATCAGGCAC
        CTGTCTCGGC CAGTGCCCGT GAGACGTCTG TCGGGGTCTG TTAGTCCGTG
          D   R   A   G   H   G   H   S   A   D   S   P   R   Q   S   G   T
```

Figure 13- continued

```
                                                                    4150
TCGTCACACA GAGTCTTCCT CTCGTGGACA GGCTGCGTCA TCCCATGAAC
AGCAGTGTGT CTCAGAAGGA GAGCACCTGT CCGACGCAGT AGGGTACTTG
  R  H  T   E  S  S   S  R  G  Q   A  A  S   S  H  E

4200
AGGCAAGATC AAGTGCAGGA GAAAGACATG GATCCCACCA CCAGCTCCAG
TCCGTTCTAG TTCACGTCCT CTTTCTGTAC CTAGGGTGGT GGTCGAGGTC
  Q  A  R  S   S  A  G   E  R  H   G  S  H  H   Q  L  Q

4250
TCAGCAGACA GCTCCAGACA CCCAGGCATT GGGCACGGAC AAGCTTCATC
AGTCGTCTGT CGAGGTCTGT GGGTCCGTAA CCCGTGCCTG TTCGAAGTAG
  S  A  D   S  S  R  H   A  G  I   G  H  G   Q  A  S  S

4300
TGCAGTCAGA GACAGTGGAC ACCGAGGGTA CAGTGGTAGT CAGGCCACTG
ACGTCAGTCT CTGTCACCTG TGGCTCCCAT GTCACCATCA GTCCGGTGAC
  A  V  R   D  S  G   H  R  G  Y   S  G  S   Q  A  T

4350
ACAGTGAGGG ACATTCAGAA GACTCAGACA CACAGTCAGT GTCAGCCCAG
TGTCACTCCC TGTAAGTCTT CTGAGTCTGT GTGTCAGTCA CAGTCGGGTC
  D  S  E  G   H  S  E   D  S  D   T  Q  S  V   S  A  Q

4400
GGAAAAGCTG GGCCCCATCA GCAGAGCCAC AAAGAGTCCG CACGTGGCCA
CCTTTTCGAC CCGGGGTAGT CGTCTCGGTG TTTCTCAGGC GTGCACCGGT
  G  K  A   G  P  H  Q   Q  S  H   K  E  S   A  R  G  Q

4450
GTCAGGGGAA AGCTCTAGAC GTTCAGGGTC TTTCCTCTAC CAGGTGAGCA
CAGTCCCCTT TCGAGATCTG CAAGTCCCAG AAAGGAGATG GTCCACTCGT
  S  G  E   S  S  R   R  S  G  S   F  L  Y   Q  V  S

Repeat 10.2                                            4500
CTCATGAACA GTCTGAGTCC ACCCATGGAC AGTCTGTGCC CAGCACTGGA
GAGTACTTGT CAGACTCAGG TGGGTACCTG TCAGACACGG GTCGTGACCT
  T  H  E  Q   S  E  S   T  H  G   Q  S  V  P   S  T  G
Repeat 10.2
                                                                    4550
GGAAGACAAG GATCCCACCA TGATCAGGCA CAAGACAGCT CCAGGCACTC
CCTTCTGTTC CTAGGGTGGT ACTAGTCCGT GTTCTGTCGA GGTCCGTGAG
  G  R  Q   G  S  H  H   D  Q  A   Q  D  S   S  R  H  S 4600
AGCATCCCAA GAGGGTCAGG ACACCATTCG TGGACACCCG GGGCCAAGCA
TCGTAGGGTT CTCCCAGTCC TGTGGTAAGC ACCTGTGGGC CCCGGTTCGT
  A  S  Q   E  G  Q   D  T  I  R   G  H  P   G  P  S 4650
GAGGAGGAAG ACAGGGGTCC CACCACGAGC AATCGGTAGA TAGGTCTGGA
CTCCTCCTTC TGTCCCCAGG GTGGTGCTCG TTAGCCATCT ATCCAGACCT
  R  G  G  R   Q  G  S   H  H  E   Q  S  V  D   R  S  G 4700
CACTCAGGGT CCCATCACAG CCACACCACA TCCCAGGGAA GGTCTGATGC
GTGAGTCCCA GGGTAGTGTC GGTGTGGTGT AGGGTCCCTT CCAGACTACG
  H  S  G   S  H  H  S   H  T  T   S  Q  G   R  S  D  A
```

Figure 13- continued

```
                              *                            * *  4750
         CTCCCGTGGG CAGTCAGGAC CCAGAAGTGC AAGCAGACAA ACACATGACA
         GAGGGCACCC GTCAGTCCTG GGTCTTCACG TTCGTCTGTT TGTGTACTGT
           S  R  G    Q  S  G    P  R  S  A    S  R  Q    T  H  D

*                    *                               4800
         AGGAACAATC AGGAGACGGC TCTAGGCACT CAGGGTCGCG TCATCATGAA
         TCCTTGTTAG TCCTCTGCCG AGATCCGTGA GTCCCAGCGC AGTAGTACTT
           K  E  Q  S    G  D  G    S  R  H    S  G  R    H  H  E

4850
         GCTTCCTCTT GGGCCGACAG CTCTAGACAC TCACAGGCAG TCCAGGGACA
         CGAAGGAGAA CCCGGCTGTC GAGATCTGTG AGTGTCCGTC AGGTCCCTGT
           A  S  S    W  A  D  S    S  R  H    S  Q  A    V  Q  G  Q

4900
         ATCAGAGGGG TCCAGGAGAA GCAGGCGCCA GGGATCCAGT GTTAGCCAGG
         TAGTCTCCCC AGGTCCTCTT CGTCCGCGGT CCCTAGGTCA CAATCGGTCC
           S  E  G    S  R  R    S  R  R  Q    G  S  S    V  S  Q

4950
         ACAGTGACAG TCAGGGACAC TCAGAAGACT CTGAGAGGCG GTCTGGGTCT
         TGTCACTGTC AGTCCCTGTG AGTCTTCTGA GACTCTCCGC CAGACCCAGA
           D  S  D  S    Q  G  H    S  E  D    S  E  R  R    S  G  S

5000
         GCTTCCAGAA ACCATCGTGG ATCTGCTCAG GAGCAGTCAA GAGATGGCTC
         CGAAGGTCTT TGGTAGCACC TAGACGAGTC CTCGTCAGTT CTCTACCGAG
           A  S  R    N  H  R  G    S  A  Q    E  Q  S    R  D  G  S

5050
         CAGACACCCC AGGTCCCATC ACGAAGACAG AGCCGGTCAT GGGCACTCTG
         GTCTGTGGGG TCCAGGGTAG TGCTTCTGTC TCGGCCAGTA CCCGTGAGAC
           R  H  P    R  S  H    H  E  D  R    A  G  H    G  H  S

5100
         CAGACAGCTC CAGACAATCA GGCACTCATC ATGCAGAGAA TTCCTCTGGT
         GTCTGTCGAG GTCTGTTAGT CCGTGAGTAG TACGTCTCTT AAGGAGACCA
           A  D  S  S    R  Q  S    G  T  H    H  A  E  N    S  S  G

*                                          5150
         GGACAGCCTG CATCATCCCA TGAACAGGCA AGATCAAGTG CAGGAGAGAG
         CCTGTCGGAC GTAGTAGGGT ACTTGTCCGT TCTAGTTCAC GTCCTCTCTC
           G  Q  P    A  S  S  H    E  Q  A    R  S  S    A  G  E  R

5200
         ACATGGATCC CACCACCAGC AGTCAGCAGA CAGCTCCAGA CACTCAGGCA
         TGTACCTAGG GTGGTGGTCG TCAGTCGTCT GTCGAGGTCT GTGAGTCCGT
           H  G  S    H  H  Q    Q  S  A  D    S  S  R    H  S  G

5250
         TTGGGCACGG ACAAGCTTCA TCTGCAGTCA GAGACAGTGG ACACCGAGGG
         AACCCGTGCC TGTTCGAAGT AGACGTCAGT CTCTGTCACC TGTGGCTCCC
           I  G  H  G    Q  A  S    S  A  V    R  D  S  G    H  R  G

5300
         TCCAGTGGTA GTCAGGCCAG TGACAGTGAG GGACATTCAG AAGACTCAGA
         AGGTCACCAT CAGTCCGGTC ACTGTCACTC CCTGTAAGTC TTCTGAGTCT
           S  S  G    S  Q  A  S    D  S  E    G  H  S    E  D  S  D
```

Figure 13- continued

```
                                                                    5350
        CACACAGTCA GTGTCAGCCC ACGGACAGGC TGGGCCCCAT CAGCAGAGCC
        GTGTGTCAGT CACAGTCGGG TGCCTGTCCG ACCCGGGGTA GTCGTCTCGG
          T  Q  S   V  S  A   H  G  Q  A   G  P  H    Q  Q  S 6                         5400
        ACCAAGAGTC CACACGTGGC CGGTCAGCAG GAAGGTCTGG ACGTTCAGGG
        TGGTTCTCAG GTGTGCACCG GCCAGTCGTC CTTCCAGACC TGCAAGTCCC
          H  Q  E  S   T  R  G   R  S  A   G  R  S  G   R  S  G

Repeat 11            5450
        TCTTTCCTCT ACCAGGTGAG CACTCATGAA CAGTCTGAGT CTGCCCATGG
        AGAAAGGAGA TGGTCCACTC GTGAGTACTT GTCAGACTCA GACGGGTACC
          S  F  L   Y  Q  V  S   T  H  E    Q  S  E   S  A  H  G
Repeat 11 (partial)
                                                                    5500
        ACGGGCTGGG CCCAGTACTG GAGGAAGACA AGGATCCCAC CACGAGCAGG
        TGCCCGACCC GGGTCATGAC CTCCTTCTGT TCCTAGGGTG GTGCTCGTCC
          R  A  G   P  S  T    G  G  R   Q  G  S  H   H  E  Q 5550
        CACGAGACAG CTCCAGGCAC TCAGCGTCCC AAGAGGGTCA GGACACCATT
        GTGCTCTGTC GAGGTCCGTG AGTCGCAGGG TTCTCCCAGT CCTGTGGTAA
          A  R  D   S  R  H    S  A  S    Q  E  G  Q   D  T  I 5600
        CGTGGACACC CGGGGTCAAG GAGAGGAGGA AGACAGGGAT CCTACCACGA
        GCACCTGTGG GCCCCAGTTC CTCTCCTCCT TCTGTCCCTA GGATGGTGCT
          R  G  H   P  G  S  R   R  G  G   R  Q  G    S  Y  H  E 5650
        GCAATCGGTA GATAGGTCTG GACACTCAGG GTCCCATCAC AGCCACACCA
        CGTTAGCCAT CTATCCAGAC CTGTGAGTCC CAGGGTAGTG TCGGTGTGGT
          Q  S  V   D  R  S    G  H  S  G   S  H  H   S  H  T 5700
        CATCCCAGGG AAGGTCTGAT GCCTCCCATG GGCAGTCAGG ATCCAGAAGT
        GTAGGGTCCC TTCCAGACTA CGGAGGGTAC CCGTCAGTCC TAGGTCTTCA
          T  S  Q  G   R  S  D   A  S  H   G  Q  S  G   S  R  S 5750
        GCAAGCAGAG AAACACGTAA TGAGGAACAG TCAGGAGACG GCTCCAGGCA
        CGTTCGTCTC TTTGTGCATT ACTCCTTGTC AGTCCTCTGC CGAGGTCCGT
          A  S  R   E  T  R  N   E  E  Q   S  G  D    G  S  R  H 5800
        CTCAGGGTCG CGTCACCATG AAGCTTCCAC TCAGGCTGAC AGCTCTAGAC
        GAGTCCCAGC GCAGTGGTAC TTCGAAGGTG AGTCCGACTG TCGAGATCTG
          S  G  S   R  H  H   E  A  S  T   Q  A  D    S  S  R 5850
        ACTCACAGTC CGGCCAGGGT GAATCAGCGG GGTCCAGGAG AAGCAGGCGC
        TGAGTGTCAG GCCGGTCCCA CTTAGTCGCC CCAGGTCCTC TTCGTCCGCG
          H  S  Q  S   G  Q  G   E  S  A   G  S  R  R   S  R  R 5900
        CAGGGATCCA GTGTTAGCCA GGACAGTGAC AGTGAGGCAT ACCCAGAGGA
        GTCCCTAGGT CACAATCGGT CCTGTCACTG TCACTCCGTA TGGGTCTCCT
          Q  G  S   S  V  S  Q   D  S  D   S  E  A    Y  P  E  D
```

Figure 13- continued

```
                                                            5950
CTCTGAGAGG CGATCTGAGT CTGCTTCCAG AAACCATCAT GGATCTTCTC
GAGACTCTCC GCTAGACTCA GACGAAGGTC TTTGGTAGTA CCTAGAAGAG
   S   E   R    R   S   E    S   A   S   R    N   H   H    G   S   S

6000
GGGAGCAGTC AAGAGATGGC TCCAGACACC CCGGATCCTC TCACCGCGAT
CCCTCGTCAG TTCTCTACCG AGGTCTGTGG GGCCTAGGAG AGTGGCGCTA
   R   E   Q   S    R   D   G    S   R   H    P   G   S    H   R   D

6050
ACAGCCAGTC ATGTACAGTC TTCACCTGTA CAGTCAGACT CTAGTACCGC
TGTCGGTCAG TACATGTCAG AAGTGGACAT GTCAGTCTGA GATCATGGCG
   T   A   S    H   V   Q   S    S   P   V    Q   S   D    S   S   T   A

6100
TAAGGAACAT GGTCACTTTA GTAGTCTTTC ACAAGATTCT GCGTATCACT
ATTCCTTGTA CCAGTGAAAT CATCAGAAAG TGTTCTAAGA CGCATAGTGA
   K   E    H   G   H   F    S   S   L    S   Q   D   S    A   Y   H

6150
CAGGAATACA GTCACGTGGC AGTCCTCACA GTTCTAGTTC TTATCATTAT
GTCCTTATGT CAGTGCACCG TCAGGAGTGT CAAGATCAAG AATAGTAATA
   S   G   I   Q    S   R   G    S   P   H    S   S   S    Y   H   Y

6200
CAATCTGAGG GCACTGAAAG GCAAAAAGGT CAATCAGGTT TAGTTTGGAG
GTTAGACTCC CGTGACTTTC CGTTTTTCCA GTTAGTCCAA ATCAAACCTC
   Q   S   E    G   T   E   R    Q   K   G    Q   S   G    L   V   W   R

6223
ACATGGCAGC TATGGTAGTG CAG
TGTACCGTCG ATACCATCAC GTC
   H   G   S    Y   G   S   A
```

// FILAGGRIN

SEQUENCE LISTING

The specification further incorporates by reference the Sequence Listing submitted herewith via EFS on Jun. 9, 2011. Pursuant to 37 C.F.R. §1.821(c), the Sequence Listing text file, identified as Ser. No. 12/097,493.txt, is 249,270 bytes, and was created on Jun. 9, 2011. The Sequence Listing, electronically filed herewith, does not extend beyond the scope of the specification and thus does not contain new matter.

FIELD OF THE INVENTION

The present invention relates to the identification of loss-of-function mutations in the filaggrin gene and their use in diagnosing ichthyosis vulgaris and/or susceptibility to other diseases including atopic dermatitis (eczema), asthma, psoriasis and allergies (including food allergy).

BACKGROUND TO THE INVENTION

Ichthyosis vulgaris (IV; OMIM#146700) is the most common inherited disorder of keratinisation and one of the most frequent single gene disorders in humans. The most widely cited incidence figure is 1 in 250 based on a survey of 6051 healthy English schoolchildren[1].

The phenotypic characteristics of IV include palmar hyperlinearity, keratosis pilaris and a fine scale most markedly seen over the lower abdomen, arms and legs[2]. Filaggrin (filament aggregating protein) is important in the formation of the stratum corneum[3-5]. Keratohyalin granules in the granular layer of interfollicular epidermis are predominantly composed of the 400 kDa protein profilaggrin. Following a short, unique N-terminal domain, most of the profilaggrin molecule consists of 10-12 repeats of the 324 amino acid filaggrin sequence[6]. Upon terminal differentiation of granular cells, profilaggrin is proteolytically cleaved into ~37 kDa filaggrin peptides and the N-terminal domain containing an S100-like calcium binding domain. Filaggrin rapidly aggregates the keratin cytoskeleton, causing collapse of the granular cells into flattened anuclear squames. This condensed cytoskeleton is cross-linked by transglutaminases during formation of the cornified cell envelope (CCE). The CCE is the outermost barrier layer of the skin which not only prevents water loss but also impedes the entry of allergens and infectious agents[7]. Filaggrin is therefore a key protein in facilitating epidermal differentiation and maintaining barrier function.

Immunoblotting studies have shown that filaggrin protein was absent or markedly reduced in IV patients' skin and/or keratinocytes[8-10]. In addition, decreased filaggrin mRNA has been demonstrated in some individuals with IV[11]. A recessive mouse mutant, flaky tail (ft), bears the histological and ultrastructural hallmarks of human IV[12] and strong genetic linkage has been obtained to the murine filaggrin locus (FLG)[13, 14]. Although biochemical analysis has shown defective profilaggrin processing in ft/ft homozygotes[12], any genomic mutation in the FLG gene has not hitherto been identified.

It is amongst the objects of the present invention to provide a method of diagnosing ichthyosis vulgaris and atopic diseases or predisposition thereto.

SUMMARY OF THE INVENTION

The present invention is based on the identification for the first time of mutations in the human filaggrin (FLG) gene which lead to a loss or partial loss of protein function.

Thus, in a first aspect, the present invention provides a genetic test for ichthyosis vulgaris (IV) comprising the steps of:
a) providing a nucleic acid sample from a subject to be tested; and
b) detecting whether or not a mutation, which would lead to a loss of function or partial loss of function of the filaggrin (FLG) protein encoded by the filaggrin (FLG) gene, is present in the FLG gene of said nucleic acid.

It will be appreciated that the test may be used to diagnose IV and/or to test if a subject is predisposed to developing IV. Additionally, due to an association of IV, in severe or mild forms, with other diseases, the test may be used to also detect whether or not a subject is likely to be predisposed or suffering from atopic dermatitis (eczema), asthma, psoriasis or allergies, such as of a contact type allergy and food allergies (for example, peanut allergy). With regards to skin conditions, low levels of filaggrin expression may lead to development of mild and/or sub-clinical disease. In this manner, the present invention may also relate to the identification and/or treatment of said mild and/or sub-clinical forms of disease. Indeed, many skin conditions go undiagnosed and as such treatments may be considered more as a cosmetic treatment.

Thus, in a further aspect, the present invention provides a genetic test for atopic dermatitis (eczema), asthma, psoriasis and/or allergies comprising the steps of:
a) providing a nucleic acid sample from a subject to be tested; and
b) detecting whether or not a mutation, which would lead to a loss of function or partial loss of function of the FLG protein encoded by the FLG gene, is present in the FLG gene of said nucleic acid.

The sample to be tested may be any suitable sample from which nucleic acid may be obtained. Typically the nucleic acid is a sample of genomic DNA or mRNA. Conveniently the sample may be a sample of saliva, buccal scraping or blood sample. The sample may also be a tissue sample, such as a skin biopsy.

The subject may be any subject requiring to be tested and may suitably be a newborn or even a foetus. The subject may however be at any stage of life, and therefore includes neonates, children and adults. As mentioned above, said tests may be carried out on a subject in order to ascertain whether or not he/she is predisposed to developing a disease. Thus, a test may be carried out, for example, in order to test a subject's suitability for a particular job, where he/she may come into contact with agents which are known to lead in some cases to the development of eczema and/or allergy. Alternatively, said test may be carried out in order to categorise a subject and predict an "at risk" status for, for example, atopic disease. In this manner subjects may be tested so as to categorise or stratify subjects for therapeutic intervention, when appropriate, based on any results obtained, so as to prevent and/or treat atopic disease.

Moreover, ascertaining a subject's FLG status and therefore degree of expression or lack of expression of the FLG protein may find use in determining suitable treatment for a subject suffering or predisposed to suffering from IV and/or any of the other aforementioned diseases. For example, depending on the degree of severity, or expected degree of severity, the skilled artisan can decide on an appropriate therapeutic and/or cosmetic regime and as such tailored treatments can be based on a subjects FLG status.

The present invention, in one embodiment, is based on the identification of previously unidentified mutations in the FLG gene, which lead to a loss of function of the profilaggrin and consequently filaggrin proteins. The present invention however extends to any mutation in the FLG gene which leads to a loss or partial loss of function of the profilaggrin and/or filaggrin proteins.

The mutation may be an addition, deletion, substitution or inversion. Typically, the mutation effects 1-10 nucleotides, such as a one-base substitution, or a 2-10 e.g. 4-base deletion. The mutation may also be due to a translocation. By partial or total loss of profilaggrin or filaggrin protein function, is understood to mean that the mutation or mutations result in incorrect processing and/or expression of the FLG gene such that one or more of the filaggrin peptides normally expressed, is not functionally expressed. Typically 10-12 copies of the filaggrin peptide are expressed from a non-mutated FLG gene[6]. It is understood therefore that the mutant FLG genes of the present invention will result in the functional expression of less than 10-12 filaggrin peptides, typically less than 7, 5, 3 or 1 from one or both copies of the FLG gene, which are present in a genome.

Depending on the location and/or type of a mutation or mutations, any reduction in functional filaggrin expression can be mild, e.g. a 1-5 reduction in functional filaggrin peptides; significant e.g. a 7-13 reduction in functional filaggrin peptides; or severe, e.g. a 15-20 reduction in functional filaggrin peptides.

The mutation or mutations may be found in any of the exons 1, 2 and/or 3 of the FLG gene and may typically be found in exon 3. If the mutation or mutations is/are located in exon 3, the most detrimental mutations, with regards to functional filaggrin expression, will be found within the 5' (N-terminal) portion of the 3rd exon, such as within the first 2000 bases, e.g. mutation(s) is/are found within the unique, partial repeat, or first filaggrin repeat portion of exon 3 (see FIG. 2a).

A significant number of mutations have been identified by the present inventors, which lead to a loss of function and in some cases, a total loss of function of one of the FLG copies. One such mutation is a 1-base substitution at position 1501 of the FLG gene herein (as shown in FIG. 5 and SEQ ID NO.: 188). 1501C>T (numbering from initiating ATG), which results in the substitution of a cytidine by a thymidine and a corresponding amino acid change at position 501 of an arginine to a stop codon. As this mutation occurs in the first filaggrin repeat (see FIG. 2) and results in the generation of a stop codon, no functional copies of the filaggrin peptide are produced.

A second mutation identified is a 4-base deletion starting at position 2282 (see FIG. 5 and SEQ ID NO.: 186). The mutation has been named 2282del4 and this causes a resulting frame-shift which leads to an alternative stop codon 107 bases downstream. Again, this mutation occurs in the first filaggrin repeat and as such no functional copy of a filaggrin peptide is expressed, although a truncated mutant form of the peptide may be expressed, which possesses a unique C-terminal portion (see FIG. 4 and SEQ ID NO.: 187).

A third mutation is a deletion of a G in the third filaggrin repeat. The deletion is at position 3702 and is shown in FIG. 5. This mutation causes a frameshift in repeat 3, such that only 2 functional copies of filaggrin from repeats 1 and 2 are made.

Further mutations which have been identified include R2477X (repeat 7), 53247X (repeat 9), R1474X (repeat 4), Q1745X (repeat 4), Q3683X (repeat 10), 11029delCA (repeat 10), E2422X (repeat 6), 5369delG (repeat 5), 7367delCA (repeat 7), 11033del4 (repeat 100, 6867delAG (repeat 6), 3321delA (repeat 2) and 52554X (repeat 7). The most prevalent and/or recurrent mutations in the European population are R510X, 2282del4, 3702delG, R2447X and S3247X.

The nomenclature used above is to be understood as follows: S3247X, for example means that there is a mutation found at codon position 3247 which results in a codon change from a codon which encodes a serine, to a stop codon. 5360delG is a deletion of a G at DNA base-pair position 5360 (numbering where the initiating ATG=1), leading to a frameshift.

Detection of a mutation in the FLG gene may be carried out by a variety of techniques including quantitative or semi-quantitative PCR, including real-time PCR, nucleic acid sequencing, hybridisation studies and/or restriction fragment length polymorphism (RFLP) analysis techniques, well known to the skilled addressee (see, for example, Sambrook & Russel, 2000).

Depending on where the mutation or mutations are located, it may be appropriate to amplify one or more exons or portions thereof. If the mutation(s) is/are located in exon 3, all or only a portion of exon 3 may be amplified using appropriate primers. If the mutation(s) is/are located in the first repeat, it may only be necessary to amplify the first repeat, or portion thereof comprising the mutation(s). By appropriate use of primers and optional labels, it can be possible to amplify a product and ascertain whether or not the product comprises a mutation. For example, primers may be designed which incorporate at (or very close to) the 3' terminal, a base capable of binding to the native or mutant base/sequence, such that only the native or mutant sequence will be amplified and detected. A selection of primers suitable for use in amplifying the entire exon 3, or certain specific regions of the repeated sequences of exon 3 are identified herein as SEQ ID NO.s: 1-182.]

SEQ ID NO.s 1-8 represent primers suitable for long range PCR and sequencing of the filaggrin repeats.

SEQ ID NO.s 9-12 represent primers suitable for generating short PCR fragments for detection of the R501X mutation.

SEQ ID NO.s 13-15 represent primers suitable for generating short PCR fragments for detection of mutation 2828del4.

SEQ ID NO.s 15-18 represent primers suitable for generating short PCR fragments for detection of mutation 3702delG.

SEQ ID NO.s 19-40 represent primers which are specific for repeat 0.

SEQ ID NO.s 41-67 represent primers which are specific for repeat 1.

SEQ ID NO.s 68-93 represent primers which are specific for repeat 2.

SEQ ID NO.s 94-136 represent primers which are specific for repeat 3.

SEQ ID NO.s 137-201 represent primers which are specific for repeat 4.

SEQ ID NO.s 202-264 represent primers which are specific for repeat 5.

SEQ ID NO.s 265-329 represent primers which are specific for repeat 6.

SEQ ID NO.s 330-377 represent primers which are specific for repeat 7.

SEQ ID NO.s 378-414 represent primers which are specific for repeat 8.

SEQ ID NO.s 415-461 represent primers which are specific for repeat 9.

SEQ ID NO.s 462-493 represent primers which are specific for repeat 10.

SEQ ID NO.s 494-497 represent primers which are specific for repeat 8.1.

SEQ ID NO.s 498-501 represent primers which are specific for repeat 8.2.

SEQ ID NO.s 502-518 represent primers which are specific for repeat 10.1.

SEQ ID NO.s 519-539 represent primers which are specific for repeat 10.2.

SEQ ID NO.s 540-544 represent primers which are specific for repeat 11.

SEQ ID NO. 545 represents a primer which is specific for the filaggrin tail.

In all cases, F at the end of a primer sequence shows that the primer is a forward primer and an R shows it is a reverse primer.

It will be appreciated that shorter or longer versions of the identified primer sequences may be used, for example, the primers may be from 12-50 bases in length. However, 3'-terminal base is critical for correct primer extension and so the 3'-end of any primer should be identical to the sequences as identified herein.

Labels, such as fluorescent, chemiluminescent, bioluminescent or radio-labels may be incorporated into the PCR primers so as to allow detection of the native or mutant sequence. The skilled man will appreciate that two separately labelled primers may be used in a PCR reaction, designed to facilitate amplification of a product comprising either the native or mutant sequence and the sequence, native or mutant, detected based on the particular label being present in the product. Other labelling techniques such as the TaqMan® system of Applied Biosystems Inc., CA, USA, may be employed.

Of course, a fragment of DNA, which includes the portion of DNA which may include the mutation, may simply be amplified and sequenced, in order to determine whether or not the FLG gene comprises a mutation. Alternatively, such a fragment may be amplified and a hybridisation study carried out using an appropriate oligonucleotide and very stringent hybridisation conditions and washing conditions employed (see for example Sambrook et al, 2000[15]) so that only exactly matching oligonucleotides bind to the amplified fragment in the region or regions comprising the mutation(s).

It may also be appropriate to first amplify a fragment of DNA comprising the sequence which may or may not comprise a mutation(s) and thereafter detecting whether or not the fragment includes the native or mutant sequence by carrying out a further PCR reaction using primers internal to the amplified fragment, in order to detect or otherwise, a mutation(s). Such a technique is commonly known as nested PCR.

Moreover, any particular mutation may generate a new restriction site which may be detected by RFLP analysis. A fragment which would encompass a mutation which, if present, can first be amplified using appropriate primers and the fragment thereafter subjected to RFLP analysis providing the mutation or native sequence has a restriction site which is not present in the corresponding native or mutant sequence. In accordance with the present invention, the exemplary mutations identified herein result in the generation of new restriction sites which can easily be detected by first amplifying a fragment comprising the mutation and thereafter restricting the fragment obtained using the appropriate restriction enzyme—only a fragment comprising the mutant sequence will be restricted (see Examples Section for further description).

The present invention also extends to kits which comprise one or more of the aforementioned oligonucleotides/primers. The kits may also comprise other reagents to facilitate, for example, sequencing, conducting PCR and/or RFLP analysis. Such kits may also comprise instructions for their use to detect one or more mutations in a filaggrin gene and optionally how to interpret whether or not a mutation may lead to development or predisposition to developing IV and/or any of the other aforementioned diseases/conditions.

The oligonucleotides/primers of the present invention may also be used in multiplex PCR techniques, known to the skilled addressee, see for example. Kuperstein G, Jack E and Narod S A; Genet Test. 10(1):1-7 (2006). so as to identify mutations in the filaggrin sequence.

In addition to mutations which lead to a loss of function or partial loss of function of profilaggrin/filaggrin protein, the present inventors have now identified the specific repeat sequences which can lead to exon 3 of the filaggrin gene consisting of 11 or 12 full filaggrin repeats, as opposed to the "normal" 10 repeats. The inventors have identified that repeats 8 and/or 10 can be essentially duplicated in certain individuals, in order to generate 11 or 12 filaggrin repeats. Desirably therefore, the present invention also extends to identifying the number of filaggrin repeats in a subject as well as detecting one or more mutations. Heterozygous mutant subjects who possess one mutant allele which results in no or little filaggrin expression, but have a second wild-type allele encoding 11 or 12, filaggrin repeats, may express sufficient filaggrin to not develop disease, or only a mild form of disease. For example, a carrier of a 12-repeat allele, will express 20% more filaggrin than a 10-repeat carrier and this difference in expression may be significant in terms of disease development.

It has been observed that the aforementioned 4-base deletion (2282del4) results in the expression of a unique peptide which comprises an N-terminal region corresponding to the N-terminal portion of the filaggrin peptide and a unique C-terminal region which has been expressed due to the frame-shift mutation. With respect to this unique peptide which is produced from the mutant sequence comprising the 4-base deletion, it is possible to detect the unique peptide using an appropriate binding agent, such as a specific antibody. It is appreciated that any such binding agent/antibody should be specific for the unique peptide and not therefore be capable of binding the native filaggrin peptide.

The skilled man will readily know how to obtain a suitable antibody, such as a monoclonal antibody, by, for example, producing the unique peptide recombinantly or using synthetic chemistry, coded for by the mutant sequence and raising antibodies thereto. Antibodies so produced can thereafter be screened to ascertain their specificity, such that only those antibodies which are specific for the unique peptide may be selected.

Such specifically reactive antibodies to the unique peptide can be optionally labelled and used in an immunoassay to detect for the presence of the unique peptide in a sample. Alternatively, the specifically reactive antibody can be used in an assay, such as an ELISA, to detect any of said unique peptide in a sample being tested.

Thus, in a further aspect there is provided a method of detecting a mutant peptide expressed from a mutant of the FLG gene, comprising the steps of:

a) providing a sample from a subject to be tested; and b) detecting whether or not a mutant peptide expressed from a mutant FLG gene is present in the sample, by using a binding agent which is specifically reactive to said mutant peptide.

In this aspect, the sample may preferably be a skin tissue sample. Typically, the binding agent is an antibody, monoclonal antibody or fragment thereof, such as a Fab fragment. Detection may be carried out by detecting a label, such as a fluorescent, chemiluminescent, bio-luminescent or radio-label coupled to the binding agent/antibody/fragment. Alternatively, the binding agent, antibody or antibody fragment may be unlabelled and detected by way of an antibody specific for said binding agent, antibody or antibody fragment, such as in an ELISA assay.

It will be understood that the nucleic acid and mutant peptide tests described herein may be conducted individually or together.

Identification of mutants in the FLG gene leading to loss or partial loss of function of the FLG protein opens up the possibility of treating prophylactically or therapeutically IV and/or any of the other aforementioned diseases by gene therapy. As such a correct non-mutant copy or copies of the FLG gene may be used to complement for a mutant version of the FLG gene present in a subject.

Thus, in a further aspect there is provided use of an FLG gene sequence or fragment thereof, capable of encoding one or more copies of the FLG protein, in the manufacture of a medicament. It is understood that the medicament may be used for the prophylactic or therapeutic treatment of IV and/or diseases including atopic dermatitis (eczema), asthma, psoriasis and allergies.

The present invention therefore also provides an FLG gene sequence or fragment thereof, which gene sequence or fragment thereof, is capable of expressing one or more copies of the filaggrin protein, for use in therapy or prophylaxis.

It will be appreciated that the present invention also extends to methods of treating prophylactically or therapeutically any of the aforementioned diseases/conditions by administering to a patient suffering or predisposed to developing any of said aforementioned diseases a DNA construct comprising an FLG gene sequence or fragment thereof, which gene sequence or fragment thereof is capable of expressing one or more copies of the FLG protein, whereby expression of said one or more copies of the FLG protein treats or ameliorates said disease(s)/condition(s).

Typically, the FLG sequence or fragment thereof will be administered to a subject in the form of a recombinant molecule comprising said FLG sequence or fragment under appropriate transcriptional/translational controls to allow expression of said filaggrin protein when administered to a subject. It will be appreciated that the FLG sequence or fragment may be under control of a suitable promoter, such as a constitutive and/or controllable promoter. Convenient promoters include the native filaggrin promoter, or an appropriate late differentiation-specific keratin promoter.

The present invention also therefore provides a recombinant molecule comprising an FLG sequence or fragment thereof for use in therapy. The recombinant molecule may be in the form of a plasmid, phagemid or viral vector. Furthermore, recombinantly expressed, or chemically synthesised filaggrin or profilaggrin protein, or functionally important fragments thereof, may be produced and applied to the skin via a suitable ointment or other pharmaceutical vehicle, as a treatment or prophylactic measure for ichthyosis vulgaris and/or atopic diseases. Such a treatment may also be of cosmetic value as it may increase the barrier function and/or moisture-retention properties of the skin. Since filaggrin is prominently expressed in hair from early in development[16], such a treatment may also improve cosmetic qualities of the hair, such as moisture retention, in individuals with either normal or reduced filaggrin expression.

Many different viral and non-viral vectors and methods of their delivery, for use in gene therapy, are known, such as adenovirus vectors, adeno-associated virus vectors, retrovirus vectors, lentiviral vectors, herpes virus vectors, liposomes, DNA vaccination and the like[17].

The present invention also provides a method of treating, preventing and/or ameliorating IV and/or any of the aforementioned diseases, comprising the steps of:

a) determining if expression of one or more copies of the FLG polypeptide would occur even if a subject's FLG gene comprises one or more mutations; and b) providing a subject carries FLG alleles capable of expressing at least one or more copies of the FLG polypeptide, treating the subject using UV light in order to seek to increase FLG expression.

The intention is to increase expression of FLG polypeptides in the skin. This may most easily be achieved in heterozygote subjects, i.e. those subjects who have one mutant copy of the FLG gene and one native copy.

The expression of the FLG gene is known to be induced by UV light[18]. Thus, UV treatment of the skin of an individual carrying a heterozygous copy of a filaggrin loss-of-function mutation could increase the expression of the normal allele and thereby produce a beneficial effect.

The present invention also relates to a transgenic non-human animal which possesses one or more mutations in one or both copies of the FLG gene which would lead to a loss or partial loss of function of the FLG protein encoded by the FLG gene. Desirably, the FLG gene of the non-human animal may be replaced with a mutant human form of the gene, in order to "humanise" the non-human animal with respect to the FLG gene.

The transgenic animals of the present invention can be used for the development of various treatments for IV and/or the other diseases mentioned herein including the identification of various therapeutically active agents including but not limited to other proteins, peptides, peptidomimetic drugs, small molecule drugs, chemicals and nucleic acid-based agents.

The term non-human animals is used herein to include all vertebrate animals, except humans. It also includes an individual animal in all stages of development, including embryonic and foetal stages. A transgenic animal is any animal containing one or more cells bearing genetic information altered or received, directly or indirectly, by deliberate genetic manipulation at a subcellular level, such as by targeted recombination or microinjection or infection with recombinant virus. The term transgenic animal is not intended to encompass classical cross-breading or in vitro fertilization, but rather is meant to encompass animals in which one or more cells are altered by, or receive, a recombinant DNA molecule.

To create a transgenic non-human animal expressing a mutant form of the FLG gene, mutant FLG nucleic acid sequences are inserted into a germ line of the animal using standard techniques of oocyte microinjection or transfection or microinjection into stem cells. Preferably, it is desired to replace the endogenous gene and homologous recombination using embryonic stem cells or foetal fibroblasts can be applied.

Mice are often used for transgenic animal models because they are easy to house, relatively inexpensive, and easy to breed. However, other non-human transgenic mammals can also be made in accordance with the present invention such as but not limited to monkeys, sheep, rabbits, dogs and rats. Transgenic animals are those which carry a transgene, that is, a cloned gene introduced and stably incorporated which is passed on to successive generations.

For oocyte injection, for example in mice, one or more copies of the nucleic acid sequences encoding FLG can be inserted into the pronucleus of a just-fertilised mouse oocyte. This oocyte is then reimplanted into a pseudo-pregnant foster mother. The live born mice can then be screened for integrants using analysis of, for example, tail DNA for the presence of the mutant FLG sequences.

Methods of making transgenic mammals are known and described, e.g. in Wall, et al. (1992) J. Cell Biochem. 49(2): 113-20[19]; McCreath, et al. (2000) Nature 405: 1066-1069[20]; Lai, et al. (2002) Science 295: 1089-92[21]; Hogan, et al. (1986) In: Manipulating the mouse embryo. A Laboratory Manual. Cold Spring Harbour Laboratory Press, Cold Spring Harbor, N.Y.[22]; in WO 91/08216 or U.S. Pat. No. 4,736,866. The mice disclosed herein can be crossed with a hairless or nude mouse background so that skin abnormalities are visible to facilitate monitoring of disease progression and/or potential therapies.

An in vivo assay for identifying an agent which is useful for treating or preventing IV and/or any of the other aforementioned diseases associated with mutant FLG expression comprising the steps of administering a test agent to a FLG mutant transgenic animal; and measuring or determining whether the agent decreases or inhibits at least one sign or symptom of IV and/or any of the other aforementioned diseases which is indicative that the test agent is capable of treating or preventing IV and/or any of the other aforementioned diseases. The results of the screening assay can be compared with a control, e.g., an animal which has not been administered a test agent or an animal which has received an agent known to reduce a sign or symptom of said diseases. The route of administration of the test agent may vary. Examples of administration routes include, but are not limited, to oral, nasal, rectal, transmucosal, intestinal, parenteral, intravenous, intraperitoneal and topical.

EXAMPLES SECTION

The present invention will now be further described by way of example and with reference to the Figures which show:

FIG. 1 Shows Pedigrees of IV Families Studied.
Pedigrees of IV families studied here where a family history was available. Families 1-3 are of Irish origin, Families 4-6 are Scottish and Family 7 is of US origin. In addition, 8 isolated IV cases were studied where a family history was not available (not shown). Of the latter, one case was Irish, 4 were Scottish and 3 were of US origin. All patients studied were White Caucasians. Black-filled symbols refer to the marked IV presentation; cross-hatched symbols refer to the very mild IV presentation; open symbols refer to no detectable IV phenotype. The genotypes for the two mutations R501X and 2282del4 are shown. Note that wt/wt refers only to the regions screened and does not preclude other sequence changes in the central regions of exon 3. Only two people with no detectable IV phenotype were found to have a filaggrin mutation: individual II-5 in Family 5, who carries R501X; and individual II-1 in Family 7, who is an obligate carrier of R501X. On this basis, we estimate the penetrance in heterozygotes as ~90%, although this is probably an overestimate due to ascertainment bias. Many individuals in these families, who carry one or other filaggrin mutation, either heterozygously or homozygously, have, in addition to ichthyosis vulgaris, atopic dermatitis (eczema) and/or asthma and/or allergies (see also FIG. 4). Thus, filaggrin mutations predispose individuals to these other conditions.

FIG. 2 Shows FLG Mutation Detection and Confirmation.
(a) Schematic diagram of the filaggrin gene (FLG), annotated to show the corresponding protein structure. Exon 1 consists of a short 5'UTR sequence. Exon 2 and the 5' end of exon 3 encode the profilaggrin N-terminal domain. The remainder of exon 3 consists of 10-12 repeats of approximately 1 kb, each encoding a filaggrin peptide separated by linker sequences, followed by a short unique coding sequence and the 3'UTR. Upon terminal differentiation of the epidermis, each profilaggrin molecule is proteolytically cleaved to release 10-12 copies of filaggrin, which aggregate the keratin cytoskeleton and cause physical collapse of the granular cells to form squamous cells. The positions of PCR fragments used here and of the two null-mutations, R501X and 2282del4 in repeat 1 of exon 3, are shown.

(b) Long-range PCR product from genomic DNA covering exon 3 and therefore all the filaggrin repeats.

(c) Normal sequence from filaggrin repeat 1 in exon 3, corresponding to codons 499-503. (SEQ ID NO: 559)

(d) The same region of the FLG as seen in (c), showing heterozygous transition mutation 1502C>T resulting in nonsense mutation R501X. (SEQ ID NO: 560)

(e) The same region of FLG as in (c) showing a homozygous mutation resulting in a nonsense codon, R501X. (SEQ ID NO: 561)

(f) Confirmation of mutation R501X by Nla III restriction digest and 2282del4 by Dra III restriction digest from some members of Family 3.

(g) Normal sequence from filaggrin repeat 1 in exon 3, corresponding to codons 713-717. (SEQ ID NO: 562)

(h) The same region of FLG as in (f), showing overlapping peaks due to a heterozygous deletion mutation, 2282del4. (SEQ ID NO: 563)

(i) The same region of the FLG as in (f), derived from a mutant clone confirming mutation 2282del4. This mutation leads to a premature stop codon 107 bp downstream and terminates translation within filaggrin repeat 1. (SEQ ID NO: 564)

FIG. 3 Shows Morphological Features of Filaggrin-Null Ichthyosis Vulgaris.

(a) Skin biopsy from a normal (non-ichthyotic) control. Haematoxylin and eosin staining of formaldehyde-fixed paraffin-embedded tissue shows prominent keratohyalin granules in the granular cell layers of the superficial epidermis (arrows).

(b) Skin biopsy from the proband in Family 4, who is homozygous for nonsense mutation R501X in the FLG gene. In contrast with the normal control seen in (a), there is a complete absence of keratohyalin granules in the upper layers of the epidermis. The degenerating nuclei seen in the uppermost living layers (arrows), indicate that this is the area where one would normally see keratohyalin granules.

(c) Transmission electron micrograph of keratinocytes at the boundary of the granular layer and stratum corneum, from a normal individual, showing prominent keratohyalin granules (arrowheads). N=nucleus; K=keratinized material in stratum corneum. Original magnification=~5,600×.

(d) Transmission electron micrograph of granular layer cells from the proband in Family 4, who is homozygous for non-sense mutation R501X in the FLG gene. There is a complete absence of keratohyalin granules (*). The stratum corneum is not fully cornified, as compared with the control (K), indicative of an epidermal barrier defect. N=nucleus. Original magnification=~5,600×.

(e) Immunohistochemical staining of formaldehyde-fixed paraffin-embedded tissue using anti-filaggrin repeat monoclonal antibody 15C10 (Novocastra), visualized by the immunoperoxidase method. In skin biopsy material from a normal control, keratohyalin granules are strongly stained in the upper suprabasal layers of the epidermis (arrows).

(f) Immunoperoxidase staining of skin biopsy material from the proband in Family 4, shows complete absence of staining in the upper suprabasal layers (arrows) with anti-filaggrin repeat monoclonal antibody 15C10 (Novocastra). This demonstrates that no filaggrin peptides are produced in patients homozygous for R501X, consistent with a nonsense mutation within the first filaggrin repeat.

(g) Immunoperoxidase staining of skin biopsy material from a normal control individual with polyclonal antibody B1, raised against an epitope within the N-terminal domain of profilaggrin, showing prominent staining of keratohyalin granules (arrows).

(h) Immunoperoxidase staining of skin biopsy material from the proband in Family 4, with profilaggrin N-terminal antibody B1. No granular staining is seen but unlike the filaggrin repeat epitope (f), there is a diffuse pattern of residual staining. This is more pronounced in the upper suprabasal cells where profilaggrin is normally expressed (arrows) but in addition there is some patchy diffuse cytoplasmic staining throughout the epidermis (arrowheads). The epitope of this antibody is upstream of the mutation and so this shows that a truncated fragment of profilaggrin is synthesized in R501X homozygotes.

FIG. 4 shows complete sequence of the filaggrin repeats and identifies the positions of the mutations identified by the inventors and positions of where the specific primers identified herein bind. These specific priming sites were identified by analysis of alignments of the individual filaggrin repeats, including the novel additional repeats identified by the inventors.

FIG. 5 shows the pedigrees of a family with IV and corresponding atopy transmission;

FIG. 9 shows a) immunostaining of skin biopsy material from a normal control and an IV patient with the R510X/R2447X genotype. b) immunoblotting of skin biopsy protein extracts from a normal control and IV patients with the genotypes R501X/R2447X and R501X/R501X;

FIG. 10 is a schematic diagram of profilaggrin proteins encoded by size variant alleles of FLG;

FIG. 11 shows the DNA sequence of FLG size variant allele FLG$^{8+}$;

FIG. 12 shows the DNA sequence of FLG size variant allele FLG$^{10+}$; and

FIG. 13 shows the sequence of a fragment from FLG size variant allele FLG$^{8+10+}$, together with annotations as follows:
Annotated Sequence—repeats in alternate plan and bold text
*=unique base pair specific to this filaggrin repeat sequence
N=base pair shared with only one other filaggrin repeat sequence, number N
N*=base pair essentially specific due to nearby differences in repeat N.

METHODS

Affected Individuals and Phenotypes

Figure 1:
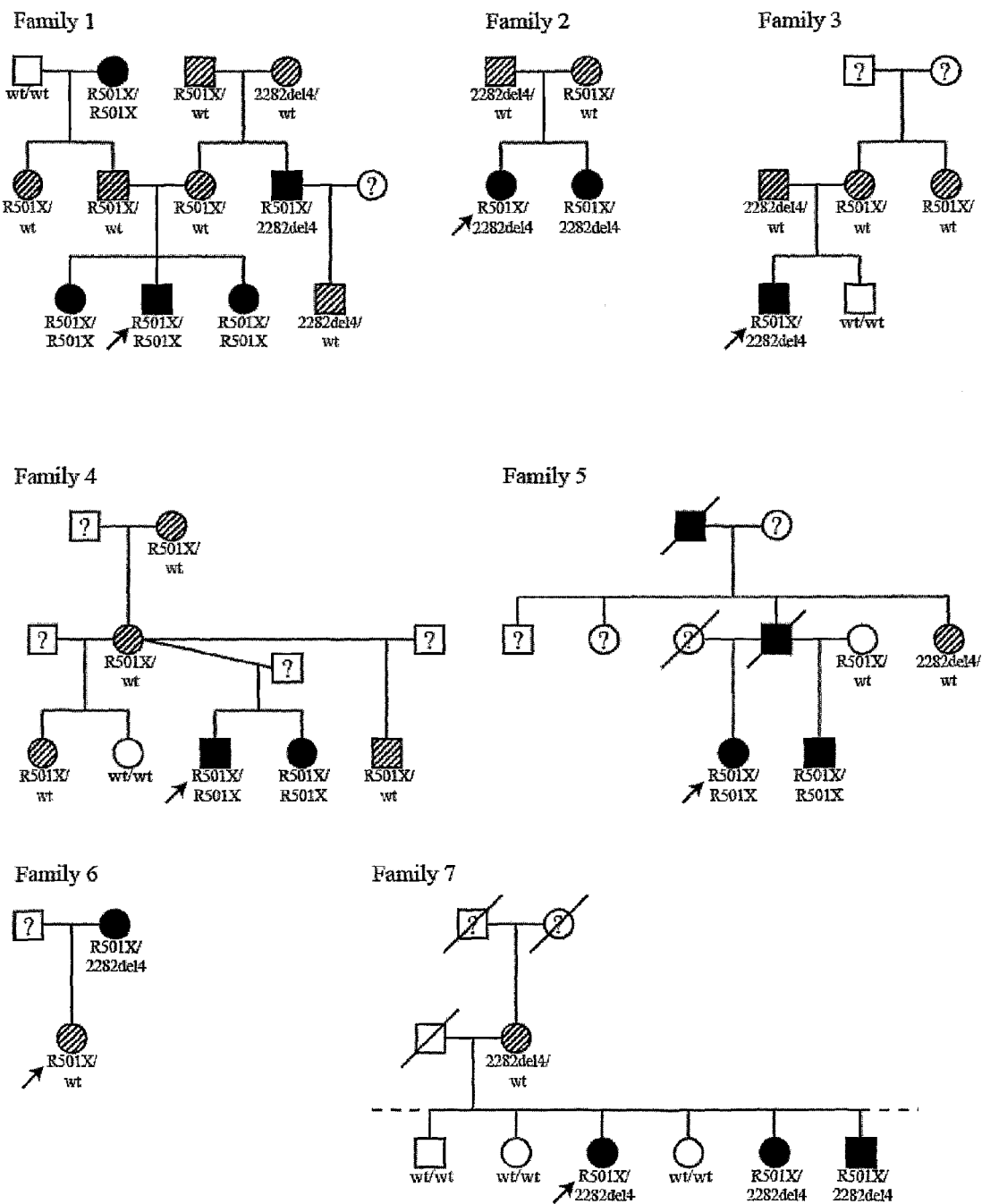

Blood samples were obtained from 15 families with IV and normal ethnically matched controls with informed consent that complies with all principles of the Helsinki Accord.

Long-Range PCR for FLG Exon 3

Primers FilLR2F (+ strand) 5' GTC ACT TAC CCC ATC AAA TC 3' (SEQ ID NO: 7) and FilLR1R (− strand) 5' CCA CCA AAC TAA TGA AAT AC 3' (SEQ ID NO: 8) were used to amplify approximately 12 kb of the filaggrin gene (including all of exon 3 and therefore all the repeat domains) from genomic DNA using the Expand Long Template PCR System (Roche Diagnostics, East Sussex, UK). A "hot start" was performed with 1 U Expand Long Template enzyme mix (Roche). Reactions were amplified using the following extended PCR program: (92° C. 5 min×1); (92° C. 10 sec, 49° C. 30 sec, 68° C. 6 min)×10; (92° C. 10 sec, 49° C. 30 sec, 68° C. 6 min plus 10 sec increment/cycle)×28; and (68° C. 10 min)×1.

R501X Mutation Analysis

A shorter PCR fragment was designed to amplify approximately 1.5 kb for mutation analysis of R501X. Primers FilF3 (+ strand) 5' GCT GAT AAT GTG ATT CTG TCT G 3' (SEQ ID NO: 1) and RPT1P6 (− strand) 5' ACC TGA GTG TCC AGA CCT ATT 3' (SEQ ID NO: 52) were used in High Fidelity PCR buffer (Roche) containing 1.5 mM MgCl$_2$, 4% DMSO and 1 U High Fidelity thermostable DNA polymerase mix (Roche). Reactions were amplified under the following conditions: (94° C. 5 min×1); (94° C. 30 sec, 57° C. 1 min, 72° C. 2 min)×30; and (72° C. 5 min)×1. Mutation R501X creates a new Nla III restriction enzyme site; this was used to confirm the mutation and screen control samples. Primers FilH1F3 (+ strand) 5' CAC GGA AAG GCT GGG CTG A 3' (SEQ ID NO: 3) and RPT1P6 (above) were used to amplify 312 bp of genomic DNA using PCR buffer (Promega) containing 1.5 mM MgCl$_2$, 4% DMSO and 1 U Taq polymerase mix (Promega). Reactions were amplified as follows: (94° C. 5 min×1); (94° C. 30 sec, 58° C. 45 sec, 72° C. 1 min)×30; and (72° C. 5 min)×1. PCR products were digested with 5 U Nla III for 4 hr at 37° C. Digests were resolved on 3% agarose gels.

2282Del4 Mutation Analysis

A PCR fragment amplifying 811 bp of genomic DNA was amplified with primers RPT1P7 (+ strand) 5' AAT AGG TCT GGA CAC TCA GGT 3' (SEQ ID NO: 51) and RPT2P1 (− strand) 5' GGG AGG ACT CAG ACT GTT T 3' (SEQ ID NO: 75) using PCR buffer (Applied Biosystems) containing 1.5 mM MgCl$_2$, 4% DMSO and 1 U Taq polymerase mix (Promega). PCR amplification conditions were: (94° C. 5 min×1); (94° C. 30 sec, 57° C. 45 sec, 72° C. 1 min 30 sec)×35; and (72° C. 5 min)×1. Mutation 2282del4 creates a new Dra III restriction enzyme site which was used to screen samples for this mutation. PCR products were digested with 5 U Dra III for 4 hr at 37° C. Digests were resolved on 2% agarose gels. A PCR fragment from a heterozygous individual was cloned into vector pCR2.1 (Invitrogen). Clones were screened by Dra III digestion and sequenced to confirm the 4 bp deletion.

Histology and Electron Microscopy

Routine hematoxylin and eosin (H&E) staining was performed to evaluate morphologic features of each specimen. Immunoperoxidase staining of frozen and paraffin-embedded sections utilized the Envision system (DakoCytomation, Denmark). Antibodies used were mouse monoclonal 15C10 against an epitope in the C-terminal portion of the human filaggrin repeat unit (Novocastra, Newcastle upon Tyne, UK) and rabbit polyclonal antiserum B1 raised against the N-terminus of profilaggrin[23]. For transmission electron microscopy, skin samples from patients were fixed in half-strength Karnovsky's fixative (containing 2.5% glutaraldehyde and 2% formaldehyde) then in 1.3% osmium tetroxide and processed using standard methods, largely as described previously[24].

Lod Score Calculations

Lod scores were calculated with MLINK algorithm of LINKAGE version 5.1, using a semidominant model of the disease where heterozygotes were assigned a mild phenotype with 90% penetrance and homozygotes or compound heterozygotes were assigned as a severe phenotype with 100% penetrance. The combined mutant allele frequency was assumed to be 0.037 (Table 1). Recalculation with 50% penetrance in heterozygotes still yielded a highly significant maximum combined lod score of 7.08 at θ=0.

Figure 2:
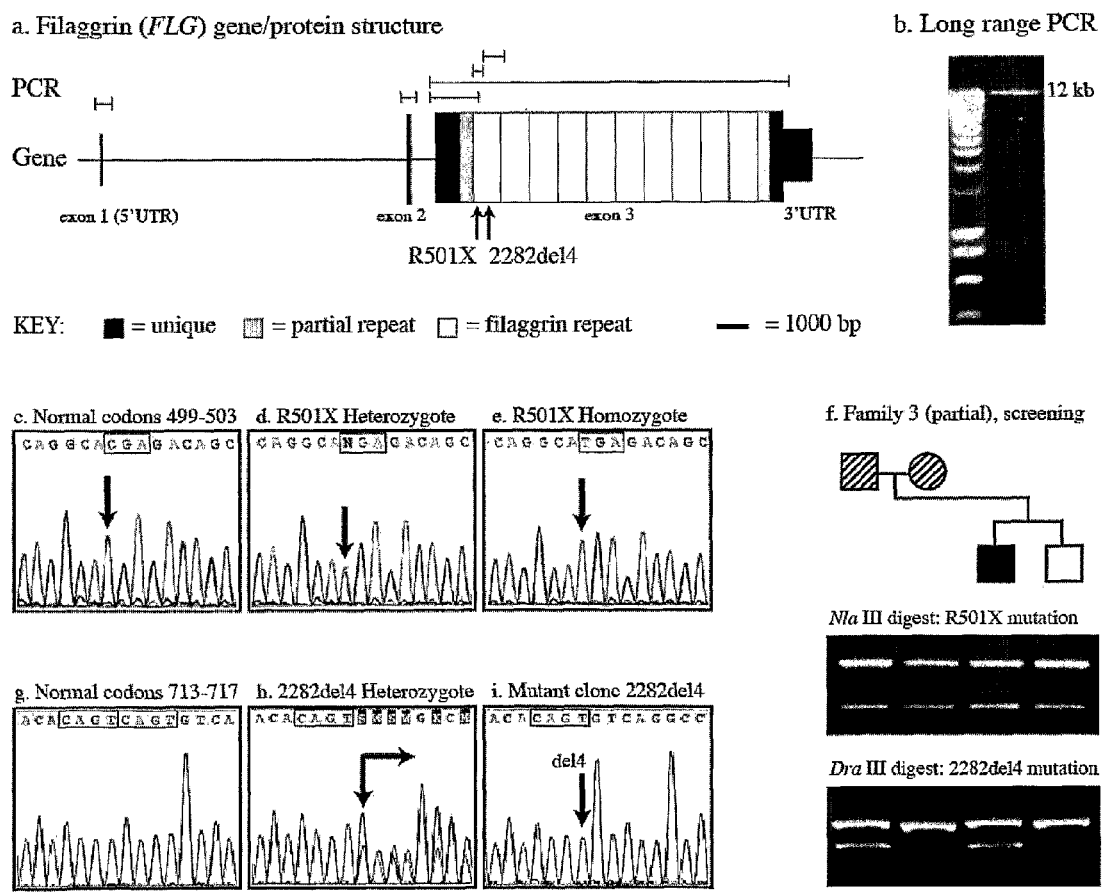

FLG consists of three exons[25,26]. Exon 1 (15 bp) consists only of 5'UTR sequences and exon 2 (159 bp) contains the initiation codon. Exon 3 is unusually large (12,753 bp) and codes for most of the N-terminal domain and all filaggrin repeats (FIG. 2a). The number of filaggrin repeats varies from 10-12 in the population[6]. The homology between the repeats at the DNA level is almost 100%, making conventional PCR-based sequencing for the internal regions of this exon almost impossible. No sequence changes were found in exons 1 or 2 in five IV families. The present inventors developed long-range PCR conditions to amplify a 12 kb genomic fragment covering exon 3 and therefore all the repeat domains (FIG. 2b). Full sequencing of this fragment is on-going, but initial sequencing has revealed a homozygous nonsense mutation R501X near the start of repeat 1 in three affected individuals from Family 1 (FIG. 2c-e). Using a smaller PCR fragment, segregation of R501X was confirmed in Family 1 and in addition, this mutation was identified in the other 14 IV kindreds studied. The mutation creates a new Nla III restriction enzyme site; this was used to confirm the mutation and screen populations (FIG. 2f). By this means, the mutation was found to be present at relatively high allele frequencies in Irish, Scottish and North American Caucasian populations (combined frequency, 0.027; see Table 1).

In 3 families, IV patients with a very pronounced phenotype were homozygous for R501X (FIG. 1). In other families and isolated cases, individuals with the marked IV phenotype were found to be heterozygous for R501X. Further sequencing in these cases revealed a second mutation, 2282del4, in exon 3 (FIG. 2g-i). This leads to a premature termination codon 107 bp downstream and, like R501X, stops protein translation within the first filaggrin repeat (FIG. 2a). Mutation 2282del4 creates a Dra III restriction enzyme site which was used to screen IV families and control samples (FIG. 2f; Table 1). This mutation segregated in 10 of the IV families studied (FIG. 1). Of the 8 "sporadic" cases of clinically significant IV where family history was not available, 4 were homozygous for R501X and the remaining 4 were R501X/2282del4 compound heterozygotes. Interestingly, part of the US family previously reported to show significant linkage to the FLG locus[27], was studied using freshly obtained high-quality DNA required for analysis of exon 3. The severely affected individuals in Family 7 were compound heterozygous for R501X/2282del4 (FIG. 1), consistent with the linkage data previously reported[27]. The semidominant mode of inheritance is best exemplified in Family 1 where there are multiple examples of IV patients with the very mild presentation as well as examples of R501X homozygotes and R501X/2282del4 compound heterozygotes with the full IV phenotype. In the studied series of families there were only two individuals who were heterozygous for a null-mutation (both R501X) and have no obvious phenotype (Families 5 & 7; FIG. 1). On the basis of these small numbers, the penetrance in heterozygotes appears to be about 90%, however, this may be an overestimate due to ascertainment bias. The allele frequency for 2282del4 in US, Irish and Scottish Caucasians was found to be ~0.01 (Table 1). Using the determined allele frequencies and assuming mildly affected heterozygotes and severely affected homozygotes, the maximum combined 2-point lod score for families 1-7 (FIG. 1), was 8.11 at θ=0.

Skin biopsy material from an R501X homozygote (proband, Family 4) was subjected to histological and ultrastructural analysis. The granular layer was found to be absent by conventional histology (FIG. 3a & b) and electron microscopy showed complete absence of keratohyalin (FIG. 3c & d). Immunohistochemistry showed that an epitope conserved in all filaggrin repeat peptides was completely absent in the R501X homozygote (FIG. 3e & f). In contrast, an epitope in the N-terminal domain of profilaggrin, encoded by sequences upstream of filaggrin repeat 1, was still present, albeit in an abnormal, diffuse distribution (FIG. 3g & h). Immunohistochemical analysis of an R501X/2282del4 compound heterozygote gave identical results (not shown). This confirms that either R501X or 2282del4 result in complete loss of filaggrin peptide production and so functionally, these are null-alleles.

Since profilaggrin is the major component of keratohyalin granules, this explains the absent granular layer associated with the more severe cases of IV[27] (FIG. 3). The presence of a truncated profilaggrin peptide in IV epidermis (FIG. 3b) is consistent with previous studies demonstrating that a peptide containing the unique N-terminal domain and a small amount of filaggrin sequence is stable in vitro[23]. In normal epidermis, the N-terminal $Ca^{2+}$-binding domain is cleaved from profilaggrin by a proprotein convertase, and subsequently localizes to different cell compartments including the nucleus[28,29]. Similar processing of the truncated peptide may occur in IV epidermis.

Here the inventors have shown that in three Caucasian populations, IV appears to be predominantly caused by two frequent null-mutations in FLG, leading to loss of filaggrin production and impaired epidermal barrier formation. In the IV families studied, most R501X mutations are in linkage disequilibrium with the same 156 bp allele of a microsatellite in intron 2 of FLG (data not shown), suggesting that, in human evolutionary terms, these are ancient mutations. Further analysis of polymorphisms near FLG will determine the approximate age of the mutations. Genetic drift may explain why these mutations have become so prevalent. Alternatively, a heterozygote advantage might explain the high frequencies of these alleles. One obvious hypothesis is that impaired barrier function leads to elevated exposure to bacterial or other antigens, leading to greater innate immunity. This "natural cutaneous vaccination" might allow heterozygotes to better survive when challenged by pandemic plagues or other pathogens. This should be testable using ft mice[12] or engineered filaggrin null-mice.

Regarding the inheritance pattern and incidence of IV; the very subtle heterozygote phenotype probably does often not come to clinical attention unless specifically sought, as was the case here. Assuming a combined null-allele frequency of ~0.037 (Table 1), and a pronounced heterozygote phenotype, then 1 in 14 people would have IV, which is clearly not the case. With this allele frequency, 1 in 730 should be homozygous or compound heterozygous and have marked IV. The subtlety of the heterozygote phenotype, combined with incomplete penetrance and seasonal variation, probably explains the reported incidence of 1 in 250[1]. With these high mutant allele frequencies, IV families will also frequently appear to have dominant or pseudo-dominant inheritance with reduced penetrance (FIG. 1). By Southern analysis, polymorphism in the number of filaggrin repeats has been shown in humans (10-12 repeats)[6] and mice (12-20 repeats)[30]. The inventors also observed this size variation using long-range PCR and determined the sequences of the longer variant alleles (described below). It is possible that a heterozygote for a null-mutation might carry an expanded exon 3 on their other allele, lessening the overall effect of the mutation. This might explain the phenotypically normal heterozygotes seen in Families 5 and 7 (FIG. 1). Due to their relatively high population frequencies, filaggrin null-mutations may themselves be modifying factors in other ichthyotic skin conditions, including congenital ichthyoses, Netherton syndrome or disorders due to defects in suprabasal keratins, where intra- and interfamilial phenotypic variation is well documented[31-34]. The association of IV with the atopic diathesis is well established; 37-50% of people with IV have atopic diseases[1,36] and conversely around 8% of atopic dermatitis patients have classical features of IV[1,35]. Thus, filaggrin may be a factor in very common skin disorders known to have a major genetic component.

In the IV families studied, many filaggrin-null or heterozygous individuals also had atopic dermatitis (AD; "eczema") and/or asthma. An example is shown in FIG. 5, where 3/6 filaggrin-null heterozygotes and 5/5 homozygotes had atopic disease. The inventors therefore sought to examine the role of these variants in common atopy associated with asthma. The two filaggrin variants were genotyped in a cohort of 800 schoolchildren with unknown disease status (population cohort) and in 550 school children and adolescents with physician-diagnosed asthma from the Dundee BREATHE study. The frequency of carriers of R501X was 5.2% and the 2282del4 variant was present in 3.6% of the schoolchildren, giving a combined carrier frequency of 8.8%. Both filaggrin variants were over-represented in the asthmatic cohort, with carriers of either allele demonstrating a dominant risk (Table 2; combined genotype OR=1.94 95% CI=1.35-2.80, p=0.0005). Homozygotes for both variants were observed in the asthma cohort, as were two compound heterozygotes. AD is known to be co-associated with asthma[1,36] and since filaggrin is a major epidermal structural protein, one would expect a stronger association with AD/asthma with filaggrin defects. Consistent with this, 75% of all the children in the asthma cohort carrying a filaggrin null-allele had AD, in contrast to only 46.7% of those without these filaggrin variants (Table 3; OR=2.81 95% CI=1.64-4.81, p=0.0001). This observation appears to be related to allergen exposure, as the risk was largely seen in individuals routinely exposed to animals (OR 5.2 95% CI=2.36-11.50, p=0.000006).

Figure 6:
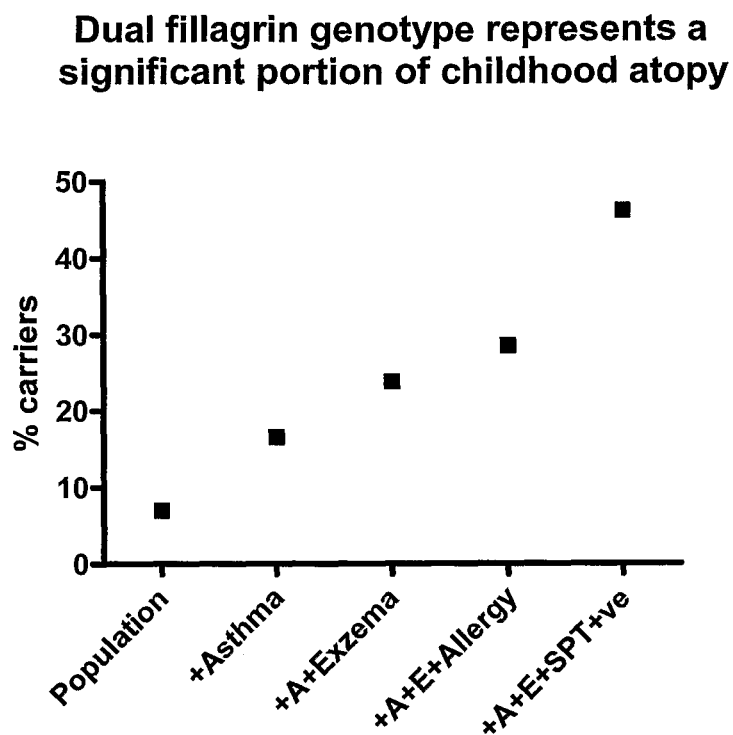
FIG. 6 is a graph showing that filaggrin variants are associated with increased atopy.
Figure 7:
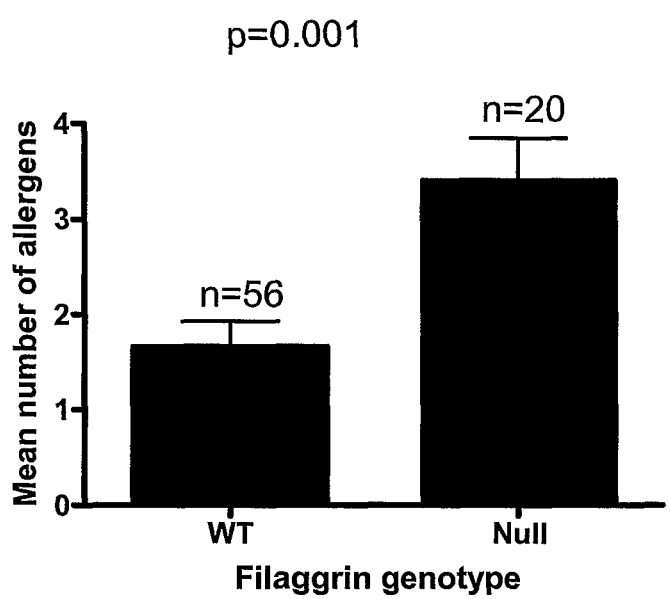
FIG. 7 is a graph showing increased number of positive allergens in carriers of filaggrin mutations.
Figure 8:
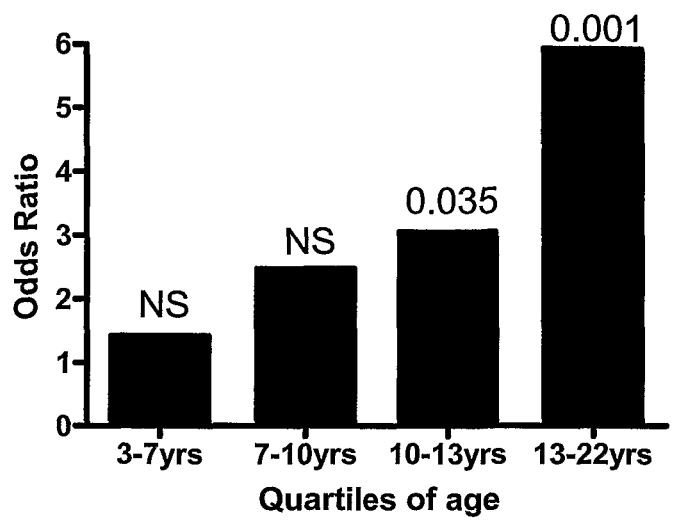
FIG. 8 is a graph showing filaggrin variants are stronger risk factors for eczema in the older asthmatics.

These data suggested that a barrier function defect may lead to greater risk of allergy and this hypothesis was supported by the observation that a significantly greater number of the children with asthma had been referred to an allergy clinic for allergy testing if they carried a filaggrin null variant (OR=1.78 95% CI=1.08-2.95, p=0.034). Even more significantly, every individual tested that carried the null variants (n=20) was positive for at least one allergen, whereas 26 out of the 56 non-carrier individuals tested negative for allergens (p=0.00006). This striking atopic phenotype resulted in a systematic increase of the carrier frequency of the null variants as we increased the definition of the degree of atopy of the cohort (FIG. 6), with 46.7% of all the individuals that had asthma, AD and immunologically-verified allergy having the filaggrin null variants (n=75). In this group, the variant was still further associated with an increased number of positive allergens, with the mean number of allergens for a null variant carrier being substantially greater that that for the wild type individuals (FIG. 7). This demonstrates that a substantial fraction of common, complex atopic disease can be accounted for by a single pair of variants in the filaggrin gene. Given the population carrier frequency of both of these variants (~9%), these observations will have a huge impact in the understanding of atopy and may lead to the development of novel treatments for asthma and allergy. Asthma and allergy can wane during adolescence and the temporal features of childhood atopy are known as the "atopic march". Here the inventors show that individuals haploinsufficient for filaggrin represent a population of persistent atopy, where the observed risk of eczema increases consistently through age in the asthmatic cohort, consistent with the atopic march (FIG. 8).

Nut and Food Allergy

The asthma cohort was analysed for people with a recorded allergy to peanuts and/or other nuts. 23 individuals had a proven nut allergy and of these, 8 carried a filaggrin-null mutation (either 2282del4 or R501X), i.e. 35% were carriers. In a population control cohort, 60 out of 621 individuals carried a filaggrin-null mutation, i.e. 9.7%. Thus, the filaggrin mutation carrier frequency is greatly increased in people with asthma and nut allergy. Fisher's exact test gave a two-sided P value of 0.0008, which is considered extremely significant (odds ratio=5.520 95% CI 2.248-13.554). Thus, filaggrin mutations are a highly significant risk factor for nut allergy and asthma. In addition, atopy is strongly associated with food allergy especially cow's milk, hen's egg, banana, kiwi, white fish, wheat, prawns/shrimp and strawberries[37-39]. Since nut allergy is regarded as the most reliable marker for food allergy, this strongly infers that filaggrin mutations are associated with food allergies in general.

A Comprehensive Mutation Detection Strategy for FLG.

Using primers ending on bases that had been determined by detailed sequence alignments to be absolutely specific for a given filaggrin repeat, or in a few cases, ending on bases that are shared by only two filaggrin repeats, a series of overlapping PCR fragments was generated that span exon 3 of the FLG gene in its entirety. These fragments were fully sequenced using the amplification primers and/or internal primers that again ended on unique bases. In some individuals, the identification of single nucleotide polymorphisms was able to show that the overlapping PCR fragments were amplifying both alleles, thus demonstrating the specificity and utility of this sequencing strategy. Using this method, individuals with a severe IV phenotype predictive of homozygous or compound heterozygous mutations were sequenced. These patients were from European populations, predominantly Irish and Scottish with some Dutch and Austrian individuals. A number of novel loss-of-function mutations were identified, all of which lead to premature termination codons, either as nonsense mutations or frameshift mutations. In many cases, these were inherited in trans with the more common mutations R501X or 2282del4. Specifically, these further mutations were 3702delG (repeat 3), R2447X (repeat 7), 53247X (repeat 9), R1474X (repeat 4), Q1745X (repeat 4), Q3683X (repeat 10), 11029delCA (repeat 10) in Irish and Scottish patients; E2422X (repeat 6), 5360delG (repeat 5), 7267delCA (repeat 7) and 11033del4 (repeat 10) in Dutch patients; and 6867delAG (repeat 6) in an Austrian patient. The IV phenotype of the patients carrying these more 3' mutations were essentially indistinguishable to patients carrying R501X or 2282del4 mutations in repeat 1. Thus, premature termination codon mutations essentially anywhere in the profilaggrin molecule appear to have similar or equivalent pathogenicity. The following mutations were recurrent and/or prevalent in the European population R501X, 2282del4, 3702delG, R2447X and 53247X. The Dutch and Austrian mutations were not detected in 188 Irish AD patients and may be population-specific or very rare. The remaining variants were not tested for prevalence.

Mutations in the 3' Half of FLG Exon 3 are Essentially Functional Null Alleles

To determine the biochemical consequences of the more 3' mutations, biopsy material was obtained from two patients with the compound heterozygote genotype R501X/R2447X. Immunostaining of skin sections with Novocastra 15C10 antibody against the filaggrin repeat domain showed that this patient has an identifiable but very restricted granular cell layer in the upper epidermis (FIG. 9A). The more quantitative technique of immunoblotting, using protein extracts from this biopsy, revealed that only a very small quantity of a truncated profilaggrin molecule is expressed and importantly, this is not processed into mature filaggrin (FIG. 9B). Essentially identical results were obtained for an R501X/11033del4 compound heterozygote (not shown). Thus, more 3' FLG mutations lead to greatly reduced expression of truncated profilaggrin and complete loss of mature filaggrin and therefore, are essentially filaggrin functional null alleles.

Mutations in More 3' Repeats and Repeat 1 of the FLG Gene Predispose to AD

A cohort of 188 Irish paediatric cases of moderate-severe AD were genotyped for 5 mutations found to be prevalent and/or recurrent in this population, R501X, 2282del4, 3702delG, R2447X and S3247X. Comparison of allele frequencies was made to an unselected Irish control population of 736 individuals genotyped for the same 5 FLG variants. Pearson chi-square analysis revealed that all 5 mutations are independently associated with the AD phenotype, giving individual statistically significant P values of <0.05 (Table 4). Combining the data for all 5 genotypes gave an extremely significant P value of $2.12 \times 10^{-51}$. About 48% of the patients in the AD cohort carried one or more of the 5 filaggrin variants. Thus, a wide range of FLG mutations contribute to genetic predisposition to atopy and this is a major gene in early-onset moderate-to-severe AD.

A Different Spectrum of FLG Mutations Predispose to Atopy in Non-European populations The European-specific mutations R501X and 2282del4 were found to be absent from 253 Japanese individuals. We therefore sequenced the FLG gene in four Japanese families with IV and identified two novel mutations, 3321delA and S2554X.

We screened 143 Japanese AD patients for these null FLG mutations and identified them in 8 AD patients (5.6%), including S2554X in 6 patients (4.2%) and 3321delA in 2 patients (1.4%). Both null variants were absent from 156 Japanese non-atopic and non-ichthyotic controls, giving a statistically significant association between the FLG mutations and AD (Chi-square P value 0.0015).

Thus, in non-European populations, in this case Japan, there appears to be a distinct set of prevalent/recurrent FLG mutations that contribute to genetic predisposition to atopy. It is likely that other human populations will have their own spectrum of FLG mutations.

Size Variants of the Filaggrin Gene (FLG)

It has been reported previously that exon 3 of the FLG gene is variable in size in the human population and these variant alleles were predicted, on the basis of their size, to consist of 10, 11 or 12 full filaggrin repeats in addition to the two partial repeats (Gan et al., 1990)[40]. However, the positions of these insertions within FLG exon 3 and the precise DNA sequences encoding these additional filaggrin repeats remained unknown.

Using specific PCR primers located in repeat 7 and repeat 11, DNA fragments were generated from unrelated individuals that, from the public sequence of the FLG gene (Human Genome, March 2006 Assembly, hg18), would be predicted to be ~4.2 kb in size. For convenience, this allele is designated as $FLG^N$. In some individuals, additional bands of ~5.2 and/or ~6.2 kb were observed. These larger alleles were cloned into plasmid vector pCR3.1 to allow full sequencing of these variant alleles. This revealed that some individual alleles contain a duplication of repeat 8, designated as $FLG^{8+}$. Another allele consisted of what was essentially a duplication of repeat 10, which was designated as $FLG^{10+}$. Both copies of the repeat 10 sequences on this allele showed some sequence divergence from the published genome sequence. Similarly, there were a smaller number of sequence differences between the two repeat 8 copies on the $FLG^{8+}$ allele. In some individuals, a larger allele was present consisting of the duplicated repeat 8 and the duplicated repeat 10, which was designated as $FLG^{8+10+}$. The size variants are shown diagrammatically in FIG. 10, compared to the hg18 genome database sequence, labelled $FLG^N$. The raw sequences of the duplicated regions of these alleles are shown in FIGS. 11-13. A fully annotated sequence of the $FLG^{8+10+}$, representing all the novel sequence data generated here, with the positions of the previously known and novel filaggrin repeat sequences, is shown in FIG. 13.

By alignment of these additional repeat sequences with all the existing filaggrin repeats, a number of priming sites were identified that would allow specific amplification, sequencing and mutation detection within these novel alleles. Forward and reverse primers ending on these specific bases are listed in the sequence listing as SEQ ID Nos. 494-539. It is recognised that the length of these primers may be varied and still allow specific PCR amplification, sequencing, or mutation analysis, provided the 3' end of the primer ends on these specific bases or very close to them. The specific bases within the duplicated repeat regions are also annotated on FIG. 13.

It is recognised that some individuals with ichthyosis vulgaris and/or atopic disease may carry loss-of-function mutations within the newly identified sequences that constitute these new size variant alleles. It is also recognised that size variation may modulate the phenotype of heterozygous carriers of a loss-of-function or other mutation in the FLG gene, i.e. a heterozygous carrier of the R501X mutation may carry a second wild-type allele encoding either 10, 11 or 12 filaggrin repeats. It is recognised that the size of the heterozygous wild-type allele may influence the phenotype observed, for example, a carrier of the 12-repeat ($FLG^{8+10+}$) allele will express 20% more filaggrin than a R501X carrier carrying a 10-repeat wild-type allele in trans. Thus, detection of these size variants may be of prognostic value in ichthyosis vulgaris and atopic disease.

REFERENCES

1. Wells, R. S. and Kerr C B, Br Med J., 1:947-949 (1966).
2. Judge, M. R., McLean, W. H. I. & Munro, C. S. Disorders of keratinization. in *Rook's Textbook of Dermatology*, Vol. 2 (eds. Burns, T., Breathnach, S., Cox, C. & Griffiths, C.) 34.54-34.56 (Blackwell Scientific Publishing, Oxford, 2004).
3. Steinert, P. M., Cantieri, J. S., Teller, D. C., Lonsdale-Eccles, J. D. & Dale, B. A. Characterization of a class of cationic proteins that specifically interact with intermediate filaments. *Proc Natl Acad Sci* 78, 4097-4101 (1981).
4. Dale, B. A., Resing, K. A. & Lonsdale-Ecccles, J. D. Filaggrin: a keratin filament associated protein. *Ann. NY Acad. Sci.* 455, 330-342 (1985).
5. Listwan, P. & Rothnagel, J. A. Keratin bundling proteins. *Methods Cell Biol* 78, 817-27 (2004).
6. Gan, S. Q., McBride, O. W., Idler, W. W., Markova, N. & Steinert, P. M. Organization, structure, and polymorphisms of the human profilaggrin gene. *Biochemistry* 29, 9432-40 (1990).
7. Candi, E., Schmidt, R. & Melino, G. The cornified envelope: a model of cell death in the skin. *Nat Rev Mol Cell Biol* 6, 328-40 (2005).

8. Fleckman, P., Holbrook, K. A., Dale, B. A. & Sybert, V. P. Keratinocytes cultured from subjects with ichthyosis vulgaris are phenotypically abnormal. *J Invest Dermatol* 88, 640-5 (1987).
9. Pena Penabad, C. et al. Differential patterns of filaggrin expression in lamellar ichthyosis. *Br J Dermatol* 139, 958-64 (1998).
10. Sybert, V. P., Dale, B. A. & Holbrook, K. A. Ichthyosis vulgaris: identification of a defect in synthesis of filaggrin correlated with an absence of keratohyaline granules. *J Invest Dermatol* 84, 191-4 (1985).
11. Nirunsuksiri, W., Zhang, S. H. & Fleckman, P. Reduced stability and bi-allelic, coequal expression of profilaggrin mRNA in keratinocytes cultured from subjects with ichthyosis vulgaris. *J Invest Dermatol* 110, 854-61 (1998).
12. Presland, R. B. et al. Loss of normal profilaggrin and filaggrin in flaky tail (ft/ft) mice: an animal model for the filaggrin-deficient skin disease ichthyosis vulgaris. *J Invest Dermatol* 115, 1072-81 (2000).
13. Lane, P. W. Two new mutations in linkage group XVI of the house mouse. Flaky tail and varitint-waddler-J. *J Hered* 63, 135-40 (1972).
14. Rothnagel, J. A. et al. Characterization of the mouse loricrin gene: linkage with profilaggrin and the flaky tail and soft coat mutant loci on chromosome 3. *Genomics* 23, 450-6 (1994).
15. Sambrook & Russel; "Molecular Cloning—A Laboratory Manual", (2000); Cold Spring Harbor Laboratory Press.
16. Dale B A, Holbrook K A, Kimball J R, Hoff M, Sun T T., Expression of epidermal keratins and filaggrin during human fetal skin development., J Cell Biol. 1985 October; 101(4):1257-60.
17. Gene Therapy (2004) 11, S57-63.
18. Lee D S, Quan G, Choi J Y, Kim S Y, Lee S C. Chronic ultraviolet radiation modulates epidermal differentiation as it up-regulates transglutaminase 1 and its substrates. Photodermatol Photoimmunol Photomed. 2005 February; 21(1):45-52.
19. Wall, et al. (1992) J. Cell Biochem. 49(2): 113-20.
20. McCreath, et al. (2000) Nature 405: 1066-1069.
21. Lai, et al. (2002) Science 295: 1089-92.
22. Hogan, et al. (1986) In: Manipulating the mouse embryo. A Laboratory Manual. Cold Spring Harbour Laboratory Press, Cold Spring Harbor, N.Y.
23. Pearton, D. J., Dale, B. A. & Presland, R. B. Functional analysis of the profilaggrin N-terminal peptide: identification of domains that regulate nuclear and cytoplasmic distribution. *J Invest Dermatol* 119, 661-9 (2002).
24. Eady, R. A. J. Transmission electron microscopy. in *Methods in Skin Research* (eds. Skerrow, D. & Skerrow, C. J.) 1-36 (John Wiley & Sons, Chichester, 1985).
25. Presland, R. B., Haydock, P. V., Fleckman, P., Nirunsuksiri, W. & Dale, B. A. Characterization of the human epidermal profilaggrin gene. Genomic organization and identification of an S-100-like calcium binding domain at the amino terminus. *J Biol Chem* 267, 23772-81 (1992).
26. Markova, N. G. et al. Profilaggrin is a major epidermal calcium-binding protein. *Mol Cell Riot* 13, 613-25 (1993).
27. Compton, J. G., DiGiovanna, J. J., Johnston, K. A., Fleckman, P. & Bale, S. J. Mapping of the associated phenotype of an absent granular layer in ichthyosis vulgaris to the epidermal differentiation complex on chromosome 1. *Exp Dermatol* 11, 518-26 (2002).
28. Presland, R. B. et al. Evidence for specific proteolytic cleavage of the N-terminal domain of human profilaggrin during epidermal differentiation. *J Invest Dermatol* 108, 170-8 (1997).
29. Ishida-Yamamoto, A., Takahashi, H., Presland, R. B., Dale, B. A. & Iizuka, H. Translocation of profilaggrin N-terminal domain into keratinocyte nuclei with fragmented DNA in normal human skin and loricrin keratoderma. *Lab Invest* 78, 1245-53 (1998).
30. Rothnagel, J. A. & Steinert, P. M. The structure of the gene for mouse filaggrin and a comparison of the repeating units. *J. Biol. Chem.* 265, 1862-1865 (1990).
31. Bale, S. J., Compton, J. G., Russell, L. J. & DiGiovanna, J. J. Genetic heterogeneity in lamellar ichthyosis. *J Invest Dermatol* 107, 140-1 (1996).
32. Bitoun, E. et al. Netherton syndrome: disease expression and spectrum of SPINK5 mutations in 21 families. *J Invest Dermatol* 118, 352-61 (2002).
33. Smith, F. J. D. et al. Genomic organization and fine mapping of the keratin 2e gene (KRT2E): K2e V1 domain polymorphism and novel mutations in ichthyosis bullosa of Siemens. *J. Invest. Dermatol.* 111, 817-821 (1998).
34. McLean, W. H. I. et al. Mutations in the rod 1A domain of keratins 1 and 10 in bullous congenital ichthyosiform erythroderma (BCIE). *J. Invest. Dermatol.* 102, 24-30 (1994).
35. Tay, Y. K., Khoo, B. P. & Goh, C. L. The epidemiology of atopic dermatitis at a tertiary referral skin center in Singapore. *Asian Pac J Allergy Immunol* 17, 137-41 (1999).
36. Koukkanen K., Ichthyosis vulgaris. A clinical and histopathological study of patients and their close relatives in the autosomal dominant and sex-linked forms of the disease. Acta Derm Venereol Suppl (Stockh). 1969; 62:1-72.
37. Werfel T, Breuer K., Curr Opin Allergy Clin Immunol. 2004 October; 4(5): 379-85. Role of food allergy in atopic dermatitis.
38. Sicherer S. H., Sampson H. A., J. Allergy Clin Immunol. 1999 September; 104 (3 Pt 2): S114-22. Food hypersensitivity and atopic dermatitis: pathophysiology, epidemiology, diagnosis and management.
39. Ellman L. K., Chatchatee P., Sicherer S. H. & Sampson H. A. Pediatr Allergy Immunol. 2002 August; 13(4): 205-8. Food hypersensitivity in two groups of children and young adults with atopic dermatitis evaluated a decade apart.
40. Gan S. Q., McBride O. W., Idler W. W., Markova N., Steinert P. M. Organization, structure, and polymorphisms of the human profilaggrin gene. Biochemistry 1990; 29: 9432-40.

TABLE 1

Allele frequencies of FLG mutations R501X and 2282del4

| Population | Allele Frequency R501X | Allele Frequency 2282del4 |
| --- | --- | --- |
| Irish Caucasian | 0.041 (n = 97) | 0.005 (n = 91) |
| Scottish Caucasian | 0.021 (n = 145) | 0.012 (n = 166) |
| US Caucasian | 0.024 (n = 124) | 0.011 (n = 133) |
| Combined | 0.027 (n = 366) | 0.01 (n = 390) |

TABLE 2

Both R501X and 2282del4 are overrepresented in a childhood asthma cohort.

| R501X | | 2282del4 | | Combined | |
|---|---|---|---|---|---|
| Population | Asthma | Population | Asthma | Population | Asthma |
| 720 | 484 | 714 | 494 | 585 | 390 |
| 38 | 46 | 27 | 35 | 52 | 69 |
| 5 | 2 | 0 | 2 | 6 | 6 |
| 763 | 532 | 741 | 531 | 643 | 465 |
|  | p = 0.04 |  | p = 0.0038 |  | p = 00045 |

TABLE 3

Characteristics of asthmatic children with and without filaggrin variants

|  | WT n = 390 | NULLcarriers n = 75 | p |
|---|---|---|---|
| SEX (% Male) | 59.2 | 59.0 | 0.522 |
| Age | 10.2(2.7-21.2) | 10.3(4.1-22) |  |
| BMI | 19.1 | 18.8 |  |
| PEFR % | 92.8 | 90.6 |  |
| FEV1 % | 98.1 | 96.8 |  |
| FVC % | 97.1 | 97.0 |  |
| Eczema | 46.7 | 73.3 | 0.0001 |
| Perennial Rhinitis | 29 | 26.7 | 0.784 |
| Seasonal Rhinitis | 14.8 | 13.3 | 0.861 |
| Cold air trigger | 41.0 | 44.4 | 0.596 |
| Exercise trigger | 36.1 | 44.4 | 0.213 |
| Viral trigger | 44.9 | 46.8 | 0.787 |
| Tested for allergy | 16.6 | 30.1 | 0.035 |

TABLE 4

Case control association study for 5 FLG mutations (188 Irish AD patients versus 736 Irish population controls)

| Genotype | R501X Population | AD | 2282del4 Population | AD | R2447X Population | AD |
|---|---|---|---|---|---|---|
| AA | 717 | 137 | 717 | 152 | 734 | 181 |
| Aa | 19 | 51 | 19 | 35 | 2 | 7 |
| aa | 0 | 0 | 0 | 1 | 0 | 0 |
| Totals | 736 | 188 | 736 | 188 | 736 | 188 |
|  | p = 7.8 × 10$^{-30}$ |  | p = 7.8 × 10$^{-17}$ |  | p = 1.7 × 10$^{-5}$ |  |

| Genotype | S3247X Population | Asthma | 3702delG Population | AD | Combined Population | AD |
|---|---|---|---|---|---|---|
| AA | 720 | 177 | 735 | 186 | 680 | 103 |
| Aa | 16 | 11 | 1 | 2 | 55 | 62 |
| aa | 0 | 0 | 0 | 0 | 1 | 23 |
|  | 736 | 188 | 736 | 188 | 736 | 188 |
|  | p = 0.008 |  | p = 0.046 |  | p = 2.12 × 10$^{-51}$ |  |

---

The invention claimed is:

1. A method for detecting ichthyosis vulgaris or a predisposition to ichthyosis vulgaris in a human subject comprising the step of:
   detecting in a sample of nucleic acid from the subject the presence of a R501X mutation in the filaggrin gene using one or more of the primers selected from SEQ ID NO: 9, 10, 11, or 12; and
   correlating the presence of the R501X mutation in the sample with detection of ichthyosis vulgaris or a predisposition to ichthyosis vulgaris in the subject.

2. A method for detecting atopic dermatitis or asthma in a human subject comprising the step of:
   detecting in a sample of nucleic acid from the subject the presence of a R501X mutation in the filaggrin gene using one or more of the primers selected from SEQ ID NO: 9, 10, 11, or 12; and
   correlating the presence of the R501X mutation in the sample with detection of atopic dermatitis or asthma in the subject.

3. The method according to claim 1, wherein the nucleic acid is genomic DNA or mRNA.

4. The method according to claim 1, wherein the human subject is a newborn or a fetus.

5. The method according to claim 1, wherein the detection step comprises an analysis technique selected from the group consisting of: quantitative PCR, semi-quantitative PCR, real-time PCR, nucleic acid sequencing, hybridization studies, and restriction fragment length polymorphism (RFLP) analysis.

6. The method according to claim 1, further comprising a step of identifying the number of filaggrin repeats in the filaggrin gene from the sample.

7. The method according to claim 2, wherein the nucleic acid is genomic DNA or mRNA.

8. The method according to claim 2, wherein the human subject is a newborn or a fetus.

9. The method according to claim 2, wherein the detection step comprises an analysis technique selected from the group consisting of: quantitative PCR, semi-quantitative PCR, real-time PCR, nucleic acid sequencing, hybridization studies, and restriction fragment length polymorphism (RFLP) analysis.

10. The method according to claim 2, further comprising a step of identifying the number of filaggrin repeats in the filaggrin gene from the sample.

* * * * *

SEQUENCE LISTING

<160> NUMBER OF SEQ ID NOS: 565

<210> SEQ ID NO 1
<211> LENGTH: 22
<212> TYPE: DNA
<213> ORGANISM: Artificial Sequence
<220> FEATURE:
<221> NAME/KEY:
<223> OTHER INFORMATION: primer

<400> SEQUENCE: 1
gctgataatg tgattctgtc tg                                      22

<210> SEQ ID NO 2
<211> LENGTH: 22
<212> TYPE: DNA
<213> ORGANISM: Artificial Sequence
<220> FEATURE:
<221> NAME/KEY:
<223> OTHER INFORMATION: Primer

<400> SEQUENCE: 2
gccacatatt acacaatcca gg                                      22

```
<210> SEQ ID NO 3
<211> LENGTH: 19
<212> TYPE: DNA
<213> ORGANISM: Artificial Sequence
<220> FEATURE:
<221> NAME/KEY:
<223> OTHER INFORMATION: Primer

<400> SEQUENCE: 3
cacggaaagg ctgggctga                                              19

<210> SEQ ID NO 4
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 4
ggtgagcact catgaacagc                                             20

<210> SEQ ID NO 5
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 5
ggtgagcact catgaacagt                                             20

<210> SEQ ID NO 6
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 6
cctctgtgac ttccctctgt a                                           21

<210> SEQ ID NO 7
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 7
gtcacttacc ccatcaaatc                                             20

<210> SEQ ID NO 8
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 8
ccaccaaact aatgaaatac                                             20

<210> SEQ ID NO 9
```

```
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 9
actggaggaa gacaaggatc g                                              21

<210> SEQ ID NO 10
<211> LENGTH: 18
<212> TYPE: DNA
<213> ORGANISM: Artificial Sequence
<220> FEATURE:
<221> NAME/KEY:
<223> OTHER INFORMATION: Primer

<400> SEQUENCE: 10
ccctcttggg acgctgaa                                                  18

<210> SEQ ID NO 11
<211> LENGTH: 19
<212> TYPE: DNA
<213> ORGANISM: Artificial Sequence
<220> FEATURE:
<221> NAME/KEY:
<223> OTHER INFORMATION: Primer

<400> SEQUENCE: 11
tggaggaaga caaggatcg                                                 19

<210> SEQ ID NO 12
<211> LENGTH: 17
<212> TYPE: DNA
<213> ORGANISM: Artificial Sequence
<220> FEATURE:
<221> NAME/KEY:
<223> OTHER INFORMATION: Primer

<400> SEQUENCE: 12
cctcttggga cgctgaa                                                   17

<210> SEQ ID NO 13
<211> LENGTH: 19
<212> TYPE: DNA
<213> ORGANISM: Artificial Sequence
<220> FEATURE:
<221> NAME/KEY:
<223> OTHER INFORMATION: Primer

<400> SEQUENCE: 13
gtggctctgc tgatggtga                                                 19

<210> SEQ ID NO 14
<211> LENGTH: 22
<212> TYPE: DNA
<213> ORGANISM: Artificial Sequence
<220> FEATURE:
<221> NAME/KEY:
<223> OTHER INFORMATION: Primer

<400> SEQUENCE: 14
cgtcacacac agaattcctc ta                                             22

<210> SEQ ID NO 15
<211> LENGTH: 16
```

```
<212> TYPE: DNA
<213> ORGANISM: Artificial Sequence
<220> FEATURE:
<221> NAME/KEY:
<223> OTHER INFORMATION: Primer

<400> SEQUENCE: 15
tcccgccacc agctcc                                                    16

<210> SEQ ID NO 16
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 16
gcaagcagac aaactcgtaa g                                              21

<210> SEQ ID NO 17
<211> LENGTH: 28
<212> TYPE: DNA
<213> ORGANISM: Artificial Sequence
<220> FEATURE:
<221> NAME/KEY:
<223> OTHER INFORMATION: Primer

<400> SEQUENCE: 17
gtttcttctc ggagtcgtct gagtgtct                                       28

<210> SEQ ID NO 18
<211> LENGTH: 27
<212> TYPE: DNA
<213> ORGANISM: Artificial Sequence
<220> FEATURE:
<221> NAME/KEY:
<223> OTHER INFORMATION: Primer

<400> SEQUENCE: 18
gtttcttcag acaacctctc ggagtcg                                        27

<210> SEQ ID NO 19
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 19
gggaaaaggc atgaatctag t                                              21

<210> SEQ ID NO 20
<211> LENGTH: 20
<212> TYPE: DNA
<213> ORGANISM: Artificial Sequence P1F
<220> FEATURE:
<221> NAME/KEY:
<223> OTHER INFORMATION: Primer

<400> SEQUENCE: 20
cagtgaggga cattcagaaa                                                20

<210> SEQ ID NO 21
<211> LENGTH: 20
<212> TYPE: DNA
```

```
<213> ORGANISM: Artificial Sequence
<220> FEATURE:
<221> NAME/KEY:
<223> OTHER INFORMATION: Primer

<400> SEQUENCE: 21
cagaaaactc agacacacaa                                                        20

<210> SEQ ID NO 22
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 22
ggccacggaa aggctgggct                                                        20

<210> SEQ ID NO 23
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 23
gccacggaaa ggctgggctg                                                        20

<210> SEQ ID NO 24
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 24
ccacggaaag gctgggctga                                                        20

<210> SEQ ID NO 25
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 25
cacggaaagg ctgggctgag                                                        20

<210> SEQ ID NO 26
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 26
acggaaaggc tgggctgaga                                                        20

<210> SEQ ID NO 27
<211> LENGTH: 20
<212> TYPE: DNA
<213> ORGANISM: Artificial Sequence
```

```
<220> FEATURE:
<221> NAME/KEY:
<223> OTHER INFORMATION: Primer

<400> SEQUENCE: 27
ggccacggaa aggctaggct                                               20

<210> SEQ ID NO 28
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 28
gccacggaaa ggctaggctg                                               20

<210> SEQ ID NO 29
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 29
ccacggaaag gctaggctga                                               20

<210> SEQ ID NO 30
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 30
cacggaaagg ctaggctgag                                               20

<210> SEQ ID NO 31
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 31
acggaaaggc taggctgaga                                               20

<210> SEQ ID NO 32
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: x = Inosine
<220> FEATURE:
<221> NAME/KEY:
<223> OTHER INFORMATION: Primer

<400> SEQUENCE: 32
ggccacggaa aggctnggct                                               20

<210> SEQ ID NO 33
```

```
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: n = Inosine
<220> FEATURE:
<221> NAME/KEY:
<223> OTHER INFORMATION: Primer

<400> SEQUENCE: 33
gccacggaaa ggctnggctg                                              20

<210> SEQ ID NO 34
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: n= Inosine
<220> FEATURE:
<221> NAME/KEY:
<223> OTHER INFORMATION: Primer

<400> SEQUENCE: 34
ccacggaaag gctnggctga                                              20

<210> SEQ ID NO 35
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: n = Inosine
<220> FEATURE:
<221> NAME/KEY:
<223> OTHER INFORMATION: Primer

<400> SEQUENCE: 35
cacggaaagg ctnggctgag                                              20

<210> SEQ ID NO 36
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: n = Inosine
<220> FEATURE:
<221> NAME/KEY:
<223> OTHER INFORMATION: Primer

<400> SEQUENCE: 36
acggaaaggc tnggctgaga                                              20

<210> SEQ ID NO 37
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 37
acgtggccgg tcaggggaac                                              20
```

-continued

```
<210> SEQ ID NO 38
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 38
tctggacgtt cagggtcttc                                              20

<210> SEQ ID NO 39
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 39
ggtgagcact catgaacagc                                              20

<210> SEQ ID NO 40
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 40
ggtgagcact catgaacagt                                              20

<210> SEQ ID NO 41
<211> LENGTH: 22
<212> TYPE: DNA
<213> ORGANISM: Artificial Sequence
<220> FEATURE:
<221> NAME/KEY:
<223> OTHER INFORMATION: Primer

<400> SEQUENCE: 41
caggccatgg acaggctggt ca                                           22

<210> SEQ ID NO 42
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 42
cgtccatggg cagagtcagg                                              20

<210> SEQ ID NO 43
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 43
cgtccatggg cagagtcaga                                              20
```

```
<210> SEQ ID NO 44
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 44
gcactcatga acagcctgac                                               20

<210> SEQ ID NO 45
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 45
ctggaggaag acaaggatcg                                               20

<210> SEQ ID NO 46
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 46
ctcgtgcctg ctcgtggtgc                                               20

<210> SEQ ID NO 47
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 47
gcacgagaca gctccaggca t                                             21

<210> SEQ ID NO 48
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 48
gaccctcttg ggacgctgaa                                               20

<210> SEQ ID NO 49
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 49
cccaccacga gcaatcggta a                                             21

<210> SEQ ID NO 50
```

```
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 50
acctgagtgt ccagacctat t                                              21

<210> SEQ ID NO 51
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 51
aataggtctg gacactcagg t                                              21

<210> SEQ ID NO 52
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 52
tggtgtggct gtgatgggaa                                                20

<210> SEQ ID NO 53
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 53
ggaacaatca ggagacggca                                                20

<210> SEQ ID NO 54
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 54
cgtgaccctg agtgcctggt                                                20

<210> SEQ ID NO 55
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 55
catcggggcc caggacaagt                                                20

<210> SEQ ID NO 56
<211> LENGTH: 20
```

```
<212> TYPE: DNA
<213> ORGANISM: Artificial Sequence
<220> FEATURE:
<221> NAME/KEY:
<223> OTHER INFORMATION: Primer

<400> SEQUENCE: 56
cactggatcc ctggttccta                                              20

<210> SEQ ID NO 57
<211> LENGTH: 18
<212> TYPE: DNA
<213> ORGANISM: Artificial Sequence
<220> FEATURE:
<221> NAME/KEY:
<223> OTHER INFORMATION: Primer

<400> SEQUENCE: 57
ctgcagacag ctccagaa                                                18

<210> SEQ ID NO 58
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 58
gtgtgacgag tgcctgattt                                              20

<210> SEQ ID NO 59
<211> LENGTH: 18
<212> TYPE: DNA
<213> ORGANISM: Artificial Sequence
<220> FEATURE:
<221> NAME/KEY:
<223> OTHER INFORMATION: Primer

<400> SEQUENCE: 59
acacacagaa ttcctcta                                                18

<210> SEQ ID NO 60
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 60
gatgacgcag cctgtccact                                              20

<210> SEQ ID NO 61
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 61
caggccatgg acaggctggt                                              20

<210> SEQ ID NO 62
<211> LENGTH: 21
<212> TYPE: DNA
```

```
<213> ORGANISM: Artificial Sequence
<220> FEATURE:
<221> NAME/KEY:
<223> OTHER INFORMATION: Primer

<400> SEQUENCE: 62
aggccatgga caggctggtc a                                              21

<210> SEQ ID NO 63
<211> LENGTH: 24
<212> TYPE: DNA
<213> ORGANISM: Artificial Sequence
<220> FEATURE:
<221> NAME/KEY:
<223> OTHER INFORMATION: Primer

<400> SEQUENCE: 63
actcttggtg gctctgctga tggt                                           24

<210> SEQ ID NO 64
<211> LENGTH: 24
<212> TYPE: DNA
<213> ORGANISM: Artificial Sequence
<220> FEATURE:
<221> NAME/KEY:
<223> OTHER INFORMATION: Primer

<400> SEQUENCE: 64
tcttggtggc tctgctgatg gtga                                           24

<210> SEQ ID NO 65
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 65
ccggtcaggg gaaaggtctc                                                20

<210> SEQ ID NO 66
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 66
aggaaagacc ctgaacgtcg                                                20

<210> SEQ ID NO 67
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 67
ctaccaggtg agcactcata                                                20

<210> SEQ ID NO 68
<211> LENGTH: 19
<212> TYPE: DNA
<213> ORGANISM: Artificial Sequence
```

```
<220> FEATURE:
<221> NAME/KEY:
<223> OTHER INFORMATION: Primer

<400> SEQUENCE: 68
ccagacaatc aggaactcc                                                   19

<210> SEQ ID NO 69
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 69
gaagtctctg cgtgaggagt t                                                21

<210> SEQ ID NO 70
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 70
agtgagggac attcagagga g                                                21

<210> SEQ ID NO 71
<211> LENGTH: 28
<212> TYPE: DNA
<213> ORGANISM: Artificial Sequence
<220> FEATURE:
<221> NAME/KEY:
<223> OTHER INFORMATION: Primer

<400> SEQUENCE: 71
gtttcttagt gagggacatt cagaggag                                         28

<210> SEQ ID NO 72
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 72
gtgtcaggcc atggacagga                                                  20

<210> SEQ ID NO 73
<211> LENGTH: 27
<212> TYPE: DNA
<213> ORGANISM: Artificial Sequence
<220> FEATURE:
<221> NAME/KEY:
<223> OTHER INFORMATION: Primer

<400> SEQUENCE: 73
gtttcttgtg tcaggccatg gacagga                                          27

<210> SEQ ID NO 74
<211> LENGTH: 21
<212> TYPE: DNA
<213> ORGANISM: Artificial Sequence
<220> FEATURE:
```

```
<221> NAME/KEY: misc_feature
<222> LOCATION: (1)..(21)
<223> OTHER INFORMATION: Carboxyfluorescein labelled adenine
<220> FEATURE:
<221> NAME/KEY:
<223> OTHER INFORMATION: Primer

<400> SEQUENCE: 74
ntgagtgctc acctggtaga t                                                 21

<210> SEQ ID NO 75
<211> LENGTH: 19
<212> TYPE: DNA
<213> ORGANISM: Artificial Sequence
<220> FEATURE:
<221> NAME/KEY:
<223> OTHER INFORMATION: Primer

<400> SEQUENCE: 75
gggaggactc agactgttt                                                    19

<210> SEQ ID NO 76
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 76
catgagcagg cacgagacaa                                                   20

<210> SEQ ID NO 77
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 77
ggatgctgag tgcctggagt                                                   20

<210> SEQ ID NO 78
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 78
ggcactcagc atcccaagat                                                   20

<210> SEQ ID NO 79
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 79
cacgaatggt gtcctgacca                                                   20

<210> SEQ ID NO 80
<211> LENGTH: 20
```

```
<212> TYPE: DNA
<213> ORGANISM: Artificial Sequence
<220> FEATURE:
<221> NAME/KEY:
<223> OTHER INFORMATION: Primer

<400> SEQUENCE: 80
acgtaatgag gaacaatcaa                                               20

<210> SEQ ID NO 81
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 81
gagtgcctgg agccgtctct                                               20

<210> SEQ ID NO 82
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 82
gacagctcca gacaatcagg a                                             21

<210> SEQ ID NO 83
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 83
tccagacaat caggaactcc                                               20

<210> SEQ ID NO 84
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 84
aagtctctgc gtgaggagtt                                               20

<210> SEQ ID NO 85
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 85
agaggaagtc tctgcgtgag                                               20

<210> SEQ ID NO 86
<211> LENGTH: 20
<212> TYPE: DNA
```

-continued

<213> ORGANISM: Artificial Sequence
<220> FEATURE:
<221> NAME/KEY:
<223> OTHER INFORMATION: Primer

<400> SEQUENCE: 86
atagtgaggg acattcagag                                              20

<210> SEQ ID NO 87
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 87
ctgactgtgt gtctgactcc                                              20

<210> SEQ ID NO 88
<211> LENGTH: 19
<212> TYPE: DNA
<213> ORGANISM: Artificial Sequence
<220> FEATURE:
<221> NAME/KEY:
<223> OTHER INFORMATION: Primer

<400> SEQUENCE: 88
tgtcaggcca tggacagga                                               19

<210> SEQ ID NO 89
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 89
gctctgctga tggggcccat                                              20

<210> SEQ ID NO 90
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 90
ccaagagtcc gcacgtgact                                              20

<210> SEQ ID NO 91
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 91
tccagacctt cccctgacc a                                             21

<210> SEQ ID NO 92
<211> LENGTH: 21
<212> TYPE: DNA
<213> ORGANISM: Artificial Sequence

```
<220> FEATURE:
<221> NAME/KEY:
<223> OTHER INFORMATION: Primer

<400> SEQUENCE: 92
ctggacgttc agggtctttc a                                              21

<210> SEQ ID NO 93
<211> LENGTH: 20
<212> TYPE: DNA
<213> ORGANISM: Artificial Sequence RPT
<220> FEATURE:
<221> NAME/KEY:
<223> OTHER INFORMATION: Primer

<400> SEQUENCE: 93
tgagtgctca cctggtagat                                                20

<210> SEQ ID NO 94
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 94
gggtcaggac accattcgtg c                                              21

<210> SEQ ID NO 95
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 95
gcaagcagac aaactcgtaa g                                              21

<210> SEQ ID NO 96
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Carboxyfluorescein labelled guanine
<220> FEATURE:
<221> NAME/KEY:
<223> OTHER INFORMATION: Primer

<400> SEQUENCE: 96
ncaagcagac aaactcgtaa g                                              21

<210> SEQ ID NO 97
<211> LENGTH: 22
<212> TYPE: DNA
<213> ORGANISM: Artificial Sequence
<220> FEATURE:
<221> NAME/KEY:
<223> OTHER INFORMATION: Primer

<400> SEQUENCE: 97
gaatgtccct cactgttagt ga                                             22

<210> SEQ ID NO 98
```

```
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 98
ctttcctcta ccaggtgagc t                                              21

<210> SEQ ID NO 99
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 99
ggtcaggaca ccattcgtgc                                                20

<210> SEQ ID NO 100
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 100
tctccttgac cccgggtgtg                                                20

<210> SEQ ID NO 101
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 101
gtgcacaccc ggggtcaagg                                                20

<210> SEQ ID NO 102
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 102
atccctgcct tcctcctctc                                                20

<210> SEQ ID NO 103
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 103
caagcagaca aactcgtaag                                                20

<210> SEQ ID NO 104
<211> LENGTH: 20
```

<212> TYPE: DNA
<213> ORGANISM: Artificial Sequence
<220> FEATURE:
<221> NAME/KEY:
<223> OTHER INFORMATION: Primer

<400> SEQUENCE: 104
cgtctcctga ttgtttgtcc                                           20

<210> SEQ ID NO 105
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 105
gtcacgtcac catgaagctg                                           20

<210> SEQ ID NO 106
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 106
gagctgtcag cccaagaggc                                           20

<210> SEQ ID NO 107
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 107
ctagacactc acaggtggga                                           20

<210> SEQ ID NO 108
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 108
accccgatga ttgttcctgt                                           20

<210> SEQ ID NO 109
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 109
gaccccgatg attgttcctg t                                         21

<210> SEQ ID NO 110
<211> LENGTH: 20
<212> TYPE: DNA

```
<213> ORGANISM: Artificial Sequence
<220> FEATURE:
<221> NAME/KEY:
<223> OTHER INFORMATION: Primer

<400> SEQUENCE: 110
cactcacagg tgggacagga                                          20

<210> SEQ ID NO 111
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 111
cctggacccc gatgattgtt                                          20

<210> SEQ ID NO 112
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 112
ccaggacagt gacagtgaga                                          20

<210> SEQ ID NO 113
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 113
tcggagtcgt ctgagtgtct                                          20

<210> SEQ ID NO 114
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 114
acagtgagag acactcagac                                          20

<210> SEQ ID NO 115
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 115
cagacaacct ctcggagtcg                                          20

<210> SEQ ID NO 116
<211> LENGTH: 20
<212> TYPE: DNA
<213> ORGANISM: Artificial Sequence
```

```
<220> FEATURE:
<221> NAME/KEY:
<223> OTHER INFORMATION: Primer

<400> SEQUENCE: 116
agagacactc agacgactcc                                              20

<210> SEQ ID NO 117
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 117
cagacccaga caacctctcg                                              20

<210> SEQ ID NO 118
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 118
tcagacgact ccgagaggtt                                              20

<210> SEQ ID NO 119
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 119
tctggaagca gacccagaca                                              20

<210> SEQ ID NO 120
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 120
cagaaaccat catggatctt                                              20

<210> SEQ ID NO 121
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 121
tctcttgact gctcccgaga                                              20

<210> SEQ ID NO 122
<211> LENGTH: 20
<212> TYPE: DNA
<213> ORGANISM: Artificial Sequence
<220> FEATURE:
```

```
<221> NAME/KEY:
<223> OTHER INFORMATION: Primer

<400> SEQUENCE: 122
ggctccagac accctgggtt                                                   20

<210> SEQ ID NO 123
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 123
tggctctgtc ttcttgatgg a                                                 21

<210> SEQ ID NO 124
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 124
cacacagagt cttcctctca                                                   20

<210> SEQ ID NO 125
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 125
ggatgacaca gcctgtccat                                                   20

<210> SEQ ID NO 126
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 126
tcctctcatg gacaggctgt                                                   20

<210> SEQ ID NO 127
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 127
tgcctgttca tgggatgaca                                                   20

<210> SEQ ID NO 128
<211> LENGTH: 20
<212> TYPE: DNA
<213> ORGANISM: Artificial Sequence
<220> FEATURE:
<221> NAME/KEY:
```

<223> OTHER INFORMATION: Primer

<400> SEQUENCE: 128
gggtccagtg gtagtcaggt                                                    20

<210> SEQ ID NO 129
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 129
atgtccctca ctgttagtga                                                    20

<210> SEQ ID NO 130
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 130
cagtggtagt caggtcacta                                                    20

<210> SEQ ID NO 131
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 131
tctgaatgtc cctcactgtt                                                    20

<210> SEQ ID NO 132
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 132
ggaaagctct ggacgttcaa                                                    20

<210> SEQ ID NO 133
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 133
acctggtaga ggaaagacct                                                    20

<210> SEQ ID NO 134
<211> LENGTH: 20
<212> TYPE: DNA
<213> ORGANISM: Artificial Sequence
<220> FEATURE:
<221> NAME/KEY:
<223> OTHER INFORMATION: Primer

```
<400> SEQUENCE: 134
tttcctctac caggtgagct                                               20

<210> SEQ ID NO 135
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 135
gactcagact gttcatgaga                                               20

<210> SEQ ID NO 136
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 136
gagtgtccag acctatctac t                                             21

<210> SEQ ID NO 137
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 137
gacaagattc atctgtagtc g                                             21

<210> SEQ ID NO 138
<211> LENGTH: 28
<212> TYPE: DNA
<213> ORGANISM: Artificial Sequence
<220> FEATURE:
<221> NAME/KEY:
<223> OTHER INFORMATION: Primer

<400> SEQUENCE: 138
gtttcttgac aagattcatc tgtagtcg                                      28

<210> SEQ ID NO 139
<211> LENGTH: 19
<212> TYPE: DNA
<213> ORGANISM: Artificial Sequence
<220> FEATURE:
<221> NAME/KEY:
<223> OTHER INFORMATION: Primer

<400> SEQUENCE: 139
gtagtcggag acagtggaa                                                19

<210> SEQ ID NO 140
<211> LENGTH: 20
<212> TYPE: DNA
<213> ORGANISM: Artificial Sequence
<220> FEATURE:
<221> NAME/KEY:
<223> OTHER INFORMATION: Primer
```

<400> SEQUENCE: 140
atgaacagtc tgagtccaca                                              20

<210> SEQ ID NO 141
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 141
tgggtgcagt ctgtccgtgt                                              20

<210> SEQ ID NO 142
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 142
aacagtctga gtccacacac                                              20

<210> SEQ ID NO 143
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 143
tgctgggtgc agtctgtccg                                              20

<210> SEQ ID NO 144
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 144
ccacacacgg acagactgca                                              20

<210> SEQ ID NO 145
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 145
gtcttcctcc agtgctgggt                                              20

<210> SEQ ID NO 146
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 146

-continued ccgccatgag caggcacgaa                                           20

<210> SEQ ID NO 147
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 147
gctgagtgcc tagagctgtt                                           20

<210> SEQ ID NO 148
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 148
agcaggcacg aaacagctct                                           20

<210> SEQ ID NO 149
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 149
cttgggatgc tgagtgccta                                           20

<210> SEQ ID NO 150
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 150
aggaggaagg cagggatcct                                           20

<210> SEQ ID NO 151
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 151
tctactgatt gctcgtggta                                           20

<210> SEQ ID NO 152
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 152
gatcctacca cgagcaatca                                                    20

<210> SEQ ID NO 153
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 153
agtgtccaga cctatctact                                                    20

<210> SEQ ID NO 154
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 154
aggtctggac actcagggta                                                    20

<210> SEQ ID NO 155
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 155
tgtggtgtgg ctgtgatggt                                                    20

<210> SEQ ID NO 156
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 156
ccatcacagc cacaccacac                                                    20

<210> SEQ ID NO 157
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 157
gcatcagacc ttccctgggg                                                    20

<210> SEQ ID NO 158
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 158
ctcccatggg cagtcaggac                                                    20

<210> SEQ ID NO 159
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 159
ttgcctgctt gcacttctgg g                                              21

<210> SEQ ID NO 160
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 160
ggacccagaa gtgcaagcag g                                              21

<210> SEQ ID NO 161
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 161
gttcctcatt tcttgtttgc                                                20

<210> SEQ ID NO 162
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 162
aagtgcaagc aggcaaacaa                                                20

<210> SEQ ID NO 163
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 163
cctgattgtt cctcatttct                                                20

<210> SEQ ID NO 164
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 164
agggtcacgt caccatgaac                                                20

```
<210> SEQ ID NO 165
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 165
ctgccggccc gagtggaagg                                              20

<210> SEQ ID NO 166
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 166
gaaccttcca ctcgggccgg                                              20

<210> SEQ ID NO 167
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 167
ctgtgagtgt ctagagctgc                                              20

<210> SEQ ID NO 168
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 168
ctcacaggtg ggccagggag                                              20

<210> SEQ ID NO 169
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 169
gtcttggacc ccgctgattc                                              20

<210> SEQ ID NO 170
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 170
gggagaatca gcggggtcca a                                            21
```

```
<210> SEQ ID NO 171
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 171
tccctggcgc ctgcttgtct                                              20

<210> SEQ ID NO 172
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 172
gccagggatc cagtgttagt                                              20

<210> SEQ ID NO 173
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 173
cctcactgtc cctgtcctga                                              20

<210> SEQ ID NO 174
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 174
gtcggcttcc agaaaccatt                                              20

<210> SEQ ID NO 175
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 175
tgctcccgag cagatccata                                              20

<210> SEQ ID NO 176
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 176
agtcaagaca tggctccagg                                              20

<210> SEQ ID NO 177
```

```
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 177 gaacccccagg tcccatcaag                                              20

<210> SEQ ID NO 178
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 178
gtcaagacat ggctccagga                                               20

<210> SEQ ID NO 179
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 179
gacaggctgc atcatcccag                                               20

<210> SEQ ID NO 180
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 180
gacaggctgc atcatcccag                                               20

<210> SEQ ID NO 181
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 181
gacttgacct tgcctgttcc                                               20

<210> SEQ ID NO 182
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 182
catcccagga acaggcaagg                                               20

<210> SEQ ID NO 183
<211> LENGTH: 20
```

```
<212> TYPE: DNA
<213> ORGANISM: Artificial Sequence
<220> FEATURE:
<221> NAME/KEY:
<223> OTHER INFORMATION: Primer

<400> SEQUENCE: 183
gtctttctcc tggacttgac                                               20

<210> SEQ ID NO 184
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 184
cagtcagcag acagctccac                                               20

<210> SEQ ID NO 185
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 185
gcgcccagtg cctgagtctg                                               20

<210> SEQ ID NO 186
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 186
gtcagcagac agctccacag                                               20

<210> SEQ ID NO 187
<211> LENGTH: 19
<212> TYPE: DNA
<213> ORGANISM: Artificial Sequence
<220> FEATURE:
<221> NAME/KEY:
<223> OTHER INFORMATION: Primer

<400> SEQUENCE: 187
tgcgcccagt gcctgagtc                                                19

<210> SEQ ID NO 188
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 188
ggcactgggc gcagacaaga                                               20

<210> SEQ ID NO 189
<211> LENGTH: 20
<212> TYPE: DNA
```

```
<213> ORGANISM: Artificial Sequence
<220> FEATURE:
<221> NAME/KEY:
<223> OTHER INFORMATION: Primer

<400> SEQUENCE: 189
gtctccgact acagatgaat                                              20

<210> SEQ ID NO 190
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 190
cgcagacaag attcatctgt                                              20

<210> SEQ ID NO 191
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 191
gtttccactg tctccgacta                                              20

<210> SEQ ID NO 192
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 192
acaagattca tctgtagtcg                                              20

<210> SEQ ID NO 193
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 193
cctcggtttc cactgtctcc                                              20

<210> SEQ ID NO 194
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 194
tgtagtcgga gacagtggaa                                              20

<210> SEQ ID NO 195
<211> LENGTH: 20
<212> TYPE: DNA
<213> ORGANISM: Artificial Sequence
```

```
<220> FEATURE:
<221> NAME/KEY:
<223> OTHER INFORMATION: Primer

<400> SEQUENCE: 195
ctaccactgg accctcggtt                                                  20

<210> SEQ ID NO 196
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 196
accgagggtc cagtggtagc                                                  20

<210> SEQ ID NO 197
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 197
cctcgctgtc actggcctgg                                                  20

<210> SEQ ID NO 198
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 198
gtagccaggc cagtgacagc                                                  20

<210> SEQ ID NO 199
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 199
actcttctga gtgtccctcg                                                  20

<210> SEQ ID NO 200
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 200
ccagtgacag cgagggacac                                                  20

<210> SEQ ID NO 201
<211> LENGTH: 20
<212> TYPE: DNA
<213> ORGANISM: Artificial Sequence
<220> FEATURE:
```

```
<221> NAME/KEY:
<223> OTHER INFORMATION: Primer

<400> SEQUENCE: 201
gtgtgtctga ctcttctgag                                               20

<210> SEQ ID NO 202
<211> LENGTH: 19
<212> TYPE: DNA
<213> ORGANISM: Artificial Sequence
<220> FEATURE:
<221> NAME/KEY:
<223> OTHER INFORMATION: Primer

<400> SEQUENCE: 202
cctgctcgtg gcgggatct                                                19

<210> SEQ ID NO 203
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Carboxyfluorescein labelled cytosine
<220> FEATURE:
<221> NAME/KEY:
<223> OTHER INFORMATION: Primer

<400> SEQUENCE: 203
nctgctcgtg gcgggatct                                                19

<210> SEQ ID NO 204
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 204
gtcccaggaa aggtctgatg t                                             21

<210> SEQ ID NO 205
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 205
acatcagacc tttcctggga c                                             21

<210> SEQ ID NO 206
<211> LENGTH: 22
<212> TYPE: DNA
<213> ORGANISM: Artificial Sequence
<220> FEATURE:
<221> NAME/KEY:
<223> OTHER INFORMATION: Primer

<400> SEQUENCE: 206
catggatccc accaccagct cc                                            22

<210> SEQ ID NO 207
<211> LENGTH: 22
```

```
<212> TYPE: DNA
<213> ORGANISM: Artificial Sequence
<220> FEATURE:
<221> NAME/KEY:
<223> OTHER INFORMATION: Primer

<400> SEQUENCE: 207
agacacacag tcagtgtcag ca                                          22

<210> SEQ ID NO 208
<211> LENGTH: 22
<212> TYPE: DNA
<213> ORGANISM: Artificial Sequence
<220> FEATURE:
<221> NAME/KEY:
<223> OTHER INFORMATION: Primer

<400> SEQUENCE: 208
cacacagtca gtgtcagcac ag                                          22

<210> SEQ ID NO 209
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 209
ctgagtccgc ccatggacgc                                             20

<210> SEQ ID NO 210
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 210
ctccagtgct gggccctgtg                                             20

<210> SEQ ID NO 211
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 211
agtccgccca tggacgcaca                                             20

<210> SEQ ID NO 212
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 212
ttcctccagt gctgggccct                                             20

<210> SEQ ID NO 213
<211> LENGTH: 20
<212> TYPE: DNA
```

```
<213> ORGANISM: Artificial Sequence
<220> FEATURE:
<221> NAME/KEY:
<223> OTHER INFORMATION: Primer

<400> SEQUENCE: 213
cagcactgga ggaagacaaa                                              20

<210> SEQ ID NO 214
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 214
gcctgctcgt ggcgggatct                                              20

<210> SEQ ID NO 215
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 215
acaccattcg tggacaccca                                              20

<210> SEQ ID NO 216
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 216
ttcctcctct gcttgaccct                                              20

<210> SEQ ID NO 217
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 217
gaaggcaggg atcccactat                                              20

<210> SEQ ID NO 218
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 218
atctatctac cgattgctca                                              20

<210> SEQ ID NO 219
<211> LENGTH: 20
<212> TYPE: DNA
<213> ORGANISM: Artificial Sequence
```

```
<220> FEATURE:
<221> NAME/KEY:
<223> OTHER INFORMATION: Primer

<400> SEQUENCE: 219
atgagcaatc ggtagatagt                                              20

<210> SEQ ID NO 220
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 220
gagaccctga gtgtccagaa                                              20

<210> SEQ ID NO 221
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 221
ctcatcacag ccacaccacg                                              20

<210> SEQ ID NO 222
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 222
catcagacct ttcctgggac                                              20

<210> SEQ ID NO 223
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 223
agccacacca cgtcccagga                                              20

<210> SEQ ID NO 224
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 224
acgggagaca tcagaccttt                                              20

<210> SEQ ID NO 225
<211> LENGTH: 20
<212> TYPE: DNA
<213> ORGANISM: Artificial Sequence
<220> FEATURE:
```

<221> NAME/KEY:
<223> OTHER INFORMATION: Primer

<400> SEQUENCE: 225
tcccaggaaa ggtctgatgt                                                    20

<210> SEQ ID NO 226
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 226
tcctgactgc ccacgggaga                                                    20

<210> SEQ ID NO 227
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 227
cagtcaggat ccagaagtgt                                                    20

<210> SEQ ID NO 228
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 228
tgtctggagc tgtctgctga                                                    20

<210> SEQ ID NO 229
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 229
agtcaggatc cagaagtgtc                                                    20

<210> SEQ ID NO 230
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 230
gtgtctggag ctgtctgctg                                                    20

<210> SEQ ID NO 231
<211> LENGTH: 20
<212> TYPE: DNA
<213> ORGANISM: Artificial Sequence
<220> FEATURE:
<221> NAME/KEY:

<223> OTHER INFORMATION: Primer

<400> SEQUENCE: 231
cagacaaaca cgtaatgaga                                               20

<210> SEQ ID NO 232
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 232
gagccgtctc ctgattgttt                                               20

<210> SEQ ID NO 233
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 233
ccgacagctc tagacactcg                                               20

<210> SEQ ID NO 234
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 234
attgtccctg gcccacctgc                                               20

<210> SEQ ID NO 235
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 235
tgggccaggg acaatcatca                                               20

<210> SEQ ID NO 236
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 236
tcctgcttgt cctgggccct                                               20

<210> SEQ ID NO 237
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 237
tctgcttcca gaaaccatct                                                    20

<210> SEQ ID NO 238
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 238
ctgctcccaa gcagatccaa                                                    20

<210> SEQ ID NO 239
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 239
aaaccatctt ggatctgctt                                                    20

<210> SEQ ID NO 240
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 240
tgtcttcgtg atgggaccca                                                    20

<210> SEQ ID NO 241
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 241
gagatggctc cagacaccct                                                    20

<210> SEQ ID NO 242
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 242
tgtcttcgtg atgggaccca                                                    20

<210> SEQ ID NO 243
<211> LENGTH: 20
<212> TYPE: DNA
<213> ORGANISM: Artificial Sequence
<220> FEATURE:
<221> NAME/KEY:
<223> OTHER INFORMATION: Primer

```
<400> SEQUENCE: 243
agatggctcc agacaccctg                                              20

<210> SEQ ID NO 244
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 244
ctgtcttcgt gatgggaccc                                              20

<210> SEQ ID NO 245
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 245
aggcactcgt cacacagagt                                              20

<210> SEQ ID NO 246
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 246
gcctgtccac gagaggaaga                                              20

<210> SEQ ID NO 247
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 247
catggatccc accaccagct                                              20

<210> SEQ ID NO 248
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 248
ggagctgtct gctgactgga                                              20

<210> SEQ ID NO 249
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 249
```
atggatccca ccaccagctc                                              20

<210> SEQ ID NO 250
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 250
tggagctgtc tgctgactgg                                              20

<210> SEQ ID NO 251
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 251
tggatcccac caccagctcc                                              20

<210> SEQ ID NO 252
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 252
ctggagctgt ctgctgactg                                              20

<210> SEQ ID NO 253
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 253
gacactcagg cattgggcat                                              20

<210> SEQ ID NO 254
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 254
ctgcagatga agcttgtcca                                              20

<210> SEQ ID NO 255
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 255
acacacagtc agtgtcagca                                              20

<210> SEQ ID NO 256
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 256
ggggcccagc ttttccctgt                                              20

<210> SEQ ID NO 257
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 257
cacagtcagt gtcagcacag                                              20

<210> SEQ ID NO 258
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 258
gatggggccc agcttttccc                                              20

<210> SEQ ID NO 259
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 259
cagtgtcagc acagggaaaa                                              20

<210> SEQ ID NO 260
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 260
tctgctgatg gggcccagct                                              20

<210> SEQ ID NO 261
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 261
gccccatcag cagagccaca                                              20

```
<210> SEQ ID NO 262
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 262
tggccacgtg cggactcttt                                          20

<210> SEQ ID NO 263
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 263
gtggccagtc aggggaaagc                                          20

<210> SEQ ID NO 264
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 264
aagaccctga acgtccagag                                          20

<210> SEQ ID NO 265
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 265
gaggaagaca aggatcccat t                                        21

<210> SEQ ID NO 266
<211> LENGTH: 22
<212> TYPE: DNA
<213> ORGANISM: Artificial Sequence
<220> FEATURE:
<221> NAME/KEY:
<223> OTHER INFORMATION: Primer

<400> SEQUENCE: 266
gctgtcttgt gcctgatcat aa                                       22

<210> SEQ ID NO 267
<211> LENGTH: 22
<212> TYPE: DNA
<213> ORGANISM: Artificial Sequence
<220> FEATURE:
<221> NAME/KEY:
<223> OTHER INFORMATION: Primer

<400> SEQUENCE: 267
gaagtgcaag cagaaaaaca ta                                       22
```

```
<210> SEQ ID NO 268
<211> LENGTH: 22
<212> TYPE: DNA
<213> ORGANISM: Artificial Sequence
<220> FEATURE:
<221> NAME/KEY:
<223> OTHER INFORMATION: Primer

<400> SEQUENCE: 268
ctcctgattg ttccttgtca ta                                              22

<210> SEQ ID NO 269
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 269
gaacaatcag gagatggctc t                                               21

<210> SEQ ID NO 270
<211> LENGTH: 22
<212> TYPE: DNA
<213> ORGANISM: Artificial Sequence
<220> FEATURE:
<221> NAME/KEY:
<223> OTHER INFORMATION: Primer

<400> SEQUENCE: 270
ccgacagctc tagacactca ct                                              22

<210> SEQ ID NO 271
<211> LENGTH: 27
<212> TYPE: DNA
<213> ORGANISM: Artificial Sequence
<220> FEATURE:
<221> NAME/KEY:
<223> OTHER INFORMATION: Primer

<400> SEQUENCE: 271
gtttcttaga ggcggtctgg gtctgcg                                         27

<210> SEQ ID NO 272
<211> LENGTH: 22
<212> TYPE: DNA
<213> ORGANISM: Artificial Sequence
<220> FEATURE:
<221> NAME/KEY:
<223> OTHER INFORMATION: Primer

<400> SEQUENCE: 272
ccagaggaat tctctgcatg at                                              22

<210> SEQ ID NO 273
<211> LENGTH: 27
<212> TYPE: DNA
<213> ORGANISM: Artificial Sequence
<220> FEATURE:
<221> NAME/KEY:
<223> OTHER INFORMATION: Primer

<400> SEQUENCE: 273
gtttcttcca cacgtggccg gtcagca                                         27
```

```
<210> SEQ ID NO 274
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 274
tcatgaacag tctgagtcca                                                  20

<210> SEQ ID NO 275
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 275
ggcgcagact gtccatgggt                                                  20

<210> SEQ ID NO 276
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 276
tctgagtcca cccatggaca                                                  20

<210> SEQ ID NO 277
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 277
tccagtgctg ggcgcagact                                                  20

<210> SEQ ID NO 278
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 278
tgagtccacc catggacagt                                                  20

<210> SEQ ID NO 279
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 279
cctccagtgc tgggcgcaga                                                  20

<210> SEQ ID NO 280
```

```
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 280
cctccagtgc tgggcgcaga                                               20

<210> SEQ ID NO 281
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 281
ttcctccagt gctgggcgca                                               20

<210> SEQ ID NO 282
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 282
tccacccatg gacagtctgc                                               20

<210> SEQ ID NO 283
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 283
tcttcctcca gtgctgggcg                                               20

<210> SEQ ID NO 284
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 284
tcagcatccc aagaggccat                                               20

<210> SEQ ID NO 285
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 285
tgtcttgtgc ctgatcataa                                               20

<210> SEQ ID NO 286
<211> LENGTH: 20
```

```
<212> TYPE: DNA
<213> ORGANISM: Artificial Sequence
<220> FEATURE:
<221> NAME/KEY:
<223> OTHER INFORMATION: Primer

<400> SEQUENCE: 286
cagcatccca agaggccatt                                                   20

<210> SEQ ID NO 287
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 287
ctgtcttgtg cctgatcata                                                   20

<210> SEQ ID NO 288
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 288
gacaaggatc ccattatgat                                                   20

<210> SEQ ID NO 289
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 289
tggagctgtc ttgtgcctga                                                   20

<210> SEQ ID NO 290
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 290
cattcgtgga cacccggggc                                                   20

<210> SEQ ID NO 291
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 291
tgtcttcctc ctctgcttgg                                                   20

<210> SEQ ID NO 292
<211> LENGTH: 20
<212> TYPE: DNA
```

```
<213> ORGANISM: Artificial Sequence
<220> FEATURE:
<221> NAME/KEY:
<223> OTHER INFORMATION: Primer

<400> SEQUENCE: 292
ggccaagcag aggaggaaga                                              20

<210> SEQ ID NO 293
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 293
gctcttggtg ggacccctgt                                              20

<210> SEQ ID NO 294
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 294
gaagacaggg gtcccaccaa                                              20

<210> SEQ ID NO 295
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 295
acctatctac cgattgctct                                              20

<210> SEQ ID NO 296
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 296
aagtgcaagc agaaaaacat                                              20

<210> SEQ ID NO 297
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 297
cctgattgtt ccttgtcata                                              20

<210> SEQ ID NO 298
<211> LENGTH: 20
<212> TYPE: DNA
<213> ORGANISM: Artificial Sequence
```

-continued

```
<220> FEATURE:
<221> NAME/KEY:
<223> OTHER INFORMATION: Primer

<400> SEQUENCE: 298
agtgcaagca gaaaaacata                                               20

<210> SEQ ID NO 299
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 299
tcctgattgt tccttgtcat                                               20

<210> SEQ ID NO 300
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 300
tgcaagcaga aaacatatg                                                20

<210> SEQ ID NO 301
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 301
tctcctgatt gttccttgtc                                               20

<210> SEQ ID NO 302
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 302
caagcagaaa aacatatgac                                               20

<210> SEQ ID NO 303
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 303
catctcctga ttgttccttg                                               20

<210> SEQ ID NO 304
<211> LENGTH: 20
<212> TYPE: DNA
<213> ORGANISM: Artificial Sequence
<220> FEATURE:
```

<221> NAME/KEY:
<223> OTHER INFORMATION: Primer

<400> SEQUENCE: 304
aagcagaaaa acatatgaca                                              20

<210> SEQ ID NO 305
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 305
ccatctcctg attgttcctt                                              20

<210> SEQ ID NO 306
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 306
acaaggaaca atcaggagat                                              20

<210> SEQ ID NO 307
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 307
accctgagtg cctagagcca                                              20

<210> SEQ ID NO 308
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 308
aacaatcagg agatggctct                                              20

<210> SEQ ID NO 309
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 309
gatgcgaccc tgagtgccta                                              20

<210> SEQ ID NO 310
<211> LENGTH: 20
<212> TYPE: DNA
<213> ORGANISM: Artificial Sequence
<220> FEATURE:
<221> NAME/KEY:

<223> OTHER INFORMATION: Primer

<400> SEQUENCE: 310
tctaggcact cagggtcgca                                          20

<210> SEQ ID NO 311
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 311
agaggaagct tcatgatgat                                          20

<210> SEQ ID NO 312
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 312
ggcactcagg gtcgcatcat                                          20

<210> SEQ ID NO 313
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 313
cccaagagga agcttcatga                                          20

<210> SEQ ID NO 314
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 314
tcatcatgaa gcttcctctt                                          20

<210> SEQ ID NO 315
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 315
tgtctagagc tgtcggccca                                          20

<210> SEQ ID NO 316
<211> LENGTH: 20
<212> TYPE: DNA
<213> ORGANISM: Artificial Sequence
<220> FEATURE:
<221> NAME/KEY:
<223> OTHER INFORMATION: Primer -continued

```
<400> SEQUENCE: 316
gacagctcta gacactcact                                           20

<210> SEQ ID NO 317
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 317
tgattgtccc tggcccacca                                           20

<210> SEQ ID NO 318
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 318
tgggccaggg acaatcatca                                           20

<210> SEQ ID NO 319
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 319
gcctgcttgt cctgggccct                                           20

<210> SEQ ID NO 320
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 320
gggcccagga caagcaggcc                                           20

<210> SEQ ID NO 321
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 321
gctaacactg gatccccggg                                           20

<210> SEQ ID NO 322
<211> LENGTH: 20
<212> TYPE: DNA
<213> ORGANISM: Artificial Sequence
<220> FEATURE:
<221> NAME/KEY:
<223> OTHER INFORMATION: Primer
```

```
<400> SEQUENCE: 322
cccaggacaa gcaggccccg                                              20

<210> SEQ ID NO 323
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 323
ctggctaaca ctggatcccc                                              20

<210> SEQ ID NO 324
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 324
agaggcggtc tgggtctgcg                                              20

<210> SEQ ID NO 325
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 325
atccatgatg gtttctggac                                              20

<210> SEQ ID NO 326
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 326
tccacacgtg gccggtcagc                                              20

<210> SEQ ID NO 327
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 327
tgaacgtcca gaccttcctg                                              20

<210> SEQ ID NO 328
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 328
```

-continued ccacacgtgg ccggtcagca                                           20

<210> SEQ ID NO 329
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 329
ctgaacgtcc agaccttcct                                           20

<210> SEQ ID NO 330
<211> LENGTH: 19
<212> TYPE: DNA
<213> ORGANISM: Artificial Sequence
<220> FEATURE:
<221> NAME/KEY:
<223> OTHER INFORMATION: Primer

<400> SEQUENCE: 330
agctgtctcg tgcctgctt                                            19

<210> SEQ ID NO 331
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 331
gtcctgaccc tcttgggacg t                                         21

<210> SEQ ID NO 332
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: hexachlorofluorescein labelled guanine
<220> FEATURE:
<221> NAME/KEY:
<223> OTHER INFORMATION: Primer

<400> SEQUENCE: 332
ntcctgaccc tcttgggacg t                                         21

<210> SEQ ID NO 333
<211> LENGTH: 19
<212> TYPE: DNA
<213> ORGANISM: Artificial Sequence
<220> FEATURE:
<221> NAME/KEY:
<223> OTHER INFORMATION: Primer

<400> SEQUENCE: 333
cccaggacaa gcaggaact                                            19

<210> SEQ ID NO 334
<211> LENGTH: 21
<212> TYPE: DNA
<213> ORGANISM: Artificial Sequence
<220> FEATURE:
<221> NAME/KEY:

<223> OTHER INFORMATION: Primer

<400> SEQUENCE: 334
ctggctaaaa ctggatcccc a                                              21

<210> SEQ ID NO 335
<211> LENGTH: 19
<212> TYPE: DNA
<213> ORGANISM: Artificial Sequence
<220> FEATURE:
<221> NAME/KEY:
<223> OTHER INFORMATION: Primer

<400> SEQUENCE: 335
ggctaaaact ggatcccca                                                 19

<210> SEQ ID NO 336
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 336
aagacaagga tcccaccaca                                                20

<210> SEQ ID NO 337
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 337
gagctgtctc gtgcctgctt                                                20

<210> SEQ ID NO 338
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 338
agacagctcc aggcactcaa                                                20

<210> SEQ ID NO 339
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 339
tcctgaccct cttgggacgt                                                20

<210> SEQ ID NO 340
<211> LENGTH: 20
<212> TYPE: DNA
<213> ORGANISM: Artificial Sequence
<220> FEATURE:
<221> NAME/KEY:
<223> OTHER INFORMATION: Primer

```
<400> SEQUENCE: 340
gagggtcagg acaccattca                                              20

<210> SEQ ID NO 341
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 341
gcttgacccc gggtgtccat                                              20

<210> SEQ ID NO 342
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 342
gacacccggg gtcaagcagt                                              20

<210> SEQ ID NO 343
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 343
gggatccctg ccttcctcca                                              20

<210> SEQ ID NO 344
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 344
ggatcccact acgagcaatt                                              20

<210> SEQ ID NO 345
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 345
gtgtccagat ctatctacca                                              20

<210> SEQ ID NO 346
<211> LENGTH: 20
<212> TYPE: DNA
<213> ORGANISM: Artificial Sequence
<220> FEATURE:
<221> NAME/KEY:
<223> OTHER INFORMATION: Primer
```

```
<400> SEQUENCE: 346
acgagcaatt ggtagataga                                              20

<210> SEQ ID NO 347
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 347
gagaccctga gtgtccagat                                              20

<210> SEQ ID NO 348
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 348
ctgatgcctc ccatgggcac                                              20

<210> SEQ ID NO 349
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 349
ttgcacttct ggatcctgag                                              20

<210> SEQ ID NO 350
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 350
caagcagaca aactcgtaac                                              20

<210> SEQ ID NO 351
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 351
cgtctcctga ttgttcatcg                                              20

<210> SEQ ID NO 352
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 352
```

```
gcagacaaac tcgtaacgat                                              20
```

<210> SEQ ID NO 353
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 353

```
agccgtctcc tgattgttca                                              20
```

<210> SEQ ID NO 354
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 354

```
agccgtctcc tgattgttca                                              20
```

<210> SEQ ID NO 355
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 355

```
tggcccacct gcgagtgtcc                                              20
```

<210> SEQ ID NO 356
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 356

```
ccgacagctc tggacactcg                                              20
```

<210> SEQ ID NO 357
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 357

```
attgtccctg gcccacctgc                                              20
```

<210> SEQ ID NO 358
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 358
gcccaggaca agcaggaact    20

<210> SEQ ID NO 359
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 359
tggctaaaac tggatcccca    20

<210> SEQ ID NO 360
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 360
cccaggacaa gcaggaactg    20

<210> SEQ ID NO 361
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 361
ctggctaaaa ctggatcccc    20

<210> SEQ ID NO 362
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 362
caggaactgg ggatccagtt    20

<210> SEQ ID NO 363
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 363
ctgtcactgt cctggctaaa    20

<210> SEQ ID NO 364
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 364
tggatctgct caggagcagc    20

```
<210> SEQ ID NO 365
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 365
tgtctggagc catctcttag                                              20

<210> SEQ ID NO 366
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 366
ggatctgctc aggagcagct                                              20

<210> SEQ ID NO 367
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 367
gtgtctggag ccatctctta                                              20

<210> SEQ ID NO 368
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 368
ggtagtcagg ccagtgacaa                                              20

<210> SEQ ID NO 369
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 369
gtcttctgaa tgtccctcat                                              20

<210> SEQ ID NO 370
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 370
agcccacgga caggctgggt                                              20
```

<210> SEQ ID NO 371
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 371
tggtggctct gctgatggga                    20

<210> SEQ ID NO 372
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 372
cgtggccggt caggggaaac                    20

<210> SEQ ID NO 373
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 373
agatcctgaa tgtccagacg                    20

<210> SEQ ID NO 374
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 374
tcaggggaaa cgtctggaca                    20

<210> SEQ ID NO 375
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 375
gtagaggaaa gatcctgaat                    20

<210> SEQ ID NO 376
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 376
aaacgtctgg acattcagga                    20

```
<210> SEQ ID NO 377
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 377
tcacctggta gaggaaagat                                                    20

<210> SEQ ID NO 378
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 378
gatggacggg gcccagcact a                                                  21

<210> SEQ ID NO 379
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 379
cttcctctag tgctgggccc c                                                  21

<210> SEQ ID NO 380
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 380
ctaccgaatg ctcgtggtgg t                                                  21

<210> SEQ ID NO 381
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 381
cacgagcatt cggtagatag c                                                  21

<210> SEQ ID NO 382
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 382
aggcgccagg gatccagtgt g                                                  21

<210> SEQ ID NO 383
```

```
<211> LENGTH: 22
<212> TYPE: DNA
<213> ORGANISM: Artificial Sequence
<220> FEATURE:
<221> NAME/KEY:
<223> OTHER INFORMATION: Primer

<400> SEQUENCE: 383
cttggtggct ctgctgatgg ga                                            22

<210> SEQ ID NO 384
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 384
gaaacgtctg gacattcagg a                                             21

<210> SEQ ID NO 385
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 385
agtcctccca tggatggacg                                               20

<210> SEQ ID NO 386
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 386
ttcctctagt gctgggcccc                                               20

<210> SEQ ID NO 387
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 387
atggacgggg cccagcacta                                               20

<210> SEQ ID NO 388
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 388
cgggatcctt gtcttcctct                                               20

<210> SEQ ID NO 389
<211> LENGTH: 20
```

```
<212> TYPE: DNA
<213> ORGANISM: Artificial Sequence
<220> FEATURE:
<221> NAME/KEY:
<223> OTHER INFORMATION: Primer

<400> SEQUENCE: 389
agaggaggaa ggcagggta                                              20

<210> SEQ ID NO 390
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 390
taccgaatgc tcgtggtggt                                             20

<210> SEQ ID NO 391
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 391
aggggtacca ccacgagcat                                             20

<210> SEQ ID NO 392
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 392
gtccagagct atctaccgaa                                             20

<210> SEQ ID NO 393
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 393
acgagcattc ggtagatagc                                             20

<210> SEQ ID NO 394
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 394
gggaccctga gtgtccagag                                             20

<210> SEQ ID NO 395
<211> LENGTH: 20
<212> TYPE: DNA
```

```
<213> ORGANISM: Artificial Sequence
<220> FEATURE:
<221> NAME/KEY:
<223> OTHER INFORMATION: Primer

<400> SEQUENCE: 395
tctagacact cacaggcagt                                               20

<210> SEQ ID NO 396
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 396
cccctctgat tgtccctgga                                               20

<210> SEQ ID NO 397
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 397
caatcagagg ggtccaggag                                               20

<210> SEQ ID NO 398
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 398
ggatccctgg cgcctgcttc                                               20

<210> SEQ ID NO 399
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 399
ggcgccaggg atccagtgtg                                               20

<210> SEQ ID NO 400
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 400
cactgtcact gtcctggctc                                               20

<210> SEQ ID NO 401
<211> LENGTH: 20
<212> TYPE: DNA
<213> ORGANISM: Artificial Sequence
```

<220> FEATURE:
<221> NAME/KEY:
<223> OTHER INFORMATION: Primer

<400> SEQUENCE: 401
tggatctgct caggagcagc                                               20

<210> SEQ ID NO 402
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 402
tgtctggagc catctcttag                                               20

<210> SEQ ID NO 403
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 403
ggatctgctc aggagcagct                                               20

<210> SEQ ID NO 404
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 404
gtgtctggag ccatctctta                                               20

<210> SEQ ID NO 405
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 405
ggtagtcagg ccagtgacaa                                               20

<210> SEQ ID NO 406
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 406
gtcttctgaa tgtccctcat                                               20

<210> SEQ ID NO 407
<211> LENGTH: 20
<212> TYPE: DNA
<213> ORGANISM: Artificial Sequence
<220> FEATURE:

```
<221> NAME/KEY:
<223> OTHER INFORMATION: Primer

<400> SEQUENCE: 407
agcccacgga caggctgggt                                              20

<210> SEQ ID NO 408
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 408
tggtggctct gctgatggga                                              20

<210> SEQ ID NO 409
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 409
cgtggccggt caggggaaac                                              20

<210> SEQ ID NO 410
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 410
agatcctgaa tgtccagacg                                              20

<210> SEQ ID NO 411
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 411 tcagggaaa cgtctggaca                                               20

<210> SEQ ID NO 412
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 412
gtagaggaaa gatcctgaat                                              20

<210> SEQ ID NO 413
<211> LENGTH: 20
<212> TYPE: DNA
<213> ORGANISM: Artificial Sequence
<220> FEATURE:
<221> NAME/KEY:
```

<223> OTHER INFORMATION: Primer

<400> SEQUENCE: 413
aaacgtctgg acattcagga                                         20

<210> SEQ ID NO 414
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 414
tcacctggta gaggaaagat                                         20

<210> SEQ ID NO 415
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 415
ccaggcactc agcatcccaa t                                       21

<210> SEQ ID NO 416
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 416
acgaatggtg tcctgaccgt a                                       21

<210> SEQ ID NO 417
<211> LENGTH: 24
<212> TYPE: DNA
<213> ORGANISM: Artificial Sequence
<220> FEATURE:
<221> NAME/KEY:
<223> OTHER INFORMATION: Primer

<400> SEQUENCE: 417
gtaatgagga acaatcagga gaca                                    24

<210> SEQ ID NO 418
<211> LENGTH: 22
<212> TYPE: DNA
<213> ORGANISM: Artificial Sequence
<220> FEATURE:
<221> NAME/KEY:
<223> OTHER INFORMATION: Primer

<400> SEQUENCE: 418
gtgacactga gtgcctggag ct                                      22

<210> SEQ ID NO 419
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 419
cagaaaccat cgtggatctg t                                              21

<210> SEQ ID NO 420
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 420
ctggggtgtc tggagccgtg c                                              21

<210> SEQ ID NO 421
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 421
gtcacgggca ctctgcagac c                                              21

<210> SEQ ID NO 422
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 422
agtcctccca tggatggacg                                                20

<210> SEQ ID NO 423
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 423
ttcctctagt gctgggcccc                                                20

<210> SEQ ID NO 424
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 424
atggacgggg cccagcacta                                                20

<210> SEQ ID NO 425
<211> LENGTH: 20
<212> TYPE: DNA
<213> ORGANISM: Artificial Sequence
<220> FEATURE:
<221> NAME/KEY:
<223> OTHER INFORMATION: Primer

```
<400> SEQUENCE: 425
cgggatcctt gtcttcctct                                              20

<210> SEQ ID NO 426
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 426
tcccgccatg agcaggcaca                                              20

<210> SEQ ID NO 427
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 427
tgagtgcctg gagctgtctt                                              20

<210> SEQ ID NO 428
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 428
caggcactca gcatcccaat                                              20

<210> SEQ ID NO 429
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 429
cgaatggtgt cctgaccgta                                              20

<210> SEQ ID NO 430
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 430
agaggaggaa ggcaggggta                                              20

<210> SEQ ID NO 431
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 431
```

```
taccgaatgc tcgtggtggt                                                    20
```

<210> SEQ ID NO 432
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 432

```
aggggtacca ccacgagcat                                                    20
```

<210> SEQ ID NO 433
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 433

```
gtccagagct atctaccgaa                                                    20
```

<210> SEQ ID NO 434
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 434

```
acgagcattc ggtagatagc                                                    20
```

<210> SEQ ID NO 435
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 435

```
gggaccctga gtgtccagag                                                    20
```

<210> SEQ ID NO 436
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 436

```
tgaggaacaa tcaggagaca                                                    20
```

<210> SEQ ID NO 437
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 437
gacactgagt gcctggagct 20

<210> SEQ ID NO 438
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 438
gacagctcca ggcactcagt 20

<210> SEQ ID NO 439
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 439
agcttcatgg tgacgtgaca 20

<210> SEQ ID NO 440
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 440
tctctagaca ctcacaggca 20

<210> SEQ ID NO 441
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 441
cctctgattg tccctggact 20

<210> SEQ ID NO 442
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 442
tctagacact cacaggcagt 20

<210> SEQ ID NO 443
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 443
cccctctgat tgtccctgga 20

```
<210> SEQ ID NO 444
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 444
ggcgccaggg atccagtgtg                                              20

<210> SEQ ID NO 445
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 445
cactgtcact gtcctggctc                                              20

<210> SEQ ID NO 446
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 446
agaaaccatc gtggatctgt                                              20

<210> SEQ ID NO 447
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 447
gtgccttgac tgctcctgaa                                              20

<210> SEQ ID NO 448
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 448
tcacgggcac tctgcagacc                                              20

<210> SEQ ID NO 449
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 449
gtgcctgatt gtctggagcg                                              20
```

<210> SEQ ID NO 450
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 450
ctccagacac tcaggcattc                                           20

<210> SEQ ID NO 451
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 451
gatgaagctt gtccacgcgg                                           20

<210> SEQ ID NO 452
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 452
tccagacact caggcattcc                                           20

<210> SEQ ID NO 453
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 453
agatgaagct tgtccacgcg                                           20

<210> SEQ ID NO 454
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 454
gacactcagg cattccgcgt                                           20

<210> SEQ ID NO 455
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 455
ctgcagatga agcttgtcca                                           20

```
<210> SEQ ID NO 456
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 456
atctgcagtc agagacagta                                              20

<210> SEQ ID NO 457
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 457
ccactggacc cccagtgtct                                              20

<210> SEQ ID NO 458
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 458
agtcagagac agtagacact                                              20

<210> SEQ ID NO 459
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 459
tgactaccac tggaccccca                                              20

<210> SEQ ID NO 460
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 460
gtggtagtca ggccagtgat                                              20

<210> SEQ ID NO 461
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 461
cttctgaatg tccctcacta                                              20

<210> SEQ ID NO 462
```

-continued

```
<211> LENGTH: 19
<212> TYPE: DNA
<213> ORGANISM: Artificial Sequence
<220> FEATURE:
<221> NAME/KEY:
<223> OTHER INFORMATION: Primer

<400> SEQUENCE: 462
gcccatgggc ggaccagga                                           19

<210> SEQ ID NO 463
<211> LENGTH: 19
<212> TYPE: DNA
<213> ORGANISM: Artificial Sequence
<220> FEATURE:
<221> NAME/KEY:
<223> OTHER INFORMATION: Primer

<400> SEQUENCE: 463
gatggctcca ggcactcat                                           19

<210> SEQ ID NO 464
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 464
gggcccagga caagcaggaa                                          20

<210> SEQ ID NO 465
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 465
gtcagagaca gtggacaccg a                                        21

<210> SEQ ID NO 466
<211> LENGTH: 28
<212> TYPE: DNA
<213> ORGANISM: Artificial Sequence
<220> FEATURE:
<221> NAME/KEY:
<223> OTHER INFORMATION: Primer

<400> SEQUENCE: 466
gtttcttgtc agagacagtg gacaccga                                 28

<210> SEQ ID NO 467
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 467
ctgaacgtcc agaccttcct g                                        21

<210> SEQ ID NO 468
<211> LENGTH: 20
```

```
<212> TYPE: DNA
<213> ORGANISM: Artificial Sequence
<220> FEATURE:
<221> NAME/KEY:
<223> OTHER INFORMATION: Primer

<400> SEQUENCE: 468
agtctgagtc tgcccatggg                                              20

<210> SEQ ID NO 469
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 469
cagtgctggt cctggtccgc                                              20

<210> SEQ ID NO 470
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 470
gtctgcccat gggcggacca                                              20

<210> SEQ ID NO 471
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 471
cttcgtccag tgctggtcct                                              20

<210> SEQ ID NO 472
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 472
gaccaggacc agcactggac                                              20

<210> SEQ ID NO 473
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 473
tggtgggatc cttgtcttcg                                              20

<210> SEQ ID NO 474
<211> LENGTH: 20
<212> TYPE: DNA
```

```
<213> ORGANISM: Artificial Sequence
<220> FEATURE:
<221> NAME/KEY:
<223> OTHER INFORMATION: Primer

<400> SEQUENCE: 474
acacccgggg tcaagcagaa                                         20

<210> SEQ ID NO 475
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 475
tgggatccct gccttcctct                                         20

<210> SEQ ID NO 476
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 476
agtcaggatc cagaagtgcc                                         20

<210> SEQ ID NO 477
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 477
cattacgagt ttgtctgctg                                         20

<210> SEQ ID NO 478
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 478
gcagacaaac tcgtaatgac                                         20

<210> SEQ ID NO 479
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 479
agccatctcc tgattgttcg                                         20

<210> SEQ ID NO 480
<211> LENGTH: 20
<212> TYPE: DNA
<213> ORGANISM: Artificial Sequence
```

```
<220> FEATURE:
<221> NAME/KEY:
<223> OTHER INFORMATION: Primer

<400> SEQUENCE: 480
atgacgaaca atcaggagat                                          20

<210> SEQ ID NO 481
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 481
accatgagtg cctggagcca                                          20

<210> SEQ ID NO 482
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 482
agatggctcc aggcactcat                                          20

<210> SEQ ID NO 483
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 483
gcttcatggt gatgcgacca                                          20

<210> SEQ ID NO 484
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 484
tccaggcact catggtcgca                                          20

<210> SEQ ID NO 485
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 485
agtggaagct tcatggtgat                                          20

<210> SEQ ID NO 486
<211> LENGTH: 20
<212> TYPE: DNA
<213> ORGANISM: Artificial Sequence
<220> FEATURE:
```

```
<221> NAME/KEY:
<223> OTHER INFORMATION: Primer

<400> SEQUENCE: 486
atgaagcttc cactcaggcg                                                  20

<210> SEQ ID NO 487
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 487
gtgagtgtct agagctgtcc                                                  20

<210> SEQ ID NO 488
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 488
cagctctaga cactcacagt                                                  20

<210> SEQ ID NO 489
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 489
gctgattgtc cctggccgga                                                  20

<210> SEQ ID NO 490
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 490
gatggctcca gacaccccac                                                  20

<210> SEQ ID NO 491
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 491
tctgtcttcg tgatgggacg                                                  20

<210> SEQ ID NO 492
<211> LENGTH: 20
<212> TYPE: DNA
<213> ORGANISM: Artificial Sequence
<220> FEATURE:
<221> NAME/KEY:
```

```
<223> OTHER INFORMATION: Primer

<400> SEQUENCE: 492
ccacacgtgg ccggtcagca                                          20

<210> SEQ ID NO 493
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 493
ctgaacgtcc agaccttcct                                          20

<210> SEQ ID NO 494
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 494
tgggcagtca ggatccagac                                          20

<210> SEQ ID NO 495
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 495
cgtgttgttc tgcttgcacg                                          20

<210> SEQ ID NO 496
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 496
cccaggtccc atcaagaagg                                          20

<210> SEQ ID NO 497
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 497
gtgcccatga ccagctctgc                                          20

<210> SEQ ID NO 498
<211> LENGTH: 20
<212> TYPE: DNA
<213> ORGANISM: Artificial Sequence
<220> FEATURE:
<221> NAME/KEY:
<223> OTHER INFORMATION: Primer
```

<400> SEQUENCE: 498
ggcactcagc atcccaagat                                               20

<210> SEQ ID NO 499
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 499
cacgaatggt gtcctgacca                                               20

<210> SEQ ID NO 500
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 500
aggcactcgt cacacacagg                                               20

<210> SEQ ID NO 501
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 501
gcctgtccac cagaggaagc                                               20

<210> SEQ ID NO 502
<211> LENGTH: 22
<212> TYPE: DNA
<213> ORGANISM: Artificial Sequence
<220> FEATURE:
<221> NAME/KEY:
<223> OTHER INFORMATION: Primer

<400> SEQUENCE: 502
catggatccc accaccagct cc                                            22

<210> SEQ ID NO 503
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 503
agacggctcc aggcactcat                                               20

<210> SEQ ID NO 504
<211> LENGTH: 20
<212> TYPE: DNA
<213> ORGANISM: Artificial Sequence
<220> FEATURE:
<221> NAME/KEY:
<223> OTHER INFORMATION: Primer

```
<400> SEQUENCE: 504
gcttcatggt gatgcgacca                                              20

<210> SEQ ID NO 505
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 505
atgaagcttc cactcaggcg                                              20

<210> SEQ ID NO 506
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 506
gtgagtgtct agagctgtcc                                              20

<210> SEQ ID NO 507
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 507
cagctctaga cactcacagt                                              20

<210> SEQ ID NO 508
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 508
gctgattgtc cctggccgga                                              20

<210> SEQ ID NO 509
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 509
gacaatcagc ggggcccagt                                              20

<210> SEQ ID NO 510
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 510
```

| | |
|---|---|
| atccctggtt cctgcttgta | 20 |

<210> SEQ ID NO 511
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 511

| | |
|---|---|
| cgggcactct gcagacagcc | 20 |

<210> SEQ ID NO 512
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 512

| | |
|---|---|
| cgagtgcctg attgtctggg | 20 |

<210> SEQ ID NO 513
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 513

| | |
|---|---|
| agcagacagc tccagacacg | 20 |

<210> SEQ ID NO 514
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 514

| | |
|---|---|
| tgtccgtgcc caatgcctgc | 20 |

<210> SEQ ID NO 515
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 515

| | |
|---|---|
| acacacagtc agtgtcagca | 20 |

<210> SEQ ID NO 516
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 516
ggggcccagc ttttccctgt                                                20

<210> SEQ ID NO 517
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 517
ccagtcaggg gaaagctcta                                                20

<210> SEQ ID NO 518
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 518
aggaaagacc ctgaacgtct                                                20

<210> SEQ ID NO 519
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 519
gtccacccat ggacagtctg t                                              21

<210> SEQ ID NO 520
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 520
tgagtccacc catggacagt                                                20

<210> SEQ ID NO 521
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 521
cctccagtgc tgggcacaga                                                20

<210> SEQ ID NO 522
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 522
gacaaggatc ccaccatgat                                                20

```
<210> SEQ ID NO 523
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 523
tggagctgtc ttgtgcctga                                         20

<210> SEQ ID NO 524
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 524
cattcgtgga cacccggggc                                         20

<210> SEQ ID NO 525
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 525
tgtcttcctc ctctgcttgg                                         20

<210> SEQ ID NO 526
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 526
ctcccgtggg cagtcaggac                                         20

<210> SEQ ID NO 527
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 527
cccagaagtg caagcagaca                                         20

<210> SEQ ID NO 528
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 528
agtgcaagca gacaaacaca                                         20
```

<210> SEQ ID NO 529
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 529
tcctgattgt tccttgtcat                                               20

<210> SEQ ID NO 530
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 530
tgcaagcaga caaacacatg                                               20

<210> SEQ ID NO 531
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 531
tctcctgatt gttccttgtc                                               20

<210> SEQ ID NO 532
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 532
agcagacaaa cacatgacaa                                               20

<210> SEQ ID NO 533
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 533
gccgtctcct gattgttcct                                               20

<210> SEQ ID NO 534
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 534
aacaatcagg agacggctct                                               20

```
<210> SEQ ID NO 535
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 535
gacgcgaccc tgagtgccta                                              20

<210> SEQ ID NO 536
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 536
gaattcctct ggtggacagc                                              20

<210> SEQ ID NO 537
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 537
tgttcatggg atgatgcagg                                              20

<210> SEQ ID NO 538
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 538
ccacacgtgg ccggtcagca                                              20

<210> SEQ ID NO 539
<211> LENGTH: 20
<212> TYPE: DNA
<213> ORGANISM: Artificial Sequence
<220> FEATURE:
<221> NAME/KEY:
<223> OTHER INFORMATION: Primer

<400> SEQUENCE: 539
ctgaacgtcc agaccttcct                                              20

<210> SEQ ID NO 540
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Carboxyfluorescein labelled guanine
<220> FEATURE:
<221> NAME/KEY:
<223> OTHER INFORMATION: Primer

<400> SEQUENCE: 540
```
natccttgtc ttcctccagt a                                          21

<210> SEQ ID NO 541
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 541
gatccttgtc ttcctccagt a                                          21

<210> SEQ ID NO 542
<211> LENGTH: 22
<212> TYPE: DNA
<213> ORGANISM: Artificial Sequence
<220> FEATURE:
<221> NAME/KEY:
<223> OTHER INFORMATION: Primer

<400> SEQUENCE: 542
ctagtaccgc taaggaacat gg                                         22

<210> SEQ ID NO 543
<211> LENGTH: 19
<212> TYPE: DNA
<213> ORGANISM: Artificial Sequence
<220> FEATURE:
<221> NAME/KEY:
<223> OTHER INFORMATION: Primer

<400> SEQUENCE: 543
ggcagctatg gtagtgcag                                             19

<210> SEQ ID NO 544
<211> LENGTH: 19
<212> TYPE: DNA
<213> ORGANISM: Artificial Sequence
<220> FEATURE:
<221> NAME/KEY:
<223> OTHER INFORMATION: Primer

<400> SEQUENCE: 544
ctgcactacc atagctgcc                                             19

<210> SEQ ID NO 545
<211> LENGTH: 21
<212> TYPE: DNA
<213> ORGANISM: Artificial Sequence
<220> FEATURE:
<221> NAME/KEY:
<223> OTHER INFORMATION: Primer

<400> SEQUENCE: 545
tggctccttc gatatttctg a                                          21

<210> SEQ ID NO 546
<211> LENGTH: 12186
<212> TYPE: DNA
<213> ORGANISM: Homo sapiens
<220> FEATURE:
<221> NAME/KEY:
<223> OTHER INFORMATION: Human Profilaggrin

<400> SEQUENCE: 546
atgtctactc tcctggaaaa catctttgcc ataattaatc ttttcaagca atattcaaaa     60

| | |
|---|---|
| aaagataaaa acactgacac attgagtaaa aaagagctga aggaacttct ggaaaaggaa | 120 |
| tttcggcaaa tcctgaagaa tccagatgac ccagatatgg ttgatgtctt catggatcac | 180 |
| ttggatatag accacaacaa gaaaattgac ttcactgagt ttcttctgat ggtattcaag | 240 |
| ttggctcaag catattatga gtctaccaga aaagagaatt taccgatatc aggacacaag | 300 |
| cacagaaagc acagtcatca tgataaacat gaagataata acaggaagaa aaacaaagaa | 360 |
| aacagaaaaa gaccctcaag tctggaaaga agaaacaata gaaaagggaa taagggaaga | 420 |
| tccaagagcc caagagaaac agggggaaa aggcatgaat ctagttctga aaaaaagaa | 480 |
| agaaaaggat attcacctac tcatagaaa gaagaatatg gaaaaaacca tcataactca | 540 |
| agtaaaaaag agaaaaacaa gactgaaaat actagattag gagacaatag gaagaggcta | 600 |
| agtgaaagac ttgaagagaa agaagacaat gaagaaggag tatatgatta tgaaaataca | 660 |
| ggaagaatga ctcaaaaatg gatacaatca ggccatattg ccacatatta cacaatccag | 720 |
| gatgaagcct atgacaccac tgatagtcta ttagaagaaa acaaaatata tgaaagatca | 780 |
| aggtcatctg atggcaaatc atcatctcaa gtgaacaggt caagacatga aaatacaagc | 840 |
| caggtaccat tgcaggagtc caggacaaga aagcgtaggg gatccagagt tagccaggac | 900 |
| agggacagtg agggacactc agaagactct gagaggcact ctgggtcggc ttccagaaac | 960 |
| catcatggat ctgcgtggga gcagtcaaga gatggctcca gacacccag gtcccatgat | 1020 |
| gaagacagag ccagtcatgg gcactctgca gacagctcca gacaatcagg cactcgtcac | 1080 |
| gcagagactt cctctcgtgg acagactgca tcatcccatg aacaggcaag atcaagtcca | 1140 |
| ggagaaagac atggatccgg ccaccagcag tcagcagaca gctccagaca ctcagccact | 1200 |
| gggcgcgggc aagcttcatc tgcagtcagc gatcgtggac accggggtc tagcggtagt | 1260 |
| caggccagtg acagtgaggg acattcagaa aactcagaca cacaatcagt gtcaggccac | 1320 |
| ggaaaggctg ggctgagaca gcagagccac caagagtcca cacgtggccg gtcaggggaa | 1380 |
| cggtctggac gttcagggtc ttccctctac caggtgagca ctcatgaaca gcctgactct | 1440 |
| gcccatggac ggaccgggac cagcactgga ggaagacaag gatcgcacca cgagcaggca | 1500 |
| cgagacagct ccaggcattc agcgtcccaa gagggtcagg acaccattcg tggacacccg | 1560 |
| gggtcaagca gaggaggaag gcagggatcc caccacgagc aatcggtaaa taggtctgga | 1620 |
| cactcaggtt cccatcacag ccacaccaca tcccagggaa ggtctgatgc ctcccatggg | 1680 |
| cagtcaggat ccagaagtgc aagcagacaa acacgaaatg aggaacaatc aggagacggc | 1740 |
| accaggcact cagggtcacg tcatcatgaa gcttcctctc aggctgacag ctctagacac | 1800 |
| tcacaggtgg gccagggaca atcatcgggg cccaggacaa gtaggaacca gggatccagt | 1860 |
| gttagccagg acagtgacag tcaggacac tcagaagact ctgagaggtg gtctgggtct | 1920 |
| gcttccagaa accatcatgg atctgctcag gagcagtcaa gagatggctc cagacacccc | 1980 |
| aggtcccatc acgaagacag agctggtcat gggcactctg cagacagctc agaaaatca | 2040 |
| ggcactcgtc acacacagaa ttcctctagt ggacaggctg cgtcatccca tgaacaggca | 2100 |
| agatcaagtg caggagaaag acatggatcc cgccaccagc tccagtcagc agacagctcc | 2160 |
| agacactcag gcactgggca cggacaagct tcatctgcag tcagagacag tggacaccga | 2220 |
| gggtccagtg gtagtcaggc cactgacagt gagggacatt cagaagactc agacacacag | 2280 |
| tcagtgtcag gccatggaca ggctggtcac catcagcaga gccaccaaga gtccgcacgt | 2340 |
| gaccggtcag gggaaaggtc tcgacgttca gggtctttcc tctaccaggt gagcactcat | 2400 |

```
aaacagtctg agtcctccca tggatggaca gggcccagca ctggagtaag acaaggatcc      2460
caccatgagc aggcacgaga caactccagg cactcagcat cccaagatgg tcaggacacc      2520
attcgtggac acccggggtc aagcagaaga ggaaggcagg ggtcccacca cgagcaatcg      2580
gtagataggt ctggacactc agggtcccat cacagccaca ccacatccca gggaaggtct      2640
gatgcctccc gtgggcagtc aggatccaga agtgcaagca gaacaacacg taatgaggaa      2700
caatcaagag acggctccag gcactcaggg tcacgtcacc atgaagcttc ctctcatgcc      2760
gacatctcta gacactcaca ggcaggccag ggacaatcag aggggtccag acaagcagg      2820
cgccagggat ccagtgttag ccaggacagt gacagtgagg gacattcaga agactctgag      2880
aggtggtctg ggtctgcttc cagaaaccat cgtggatctg ctcaggagca gtcaagacat      2940
ggctccagac accccaggtc ccatcacgaa gacagagccg gtcacgggca ctctgcagac      3000
agctccagac aatcaggaac tcctcacgca gagacttcct ctggtggaca ggctgcgtca      3060
tcccatgaac aggcaagatc aagtccagga gaaagacacg gatcccgcca ccagcagtca      3120
gcagacagct ccagacactc aggcattccg cgcagacaag cttcatctgc agtcagagac      3180
agtggacact gggggtccag tggtagtcag gccagtgata gtgagggaca ttcagaggag      3240
tcagacacac agtcagtgtc aggccatgga caggatgggc cccatcagca gagccaccaa      3300
gagtccgcac gtgactggtc aggggggaagg tctggacgtt cagggtcttt catctaccag      3360
gtgagcactc atgaacagtc tgagtctgcc catgggcgga ccaggaccag cactggacga      3420
agacaaggat cccaccacga gcaggcacga gacagctcca ggcactcagc gtcccaagag      3480
ggtcaggaca ccattcgtgc acacccgggg tcaaggagag gaggaaggca gggatcccac      3540
catgagcaat cggtagatag atctggacac tcagggtccc atcacagcca caccacatcc      3600
cagggaaggt ctgatgcctc ccatgggcag tcaggatcca gaagtgcaag cagacaaact      3660
cgtaaggaca acaatcagg agacggctcc aggcactcag ggtcacgtca ccatgaagct      3720
gcctcttggg ctgacagctc tagacactca caggtgggac aggaacaatc atcgggtcc      3780
aggacaagca ggcaccaggg atccagtgtt agccaggaca gtgacagtga gagacactca      3840
gacgactccg agaggttgtc tgggtctgct tccagaaacc atcatggatc ttctcgggag      3900
cagtcaagag atggctccag acaccctggg ttccatcaag aagacagagc cagtcacggg      3960
cactctgcag acagctccag acaatcaggc actcatcaca cagagtcttc ctctcatgga      4020
caggctgtgt catcccatga acaggcaaga tcaagtccag gagaaagaca tggatcccgc      4080
caccagcagt cagcagacag ctccagacac tcaggcattg gcacagaca agcttcatct      4140
gcagtcagag acagtggaca ccgagggtcc agtggtagtc aggtcactaa cagtgaggga      4200
cattcagaag actcagacac acagtcagtg tcagcccacg gacaagctgg gccccatcag      4260
cagagccaca aagagtccgc acgtggccag tcaggggaaa gctctggacg ttcaaggtct      4320
ttcctctacc aggtgagctc tcatgaacag tctgagtcca cacacggaca gactgcaccc      4380
agcactggag gaagacaagg atcccgccat gagcaggcac gaaacagctc taggcactca      4440
gcatcccaag acggtcagga caccattcgt ggacacccgg ggtcaagcag aggaggaagg      4500
cagggatcct accacgagca atcagtgat aggtctggac actcagggta ccatcacagc      4560
cacaccacac cccagggaag gtctgatgcc tcccatgggc agtcaggacc agaagtgca      4620
agcaggcaaa caagaaatga ggaacaatca ggagacggct ccaggcactc agggtcacgt      4680
caccatgaac cttccactcg ggccggcagc tctagacact cacaggtggg ccagggagaa      4740
tcagcggggt ccaagacaag caggcgccag ggatccagtg ttagtcagga cagggacagt      4800
```

```
gagggacact cagaagactc tgagaggcgg tctgagtcgg cttccagaaa ccattatgga    4860
tctgctcggg agcagtcaag acatggctcc aggaacccca ggtcccatca agaagataga    4920
gccagtcatg ggcactctgc agagagctcc agacaatcag gcactcgtca tgcagagact    4980
tcctctggtg gacaggctgc atcatcccag gaacaggcaa ggtcaagtcc aggagaaaga    5040
catggatccc gccaccagca gtcagcagac agctccacag actcaggcac tgggcgcaga    5100
caagattcat ctgtagtcgg agacagtgga aaccgagggt ccagtggtag ccaggccagt    5160
gacagcgagg gacactcaga agagtcagac acacagtcag tgtcagccca cggacaggct    5220 gggcccatc agcagagcca ccaagagtcc acacgtggcc agtcagggga aaggtctgga    5280
cgttcagggt ctttcctcta ccaggtgagc actcatgaac agtctgagtc cgcccatgga    5340
cgcacagggc ccagcactgg aggaagacaa agatcccgcc acgagcaggc acgagacagc    5400
tccaggcact cagcgtccca agagggtcag gacaccattc gtggacaccc agggtcaagc    5460
agaggaggaa ggcagggatc ccactatgag caatcggtag atagttctgg acactcaggg    5520
tctcatcaca gccacaccac gtcccaggaa aggtctgatg tctcccgtgg gcagtcagga    5580
tccagaagtg tcagcagaca aacacgtaat gagaaacaat caggacggg ctccaggcac    5640 tcagggtcgc gtcaccatga agcttcctct cgggccgaca gctctagaca ctcgcaggtg    5700
ggccagggac aatcatcagg gcccaggaca agcaggaacc agggatccag tgttagccag    5760
gacagtgaca gtcagggaca ctcagaagac tctgagaggt ggtctgggtc tgcttccaga    5820
aaccatcttg gatctgcttg ggagcagtca agagatggct ccagacaccc tgggtcccat    5880
cacgaagaca gagccggtca cgggcactct gcagacagct ccagacaatc aggcactcgt    5940
cacacagagt cttcctctcg tggacaggct gcgtcatccc atgaacaggc aagatcaagt    6000
gcaggagaaa gacatggatc ccaccaccag ctccagtcag cagacagctc cagacactca    6060
ggcattgggc atggacaagc ttcatctgca gtcagagaca gtggacaccg agggtacagt    6120
ggtagtcagg ccagtgacag tgagggacat tcagaagact cagacacaca gtcagtgtca    6180
gcacagggaa aagctgggcc ccatcagcag agccacaaag agtccgcacg tggccagtca    6240
ggggaaagct ctggacgttc agggtctttc ctctaccagg tgagcactca tgaacagtct    6300
gagtccaccc atggacagtc tgcgcccagc actggaggaa gacaaggatc ccattatgat    6360
caggcacaag acagctccag gcactcagca tcccaagagg gtcaggacac cattcgtgga    6420
cacccggggc caagcagagg aggaagacag gggtcccacc aagagcaatc ggtagatagg    6480
tctggacact cagggtctca tcacagccac accacatccc agggaaggtc tgatgcctcc    6540
cgtgggcagt caggatccag aagtgcaagc agaaaaacat atgacaagga acaatcagga    6600
gatggctcta ggcactcagg gtcgcatcat catgaagctt cctcttgggc cgacagctct    6660
agacactcac tggtgggcca gggacaatca tcagggccca ggacaagcag gccccgggga    6720
tccagtgtta gccaggacag tgacagtgag ggacactcag aagattctga gaggcggtct    6780
gggtctgcgt ccagaaacca tcatggatct gctcaggagc agtcaagaga tggctccaga    6840
caccccaggt cccatcacga agacagagcc ggtcatgggc actctgcaga gagctccaga    6900
caatcaggca ctcatcatgc agagaattcc tctggtggaa aggctgcatc atcccatgaa    6960
caggcaagat caagtgcagg agagagacac ggatcccacc accagcagtc agcagacagc    7020
tccagacact caggcattgg gcacggacaa gcttcatctg cagtcagaga cagtggacac    7080
cgagggtcca gtggtagtca ggccagtgac agtgagggac attcagaaga ctcagacaca    7140
```

```
cagtcagtgt cagcccacgg acaggctggg ccccatcagc agagccacca agagtccaca    7200
cgtggccggt cagcaggaag gtctggacgt tcagggtctt tcctctacca ggtgagcact    7260
catgaacagt ctgagtccgc ccatggacgg accgggacca gcactggagg aagacaagga    7320
tcccaccaca agcaggcacg agacagctcc aggcactcaa cgtcccaaga gggtcaggac    7380
accattcatg gacacccggg gtcaagcagt ggaggaaggc agggatccca ctacgagcaa    7440
ttggtagata gatctggaca ctcagggtct catcacagcc acaccacatc ccagggaagg    7500
tctgatgcct cccatgggca ctcaggatcc agaagtgcaa gcagacaaac tcgtaacgat    7560
gaacaatcag gagacggctc caggcactca gggtcgcgtc accatgaagc ttcctctcgg    7620
gccgacagct ctggacactc gcaggtgggc caggacaat cagaggggcc caggacaagc    7680
aggaactggg gatccagttt tagccaggac agtgacagtc agggacactc agaagactct    7740
gagaggtggt ctgggtctgc ttccagaaac catcatggat ctgctcagga gcagctaaga    7800
gatggctcca gacaccccag gtcccatcaa gaagacagag ctggtcatgg gcactctgca    7860
gacagctcca gacaatcagg cactcgtcac acacagactt cctctggtgg acaggctgca    7920
tcatcccatg aacaggcaag atcaagtgca ggagaaagac atggatccca ccaccagcag    7980
tcagcagaca gctccagaca ctcaggcatt gggcacggac aagcttcatc tgcagtcaga    8040
gacagtggac accgagggta cagtggtagt caggccagtg acaatgaggg acattcagaa    8100
gactcagaca cacagtcagt gtcagcccac ggacaggctg gtcccatca gcagagccac    8160 caagagtccg cacgtggccg gtcagggaa acgtctggac attcaggatc tttcctctac    8220
caggtgagca ctcatgaaca gtctgagtcc tcccatggat ggacggggcc cagcactaga    8280
ggaagacaag gatcccgcca tgagcaggca caagacagct ccaggcactc agcatcccaa    8340
gacggtcagg acaccattcg tggacacccg gggtcaagca gaggaggaag gcaggggtac    8400
caccacgagc attcggtaga tagctctgga cactcagggt cccatcacag ccacaccaca    8460
tcccagggaa ggtctgatgc ctcccgtggg cagtcaggat ccagaagtgc aagcagaaca    8520
acacgtaatg aggaacaatc aggagacggc tccaggcact cagggtcgcg tcaccatgaa    8580
gcttccactc atgccgacat ctctagacac tcacaggcag tccagggaca atcagagggg    8640
tccaggagaa gcaggcgcca gggatccagt gtgagccagg acagtgacag tgagggacat    8700
tcagaagact ctgagaggtg gtctgggtct gcttccagaa accatcatgg atctgctcag    8760
gagcagctaa gagatggctc cagacacccc aggtcccatc aagaagacag agctggtcat    8820
gggcactctg cagacagctc cagacaatca ggcactcgtc acacacagac ttcctctggt    8880
ggacaggctg catcatccca tgaacaggca agatcaagtg caggagaaag acatggatcc    8940
caccaccagc agtcagcaga cagctccaga cactcaggca ttgggcacgg acaagcttca    9000
tctgcagtca gagacagtgg acaccgaggg tacagtggta gtcaggccag tgacaatgag    9060
ggacattcag aagactcaga cacacagtca gtgtcagccc acggacaggc tgggtcccat    9120
cagcagagcc accaagagtc cgcacgtggc cggtcagggg aaacgtctgg acattcagga    9180
tctttcctct accaggtgag cactcatgaa cagtctgagt cctcccatgg atggacgggg    9240
cccagcacta gaggaagaca aggatcccgc catgagcagg cacaagacag ctccaggcac    9300
tcagcatccc aatacggtca ggacaccatt cgtggacacc cggggtcaag cagaggagga    9360
aggcaggggt accaccacga gcattcggta gatagctctg gacactcagg tcccatcac    9420 agccacacca catcccaggg aaggtctgat gcctcccgtg ggcagtcagg atccagaagt    9480
gcaagcagaa caacacgtaa tgaggaacaa tcaggagaca gctccaggca ctcagtgtca    9540
```

```
cgtcaccatg aagcttccac tcatgccgac atctctagac actcacaggc agtccaggga   9600
caatcagagg ggtccaggag aagcaggcgc cagggatcca gtgtgagcca ggacagtgac   9660
agtgagggac attcagaaga ctctgagagg tggtctgggt ctgcttccag aaaccatcgt   9720
ggatctgttc aggagcagtc aaggcacggc tccagacacc ccaggtccca tcacgaagac   9780
agagccggtc acgggcactc tgcagaccgc tccagacaat caggcactcg tcacgcagag   9840
acttcctctg gtggacaggc tgcatcatcc catgaacagg caagatcaag tccaggagag   9900
agacacggat cccgccacca gcagtcagca gacagctcca gacactcagg cattccgcgt   9960
ggacaagctt catctgcagt cagagacagt agacactggg ggtccagtgg tagtcaggcc  10020
agtgatagtg agggacattc agaagagtca gacacacagt cagtgtcagg ccatggacag  10080
gctgggcccc atcagcagag ccaccaagag tccgcacgtg accggtcagg gggaaggtct  10140
ggacgttcag ggtcttttcct ctaccaggtg agcactcatg aacagtctga gtctgcccat  10200
gggcggacca ggaccagcac tggacgaaga caaggatccc accacgagca ggcacgagac  10260
agctccaggc actcagcgtc ccaagagggt caggacacca ttcgtggaca cccggggtca  10320
agcagaagag gaaggcaggg atcccactac gagcaatcgg tagataggtc tggacactca  10380
gggtcccatc acagccacac cacatcccag ggaaggtctg atgcctcccg tgggcagtca  10440
ggatccagaa gtgccagcag acaaactcgt aatgacgaac aatcaggaga tggctccagg  10500
cactcatggt cgcatcacca tgaagcttcc actcaggcgg acagctctag acactcacag  10560
tccggccagg gacaatcagc ggggcccagg acaagcagga accagggatc cagtgttagc  10620
caggacagtg acagtcaggg acactcagaa gactctgaga ggtggtctgg gtctgcttcc  10680
agaaaccatc gtggatctgc tcaggagcag tcaagagatg gctccagaca ccccacgtcc  10740
catcacgaag acagagccgg tcacgggcac tctgcagaga gctccagaca atcaggcact  10800
catcatgcag agaattcctc tggtggacag gctgcatcat cccatgaaca ggcaagatca  10860
agtgcaggag agagacatgg atcccaccac cagcagtcag cagacagctc cagacactca  10920
ggcattgggc acggacaagc ttcatctgca gtcagagaca gtggacaccg agggtccagt  10980
ggtagtcagg ccagtgacag tgagggacat tcagaagact cagacacaca gtcagtgtca  11040
gcccacggac aggctgggcc ccatcagcag agccaccaag agtccacacg tggccggtca  11100
gcaggaaggt ctggacgttc aggtctcttc ctctaccagg tgagcactca tgaacagtct  11160
gagtctgccc atggacgggc tgggcccagt actggaggaa gacaaggatc cgccacgag  11220 caggcacgag acagctccag gcactcagcg tcccaagagg gtcaggacac cattcgtgga  11280
cacccggggt caaggagagg aggaagacag ggatcctacc acgagcaatc ggtagatagg  11340
tctggacact cagggtccca tcacagccac accacatccc agggaaggtc tgatgcctcc  11400
catgggcagt caggatccag aagtgcaagc agagaaacac gtaatgagga acagtcagga  11460
gacggctcca ggcactcagg gtcgcgtcac catgaagctt ccactcaggc tgacagctct  11520
agacactcac agtccggcca gggtgaatca gcggggtcca ggagaagcag cgccaggga   11580 tccagtgtta gccaggacag tgacagtgag gcatacccag aggactctga gaggcgatct  11640
gagtctgctt ccagaaacca tcatggatct tctcgggagc agtcaagaga tggctccaga  11700
caccccggat cctctcaccg cgatacagcc agtcatgtac agtcttcacc tgtacagtca  11760
gactctagta ccgctaagga acatggtcac tttagtagtc tttcacaaga ttctgcgtat  11820
cactcaggaa tacagtcacg tggcagtcct cacagttcta gttcttatca ttatcaatct  11880
```

```
gagggcactg aaaggcaaaa aggtcaatca ggtttagttt ggagacatgg cagctatggt    11940
agtgcagatt atgattatgg tgaatccggg tttagacact ctcagcacgg aagtgttagt    12000
tacaattcca atcctgttgt tttcaaggaa agatctgata tctgtaaagc aagtgcgttt    12060
ggtaaagatc atccaaggta ttatgcaacg tatattaata aggacccagg tttatgtggc    12120
cattctagtg atatatcgaa acaactggga tttagtcagt cacagagata ctattactat    12180
gagtaa                                                               12186
```

<210> SEQ ID NO 547
<211> LENGTH: 975
<212> TYPE: DNA
<213> ORGANISM: Homo sapiens
<220> FEATURE:
<221> NAME/KEY:
<223> OTHER INFORMATION: Human Profilaggrin Repeat 1

<400> SEQUENCE: 547

```
cctgactctg cccatggacg gaccgggacc agcactggag gaagacaagg atcgcaccac      60
gagcaggcac gagacagctc caggcattca gcgtcccaag agggtcagga caccattcgt     120
ggacacccgg ggtcaagcag aggaggaagg cagggatccc accacgagca atcggtaaat     180
aggtctggac actcaggttc ccatcacagc cacaccacat cccagggaag gtctgatgcc     240
tcccatgggc agtcaggatc cagaagtgca agcagacaaa cacgaaatga ggaacaatca     300
ggagacggca ccaggcactc agggtcacgt catcatgaag cttcctctca ggctgacagc     360
tctagacact cacaggtggg ccagggacaa tcatcggggc ccaggacaag taggaaccag     420
ggatccagtg ttagccagga cagtgacagt cagggacact cagaagactc tgagaggtgg     480
tctgggtctg cttccagaaa ccatcatgga tctgctcagg agcagtcaag agatggctcc     540
agacacccca ggtcccatca cgaagacaga gctggtcatg ggcactctgc agacagctcc     600
agaaaatcag gcactcgtca cacacagaat tcctctagtg acaggctgc gtcatcccat      660 gaacaggcaa gatcaagtgc aggagaaaga catggatccc gccaccagct ccagtcagca     720
gacagctcca gacactcagg cactgggcac ggacaagctt catctgcagt cagagacagt     780
ggacaccgag ggtccagtgg tagtcaggcc actgacagtg agggacattc agaagactca     840
gacacacagt cagtgtcagg ccatggacag gctggtcacc atcagcagag ccaccaagag     900
tccgcacgtg accggtcagg ggaaaggtct cgacgttcag ggtctttcct ctaccaggtg     960
agcactcata aacag                                                     975
```

<210> SEQ ID NO 548
<211> LENGTH: 325
<212> TYPE: PRT
<213> ORGANISM: Homo sapiens
<220> FEATURE:
<221> NAME/KEY:
<223> OTHER INFORMATION: Human Profilaggrin Repeat 1

<400> SEQUENCE: 548

```
Pro Asp Ser Ala His Gly Arg Thr Gly Thr Ser Thr Gly Gly Arg Gln
1               5                   10                  15

Gly Ser His His Glu Gln Ala Arg Asp Ser Ser Arg His Ser Ala Ser
            20                  25                  30

Gln Glu Gly Gln Asp Thr Ile Arg Gly His Pro Gly Ser Ser Arg Gly
        35                  40                  45

Gly Arg Gln Gly Ser His His Glu Gln Ser Val Asn Arg Ser Gly His
    50                  55                  60
```

```
Ser Gly Ser His His Ser His Thr Thr Ser Gln Gly Arg Ser Asp Ala
 65                  70                  75                  80

Ser His Gly Gln Ser Gly Ser Arg Ser Ala Ser Arg Gln Thr Arg Asn
             85                  90                  95

Glu Glu Gln Ser Gly Asp Gly Thr Arg His Ser Gly Ser Arg His His
            100                 105                 110

Glu Ala Ser Ser Gln Ala Asp Ser Ser Arg His Ser Gln Val Gly Gln
        115                 120                 125

Gly Gln Ser Ser Gly Pro Arg Thr Ser Arg Asn Gln Gly Ser Ser Val
130                 135                 140

Ser Gln Asp Ser Asp Ser Gln Gly His Ser Glu Asp Ser Glu Arg Trp
145                 150                 155                 160

Ser Gly Ser Ala Ser Arg Asn His His Gly Ser Ala Gln Glu Gln Ser
                165                 170                 175

Arg Asp Gly Ser Arg His Pro Arg Ser His His Glu Asp Arg Ala Gly
            180                 185                 190

His Gly His Ser Ala Asp Ser Ser Arg Lys Ser Gly Thr Arg His Thr
        195                 200                 205

Gln Asn Ser Ser Gly Gln Ala Ala Ser Ser His Glu Gln Ala Arg
210                 215                 220

Ser Ser Ala Gly Glu Arg His Gly Ser Arg His Gln Leu Gln Ser Ala
225                 230                 235                 240

Asp Ser Ser Arg His Ser Gly Thr Gly His Gly Gln Ala Ser Ser Ala
                245                 250                 255

Val Arg Asp Ser Gly His Arg Gly Ser Ser Gly Ser Gln Ala Thr Asp
            260                 265                 270

Ser Glu Gly His Ser Glu Asp Ser Asp Thr Gln Ser Val Ser Gly His
        275                 280                 285

Gly Gln Ala Gly His His Gln Gln Ser His Gln Glu Ser Ala Arg Asp
290                 295                 300

Arg Ser Gly Glu Arg Ser Arg Arg Ser Gly Ser Phe Leu Tyr Gln Val
305                 310                 315                 320

Ser Thr His Lys Gln
            325

<210> SEQ ID NO 549
<211> LENGTH: 971
<212> TYPE: DNA
<213> ORGANISM: Homo sapiens
<220> FEATURE:
<221> NAME/KEY:
<223> OTHER INFORMATION: Human Profilaggrin Repeat 1 - 2282del4

<400> SEQUENCE: 549
cctgactctg cccatggacg gaccgggacc agcactggag gaagacaagg atcgcaccac      60
gagcaggcac gagacagctc caggcattca gcgtcccaag agggtcagga caccattcgt     120
ggacacccgg ggtcaagcag aggaggaagg cagggatccc accacgagca atcggtaaat     180
aggtctggac actcaggttc ccatcacagc cacaccacat cccagggaag gtctgatgcc     240
tcccatgggc agtcaggatc agaagtgcaa gcagacaaa cacgaaatga ggaacaatca     300
ggagacggca ccaggcactc agggtcacgt catcatgaag cttcctctca ggctgacagc     360
tctagacact cacaggtggg ccagggacaa tcatcgggc caggacaag taggaaccag     420 ggatccagtg ttagccagga cagtgacagt cagggacact cagaagactc tgagaggtgg     480
```

-continued

```
tctgggtctg cttccagaaa ccatcatgga tctgctcagg agcagtcaag agatggctcc    540
agacacccca ggtccatca cgaagacaga gctggtcatg ggcactctgc agacagctcc    600
agaaaatcag gcactcgtca cacacagaat tcctctagtg acaggctgc gtcatcccat    660 gaacaggcaa gatcaagtgc aggagaaaga catggatccc gccaccagct ccagtcagca    720
gacagctcca gacactcagg cactgggcac ggacaagctt catctgcagt cagagacagt    780
ggacaccgag ggtccagtgg tagtcaggcc actgacagtg agggacattc agaagactca    840
gacacacagt gtcaggccat ggacaggctg gtcaccatca gcagagccac caagagtccg    900
cacgtgaccg gtcaggggaa aggtctcgac gttcagggtc tttcctctac caggtgagca    960
ctcataaaca g                                                        971
```

```
<210> SEQ ID NO 550
<211> LENGTH: 323
<212> TYPE: PRT
<213> ORGANISM: Homo sapiens
<220> FEATURE:
<221> NAME/KEY:
<223> OTHER INFORMATION: Human Profilaggrin Repeat 1 - 2282del4
<220> FEATURE:
<221> NAME/KEY: MISC_FEATURE
<222> LOCATION: (319)..()
<223> OTHER INFORMATION: X = STOP
<220> FEATURE:
<221> NAME/KEY: MISC_FEATURE
<222> LOCATION: (1)..(323)
<223> OTHER INFORMATION: X = STOP

<400> SEQUENCE: 550

Pro Asp Ser Ala His Gly Arg Thr Gly Thr Ser Thr Gly Gly Arg Gln
1               5                   10                  15

Gly Ser His His Glu Gln Ala Arg Asp Ser Ser Arg His Ser Ala Ser
            20                  25                  30

Gln Glu Gly Gln Asp Thr Ile Arg Gly His Pro Gly Ser Ser Arg Gly
        35                  40                  45

Gly Arg Gln Gly Ser His His Glu Gln Ser Val Asn Arg Ser Gly His
    50                  55                  60

Ser Gly Ser His His Ser His Thr Thr Ser Gln Gly Arg Ser Asp Ala
65                  70                  75                  80

Ser His Gly Gln Ser Gly Ser Arg Ser Ala Ser Arg Gln Thr Arg Asn
                85                  90                  95

Glu Glu Gln Ser Gly Asp Gly Thr Arg His Ser Gly Ser Arg His His
            100                 105                 110

Glu Ala Ser Ser Gln Ala Asp Ser Ser Arg His Ser Gln Val Gly Gln
        115                 120                 125

Gly Gln Ser Ser Gly Pro Arg Thr Ser Arg Asn Gln Gly Ser Ser Val
    130                 135                 140

Ser Gln Asp Ser Asp Ser Gln Gly His Ser Glu Asp Ser Glu Arg Trp
145                 150                 155                 160

Ser Gly Ser Ala Ser Arg Asn His His Gly Ser Ala Gln Glu Gln Ser
                165                 170                 175

Arg Asp Gly Ser Arg His Pro Arg Ser His His Glu Asp Arg Ala Gly
            180                 185                 190

His Gly His Ser Ala Asp Ser Ser Arg Lys Ser Gly Thr Arg His Thr
        195                 200                 205

Gln Asn Ser Ser Ser Gly Gln Ala Ala Ser Ser His Glu Gln Ala Arg
    210                 215                 220
```

```
Ser Ser Ala Gly Glu Arg His Gly Ser Arg His Gln Leu Gln Ser Ala
225                 230                 235                 240

Asp Ser Ser Arg His Ser Gly Thr Gly His Gly Gln Ala Ser Ser Ala
            245                 250                 255

Val Arg Asp Ser Gly His Arg Gly Ser Ser Gly Ser Gln Ala Thr Asp
        260                 265                 270

Ser Glu Gly His Ser Glu Asp Ser Asp Thr Gln Cys Gln Ala Met Asp
    275                 280                 285

Arg Leu Val Thr Ile Ser Arg Ala Thr Lys Ser Pro His Val Thr Gly
290                 295                 300

Gln Gly Lys Gly Leu Asp Val Gln Gly Leu Ser Ser Thr Arg Xaa Ala
305                 310                 315                 320

Leu Ile Asn

<210> SEQ ID NO 551
<211> LENGTH: 975
<212> TYPE: DNA
<213> ORGANISM: Homo sapiens
<220> FEATURE:
<221> NAME/KEY:
<223> OTHER INFORMATION: Human Profilaggrin repeat 1 - R501X C>T

<400> SEQUENCE: 551
cctgactctg cccatggacg gaccgggacc agcactggag gaagacaagg atcgcaccac      60
gagcaggcat gagacagctc caggcattca gcgtcccaag agggtcagga caccattcgt     120
ggacacccgg ggtcaagcag aggaggaagg cagggatccc accacgagca atcggtaaat     180
aggtctggac actcaggttc ccatcacagc cacaccacat cccagggaag gtctgatgcc     240
tcccatgggc agtcaggatc agaagtgcaa gcagacaaaa cacgaaatga ggaacaatca     300
ggagacggca ccaggcactc agggtcacgt catcatgaag cttcctctca ggctgacagc     360
tctagacact cacaggtggg ccagggacaa tcatcggggc caggacaag taggaaccag      420
ggatccagtg ttagccagga cagtgacagt cagggacact cagaagactc tgagaggtgg     480
tctgggtctg cttccagaaa ccatcatgga tctgctcagg agcagtcaag agatggctcc     540
agacacccca ggtcccatca cgaagacaga gctggtcatg ggcactctgc agacagctcc     600
agaaaatcag gcactcgtca cacacagaat tcctctagtg acaggctgc gtcatcccat       660
gaacaggcaa gatcaagtgc aggagaaaga catggatccc gccaccagct ccagtcagca     720
gacagctcca gacactcagg cactgggcac ggacaagctt catctgcagt cagagacagt     780
ggacaccgag ggtccagtgg tagtcaggcc actgacagtg agggacattc agaagactca     840
gacacacagt cagtgtcagg ccatggacag gctggtcacc atcagcagag ccaccaagag     900
tccgcacgtg accggtcagg ggaaaggtct cgacgttcag ggtctttcct ctaccaggtg     960
agcactcata aacag                                                      975

<210> SEQ ID NO 552
<211> LENGTH: 325
<212> TYPE: PRT
<213> ORGANISM: Homo sapiens
<220> FEATURE:
<221> NAME/KEY:
<223> OTHER INFORMATION: Human Profilaggrin Repeat 1 R501X C>T
<220> FEATURE:
<221> NAME/KEY: MISC_FEATURE
<222> LOCATION: (1)..(325)
<223> OTHER INFORMATION: X = STOP

<400> SEQUENCE: 552
```

```
Pro Asp Ser Ala His Gly Arg Thr Gly Thr Ser Thr Gly Gly Arg Gln
1               5                   10                  15

Gly Ser His His Glu Gln Ala Xaa Asp Ser Ser Arg His Ser Ala Ser
            20                  25                  30

Gln Glu Gly Gln Asp Thr Ile Arg Gly His Pro Gly Ser Ser Arg Gly
        35                  40                  45

Gly Arg Gln Gly Ser His His Glu Gln Ser Val Asn Arg Ser Gly His
    50                  55                  60

Ser Gly Ser His His Ser His Thr Thr Ser Gln Gly Arg Ser Asp Ala
65                  70                  75                  80

Ser His Gly Gln Ser Gly Ser Arg Ser Ala Ser Arg Gln Thr Arg Asn
                85                  90                  95

Glu Glu Gln Ser Gly Asp Gly Thr Arg His Ser Gly Ser Arg His His
            100                 105                 110

Glu Ala Ser Ser Gln Ala Asp Ser Ser Arg His Ser Gln Val Gly Gln
        115                 120                 125

Gly Gln Ser Ser Gly Pro Arg Thr Ser Arg Asn Gln Gly Ser Ser Val
    130                 135                 140

Ser Gln Asp Ser Asp Ser Gln Gly His Ser Glu Asp Ser Glu Arg Trp
145                 150                 155                 160

Ser Gly Ser Ala Ser Arg Asn His His Gly Ser Ala Gln Glu Gln Ser
                165                 170                 175

Arg Asp Gly Ser Arg His Pro Arg Ser His His Glu Asp Arg Ala Gly
            180                 185                 190

His Gly His Ser Ala Asp Ser Ser Arg Lys Ser Gly Thr Arg His Thr
        195                 200                 205

Gln Asn Ser Ser Gly Gln Ala Ala Ser Ser His Glu Gln Ala Arg
    210                 215                 220

Ser Ser Ala Gly Glu Arg His Gly Ser Arg His Gln Leu Gln Ser Ala
225                 230                 235                 240

Asp Ser Ser Arg His Ser Gly Thr Gly His Gly Gln Ala Ser Ser Ala
                245                 250                 255

Val Arg Asp Ser Gly His Arg Gly Ser Ser Gly Ser Gln Ala Thr Asp
            260                 265                 270

Ser Glu Gly His Ser Glu Asp Ser Asp Thr Gln Ser Val Ser Gly His
        275                 280                 285

Gly Gln Ala Gly His His Gln Gln Ser His Gln Glu Ser Ala Arg Asp
    290                 295                 300

Arg Ser Gly Glu Arg Ser Arg Arg Ser Gly Ser Phe Leu Tyr Gln Val
305                 310                 315                 320

Ser Thr His Lys Gln
            325

<210> SEQ ID NO 553
<211> LENGTH: 5251
<212> TYPE: DNA
<213> ORGANISM: Homo sapiens

<400> SEQUENCE: 553
aggacaagca ggaaccgggg atccagtttt agccaggaca gtgacagtca gggacactca    60
gaagactctg agaggtggtc tgggtctgct tccagaaacc atcatggatc tgctcaggag   120
cagctaagag atggctccag acaccccagg tcccatcaag aagacagagc tggtcatggg   180
cactctgcag acagctccag acaatcaggc actcgtcaca cacagacttc ctctggtgga   240
```

-continued

```
caggctgcat catcccatga acaggcaaga tcaagtgcag gagaaagaca tggatcccac    300
caccagcagt cagcagacag ctccagacac tcaggcattg ggcacggaca agcttcatct    360
gcagtcagag acagtggaca ccgagggtac agtggtagtc aggccagtga caatgaggga    420
cattcagaag actcagacac acagtcagtg tcagcccacg acaggctgg gtcccatcag     480
cagagccacc aagagtccgc acgtggccgg tcaggggaaa cgtctggaca ttcagggtct    540
ttcctctacc aggtgagcac tcatgaacag tctgagtcct cccatggatg gacgggccc     600
agcactagag gaagacaagg atcccgccat gagcaggcac aagacagctc caggcactca    660
gcatcccaag acgtcagga caccattcgt ggacacccgg ggtcaagcag aggaggaagg     720
caggggtacc accacgagca ttcggtagat agctctggac actcagggtc ccatcacagc    780
cacaccacat cccagggaag gtctgatgcc tcccgtgggc agtcaggatc cagacgtgca    840
agcagaacaa cacgtaatga ggaacaatca ggagacggct ccaggcactc agggtcgcgt    900
caccatgaag cttccactca tgccgacatc tctagacact cacaggcagt ccagggacaa    960
tcagaggggt ccaggagaag caggcgccag ggatccagtg ttagccagga cagtgacagt   1020
gagggacatt cagaagactc tgagaggtgg tctgggtctg cttccagaaa ccatcatgga   1080
tctgctcagg agcagctaag agatggctcc agacacccca ggtcccatca agaaggcaga   1140
gctggtcatg ggcactctgc agacagctcc agacaatcag gcactcgtca cacacagact   1200
tcctctggtg acaggctgc atcatcycat gaacaggcaa gatcaagtgc aggagaaaga    1260
catggatccc accaccagca gtcagcgac agctccagac actcaggcat gggcacggaa    1320
caagcttcat ctgcagtcag agacagtgga caccgagggt acagtggtag tcaggccagt   1380
gacaatgagg gacattcaga agactcagac acacagtcag tgtcagccca cggacaggct   1440
gggtcccatc agcagagcca caagagtcc gcacgtggcc ggtcagggga acgtctgga    1500
cattcaggat ctttcctcta ccaggtgagc actcatgaac agtctgagtc ctcccatgga   1560
tggacgggc ccagcactag aggaagacaa ggatcccgcc atgagcaggc acaagacagc    1620
tccaggcact cagcatccca agatggtcag gacaccattc gtggacaccc ggggtcaagc   1680
agaggaggaa ggcaggggta ccaccacgag cattcggtag atagctctgg acactcaggg   1740
tcccatcaca gccacaccac atcccaggga aggtctgatg cctcccgtgg gcagtcagga   1800
tccagaagtg caagcagaac aacacgtaat gaggaacaat caggagacgg ctccaggcac   1860
tcagggtcgc gtcaccatga agcttccact catgccgaca tctctagaca ctcacaggca   1920
gtccaggac aatcagaggg gtccaggaga agcaggcgcc agggatccag tgttagccag    1980
gacagtgaca gtgagggaca ttcagaagac tctgagaggt ggtctgggtc tgcttccaga   2040
aaccatcatg gatctgctca ggagcagcta agagatggct ccagacaccc caggtcccat   2100
caagaagaca gagctggtca tgggcactct gcagacagct ccagacaatc aggcactcgt   2160
cacacacagg cttcctctgg tggacaggct gcatcatccc atgaacaggc aagatcaagt   2220
gcaggagaaa gacatggatc ccaccaccag cagtcagcag acagctccag acactcaggc   2280
attgggcacg gacaagcttc atctgcagtc agacagtg acaccgagg gtacagtggt      2340
agtcaggcca gtgacaatga gggacattca gaagactcag acacacagtc agtgtcagcc   2400
cacggacagg ctgggtccca tcagcagagc caccaagagt ccgcacgtgg ccggtcaggg   2460
gaaacgtctg gacattcagg atctttcctc taccaggtga gcactcatga acagtctgag   2520
tcctcccatg gatggacggg gcccagcact agaggaagac aaggatcccg ccatgagcag   2580
```

```
gcacaagaca gctccaggca ctcagcatcc caagacggtc aggacaccat tcgtggacac      2640
ccggggtcaa gcagaggagg aaggcagggg taccaccacg agcattcggt agatagctct      2700
ggacactcag ggtcccatca cagccacacc acatcccagg gaaggtctga tgcctcccgt      2760
gggcagtcag gatccagaag tgcaagcaga acaacacgta atgaggaaca atcaggagac      2820
agctccaggc actcagggtc gcgtcaccat gaagcttcca ctcatgccga catctctaga      2880
cactcacagg cagtccaggg acaatcagag gggtccagga gaagcaggcg ccagggatcc      2940
agtgttagcc aggacagtga cagtgaggga cattcagaag actctgagag gtggtctggg      3000
tctgcttcca gaaaccatcg tggatctgtt caggagcagt caaggcacgg ctccagacac      3060
cccaggtccc atcacgaaga cagagccggt cacgggcact ctgcagaccg ctccagacaa      3120
tcaggcactc gtcacgcaga gacttcctct ggtggacagg ctgcatcatc ccatgaacag      3180
gcaagatcaa gtccaggaga gagacacgga tcccgccacc agcagtcagc agacagctcc      3240
agacactcag gcattccgcg tggacaggct tcatctgcag tcagacagag tagacactgg      3300
gggtccagtg gtagtcaagc cagtgatagt gagggacatt cagaagagtc agacacacag      3360
tcagtgtcag gccatggaca ggctgggccc catcagcaga gccaccaaga gtccgcacgt      3420
gaccggtcag ggggaaggtc tggacgttca gggtctttcc tctaccaggt gagcactcat      3480
gaacagtctg agtccgccca tgggcggacc aggaccagca ctggacgaag acaaggatcc      3540
caccacgagc aggcacgaga cagctccagg cactcagcgt cccaagaggg tcaggacacc      3600
attcgtgcac acccggggtc aagcagaaga ggaaggcagg gatcccacta cgagcaatcg      3660
gtagataggt ctggacactc agggtcccat cacagccaca ccacatccca gggaaggtct      3720
gatgcctccc gtgggcagtc aggatccaga agtgccagca gacaaactcg taacgacgaa      3780
caatcaggag acggctccag gcactcatgg tcgcatcacc atgaagcttc cactcaggcg      3840
gacagctcta gacactcaca gtccggccag ggacaatcag cggggcccag tacaagcagg      3900
aaccagggat ccagtgttag ccaggacagt gacagtcagg gacactcaga agactctgag      3960
aggtggtctg ggtctgcttc cagaaaccat catggatctg ctggggagca gtcaagagat      4020
ggctccagac accctgggtc ccatcaagaa gacagagccg gtcacgggca ctctgcagac      4080
agccccagac aatcaggcac tcgtcacaca gagtcttcct ctcgtggaca ggctgcgtca      4140
tcccatgaac aggcaagatc aagtgcagga gaaagacatg gatcccacca ccagctccag      4200
tcagcagaca gctccagaca cgcaggcatt gggcacggac aagcttcatc tgcagtcaga      4260
gacagtggac accgagggta cagtggtagt caggccactg acagtgaggg acattcagaa      4320
gactcagaca cacagtcagt gtcagcacag ggaaaagctg gcccccatca gcagagccac      4380
aaagagtccg cacgtggcca gtcagggaa agctctagac gttcagggtc tttcctctac      4440
caggtgagca ctcatgaaca gtctgagtct gcccatggac gggctgggcc cagtactgga      4500
ggaagacaag gatcccacca cgagcaggca cgagacagct ccaggcactc agcgtcccaa      4560
gagggtcagg acaccattcg tggacacccg gggtcaagga gaggaggaag acagggatcc      4620
taccacgagc aatcggtaga taggtctgga cactcagggt cccatcacag ccacaccaca      4680 tcccaggaa ggtctgatgc ctcccatggg cagtcaggat ccagaagtgc aagcagaaa       4740 acacgtaatg aggaacagtc aggagacggc tccaggcact cagggtcgcg tcaccatgaa      4800
gcttccactc aggctgacag ctctagacac tcacagtccg gccagggtga atcagcgggg      4860
tccaggagaa gcaggcgcca gggatccagt gttagccagg acagtgacag tgaggcatac      4920
ccagaggact ctgagaggcg atctgagtct gcttccagaa accatcatgg atcttctcgg      4980
```

```
gagcagtcaa gagatggctc cagacacccc ggatcctctc accgcgatac agccagtcat    5040
gtacagtctt cacctgtaca gtcagactct agtaccgcta aggaacatgg tcactttagt    5100
agtctttcac aagattctgc gtatcactca ggaatacagt cacgtggcag tcctcacagt    5160
tctagttctt atcattatca atctgagggc actgaaaggc aaaaaggtca atcaggttta    5220
gtttggagac atggcagcta tggtagtgca g                                    5251
```

<210> SEQ ID NO 554
<211> LENGTH: 1750
<212> TYPE: PRT
<213> ORGANISM: Homo sapiens

<400> SEQUENCE: 554

```
Arg Thr Ser Arg Asn Arg Gly Ser Ser Phe Ser Gln Asp Ser Asp Ser
1               5                   10                  15

Gln Gly His Ser Glu Asp Ser Glu Arg Trp Ser Gly Ser Ala Ser Arg
            20                  25                  30

Asn His His Gly Ser Ala Gln Glu Gln Leu Arg Asp Gly Ser Arg His
        35                  40                  45

Pro Arg Ser His Gln Glu Asp Arg Ala Gly His Gly His Ser Ala Asp
    50                  55                  60

Ser Ser Arg Gln Ser Gly Thr Arg His Thr Gln Thr Ser Ser Gly Gly
65                  70                  75                  80

Gln Ala Ala Ser Ser His Glu Gln Ala Arg Ser Ser Ala Gly Glu Arg
                85                  90                  95

His Gly Ser His His Gln Ser Ala Asp Ser Ser Arg His Ser Gly
            100                 105                 110

Ile Gly His Gly Gln Ala Ser Ser Ala Val Arg Asp Ser Gly His Arg
        115                 120                 125

Gly Tyr Ser Gly Ser Gln Ala Ser Asp Asn Glu Gly His Ser Glu Asp
    130                 135                 140

Ser Asp Thr Gln Ser Val Ser Ala His Gly Gln Ala Gly Ser His Gln
145                 150                 155                 160

Gln Ser His Gln Glu Ser Ala Arg Gly Arg Ser Gly Glu Thr Ser Gly
                165                 170                 175

His Ser Gly Ser Phe Leu Tyr Gln Val Ser Thr His Glu Gln Ser Glu
            180                 185                 190

Ser Ser His Gly Trp Thr Gly Pro Ser Thr Arg Gly Arg Gln Gly Ser
        195                 200                 205

Arg His Glu Gln Ala Gln Asp Ser Ser Arg His Ser Ala Ser Gln Asp
    210                 215                 220

Gly Gln Asp Thr Ile Arg Gly His Pro Gly Ser Ser Arg Gly Gly Arg
225                 230                 235                 240

Gln Gly Tyr His His Glu His Ser Val Asp Ser Ser Gly His Ser Gly
                245                 250                 255

Ser His His Ser His Thr Thr Ser Gln Gly Arg Ser Asp Ala Ser Arg
            260                 265                 270

Gly Gln Ser Gly Ser Arg Arg Ala Ser Arg Thr Thr Arg Asn Glu Glu
        275                 280                 285

Gln Ser Gly Asp Gly Ser Arg His Ser Gly Ser Arg His His Glu Ala
    290                 295                 300

Ser Thr His Ala Asp Ile Ser Arg His Ser Gln Ala Val Gln Gly Gln
305                 310                 315                 320
```

```
Ser Glu Gly Ser Arg Ser Arg Gln Gly Ser Val Ser Gln
            325                 330             335

Asp Ser Asp Ser Glu Gly His Ser Glu Asp Ser Glu Arg Trp Ser Gly
            340                 345                 350

Ser Ala Ser Arg Asn His His Gly Ser Ala Gln Glu Gln Leu Arg Asp
            355                 360                 365

Gly Ser Arg His Pro Arg Ser His Gln Glu Gly Arg Ala Gly His Gly
            370                 375                 380

His Ser Ala Asp Ser Ser Arg Gln Ser Gly Thr Arg His Thr Gln Thr
385                 390                 395                 400

Ser Ser Gly Gly Gln Ala Ala Ser Ser His Glu Gln Ala Arg Ser Ser
            405                 410                 415

Ala Gly Glu Arg His Gly Ser His His Gln Gln Ser Ala Asp Ser Ser
            420                 425                 430

Arg His Ser Gly Ile Gly His Gly Gln Ala Ser Ser Ala Val Arg Asp
            435                 440                 445

Ser Gly His Arg Gly Tyr Ser Gly Ser Gln Ala Ser Asp Asn Glu Gly
            450                 455                 460

His Ser Glu Asp Ser Asp Thr Gln Ser Val Ser Ala His Gly Gln Ala
465                 470                 475                 480

Gly Ser His Gln Gln Ser His Gln Glu Ser Ala Arg Gly Arg Ser Gly
            485                 490                 495

Glu Thr Ser Gly His Ser Gly Ser Phe Leu Tyr Gln Val Ser Thr His
            500                 505                 510

Glu Gln Ser Glu Ser Ser His Gly Trp Thr Gly Pro Ser Thr Arg Gly
            515                 520                 525

Arg Gln Gly Ser Arg His Glu Gln Ala Gln Asp Ser Ser Arg His Ser
            530                 535                 540

Ala Ser Gln Asp Gly Gln Asp Thr Ile Arg Gly His Pro Gly Ser Ser
545                 550                 555                 560

Arg Gly Gly Arg Gln Gly Tyr His His Glu His Ser Val Asp Ser Ser
            565                 570                 575

Gly His Ser Gly Ser His His Ser His Thr Thr Ser Gln Gly Arg Ser
            580                 585                 590

Asp Ala Ser Arg Gly Gln Ser Gly Ser Arg Ser Ala Ser Arg Thr Thr
            595                 600                 605

Arg Asn Glu Glu Gln Ser Gly Asp Gly Ser Arg His Ser Gly Ser Arg
            610                 615                 620

His His Glu Ala Ser Thr His Ala Asp Ile Ser Arg His Ser Gln Ala
625                 630                 635                 640

Val Gln Gly Gln Ser Glu Gly Ser Arg Arg Ser Arg Arg Gln Gly Ser
            645                 650                 655

Ser Val Ser Gln Asp Ser Asp Ser Glu Gly His Ser Glu Asp Ser Glu
            660                 665                 670

Arg Trp Ser Gly Ser Ala Ser Arg Asn His His Gly Ser Ala Gln Glu
            675                 680                 685

Gln Leu Arg Asp Gly Ser Arg His Pro Arg Ser His Gln Glu Asp Arg
            690                 695                 700

Ala Gly His Gly His Ser Ala Asp Ser Ser Arg Gln Ser Gly Thr Arg
705                 710                 715                 720

His Thr Gln Ala Ser Ser Gly Gly Gln Ala Ala Ser Ser His Glu Gln
            725                 730                 735

Ala Arg Ser Ser Ala Gly Glu Arg His Gly Ser His His Gln Gln Ser
```

-continued

```
                740                 745                 750
Ala Asp Ser Ser Arg His Ser Gly Ile Gly His Gly Gln Ala Ser Ser
                755                 760                 765
Ala Val Arg Asp Ser Gly His Arg Gly Tyr Ser Gly Ser Gln Ala Ser
                770                 775             780
Asp Asn Glu Gly His Ser Glu Asp Ser Asp Thr Gln Ser Val Ser Ala
785                 790                 795                 800
His Gly Gln Ala Gly Ser His Gln Gln Ser His Gln Glu Ser Ala Arg
                    805                 810                 815
Gly Arg Ser Gly Glu Thr Ser Gly His Ser Gly Ser Phe Leu Tyr Gln
                820                 825                 830
Val Ser Thr His Glu Gln Ser Glu Ser Ser His Gly Trp Thr Gly Pro
                835                 840                 845
Ser Thr Arg Gly Arg Gln Gly Ser Arg His Glu Gln Ala Gln Asp Ser
                850                 855                 860
Ser Arg His Ser Ala Ser Gln Asp Gly Gln Asp Thr Ile Arg Gly His
865                 870                 875                 880
Pro Gly Ser Ser Arg Gly Gly Arg Gln Gly Tyr His His Glu His Ser
                    885                 890                 895
Val Asp Ser Ser Gly His Ser Gly Ser His His Ser His Thr Thr Ser
                900                 905                 910
Gln Gly Arg Ser Asp Ala Ser Arg Gly Gln Ser Gly Ser Arg Ser Ala
                915                 920                 925
Ser Arg Thr Thr Arg Asn Glu Glu Gln Ser Gly Asp Ser Ser Arg His
                930                 935                 940
Ser Gly Ser Arg His His Glu Ala Ser Thr His Ala Asp Ile Ser Arg
945                 950                 955                 960
His Ser Gln Ala Val Gln Gly Gln Ser Glu Gly Ser Arg Ser Arg
                    965                 970                 975
Arg Gln Gly Ser Ser Val Ser Gln Asp Ser Asp Ser Glu Gly His Ser
                980                 985                 990
Glu Asp Ser Glu Arg Trp Ser Gly  Ser Ala Ser Arg Asn  His Arg Gly
                995                 1000                1005
Ser Val  Gln Glu Gln Ser Arg  His Gly Ser Arg His  Pro Arg Ser
    1010                1015                1020
His His  Glu Asp Arg Ala Gly  His Gly His Ser Ala  Asp Arg Ser
    1025                1030                1035
Arg Gln  Ser Gly Thr Arg His  Ala Glu Thr Ser  Gly Gly Gln
    1040                1045                1050
Ala Ala  Ser Ser His Glu Gln  Ala Arg Ser Ser Pro  Gly Glu Arg
    1055                1060                1065
His Gly  Ser Arg His Gln Gln  Ser Ala Asp Ser Ser  Arg His Ser
    1070                1075                1080
Gly Ile  Pro Arg Gly Gln Ala  Ser Ser Ala Val Arg  Asp Ser Arg
    1085                1090                1095
His Trp  Gly Ser Ser Gly Ser  Gln Ala Ser Asp Ser  Glu Gly His
    1100                1105                1110
Ser Glu  Glu Ser Asp Thr Gln  Ser Val Ser Gly His  Gly Gln Ala
    1115                1120                1125
Gly Pro  His Gln Gln Ser His  Gln Glu Ser Ala Arg  Asp Arg Ser
    1130                1135                1140
Gly Gly  Arg Ser Gly Arg Ser  Gly Ser Phe Leu Tyr  Gln Val Ser
    1145                1150                1155
```

```
Thr His Glu Gln Ser Glu Ser Ala His Gly Arg Thr Arg Thr Ser
1160                1165                1170

Thr Gly Arg Arg Gln Gly Ser His His Glu Gln Ala Arg Asp Ser
1175                1180                1185

Ser Arg His Ser Ala Ser Gln Glu Gly Gln Asp Thr Ile Arg Ala
1190                1195                1200

His Pro Gly Ser Ser Arg Arg Gly Arg Gln Gly Ser His Tyr Glu
1205                1210                1215

Gln Ser Val Asp Arg Ser Gly His Ser Gly Ser His His Ser His
1220                1225                1230

Thr Thr Ser Gln Gly Arg Ser Asp Ala Ser Arg Gly Gln Ser Gly
1235                1240                1245

Ser Arg Ser Ala Ser Arg Gln Thr Arg Asn Asp Glu Gln Ser Gly
1250                1255                1260

Asp Gly Ser Arg His Ser Trp Ser His His Glu Ala Ser Thr
1265                1270                1275

Gln Ala Asp Ser Ser Arg His Ser Gln Ser Gly Gln Gly Gln Ser
1280                1285                1290

Ala Gly Pro Ser Thr Ser Arg Asn Gln Gly Ser Ser Val Ser Gln
1295                1300                1305

Asp Ser Asp Ser Gln Gly His Ser Glu Asp Ser Glu Arg Trp Ser
1310                1315                1320

Gly Ser Ala Ser Arg Asn His His Gly Ser Ala Gly Glu Gln Ser
1325                1330                1335

Arg Asp Gly Ser Arg His Pro Gly Ser His Gln Glu Asp Arg Ala
1340                1345                1350

Gly His Gly His Ser Ala Asp Ser Pro Arg Gln Ser Gly Thr Arg
1355                1360                1365

His Thr Glu Ser Ser Ser Arg Gly Gln Ala Ala Ser Ser His Glu
1370                1375                1380

Gln Ala Arg Ser Ser Ala Gly Glu Arg His Gly Ser His His Gln
1385                1390                1395

Leu Gln Ser Ala Asp Ser Ser Arg His Ala Gly Ile Gly His Gly
1400                1405                1410

Gln Ala Ser Ser Ala Val Arg Asp Ser Gly His Arg Gly Tyr Ser
1415                1420                1425

Gly Ser Gln Ala Thr Asp Ser Glu Gly His Ser Glu Asp Ser Asp
1430                1435                1440

Thr Gln Ser Val Ser Ala Gln Gly Lys Ala Gly Pro His Gln Gln
1445                1450                1455

Ser His Lys Glu Ser Ala Arg Gly Gln Ser Gly Glu Ser Ser Arg
1460                1465                1470

Arg Ser Gly Ser Phe Leu Tyr Gln Val Ser Thr His Glu Gln Ser
1475                1480                1485

Glu Ser Ala His Gly Arg Ala Gly Pro Ser Thr Gly Gly Arg Gln
1490                1495                1500

Gly Ser His His Glu Gln Ala Arg Asp Ser Ser Arg His Ser Ala
1505                1510                1515

Ser Gln Glu Gly Gln Asp Thr Ile Arg Gly His Pro Gly Ser Arg
1520                1525                1530

Arg Gly Gly Arg Gln Gly Ser Tyr His Glu Gln Ser Val Asp Arg
1535                1540                1545
```

| | | | | | | | | | | |
|---|---|---|---|---|---|---|---|---|---|---|
| Ser | Gly | His | Ser | Gly | Ser | His | His | Ser | His | Thr | Thr | Ser | Gln | Gly |
| 1550 | | | | | 1555 | | | | | 1560 | | | | |

Arg Ser Asp Ala Ser His Gly Gln Ser Gly Ser Arg Ser Ala Ser
1565 1570 1575

Arg Glu Thr Arg Asn Glu Glu Gln Ser Gly Asp Gly Ser Arg His
1580 1585 1590

Ser Gly Ser Arg His His Glu Ala Ser Thr Gln Ala Asp Ser Ser
1595 1600 1605

Arg His Ser Gln Ser Gly Gln Gly Glu Ser Ala Gly Ser Arg Arg
1610 1615 1620

Ser Arg Arg Gln Gly Ser Ser Val Ser Gln Asp Ser Asp Ser Glu
1625 1630 1635

Ala Tyr Pro Glu Asp Ser Glu Arg Arg Ser Glu Ser Ala Ser Arg
1640 1645 1650

Asn His His Gly Ser Ser Arg Glu Gln Ser Arg Asp Gly Ser Arg
1655 1660 1665

His Pro Gly Ser Ser His Arg Asp Thr Ala Ser His Val Gln Ser
1670 1675 1680

Ser Pro Val Gln Ser Asp Ser Ser Thr Ala Lys Glu His Gly His
1685 1690 1695

Phe Ser Ser Leu Ser Gln Asp Ser Ala Tyr His Ser Gly Ile Gln
1700 1705 1710

Ser Arg Gly Ser Pro His Ser Ser Ser Tyr His Tyr Gln Ser
1715 1720 1725

Glu Gly Thr Glu Arg Gln Lys Gly Gln Ser Gly Leu Val Trp Arg
1730 1735 1740

His Gly Ser Tyr Gly Ser Ala
1745 1750

<210> SEQ ID NO 555
<211> LENGTH: 5251
<212> TYPE: DNA
<213> ORGANISM: Homo sapiens

<400> SEQUENCE: 555

```
aggacaagca ggaaccgggg atccagtttt agccaggaca gtgacagtca gggacactca      60
gaagactctg agaggtggtc tgggtctgct tccagaaacc atcatggatc tgctcaggag     120
cagctaagag atggctccag acaccccagg tcccatcaag aagacagagc tggtcatggg     180
cactctgcag acagctccag acaatcaggc actcgtcaca cacagacttc ctctggtgga     240
caggctgcat catcccatga acaggcaaga tcaagtgcag gagaaagaca tggatcccac     300
caccagcagt cagcagacag ctccagacac tcaggcattg gcacggacag agcttcatct     360
gcagtcagag acagtggaca ccgagggtac agtggtagtc aggccagtga caatgaggga     420
cattcagaag actcagacac acagtcagtg tcagcccacg acaggctggg tcccatcag      480
cagagccacc aagagtccgc acgtggccgg tcaggggaaa cgtctggaca ttcagggtct     540
ttcctctacc aggtgagcac tcatgaacag tctgagtcct cccatggatg acggggccc      600
agcactagag gaagacaagg atcccgccat gagcaggcac aagacagctc caggcactca     660
gcatcccaag acggtcagga caccattcgt ggacacccgg ggtcaagcag aggaggaagg     720
caggggtacc accacgagca ttcggtagat agctctggac actcagggtc ccatcacagc     780
cacaccacat cccagggaag gtctgatgcc tcccgtgggc agtcaggatc cagacgtgca     840
agcagaacaa cacgtaatga ggaacaatca ggagacggct ccaggcactc agggtcgcgt     900
```

```
caccatgaag cttccactca tgccgacatc tctagacact cacaggcagt ccagggacaa      960
tcagagggt  ccaggagaag caggcgccag ggatccagtg ttagccagga cagtgacagt     1020
gagggacatt cagaagactc tgagaggtgg tctgggtctg cttccagaaa ccatcatgga     1080
tctgctcagg agcagctaag agatggctcc agacacccca ggtccatca  agaaggcaga     1140
gctggtcatg ggcactctgc agacagctcc agacaatcag gcactcgtca cacacagact     1200
tcctctggtg gacaggctgc atcatcycat gaacaggcaa gatcaagtgc aggagaaaga     1260
catggatccc accaccagca gtcagcagac agctccagac actcaggcat gggcacgga      1320
caagcttcat ctgcagtcag agacagtgga caccgagggt acagtggtag tcaggccagt     1380
gacaatgagg gacattcaga agactcagac acacagtcag tgtcagccca cggacaggct     1440
gggtcccatc agcagagcca ccaagagtcc gcacgtggcc ggtcagggga aacgtctgga     1500
cattcaggat ctttcctcta ccaggtgagc actcatgaac agtctgagtc ctcccatgga     1560
tggacgggc  ccagcactag aggaagacaa ggatcccgcc atgagcaggc acaagacagc     1620
tccaggcact cagcatccca agacggtcag gacaccattc gtggacaccc ggggtcaagc     1680
agaggaggaa ggcaggggta ccaccacgag cattcggtag atagctctgg acactcaggg     1740
tcccatcaca gccacaccac atcccaggga aggtctgatg cctcccgtgg gcagtcagga     1800
tccagaagtg caagcagaac aacacgtaat gaggaacaat caggagacag ctccaggcac     1860
tcagggtcgc gtcaccatga agcttccact catgccgaca tctctagaca ctcacaggca     1920
gtccagggac aatcagaggg gtccaggaga agcaggcgcc agggatccag tgttagccag     1980
gacagtgaca gtgagggaca ttcagaagac tctgagaggt ggtctgggtc tgcttccaga     2040
aaccatcgtg gatctgttca ggagcagtca aggcacggct ccagacaccc caggtcccat     2100
cacgaagaca gagccggtca cgggcactct gcagaccgct ccagacaatc aggcactcgt     2160
cacgcagaga cttcctctgg tggacaggct gcatcatccc atgaacaggc aagatcaagt     2220
ccaggagaga gacacggatc ccgccaccag cagtcagcag acagctccag acactcaggc     2280
attccgcgtg gacaggcttc atctgcagtc agagacagta gacactgggg gtccagtggt     2340
agtcaagcca gtgatagtga gggacattca gaagagtcag acacacagtc agtgtcaggc     2400
catggacagg ctgggcccca tcagcagagc caccaagagt ccgcacgtga ccggtcaggg     2460
ggaaggtctg gacgttcagg gtcttcctc  taccaggtga gcactcatga acagtctgag     2520
tccgcccatg ggcggaccag gaccagcact ggacgaagac aaggatccca ccacgagcag     2580
gcacgagaca gctccaggca ctcagcgtcc aagagggtc  aggacaccat tcgtgcacac     2640
ccggggtcaa gcagaagagg aaggcaggga tcccactacg agcaatcggt agataggtct     2700
ggacactcag ggtcccatca cagccacacc acatcccagg gaaggtctga tgcctcccgt     2760
gggcagtcag gatccagaag tgccagcaga caaactcgta acgacgaaca atcaggagac     2820
ggctccaggc actcatggtc gcatcaccat gaagcttcca ctcaggcgga cagctctaga     2880
cactcacagt ccggccaggg acaatcagcg gggcccagta caagcaggaa ccagggatcc     2940
agtgttagcc aggacagtga cagtcaggga cactcagaag actctgagag gtggtctggg     3000
tctgcttcca gaaaccatca tggatctgct ggggagcagt caagagatgg ctccagacac     3060
cctgggtccc atcaagaaga cagagccggt cacgggcact ctgcagacag ccccagacaa     3120
tcaggcactc gtcacacaga gtcttcctct cgtggacagg ctgcgtcatc ccatgaacag     3180
gcaagatcaa gtgcaggaga aagacatgga tcccaccacc agctccagtc agcagacagc     3240
```

| | | |
|---|---|---|
| tccagacacg caggcattgg gcacggacaa gcttcatctg cagtcagaga cagtggacac | 3300 | |
| cgagggtaca gtggtagtca ggccactgac agtgagggac attcagaaga ctcagacaca | 3360 | |
| cagtcagtgt cagcacaggg aaaagctggg ccccatcagc agagccacaa agagtccgca | 3420 | |
| cgtggccagt caggggaaag ctctagacgt tcagggtctt tcctctacca ggtgagcact | 3480 | |
| catgaacagt ctgagtccac ccatggacag tctgtgccca gcactggagg aagacaagga | 3540 | |
| tcccaccatg atcaggcaca agacagctcc aggcactcag catcccaaga gggtcaggac | 3600 | |
| accattcgtg gacacccggg gccaagcaga ggaggaagac aggggtccca ccacgagcaa | 3660 | |
| tcggtagata ggtctggaca ctcagggtcc catcacagcc acaccacatc ccagggaagg | 3720 | |
| tctgatgcct cccgtgggca gtcaggaccc agaagtgcaa gcagacaaac acatgacaag | 3780 | |
| gaacaatcag gagacggctc taggcactca gggtcgcgtc atcatgaagc ttcctcttgg | 3840 | |
| gccgacagct ctagacactc acaggcagtc caggacaat cagaggggtc caggagaagc | 3900 | |
| aggcgccagg gatccagtgt tagccaggac agtgacagtc agggacactc agaagactct | 3960 | |
| gagaggcggt ctgggtctgc ttccagaaac catcgtggat ctgctcagga gcagtcaaga | 4020 | |
| gatggctcca gacaccccag gtcccatcac gaagacagag ccggtcatgg gcactctgca | 4080 | |
| gacagctcca gacaatcagg cactcatcat gcagagaatt cctctggtgg acagcctgca | 4140 | |
| tcatcccatg aacaggcaag atcaagtgca ggagagagac atggatccca ccaccagcag | 4200 | |
| tcagcagaca gctccagaca ctcaggcatt gggcacggac aagcttcatc tgcagtcaga | 4260 | |
| gacagtggac accgagggtc cagtggtagt caggccagtg acagtgaggg acattcagaa | 4320 | |
| gactcagaca cacagtcagt gtcagcccac ggacaggctg ggccccatca gcagagccac | 4380 | |
| caagagtcca cacgtggccg gtcagcagga aggtctggac gttcagggtc tttcctctac | 4440 | |
| caggtgagca ctcatgaaca gtctgagtct gcccatggac gggctgggcc cagtactgga | 4500 | |
| ggaagacaag gatcccacca cgagcaggca cgagacagct ccaggcactc agcgtcccaa | 4560 | |
| gagggtcagg acaccattcg tggacacccg gggtcaagga ggaggaagag acagggatcc | 4620 | |
| taccacgagc aatcggtaga taggtctgga cactcagggt cccatcacag ccacaccaca | 4680 | |
| tcccagggaa ggtctgatgc ctcccatggg cagtcaggat ccagaagtgc aagcagagaa | 4740 | |
| acacgtaatg aggaacagtc aggagacggc tccaggcact cagggtcgcg tcaccatgaa | 4800 | |
| gcttccactc aggctgacag ctctagacac tcacagtccg gccagggtga atcagcgggg | 4860 | |
| tccaggagaa gcaggcgcca gggatccagt gttagccagg acagtgacag tgaggcatac | 4920 | |
| ccagaggact ctgagaggcg atctgagtct gcttccagaa accatcatgg atcttctcgg | 4980 | |
| gagcagtcaa gagatggctc cagacacccc ggatcctctc accgcgatac agccagtcat | 5040 | |
| gtacagtctt cacctgtaca gtcagactct agtaccgcta aggaacatgg tcactttagt | 5100 | |
| agtctttcac aagattctgc gtatcactca ggaatacagt cacgtggcag tcctcacagt | 5160 | |
| tctagttctt atcattatca atctgagggc actgaaaggc aaaaaggtca atcaggttta | 5220 | |
| gtttggagac atggcagcta tggtagtgca g | 5251 | |

<210> SEQ ID NO 556
<211> LENGTH: 1750
<212> TYPE: PRT
<213> ORGANISM: Homo sapiens

<400> SEQUENCE: 556

Arg Thr Ser Arg Asn Arg Gly Ser Ser Phe Ser Gln Asp Ser Asp Ser
1               5                   10                  15

-continued

```
Gln Gly His Ser Glu Asp Ser Glu Arg Trp Ser Gly Ser Ala Ser Arg
             20                  25                  30

Asn His His Gly Ser Ala Gln Glu Gln Leu Arg Asp Gly Ser Arg His
         35                  40                  45

Pro Arg Ser His Gln Glu Asp Arg Ala Gly His Gly His Ser Ala Asp
     50                  55                  60

Ser Ser Arg Gln Ser Gly Thr Arg His Thr Gln Thr Ser Ser Gly Gly
65                  70                  75                  80

Gln Ala Ala Ser Ser His Glu Gln Ala Arg Ser Ser Ala Gly Glu Arg
                 85                  90                  95

His Gly Ser His His Gln Gln Ser Ala Asp Ser Ser Arg His Ser Gly
            100                 105                 110

Ile Gly His Gly Gln Ala Ser Ser Ala Val Arg Asp Ser Gly His Arg
        115                 120                 125

Gly Tyr Ser Gly Ser Gln Ala Ser Asp Asn Glu Gly His Ser Glu Asp
    130                 135                 140

Ser Asp Thr Gln Ser Val Ser Ala His Gly Ala Gly Ser His Gln
145                 150                 155                 160

Gln Ser His Gln Glu Ser Ala Arg Gly Arg Ser Gly Glu Thr Ser Gly
                165                 170                 175

His Ser Gly Ser Phe Leu Tyr Gln Val Ser Thr His Glu Gln Ser Glu
            180                 185                 190

Ser Ser His Gly Trp Thr Gly Pro Ser Thr Arg Gly Arg Gln Gly Ser
        195                 200                 205

Arg His Glu Gln Ala Gln Asp Ser Ser Arg His Ser Ala Ser Gln Asp
    210                 215                 220

Gly Gln Asp Thr Ile Arg Gly His Pro Gly Ser Ser Arg Gly Gly Arg
225                 230                 235                 240

Gln Gly Tyr His His Glu His Ser Val Asp Ser Ser Gly His Ser Gly
                245                 250                 255

Ser His His Ser His Thr Thr Ser Gln Gly Arg Ser Asp Ala Ser Arg
            260                 265                 270

Gly Gln Ser Gly Ser Arg Arg Ala Ser Arg Thr Thr Arg Asn Glu Glu
        275                 280                 285

Gln Ser Gly Asp Gly Ser Arg His Ser Gly Ser Arg His His Glu Ala
    290                 295                 300

Ser Thr His Ala Asp Ile Ser Arg His Ser Gln Ala Val Gln Gly Gln
305                 310                 315                 320

Ser Glu Gly Ser Arg Arg Ser Arg Gln Gly Ser Ser Val Ser Gln
                325                 330                 335

Asp Ser Asp Ser Glu Gly His Ser Glu Asp Ser Glu Arg Trp Ser Gly
            340                 345                 350

Ser Ala Ser Arg Asn His His Gly Ser Ala Gln Glu Gln Leu Arg Asp
        355                 360                 365

Gly Ser Arg His Pro Arg Ser His Gln Glu Gly Arg Ala Gly His Gly
    370                 375                 380

His Ser Ala Asp Ser Ser Arg Gln Ser Gly Thr Arg His Thr Gln Thr
385                 390                 395                 400

Ser Ser Gly Gly Gln Ala Ala Ser Ser His Glu Gln Ala Arg Ser Ser
                405                 410                 415

Ala Gly Glu Arg His Gly Ser His His Gln Gln Ser Ala Asp Ser Ser
            420                 425                 430

Arg His Ser Gly Ile Gly His Gly Gln Ala Ser Ser Ala Val Arg Asp
```

-continued

```
            435                 440                 445
Ser Gly His Arg Gly Tyr Ser Gly Ser Gln Ala Ser Asp Asn Glu Gly
        450                 455                 460
His Ser Glu Asp Ser Asp Thr Gln Ser Val Ser Ala His Gly Gln Ala
465                 470                 475                 480
Gly Ser His Gln Gln Ser His Gln Glu Ser Ala Arg Gly Arg Ser Gly
                    485                 490                 495
Glu Thr Ser Gly His Ser Gly Ser Phe Leu Tyr Gln Val Ser Thr His
                500                 505                 510
Glu Gln Ser Glu Ser Ser His Gly Trp Thr Gly Pro Ser Thr Arg Gly
            515                 520                 525
Arg Gln Gly Ser Arg His Glu Gln Ala Gln Asp Ser Ser Arg His Ser
        530                 535                 540
Ala Ser Gln Asp Gly Gln Asp Thr Ile Arg Gly His Pro Gly Ser Ser
545                 550                 555                 560
Arg Gly Gly Arg Gln Gly Tyr His His Glu His Ser Val Asp Ser Ser
                    565                 570                 575
Gly His Ser Gly Ser His His Ser His Thr Thr Ser Gln Gly Arg Ser
                580                 585                 590
Asp Ala Ser Arg Gly Gln Ser Gly Ser Arg Ser Ala Ser Arg Thr Thr
            595                 600                 605
Arg Asn Glu Glu Gln Ser Gly Asp Ser Ser Arg His Ser Gly Ser Arg
        610                 615                 620
His His Glu Ala Ser Thr His Ala Asp Ile Ser Arg His Ser Gln Ala
625                 630                 635                 640
Val Gln Gly Gln Ser Glu Gly Ser Arg Arg Ser Arg Arg Gln Gly Ser
                    645                 650                 655
Ser Val Ser Gln Asp Ser Asp Ser Glu Gly His Ser Glu Asp Ser Glu
                660                 665                 670
Arg Trp Ser Gly Ser Ala Ser Arg Asn His Arg Gly Ser Val Gln Glu
            675                 680                 685
Gln Ser Arg His Gly Ser Arg His Pro Arg Ser His His Glu Asp Arg
        690                 695                 700
Ala Gly His Gly His Ser Ala Asp Arg Ser Arg Gln Ser Gly Thr Arg
705                 710                 715                 720
His Ala Glu Thr Ser Ser Gly Gly Gln Ala Ala Ser Ser His Glu Gln
                    725                 730                 735
Ala Arg Ser Ser Pro Gly Glu Arg His Gly Ser Arg His Gln Gln Ser
                740                 745                 750
Ala Asp Ser Ser Arg His Ser Gly Ile Pro Arg Gly Gln Ala Ser Ser
            755                 760                 765
Ala Val Arg Asp Ser Arg His Trp Gly Ser Ser Gly Ser Gln Ala Ser
        770                 775                 780
Asp Ser Glu Gly His Ser Glu Glu Ser Asp Thr Gln Ser Val Ser Gly
785                 790                 795                 800
His Gly Gln Ala Gly Pro His Gln Gln Ser His Gln Glu Ser Ala Arg
                    805                 810                 815
Asp Arg Ser Gly Gly Arg Ser Gly Arg Ser Gly Ser Phe Leu Tyr Gln
                820                 825                 830
Val Ser Thr His Glu Gln Ser Glu Ser Ala His Gly Arg Thr Arg Thr
            835                 840                 845
Ser Thr Gly Arg Arg Gln Gly Ser His His Glu Gln Ala Arg Asp Ser
        850                 855                 860
```

```
Ser Arg His Ser Ala Ser Gln Glu Gly Gln Asp Thr Ile Arg Ala His
865                 870                 875                 880

Pro Gly Ser Ser Arg Gly Arg Gln Gly Ser His Tyr Glu Gln Ser
                885                 890                 895

Val Asp Arg Ser Gly His Ser Gly Ser His His Ser His Thr Thr Ser
                900                 905                 910

Gln Gly Arg Ser Asp Ala Ser Arg Gly Gln Ser Gly Ser Arg Ser Ala
                915                 920                 925

Ser Arg Gln Thr Arg Asn Asp Glu Gln Ser Gly Asp Gly Ser Arg His
930                 935                 940

Ser Trp Ser His His Glu Ala Ser Thr Gln Ala Asp Ser Ser Arg
945                 950                 955                 960

His Ser Gln Ser Gly Gln Gly Gln Ser Ala Gly Pro Ser Thr Ser Arg
                965                 970                 975

Asn Gln Gly Ser Ser Val Ser Gln Asp Ser Asp Ser Gln Gly His Ser
                980                 985                 990

Glu Asp Ser Glu Arg Trp Ser Gly Ser Ala Ser Arg Asn His His Gly
                995                 1000                1005

Ser Ala Gly Glu Gln Ser Arg Asp Gly Ser Arg His Pro Gly Ser
    1010                1015                1020

His Gln Glu Asp Arg Ala Gly His Gly His Ser Ala Asp Ser Pro
    1025                1030                1035

Arg Gln Ser Gly Thr Arg His Thr Glu Ser Ser Ser Arg Gly Gln
    1040                1045                1050

Ala Ala Ser Ser His Glu Gln Ala Arg Ser Ser Ala Gly Glu Arg
    1055                1060                1065

His Gly Ser His His Gln Leu Gln Ser Ala Asp Ser Ser Arg His
    1070                1075                1080

Ala Gly Ile Gly His Gly Gln Ala Ser Ser Ala Val Arg Asp Ser
    1085                1090                1095

Gly His Arg Gly Tyr Ser Gly Ser Gln Ala Thr Asp Ser Glu Gly
    1100                1105                1110

His Ser Glu Asp Ser Asp Thr Gln Ser Val Ser Ala Gln Gly Lys
    1115                1120                1125

Ala Gly Pro His Gln Gln Ser His Lys Glu Ser Ala Arg Gly Gln
    1130                1135                1140

Ser Gly Glu Ser Ser Arg Arg Ser Gly Ser Phe Leu Tyr Gln Val
    1145                1150                1155

Ser Thr His Glu Gln Ser Glu Ser Thr His Gly Gln Ser Val Pro
    1160                1165                1170

Ser Thr Gly Gly Arg Gln Gly Ser His His Asp Gln Ala Gln Asp
    1175                1180                1185

Ser Ser Arg His Ser Ala Ser Gln Glu Gly Gln Asp Thr Ile Arg
    1190                1195                1200

Gly His Pro Gly Pro Ser Arg Gly Gly Arg Gln Gly Ser His His
    1205                1210                1215

Glu Gln Ser Val Asp Arg Ser Gly His Ser Gly Ser His His Ser
    1220                1225                1230

His Thr Thr Ser Gln Gly Arg Ser Asp Ala Ser Arg Gly Gln Ser
    1235                1240                1245

Gly Pro Arg Ser Ala Ser Arg Gln Thr His Asp Lys Glu Gln Ser
    1250                1255                1260
```

```
Gly Asp Gly Ser Arg His Ser Gly Ser Arg His His Glu Ala Ser
    1265                1270                1275

Ser Trp Ala Asp Ser Ser Arg His Ser Gln Ala Val Gln Gly Gln
    1280                1285                1290

Ser Glu Gly Ser Arg Arg Ser Arg Arg Gln Gly Ser Ser Val Ser
    1295                1300                1305

Gln Asp Ser Asp Ser Gln Gly His Ser Glu Asp Ser Glu Arg Arg
    1310                1315                1320

Ser Gly Ser Ala Ser Arg Asn His Arg Gly Ser Ala Gln Glu Gln
    1325                1330                1335

Ser Arg Asp Gly Ser Arg His Pro Arg Ser His His Glu Asp Arg
    1340                1345                1350

Ala Gly His Gly His Ser Ala Asp Ser Ser Arg Gln Ser Gly Thr
    1355                1360                1365

His His Ala Glu Asn Ser Ser Gly Gly Gln Pro Ala Ser Ser His
    1370                1375                1380

Glu Gln Ala Arg Ser Ser Ala Gly Glu Arg His Gly Ser His His
    1385                1390                1395

Gln Gln Ser Ala Asp Ser Ser Arg His Ser Gly Ile Gly His Gly
    1400                1405                1410

Gln Ala Ser Ser Ala Val Arg Asp Ser Gly His Arg Gly Ser Ser
    1415                1420                1425

Gly Ser Gln Ala Ser Asp Ser Glu Gly His Ser Glu Asp Ser Asp
    1430                1435                1440

Thr Gln Ser Val Ser Ala His Gly Gln Ala Gly Pro His Gln Gln
    1445                1450                1455

Ser His Gln Glu Ser Thr Arg Gly Arg Ser Ala Gly Arg Ser Gly
    1460                1465                1470

Arg Ser Gly Ser Phe Leu Tyr Gln Val Ser Thr His Glu Gln Ser
    1475                1480                1485

Glu Ser Ala His Gly Arg Ala Gly Pro Ser Thr Gly Gly Arg Gln
    1490                1495                1500

Gly Ser His His Glu Gln Ala Arg Asp Ser Ser Arg His Ser Ala
    1505                1510                1515

Ser Gln Glu Gly Gln Asp Thr Ile Arg Gly His Pro Gly Ser Arg
    1520                1525                1530

Arg Gly Gly Arg Gln Gly Ser Tyr His Glu Gln Ser Val Asp Arg
    1535                1540                1545

Ser Gly His Ser Gly Ser His His Ser His Thr Thr Ser Gln Gly
    1550                1555                1560

Arg Ser Asp Ala Ser His Gly Gln Ser Gly Ser Arg Ser Ala Ser
    1565                1570                1575

Arg Glu Thr Arg Asn Glu Glu Gln Ser Gly Asp Gly Ser Arg His
    1580                1585                1590

Ser Gly Ser Arg His His Glu Ala Ser Thr Gln Ala Asp Ser Ser
    1595                1600                1605

Arg His Ser Gln Ser Gly Gln Gly Glu Ser Ala Gly Ser Arg Arg
    1610                1615                1620

Ser Arg Arg Gln Gly Ser Ser Val Ser Gln Asp Ser Asp Ser Glu
    1625                1630                1635

Ala Tyr Pro Glu Asp Ser Glu Arg Arg Ser Glu Ser Ala Ser Arg
    1640                1645                1650

Asn His His Gly Ser Ser Arg Glu Gln Ser Arg Asp Gly Ser Arg
```

```
            1655              1660              1665
His Pro Gly Ser Ser His Arg Asp Thr Ala Ser His Val Gln Ser
    1670              1675              1680

Ser Pro Val Gln Ser Asp Ser Ser Thr Ala Lys Glu His Gly His
    1685              1690              1695

Phe Ser Ser Leu Ser Gln Asp Ser Ala Tyr His Ser Gly Ile Gln
    1700              1705              1710

Ser Arg Gly Ser Pro His Ser Ser Ser Tyr His Tyr Gln Ser
    1715              1720              1725

Glu Gly Thr Glu Arg Gln Lys Gly Gln Ser Gly Leu Val Trp Arg
    1730              1735              1740

His Gly Ser Tyr Gly Ser Ala
    1745              1750

<210> SEQ ID NO 557
<211> LENGTH: 6173
<212> TYPE: DNA
<213> ORGANISM: Homo sapiens

<400> SEQUENCE: 557
aggacaagca ggaaccgggg atccagtttt agccaggaca gtgacagtca gggacactca      60
gaagactctg agaggtggtc tgggtctgct tccagaaacc atcatggatc tgctcaggag     120
cagctaagag atggctccag acaccccagg tcccatcaag aagacagagc tggtcatggg     180
cactctgcag acagctccag acaatcaggc actcgtcaca cacagacttc ctctggtgga     240
caggctgcat catcccatga acaggcaaga tcaagtgcag gagaaagaca tggatcccac     300
caccagcagt cagcagacag ctccagacac tcaggcattg gcacggacag agcttcatct     360
gcagtcagag acagtggaca ccgagggtac agtggtagtc aggccagtga caatgaggga     420
cattcagaag actcagacac acagtcagtg tcagcccacg gacaggctgg gtcccatcag     480
cagagccacc aagagtccgc acgtggccgg tcaggggaaa cgtctggaca ttcagggtct     540
ttcctctacc aggtgagcac tcatgaacag tctgagtcct cccatggatg gacggggccc     600
agcactagag gaagacaagg atcccgccat gagcaggcac aagacagctc aggcactca     660
gcatcccaag acggtcagga caccattcgt ggacacccgg ggtcaagcag aggaggaagg     720
cagggggtacc accacgagca ttcggtagat agctctggac actcagggtc ccatcacagc     780
cacaccacat cccagggaag gtctgatgcc tcccgtgggc agtcaggatc cagacgtgca     840
agcagaacaa cacgtaatga ggaacaatca ggagacggct ccaggcactc agggtcgcgt     900
caccatgaag cttccactca tgccgacatc tctagacact cacaggcagt ccagggacaa     960
tcagaggggt ccaggagaag caggcgccag ggatccagtg ttagccagga cagtgacagt    1020
gagggacatt cagaagactc tgagaggtgg tctgggtctg cttccagaaa ccatcatgga    1080
tctgctcagg agcagctaag agatggctcc agacacccca ggtcccatca agaaggcaga    1140
gctggtcatg tcctctggtg gacaggctgc atcatcccat gaacaggcaa gatcaagtgc    1200
aggagaaaga catggatccc accaccagca gtcagcagac agctccagac actcaggcat    1260
tgggcacgga caagcttcat ctgcagtcag agacagtgga caccgagggt acagtggtag    1320
tcaggccagt gacaatgagg gacattcaga agactcagac acacagtcag tgtcagccca    1380
cggacaggct gggtcccatc agcagagcca ccaagagtcc gcacgtggcc ggtcagggga    1440
aacgtctgga cattcaggat cttcctctca ccaggtgagc actcatgaac agtctgagtc    1500
ctcccatgga tggacggggc ccagcactag aggaagacaa ggatcccgcc atgagcaggc    1560
```

```
acaagacagc tccaggcact cagcatccca agatggtcag gacaccattc gtggacaccc    1620
ggggtcaagc agaggaggaa ggcaggggta ccaccacgag cattcggtag atagctctgg    1680
acactcaggg tcccatcaca gccacaccac atcccaggga aggtctgatg cctcccgtgg    1740
gcagtcagga tccagaagtg caagcagaac aacacgtaat gaggaacaat caggagacgg    1800
ctccaggcac tcagggtcgc gtcaccatga agcttccact catgccgaca tctctagaca    1860
ctcacaggca gtccagggac aatcagaggg gtccaggaga agcaggcgcc agggatccag    1920
tgttagccag gacagtgaca gtgagggaca ttcagaagac tctgagaggt ggtctgggtc    1980
tgcttccaga aaccatcatg gatctgctca ggagcagcta agagatggct ccagacaccc    2040
caggtcccat caagaagaca gagctggtca tgggcactct gcagacagct ccagacaatc    2100
aggcactcgt cacacacagg cttcctctgg tggacaggct gcatcatccc atgaacaggc    2160
aagatcaagt gcaggagaaa gacatggatc ccaccaccag cagtcagcag acagctccag    2220
acactcaggc attgggcacg gacaagcttc atctgcagtc agagacagtg gacaccgagg    2280
gtacagtggt agtcaggcca gtgacaatga gggacattca gaagactcag acacacagtc    2340
agtgtcagcc cacggacagg ctgggtccca tcagcagagc caccaagagt ccgcacgtgg    2400
ccggtcaggg gaaacgtctg gacattcagg atctttcctc taccaggtga gcactcatga    2460
acagtctgag tcctcccatg gatggacggg gcccagcact agaggaagac aaggatcccg    2520
ccatgagcag gcacaagaca gctccaggca ctcagcatcc aagacggtc aggacaccat    2580
tcgtggacac ccggggtcaa gcagaggagg aaggcagggg taccaccacg agcattcggt    2640
agatagctct ggacactcag ggtcccatca cagccacacc acatcccagg gaaggtctga    2700
tgcctcccgt gggcagtcag gatccagaag tgcaagcaga acaacacgta atgaggaaca    2760
atcaggagac agctccaggc actcagggtc gcgtcaccat gaagcttcca ctcatgccga    2820
catctctaga cactcacagg cagtccaggg acaatcagag gggtccagga gaagcaggcg    2880
ccagggatcc agtgttagcc aggacagtga cagtgaggga cattcagaag actctgagag    2940
gtggtctggg tctgcttcca gaaaccatcg tggatctgtt caggagcagt caaggcacgg    3000
ctccagacac cccaggtccc atcacgaaga cagagccggt cacgggcact ctgcagaccg    3060
ctccagacaa tcaggcactc gtcacgcaga gacttcctct ggtggacagg ctgcatcatc    3120
ccatgaacag gcaagatcaa gtccaggaga gagacacgga tcccgccacc agcagtcagc    3180
agacagctcc agacactcag gcattccgcg tggacaggct tcatctgcag tcagagacag    3240
tagacactgg gggtccagtg gtagtcaagc cagtgatagt gagggacatt cagaagagtc    3300
agacacacag tcagtgtcag gccatggaca ggctgggccc catcagcaga gccaccaaga    3360
gtccgcacgt gaccggtcag ggggaaggtc tggacgttca gggtctttcc tctaccaggt    3420
gagcactcat gaacagtctg agtccgccca tgggcggacc aggaccagca ctggacgaag    3480
acaaggatcc caccacgagc aggcacgaga cagctccagg cactcagcgt cccaagaggg    3540
tcaggacacc attcgtgcac acccggggtc aagcagaaga ggaaggcagg gatcccacta    3600
cgagcaatcg gtagataggt ctggacactc agggtcccat cacagccaca ccacatccca    3660
gggaaggtct gatgcctccc gtgggcagtc aggatccaga agtgccagca gacaaactcg    3720
taacgacgaa caatcaggag acggctccag gcactcatgg tcgcatcacc atgaagcttc    3780
cactcaggcg gacagctcta gacactcaca gtccggccag ggacaatcag cggggcccag    3840
tacaagcagg aaccagggat ccagtgttag ccaggacagt gacagtcagg gacactcaga    3900
```

```
agactctgag aggtggtctg ggtctgcttc cagaaaccat catggatctg ctggggagca    3960
gtcaagagat ggctccagac accctgggtc ccatcaagaa gacagagccg gtcacgggca    4020
ctctgcagac agccccagac aatcaggcac tcgtcacaca gagtcttcct ctcgtggaca    4080
ggctgcgtca tcccatgaac aggcaagatc aagtgcagga gaaagacatg gatcccacca    4140
ccagctccag tcagcagaca gctccagaca cgcaggcatt gggcacggac aagcttcatc    4200
tgcagtcaga gacagtggac accgagggta cagtggtagt caggccactg acagtgaggg    4260
acattcagaa gactcagaca cacagtcagt gtcagcacag ggaaaagctg gccccatca    4320
gcagagccac aaagagtccg cacgtggcca gtcaggggaa agctctagac gttcagggtc    4380
tttcctctac caggtgagca ctcatgaaca gtctgagtcc acccatggac agtctgtgcc    4440
cagcactgga ggaagacaag gatcccacca tgatcaggca caagacagct ccaggcactc    4500
agcatcccaa gagggtcagg acaccattcg tggacacccg gggccaagca gaggaggaag    4560
acagggtcc caccacgagc aatcggtaga taggtctgga cactcagggt cccatcacag    4620
ccacaccaca tcccagggaa ggtctgatgc ctcccgtggg cagtcaggac ccagaagtgc    4680
aagcagacaa acacatgaca aggaacaatc aggagacggc tctaggcact cagggtcgcg    4740
tcatcatgaa gcttcctctt gggccgacag ctctagacac tcacaggcag tccagggaca    4800
atcagagggg tccaggagaa gcaggcgcca gggatccagt gttagccagg acagtgacag    4860
tcaggacac tcagaagact ctgagaggcg gtctgggtct gcttccagaa accatcgtgg    4920
atctgctcag gagcagtcaa gagatggctc cagacacccc aggtcccatc acgaagacag    4980
agccggtcat gggcactctg cagacagctc cagacaatca ggcactcatc atgcagagaa    5040
ttcctctggt ggacagcctg catcatccca tgaacaggca agatcaagtg caggagagag    5100
acatggatcc caccaccagc agtcagcaga cagctccaga cactcaggca ttgggcacgg    5160
acaagcttca tctgcagtca gagacagtgg acaccgaggg tccagtggta gtcaggccag    5220
tgacagtgag ggacattcag aagactcaga cacacagtca gtgtcagccc acggacaggc    5280
tgggccccat cagcagagcc accaagagtc cacacgtggc cggtcagcag aaggtctgg    5340
acgttcaggg tctttcctct accaggtgag cactcatgaa cagtctgagt ctgcccatgg    5400
acgggctggg cccagtactg gaggaagaca aggatcccac cacgagcagg cacgagacag    5460
ctccaggcac tcagcgtccc aagagggtca ggacaccatt cgtggacacc cggggtcaag    5520
gagaggagga agacagggat cctaccacga gcaatcggta gataggtctg gacactcagg    5580
gtcccatcac agccacacca catcccaggg aaggtctgat gcctcccatg ggcagtcagg    5640
atccagaagt gcaagcagag aaacacgtaa tgaggaacag tcaggagacg gctccaggca    5700
ctcagggtcg cgtcaccatg aagcttccac tcaggctgac agctctagac actcacagtc    5760
cggccaggt gaatcagcgg ggtccaggag aagcaggcgc cagggatcca gtgttagcca    5820
ggacagtgac agtgaggcat acccagagga ctctgagagg cgatctgagt ctgcttccag    5880
aaaccatcat ggatcttctc gggagcagtc aagagatggc tccagacacc ccggatcctc    5940
tcaccgcgat acagccagtc atgtacagtc ttcacctgta cagtcagact ctagtaccgc    6000
taaggaacat ggtcactta gtagtctttc acaagattct gcgtatcact caggaataca    6060
gtcacgtggc agtcctcaca gttctagttc ttatcattat caatctgagg gcactgaaag    6120
gcaaaaaggt caatcaggtt tagtttggag acatggcagc tatggtagtg cag          6173
```

<210> SEQ ID NO 558
<211> LENGTH: 2074

<212> TYPE: PRT
<213> ORGANISM: Homo sapiens

<400> SEQUENCE: 558

```
Arg Thr Ser Arg Asn Arg Gly Ser Ser Phe Ser Gln Asp Ser Asp Ser
1               5                   10                  15

Gln Gly His Ser Glu Asp Ser Glu Arg Trp Ser Gly Ser Ala Ser Arg
            20                  25                  30

Asn His His Gly Ser Ala Gln Glu Gln Leu Arg Asp Gly Ser Arg His
        35                  40                  45

Pro Arg Ser His Gln Glu Asp Arg Ala Gly His Gly His Ser Ala Asp
    50                  55                  60

Ser Ser Arg Gln Ser Gly Thr Arg His Thr Gln Thr Ser Ser Gly Gly
65                  70                  75                  80

Gln Ala Ala Ser Ser His Glu Gln Ala Arg Ser Ser Ala Gly Glu Arg
                85                  90                  95

His Gly Ser His His Gln Gln Ser Ala Asp Ser Ser Arg His Ser Gly
            100                 105                 110

Ile Gly His Gly Gln Ala Ser Ser Ala Val Arg Asp Ser Gly His Arg
        115                 120                 125

Gly Tyr Ser Gly Ser Gln Ala Ser Asp Asn Glu Gly His Ser Glu Asp
    130                 135                 140

Ser Asp Thr Gln Ser Val Ser Ala His Gly Gln Ala Gly Ser His Gln
145                 150                 155                 160

Gln Ser His Gln Glu Ser Ala Arg Gly Arg Ser Gly Glu Thr Ser Gly
                165                 170                 175

His Ser Gly Ser Phe Leu Tyr Gln Val Ser Thr His Glu Gln Ser Glu
            180                 185                 190

Ser Ser His Gly Trp Thr Gly Pro Ser Thr Arg Gly Arg Gln Gly Ser
        195                 200                 205

Arg His Glu Gln Ala Gln Asp Ser Ser Arg His Ser Ala Ser Gln Asp
    210                 215                 220

Gly Gln Asp Thr Ile Arg Gly His Pro Gly Ser Ser Arg Gly Gly Arg
225                 230                 235                 240

Gln Gly Tyr His His Glu His Ser Val Asp Ser Ser Gly His Ser Gly
                245                 250                 255

Ser His His Ser His Thr Thr Ser Gln Gly Arg Ser Asp Ala Ser Arg
            260                 265                 270

Gly Gln Ser Gly Ser Arg Arg Ala Ser Arg Thr Thr Arg Asn Glu Glu
        275                 280                 285

Gln Ser Gly Asp Gly Ser Arg His Ser Gly Ser Arg His His Glu Ala
    290                 295                 300

Ser Thr His Ala Asp Ile Ser Arg His Ser Gln Ala Val Gln Gly Gln
305                 310                 315                 320

Ser Glu Gly Ser Arg Arg Ser Arg Gln Gly Ser Ser Val Ser Gln
                325                 330                 335

Asp Ser Asp Ser Glu Gly His Ser Glu Asp Ser Glu Arg Trp Ser Gly
            340                 345                 350

Ser Ala Ser Arg Asn His His Gly Ser Ala Gln Glu Gln Leu Arg Asp
        355                 360                 365

Gly Ser Arg His Pro Arg Ser His Gln Glu Gly Arg Ala Gly His Gly
    370                 375                 380

His Ser Ala Asp Ser Ser Arg Gln Ser Gly Thr Arg His Thr Gln Thr
385                 390                 395                 400
```

```
Ser Ser Gly Gly Gln Ala Ala Ser Ser His Glu Gln Ala Arg Ser Ser
                405                 410                 415

Ala Gly Glu Arg His Gly Ser His His Gln Gln Ser Ala Asp Ser Ser
            420                 425                 430

Arg His Ser Gly Ile Gly His Gly Gln Ala Ser Ser Ala Val Arg Asp
            435                 440                 445

Ser Gly His Arg Gly Tyr Ser Gly Ser Gln Ala Ser Asp Asn Glu Gly
        450                 455                 460

His Ser Glu Asp Ser Asp Thr Gln Ser Val Ser Ala His Gly Gln Ala
465                 470                 475                 480

Gly Ser His Gln Gln Ser His Gln Glu Ser Ala Arg Gly Arg Ser Gly
                485                 490                 495

Glu Thr Ser Gly His Ser Gly Ser Phe Leu Tyr Gln Val Ser Thr His
            500                 505                 510

Glu Gln Ser Glu Ser Ser His Gly Trp Thr Gly Pro Ser Thr Arg Gly
            515                 520                 525

Arg Gln Gly Ser Arg His Glu Gln Ala Gln Asp Ser Ser Arg His Ser
        530                 535                 540

Ala Ser Gln Asp Gly Gln Asp Thr Ile Arg Gly His Pro Gly Ser Ser
545                 550                 555                 560

Arg Gly Gly Arg Gln Gly Tyr His His Glu His Ser Val Asp Ser Ser
                565                 570                 575

Gly His Ser Gly Ser His His Ser His Thr Thr Ser Gln Gly Arg Ser
            580                 585                 590

Asp Ala Ser Arg Gly Gln Ser Gly Ser Arg Ser Ala Ser Arg Thr Thr
            595                 600                 605

Arg Asn Glu Glu Gln Ser Gly Asp Gly Ser Arg His Ser Gly Ser Arg
        610                 615                 620

His His Glu Ala Ser Thr His Ala Asp Ile Ser Arg His Ser Gln Ala
625                 630                 635                 640

Val Gln Gly Gln Ser Glu Gly Ser Arg Arg Ser Arg Arg Gln Gly Ser
                645                 650                 655

Ser Val Ser Gln Asp Ser Asp Ser Glu Gly His Ser Glu Asp Ser Glu
            660                 665                 670

Arg Trp Ser Gly Ser Ala Ser Arg Asn His His Gly Ser Ala Gln Glu
            675                 680                 685

Gln Leu Arg Asp Gly Ser Arg His Pro Arg Ser His Gln Glu Asp Arg
        690                 695                 700

Ala Gly His Gly His Ser Ala Asp Ser Ser Arg Gln Ser Gly Thr Arg
705                 710                 715                 720

His Thr Gln Ala Ser Ser Gly Gly Gln Ala Ala Ser Ser His Glu Gln
                725                 730                 735

Ala Arg Ser Ser Ala Gly Glu Arg His Gly Ser His His Gln Gln Ser
            740                 745                 750

Ala Asp Ser Ser Arg His Ser Gly Ile Gly His Gly Gln Ala Ser Ser
            755                 760                 765

Ala Val Arg Asp Ser Gly His Arg Gly Tyr Ser Gly Ser Gln Ala Ser
        770                 775                 780

Asp Asn Glu Gly His Ser Glu Asp Ser Asp Thr Gln Ser Val Ser Ala
785                 790                 795                 800

His Gly Gln Ala Gly Ser His Gln Gln Ser His Gln Glu Ser Ala Arg
                805                 810                 815
```

```
Gly Arg Ser Gly Glu Thr Ser Gly His Ser Gly Ser Phe Leu Tyr Gln
                820                 825                 830

Val Ser Thr His Glu Gln Ser Glu Ser Ser His Gly Trp Thr Gly Pro
            835                 840                 845

Ser Thr Arg Gly Arg Gln Gly Ser Arg His Glu Gln Ala Gln Asp Ser
        850                 855                 860

Ser Arg His Ser Ala Ser Gln Asp Gly Gln Asp Thr Ile Arg Gly His
865                 870                 875                 880

Pro Gly Ser Ser Arg Gly Gly Arg Gln Gly Tyr His His Glu His Ser
                885                 890                 895

Val Asp Ser Ser Gly His Ser Gly Ser His His Ser His Thr Thr Ser
            900                 905                 910

Gln Gly Arg Ser Asp Ala Ser Arg Gly Gln Ser Gly Ser Arg Ser Ala
        915                 920                 925

Ser Arg Thr Thr Arg Asn Glu Glu Gln Ser Gly Asp Ser Ser Arg His
930                 935                 940

Ser Gly Ser Arg His His Glu Ala Ser Thr His Ala Asp Ile Ser Arg
945                 950                 955                 960

His Ser Gln Ala Val Gln Gly Gln Ser Glu Gly Ser Arg Arg Ser Arg
                965                 970                 975

Arg Gln Gly Ser Ser Val Ser Gln Asp Ser Asp Ser Glu Gly His Ser
            980                 985                 990

Glu Asp Ser Glu Arg Trp Ser Gly Ser Ala Ser Arg Asn His Arg Gly
        995                 1000                1005

Ser Val Gln Glu Gln Ser Arg His Gly Ser Arg His Pro Arg Ser
    1010                1015                1020

His His Glu Asp Arg Ala Gly His Gly His Ser Ala Asp Arg Ser
    1025                1030                1035

Arg Gln Ser Gly Thr Arg His Ala Glu Thr Ser Gly Gly Gln
    1040                1045                1050

Ala Ala Ser Ser His Glu Gln Ala Arg Ser Pro Gly Glu Arg
    1055                1060                1065

His Gly Ser Arg His Gln Gln Ser Ala Asp Ser Ser Arg His Ser
    1070                1075                1080

Gly Ile Pro Arg Gly Gln Ala Ser Ser Ala Val Arg Asp Ser Arg
    1085                1090                1095

His Trp Gly Ser Ser Gly Ser Gln Ala Ser Asp Ser Glu Gly His
    1100                1105                1110

Ser Glu Glu Ser Asp Thr Gln Ser Val Ser Gly His Gly Gln Ala
    1115                1120                1125

Gly Pro His Gln Gln Ser His Gln Glu Ser Ala Arg Asp Arg Ser
    1130                1135                1140

Gly Gly Arg Ser Gly Arg Ser Gly Ser Phe Leu Tyr Gln Val Ser
    1145                1150                1155

Thr His Glu Gln Ser Glu Ser Ala His Gly Arg Thr Arg Thr Ser
    1160                1165                1170

Thr Gly Arg Arg Gln Gly Ser His His Glu Gln Ala Arg Asp Ser
    1175                1180                1185

Ser Arg His Ser Ala Ser Gln Glu Gly Gln Asp Thr Ile Arg Ala
    1190                1195                1200

His Pro Gly Ser Ser Arg Arg Gly Arg Gln Gly Ser His Tyr Glu
    1205                1210                1215

Gln Ser Val Asp Arg Ser Gly His Ser Gly Ser His His Ser His
```

```
                1220                1225                1230

Thr  Thr  Ser  Gln  Gly  Arg  Ser  Asp  Ala  Ser  Arg  Gly  Gln  Ser  Gly
     1235                1240                1245

Ser  Arg  Ser  Ala  Ser  Arg  Gln  Thr  Arg  Asn  Asp  Glu  Gln  Ser  Gly
     1250                1255                1260

Asp  Gly  Ser  Arg  His  Ser  Trp  Ser  His  His  Glu  Ala  Ser  Thr
     1265                1270                1275

Gln  Ala  Asp  Ser  Ser  Arg  His  Ser  Gln  Ser  Gly  Gln  Gly  Gln  Ser
     1280                1285                1290

Ala  Gly  Pro  Ser  Thr  Ser  Arg  Asn  Gln  Gly  Ser  Ser  Val  Ser  Gln
     1295                1300                1305

Asp  Ser  Asp  Ser  Gln  Gly  His  Ser  Glu  Asp  Ser  Glu  Arg  Trp  Ser
     1310                1315                1320

Gly  Ser  Ala  Ser  Arg  Asn  His  His  Gly  Ser  Ala  Gly  Glu  Gln  Ser
     1325                1330                1335

Arg  Asp  Gly  Ser  Arg  His  Pro  Gly  Ser  His  Gln  Glu  Asp  Arg  Ala
     1340                1345                1350

Gly  His  Gly  His  Ser  Ala  Asp  Ser  Pro  Arg  Gln  Ser  Gly  Thr  Arg
     1355                1360                1365

His  Thr  Glu  Ser  Ser  Ser  Arg  Gly  Gln  Ala  Ala  Ser  Ser  His  Glu
     1370                1375                1380

Gln  Ala  Arg  Ser  Ser  Ala  Gly  Glu  Arg  His  Gly  Ser  His  His  Gln
     1385                1390                1395

Leu  Gln  Ser  Ala  Asp  Ser  Ser  Arg  His  Ala  Gly  Ile  Gly  His  Gly
     1400                1405                1410

Gln  Ala  Ser  Ser  Ala  Val  Arg  Asp  Ser  Gly  His  Arg  Gly  Tyr  Ser
     1415                1420                1425

Gly  Ser  Gln  Ala  Thr  Asp  Ser  Glu  Gly  His  Ser  Glu  Asp  Ser  Asp
     1430                1435                1440

Thr  Gln  Ser  Val  Ser  Ala  Gln  Gly  Lys  Ala  Gly  Pro  His  Gln  Gln
     1445                1450                1455

Ser  His  Lys  Glu  Ser  Ala  Arg  Gly  Gln  Ser  Gly  Glu  Ser  Ser  Arg
     1460                1465                1470

Arg  Ser  Gly  Ser  Phe  Leu  Tyr  Gln  Val  Ser  Thr  His  Glu  Gln  Ser
     1475                1480                1485

Glu  Ser  Thr  His  Gly  Gln  Ser  Val  Pro  Ser  Thr  Gly  Gly  Arg  Gln
     1490                1495                1500

Gly  Ser  His  His  Asp  Gln  Ala  Gln  Asp  Ser  Ser  Arg  His  Ser  Ala
     1505                1510                1515

Ser  Gln  Glu  Gly  Gln  Asp  Thr  Ile  Arg  Gly  His  Pro  Gly  Pro  Ser
     1520                1525                1530

Arg  Gly  Gly  Arg  Gln  Gly  Ser  His  His  Glu  Gln  Ser  Val  Asp  Arg
     1535                1540                1545

Ser  Gly  His  Ser  Gly  Ser  His  His  Ser  His  Thr  Thr  Ser  Gln  Gly
     1550                1555                1560

Arg  Ser  Asp  Ala  Ser  Arg  Gly  Gln  Ser  Gly  Pro  Arg  Ser  Ala  Ser
     1565                1570                1575

Arg  Gln  Thr  His  Asp  Lys  Glu  Gln  Ser  Gly  Asp  Gly  Ser  Arg  His
     1580                1585                1590

Ser  Gly  Ser  Arg  His  His  Glu  Ala  Ser  Ser  Trp  Ala  Asp  Ser  Ser
     1595                1600                1605

Arg  His  Ser  Gln  Ala  Val  Gln  Gly  Gln  Ser  Glu  Gly  Ser  Arg  Arg
     1610                1615                1620
```

```
Ser Arg Arg Gln Gly Ser Ser Val Ser Gln Asp Ser Asp Ser Gln
1625                1630                1635
Gly His Ser Glu Asp Ser Glu Arg Arg Ser Gly Ser Ala Ser Arg
1640                1645                1650
Asn His Arg Gly Ser Ala Gln Glu Gln Ser Arg Asp Gly Ser Arg
1655                1660                1665
His Pro Arg Ser His His Glu Asp Arg Ala Gly His Gly His Ser
1670                1675                1680
Ala Asp Ser Ser Arg Gln Ser Gly Thr His His Ala Glu Asn Ser
1685                1690                1695
Ser Gly Gly Gln Pro Ala Ser Ser His Glu Gln Ala Arg Ser Ser
1700                1705                1710
Ala Gly Glu Arg His Gly Ser His His Gln Gln Ser Ala Asp Ser
1715                1720                1725
Ser Arg His Ser Gly Ile Gly His Gly Gln Ala Ser Ser Ala Val
1730                1735                1740
Arg Asp Ser Gly His Arg Gly Ser Ser Gly Ser Gln Ala Ser Asp
1745                1750                1755
Ser Glu Gly His Ser Glu Asp Ser Asp Thr Gln Ser Val Ser Ala
1760                1765                1770
His Gly Gln Ala Gly Pro His Gln Gln Ser His Gln Glu Ser Thr
1775                1780                1785
Arg Gly Arg Ser Ala Gly Arg Ser Gly Arg Ser Gly Ser Phe Leu
1790                1795                1800
Tyr Gln Val Ser Thr His Glu Gln Ser Glu Ser Ala His Gly Arg
1805                1810                1815
Ala Gly Pro Ser Thr Gly Gly Arg Gln Gly Ser His His Glu Gln
1820                1825                1830
Ala Arg Asp Ser Ser Arg His Ser Ala Ser Gln Glu Gly Gln Asp
1835                1840                1845
Thr Ile Arg Gly His Pro Gly Ser Arg Arg Gly Gly Arg Gln Gly
1850                1855                1860
Ser Tyr His Glu Gln Ser Val Asp Arg Ser Gly His Ser Gly Ser
1865                1870                1875
His His Ser His Thr Thr Ser Gln Gly Arg Ser Asp Ala Ser His
1880                1885                1890
Gly Gln Ser Gly Ser Arg Ser Ala Ser Arg Glu Thr Arg Asn Glu
1895                1900                1905
Glu Gln Ser Gly Asp Gly Ser Arg His Ser Gly Ser Arg His His
1910                1915                1920
Glu Ala Ser Thr Gln Ala Asp Ser Ser Arg His Ser Gln Ser Gly
1925                1930                1935
Gln Gly Glu Ser Ala Gly Ser Arg Arg Ser Arg Arg Gln Gly Ser
1940                1945                1950
Ser Val Ser Gln Asp Ser Asp Ser Glu Ala Tyr Pro Glu Asp Ser
1955                1960                1965
Glu Arg Arg Ser Glu Ser Ala Ser Arg Asn His His Gly Ser Ser
1970                1975                1980
Arg Glu Gln Ser Arg Asp Gly Ser Arg His Pro Gly Ser Ser His
1985                1990                1995
Arg Asp Thr Ala Ser His Val Gln Ser Ser Pro Val Gln Ser Asp
2000                2005                2010
```

-continued

| Ser | Ser | Thr | Ala | Lys | Glu | His | Gly | His | Phe | Ser | Ser | Leu | Ser | Gln |
|---|---|---|---|---|---|---|---|---|---|---|---|---|---|---|
| | 2015 | | | | 2020 | | | | 2025 | | | | | |

Asp Ser Ala Tyr His Ser Gly Ile Gln Ser Arg Gly Ser Pro His
    2030            2035            2040

Ser Ser Ser Ser Tyr His Tyr Gln Ser Glu Gly Thr Glu Arg Gln
    2045            2050            2055

Lys Gly Gln Ser Gly Leu Val Trp Arg His Gly Ser Tyr Gly Ser
    2060            2065            2070

Ala

<210> SEQ ID NO 559
<211> LENGTH: 15
<212> TYPE: DNA
<213> ORGANISM: Homo sapiens

<400> SEQUENCE: 559
caggcacgag acagc                                                    15

<210> SEQ ID NO 560
<211> LENGTH: 15
<212> TYPE: DNA
<213> ORGANISM: Homo sapiens
<220> FEATURE:
<221> NAME/KEY: misc_feature
<222> LOCATION: (7)..(7)
<223> OTHER INFORMATION: n is a, c, g, or t

<400> SEQUENCE: 560
caggcangag acagc                                                    15

<210> SEQ ID NO 561
<211> LENGTH: 15
<212> TYPE: DNA
<213> ORGANISM: Homo sapiens

<400> SEQUENCE: 561
caggcatgag acagc                                                    15

<210> SEQ ID NO 562
<211> LENGTH: 15
<212> TYPE: DNA
<213> ORGANISM: Homo sapiens

<400> SEQUENCE: 562
acacagtcag tgtca                                                    15

<210> SEQ ID NO 563
<211> LENGTH: 15
<212> TYPE: DNA
<213> ORGANISM: Homo sapiens

<400> SEQUENCE: 563
acacagtsws wgkcm                                                    15

<210> SEQ ID NO 564
<211> LENGTH: 15
<212> TYPE: DNA
<213> ORGANISM: Homo sapiens

<400> SEQUENCE: 564
acacagtgtc aggcc                                                    15

```
<210> SEQ ID NO 565
<211> LENGTH: 3982
<212> TYPE: PRT
<213> ORGANISM: Homo sapiens

<400> SEQUENCE: 565

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
            20                  25                  30

Leu Lys Glu Leu Leu Glu Lys Glu Phe Arg Gln Ile Leu Lys Asn Pro
        35                  40                  45

Asp Asp Pro Asp Met Val Asp Val Phe Met Asp His Leu Asp Ile Asp
    50                  55                  60

His Asn Lys Lys Ile Asp Phe Thr Glu Phe Leu Leu Met Val Phe Lys
65                  70                  75                  80

Leu Ala Gln Ala Tyr Tyr Glu Ser Thr Arg Lys Glu Asn Leu Pro Ile
                85                  90                  95

Ser Gly His Lys His Arg Lys His Ser His His Asp Lys His Glu Asp
            100                 105                 110

Asn Lys Gln Glu Glu Asn Lys Glu Asn Arg Lys Arg Pro Ser Ser Leu
        115                 120                 125

Glu Arg Arg Asn Asn Arg Lys Gly Asn Lys Gly Arg Ser Lys Ser Pro
130                 135                 140

Arg Glu Thr Gly Gly Lys Arg His Glu Ser Ser Ser Glu Lys Lys Glu
145                 150                 155                 160

Arg Lys Gly Tyr Ser Pro Thr His Arg Glu Glu Glu Tyr Gly Lys Asn
                165                 170                 175

His His Asn Ser Ser Lys Lys Glu Lys Asn Lys Thr Glu Asn Thr Arg
            180                 185                 190

Leu Gly Asp Asn Arg Lys Arg Leu Ser Glu Arg Leu Glu Glu Lys Glu
        195                 200                 205

Asp Asn Glu Glu Gly Val Tyr Asp Tyr Glu Asn Thr Gly Arg Met Thr
    210                 215                 220

Gln Lys Trp Ile Gln Ser Gly His Ile Ala Thr Tyr Tyr Thr Ile Gln
225                 230                 235                 240

Asp Glu Ala Tyr Asp Thr Thr Asp Ser Leu Leu Glu Glu Asn Lys Ile
                245                 250                 255

Tyr Glu Arg Ser Arg Ser Ser Asp Gly Lys Ser Ser Ser Gln Val Asn
            260                 265                 270

Arg Ser Arg His Glu Asn Thr Ser Gln Val Pro Leu Gln Glu Ser Arg
        275                 280                 285

Thr Arg Lys Arg Arg Gly Ser Arg Val Ser Gln Asp Arg Asp Ser Glu
    290                 295                 300

Gly His Ser Glu Asp Ser Glu Arg His Ser Gly Ser Ala Ser Arg Asn
305                 310                 315                 320

His His Gly Ser Ala Trp Glu Gln Ser Arg Asp Gly Ser Arg His Pro
                325                 330                 335

Arg Ser His Asp Glu Asp Arg Ala Ser His Gly His Ser Ala Asp Ser
            340                 345                 350

Ser Arg Gln Ser Gly Thr Arg His Ala Glu Thr Ser Ser Arg Gly Gln
        355                 360                 365

Thr Ala Ser Ser His Glu Gln Ala Arg Ser Ser Pro Gly Glu Arg His
    370                 375                 380
```

```
Gly Ser Gly His Gln Gln Ser Ala Asp Ser Ser Arg His Ser Ala Thr
385                 390                 395                 400

Gly Arg Gly Gln Ala Ser Ser Ala Val Ser Asp Arg Gly His Arg Gly
            405                 410                 415

Ser Ser Gly Ser Gln Ala Ser Asp Ser Glu Gly His Ser Glu Asn Ser
            420                 425                 430

Asp Thr Gln Ser Val Ser Gly His Gly Lys Ala Gly Leu Arg Gln Gln
        435                 440                 445

Ser His Gln Glu Ser Thr Arg Gly Arg Ser Gly Glu Arg Ser Gly Arg
    450                 455                 460

Ser Gly Ser Ser Leu Tyr Gln Val Ser Thr His Glu Gln Pro Asp Ser
465                 470                 475                 480

Ala His Gly Arg Thr Gly Thr Ser Thr Gly Gly Arg Gln Gly Ser His
            485                 490                 495

His Glu Gln Ala Arg Asp Ser Ser Arg His Ser Ala Ser Gln Glu Gly
            500                 505                 510

Gln Asp Thr Ile Arg Gly His Pro Gly Ser Ser Arg Gly Gly Arg Gln
        515                 520                 525

Gly Ser His His Glu Gln Ser Val Asn Arg Ser Gly His Ser Gly Ser
    530                 535                 540

His His Ser His Thr Thr Ser Gln Gly Arg Ser Asp Ala Ser His Gly
545                 550                 555                 560

Gln Ser Gly Ser Arg Ser Ala Ser Arg Gln Thr Arg Asn Glu Glu Gln
            565                 570                 575

Ser Gly Asp Gly Thr Arg His Ser Gly Ser Arg His His Glu Ala Ser
            580                 585                 590

Ser Gln Ala Asp Ser Ser Arg His Ser Gln Val Gly Gln Gly Gln Ser
        595                 600                 605

Ser Gly Pro Arg Thr Ser Arg Asn Gln Gly Ser Ser Val Ser Gln Asp
    610                 615                 620

Ser Asp Ser Gln Gly His Ser Glu Asp Ser Glu Arg Trp Ser Gly Ser
625                 630                 635                 640

Ala Ser Arg Asn His His Gly Ser Ala Gln Glu Gln Ser Arg Asp Gly
            645                 650                 655

Ser Arg His Pro Arg Ser His His Glu Asp Arg Ala Gly His Gly His
            660                 665                 670

Ser Ala Asp Ser Ser Arg Lys Ser Gly Thr Arg His Thr Gln Asn Ser
        675                 680                 685

Ser Ser Gly Gln Ala Ala Ser Ser His Glu Gln Ala Arg Ser Ser Ala
    690                 695                 700

Gly Glu Arg His Gly Ser Arg His Gln Leu Gln Ser Ala Asp Ser Ser
705                 710                 715                 720

Arg His Ser Gly Thr Gly His Gly Gln Ala Ser Ser Ala Val Arg Asp
            725                 730                 735

Ser Gly His Arg Gly Ser Ser Gly Ser Gln Ala Thr Asp Ser Glu Gly
            740                 745                 750

His Ser Glu Asp Ser Asp Thr Gln Ser Val Ser Gly His Gly Gln Ala
        755                 760                 765

Gly His His Gln Gln Ser His Gln Glu Ser Ala Arg Asp Arg Ser Gly
    770                 775                 780

Glu Arg Ser Arg Arg Ser Gly Ser Phe Leu Tyr Gln Val Ser Thr His
785                 790                 795                 800

Lys Gln Ser Glu Ser Ser His Gly Trp Thr Gly Pro Ser Thr Gly Val
```

```
                805                 810                 815
Arg Gln Gly Ser His His Glu Gln Ala Arg Asp Asn Ser Arg His Ser
                820                 825                 830

Ala Ser Gln Asp Gly Gln Asp Thr Ile Arg Gly His Pro Gly Ser Ser
                835                 840                 845

Arg Arg Gly Arg Gln Gly Ser His His Glu Gln Ser Val Asp Arg Ser
        850                 855                 860

Gly His Ser Gly Ser His His Ser His Thr Thr Ser Gln Gly Arg Ser
865                 870                 875                 880

Asp Ala Ser Arg Gly Gln Ser Gly Ser Arg Ser Ala Ser Arg Thr Thr
                885                 890                 895

Arg Asn Glu Glu Gln Ser Arg Asp Gly Ser Arg His Ser Gly Ser Arg
                900                 905                 910

His His Glu Ala Ser Ser His Ala Asp Ile Ser Arg His Ser Gln Ala
                915                 920                 925

Gly Gln Gly Gln Ser Glu Gly Ser Arg Thr Ser Arg Arg Gln Gly Ser
        930                 935                 940

Ser Val Ser Gln Asp Ser Asp Ser Glu Gly His Ser Glu Asp Ser Glu
945                 950                 955                 960

Arg Trp Ser Gly Ser Ala Ser Arg Asn His Arg Gly Ser Ala Gln Glu
                965                 970                 975

Gln Ser Arg His Gly Ser Arg His Pro Arg Ser His Glu Asp Arg
                980                 985                 990

Ala Gly His Gly His Ser Ala Asp  Ser Ser Arg Gln Ser  Gly Thr Pro
        995                 1000                1005

His Ala  Glu Thr Ser Ser Gly  Gly Gln Ala Ala Ser  Ser His Glu
    1010                1015                1020

Gln Ala  Arg Ser Ser Pro Gly  Glu Arg His Gly Ser  Arg His Gln
    1025                1030                1035

Gln Ser  Ala Asp Ser Ser Arg  His Ser Gly Ile Pro  Arg Arg Gln
    1040                1045                1050

Ala Ser  Ser Ala Val Arg Asp  Ser Gly His Trp Gly  Ser Ser Gly
    1055                1060                1065

Ser Gln  Ala Ser Asp Ser Glu  Gly His Ser Glu Glu  Ser Asp Thr
    1070                1075                1080

Gln Ser  Val Ser Gly His Gly  Gln Asp Gly Pro His  Gln Gln Ser
    1085                1090                1095

His Gln  Glu Ser Ala Arg Asp  Trp Ser Gly Gly Arg  Ser Gly Arg
    1100                1105                1110

Ser Gly  Ser Phe Ile Tyr Gln  Val Ser Thr His Glu  Gln Ser Glu
    1115                1120                1125

Ser Ala  His Gly Arg Thr Arg  Thr Ser Thr Gly Arg  Arg Gln Gly
    1130                1135                1140

Ser His  His Glu Gln Ala Arg  Asp Ser Ser Arg His  Ser Ala Ser
    1145                1150                1155

Gln Glu  Gly Gln Asp Thr Ile  Arg Ala His Pro Gly  Ser Arg Arg
    1160                1165                1170

Gly Gly  Arg Gln Gly Ser His  His Glu Gln Ser Val  Asp Arg Ser
    1175                1180                1185

Gly His  Ser Gly Ser His His  Ser His Thr Thr Ser  Gln Gly Arg
    1190                1195                1200

Ser Asp  Ala Ser His Gly Gln  Ser Gly Ser Arg Ser  Ala Ser Arg
    1205                1210                1215
```

-continued

```
Gln Thr Arg Lys Asp Lys Gln Ser Gly Asp Gly Ser Arg His Ser
    1220                1225                1230

Gly Ser Arg His His Glu Ala Ala Ser Trp Ala Asp Ser Ser Arg
    1235                1240                1245

His Ser Gln Val Gly Gln Glu Gln Ser Ser Gly Ser Arg Thr Ser
    1250                1255                1260

Arg His Gln Gly Ser Ser Val Ser Gln Asp Ser Asp Ser Glu Arg
    1265                1270                1275

His Ser Asp Asp Ser Glu Arg Leu Ser Gly Ser Ala Ser Arg Asn
    1280                1285                1290

His His Gly Ser Ser Arg Glu Gln Ser Arg Asp Gly Ser Arg His
    1295                1300                1305

Pro Gly Phe His Gln Glu Asp Arg Ala Ser His Gly His Ser Ala
    1310                1315                1320

Asp Ser Ser Arg Gln Ser Gly Thr His His Thr Glu Ser Ser Ser
    1325                1330                1335

His Gly Gln Ala Val Ser Ser His Glu Gln Ala Arg Ser Ser Pro
    1340                1345                1350

Gly Glu Arg His Gly Ser Arg His Gln Gln Ser Ala Asp Ser Ser
    1355                1360                1365

Arg His Ser Gly Ile Gly His Arg Gln Ala Ser Ala Val Arg
    1370                1375                1380

Asp Ser Gly His Arg Gly Ser Gly Ser Gln Val Thr Asn Ser
    1385                1390                1395

Glu Gly His Ser Glu Asp Ser Asp Thr Gln Ser Val Ser Ala His
    1400                1405                1410

Gly Gln Ala Gly Pro His Gln Ser His Lys Glu Ser Ala Arg
    1415                1420                1425

Gly Gln Ser Gly Glu Ser Ser Gly Arg Ser Arg Ser Phe Leu Tyr
    1430                1435                1440

Gln Val Ser Ser His Glu Gln Ser Glu Ser Thr His Gly Gln Thr
    1445                1450                1455

Ala Pro Ser Thr Gly Gly Arg Gln Gly Ser Arg His Glu Gln Ala
    1460                1465                1470

Arg Asn Ser Ser Arg His Ser Ala Ser Gln Asp Gly Gln Asp Thr
    1475                1480                1485

Ile Arg Gly His Pro Gly Ser Ser Arg Gly Gly Arg Gln Gly Ser
    1490                1495                1500

Tyr His Glu Gln Ser Val Asp Arg Ser Gly His Ser Gly Tyr His
    1505                1510                1515

His Ser His Thr Thr Pro Gln Gly Arg Ser Asp Ala Ser His Gly
    1520                1525                1530

Gln Ser Gly Pro Arg Ser Ala Ser Arg Gln Thr Arg Asn Glu Glu
    1535                1540                1545

Gln Ser Gly Asp Gly Ser Arg His Ser Gly Ser Arg His His Glu
    1550                1555                1560

Pro Ser Thr Arg Ala Gly Ser Ser Arg His Ser Gln Val Gly Gln
    1565                1570                1575

Gly Glu Ser Ala Gly Ser Lys Thr Ser Arg Arg Gln Gly Ser Ser
    1580                1585                1590

Val Ser Gln Asp Arg Asp Ser Glu Gly His Ser Glu Asp Ser Glu
    1595                1600                1605
```

```
Arg Arg Ser Glu Ser Ala Ser Arg Asn His Tyr Gly Ser Ala Arg
1610            1615                1620

Glu Gln Ser Arg His Gly Ser Arg Asn Pro Arg Ser His Gln Glu
1625            1630                1635

Asp Arg Ala Ser His Gly His Ser Ala Glu Ser Ser Arg Gln Ser
1640            1645                1650

Gly Thr Arg His Ala Glu Thr Ser Ser Gly Gly Gln Ala Ala Ser
1655            1660                1665

Ser Gln Glu Gln Ala Arg Ser Ser Pro Gly Glu Arg His Gly Ser
1670            1675                1680

Arg His Gln Gln Ser Ala Asp Ser Ser Thr Asp Ser Gly Thr Gly
1685            1690                1695

Arg Arg Gln Asp Ser Ser Val Val Gly Asp Ser Gly Asn Arg Gly
1700            1705                1710

Ser Ser Gly Ser Gln Ala Ser Asp Ser Glu Gly His Ser Glu Glu
1715            1720                1725

Ser Asp Thr Gln Ser Val Ser Ala His Gly Gln Ala Gly Pro His
1730            1735                1740

Gln Gln Ser His Gln Glu Ser Thr Arg Gly Gln Ser Gly Glu Arg
1745            1750                1755

Ser Gly Arg Ser Gly Ser Phe Leu Tyr Gln Val Ser Thr His Glu
1760            1765                1770

Gln Ser Glu Ser Ala His Gly Arg Thr Gly Pro Ser Thr Gly Gly
1775            1780                1785

Arg Gln Arg Ser Arg His Glu Gln Ala Arg Asp Ser Ser Arg His
1790            1795                1800

Ser Ala Ser Gln Glu Gly Gln Asp Thr Ile Arg Gly His Pro Gly
1805            1810                1815

Ser Ser Arg Gly Gly Arg Gln Gly Ser His Tyr Glu Gln Ser Val
1820            1825                1830

Asp Ser Ser Gly His Ser Gly Ser His His Ser His Thr Thr Ser
1835            1840                1845

Gln Glu Arg Ser Asp Val Ser Arg Gly Gln Ser Gly Ser Arg Ser
1850            1855                1860

Val Ser Arg Gln Thr Arg Asn Glu Lys Gln Ser Gly Asp Gly Ser
1865            1870                1875

Arg His Ser Gly Ser Arg His His Glu Ala Ser Arg Ala Asp
1880            1885                1890

Ser Ser Arg His Ser Gln Val Gly Gln Gly Gln Ser Ser Gly Pro
1895            1900                1905

Arg Thr Ser Arg Asn Gln Gly Ser Ser Val Ser Gln Asp Ser Asp
1910            1915                1920

Ser Gln Gly His Ser Glu Asp Ser Glu Arg Trp Ser Gly Ser Ala
1925            1930                1935

Ser Arg Asn His Leu Gly Ser Ala Trp Glu Gln Ser Arg Asp Gly
1940            1945                1950

Ser Arg His Pro Gly Ser His His Glu Asp Arg Ala Gly His Gly
1955            1960                1965

His Ser Ala Asp Ser Ser Arg Gln Ser Gly Thr Arg His Thr Glu
1970            1975                1980

Ser Ser Ser Arg Gly Gln Ala Ala Ser Ser His Glu Gln Ala Arg
1985            1990                1995

Ser Ser Ala Gly Glu Arg His Gly Ser His His Gln Leu Gln Ser
```

```
                 2000                 2005                    2010
Ala Asp Ser Ser Arg His Ser  Gly Ile Gly His  Gly Gln Ala Ser
                 2015                 2020                    2025

Ser Ala Val Arg Asp Ser Gly  His Arg Gly Tyr  Ser Gly Ser Gln
                 2030                 2035                    2040

Ala Ser Asp Ser Glu Gly His  Ser Glu Asp Ser  Asp Thr Gln Ser
                 2045                 2050                    2055

Val Ser Ala Gln Gly Lys Ala  Gly Pro His Gln  Gln Ser His Lys
                 2060                 2065                    2070

Glu Ser Ala Arg Gly Gln Ser  Gly Glu Ser Ser  Gly Arg Ser Gly
                 2075                 2080                    2085

Ser Phe Leu Tyr Gln Val Ser  Thr His Glu Gln  Ser Glu Ser Thr
                 2090                 2095                    2100

His Gly Gln Ser Ala Pro Ser  Thr Gly Gly Arg  Gln Gly Ser His
                 2105                 2110                    2115

Tyr Asp Gln Ala Gln Asp Ser  Ser Arg His Ser  Ala Ser Gln Glu
                 2120                 2125                    2130

Gly Gln Asp Thr Ile Arg Gly  His Pro Gly Pro  Ser Arg Gly Gly
                 2135                 2140                    2145

Arg Gln Gly Ser His Gln Glu  Gln Ser Val Asp  Arg Ser Gly His
                 2150                 2155                    2160

Ser Gly Ser His His Ser His  Thr Thr Ser Gln  Gly Arg Ser Asp
                 2165                 2170                    2175

Ala Ser Arg Gly Gln Ser Gly  Ser Arg Ser Ala  Ser Arg Lys Thr
                 2180                 2185                    2190

Tyr Asp Lys Glu Gln Ser Gly  Asp Gly Ser Arg  His Ser Gly Ser
                 2195                 2200                    2205

His His His Glu Ala Ser Ser  Trp Ala Asp Ser  Ser Arg His Ser
                 2210                 2215                    2220

Leu Val Gly Gln Gly Gln Ser  Ser Gly Pro Arg  Thr Ser Arg Pro
                 2225                 2230                    2235

Arg Gly Ser Ser Val Ser Gln  Asp Ser Asp Ser  Glu Gly His Ser
                 2240                 2245                    2250

Glu Asp Ser Glu Arg Arg Ser  Gly Ser Ala Ser  Arg Asn His His
                 2255                 2260                    2265

Gly Ser Ala Gln Glu Gln Ser  Arg Asp Gly Ser  Arg His Pro Arg
                 2270                 2275                    2280

Ser His His Glu Asp Arg Ala  Gly His Gly His  Ser Ala Glu Ser
                 2285                 2290                    2295

Ser Arg Gln Ser Gly Thr His  His Ala Glu Asn  Ser Ser Gly Gly
                 2300                 2305                    2310

Gln Ala Ala Ser Ser His Glu  Gln Ala Arg Ser  Ser Ala Gly Glu
                 2315                 2320                    2325

Arg His Gly Ser His His Gln  Gln Ser Ala Asp  Ser Ser Arg His
                 2330                 2335                    2340

Ser Gly Ile Gly His Gly Gln  Ala Ser Ser Ala  Val Arg Asp Ser
                 2345                 2350                    2355

Gly His Arg Gly Ser Ser Gly  Ser Gln Ala Ser  Asp Ser Glu Gly
                 2360                 2365                    2370

His Ser Glu Asp Ser Asp Thr  Gln Ser Val Ser  Ala His Gly Gln
                 2375                 2380                    2385

Ala Gly Pro His Gln Gln Ser  His Gln Glu Ser  Thr Arg Gly Arg
                 2390                 2395                    2400
```

```
Ser Ala Gly Arg Ser Gly Arg Ser Gly Ser Phe Leu Tyr Gln Val
2405                2410                2415

Ser Thr His Glu Gln Ser Glu Ser Ala His Gly Arg Thr Gly Thr
2420                2425                2430

Ser Thr Gly Gly Arg Gln Gly Ser His His Lys Gln Ala Arg Asp
2435                2440                2445

Ser Ser Arg His Ser Thr Ser Gln Glu Gly Gln Asp Thr Ile His
2450                2455                2460

Gly His Pro Gly Ser Ser Gly Gly Arg Gln Gly Ser His Tyr
2465                2470                2475

Glu Gln Leu Val Asp Arg Ser Gly His Ser Gly Ser His His Ser
2480                2485                2490

His Thr Thr Ser Gln Gly Arg Ser Asp Ala Ser His Gly His Ser
2495                2500                2505

Gly Ser Arg Ser Ala Ser Arg Gln Thr Arg Asn Asp Glu Gln Ser
2510                2515                2520

Gly Asp Gly Ser Arg His Ser Gly Ser Arg His His Glu Ala Ser
2525                2530                2535

Ser Arg Ala Asp Ser Ser Gly His Ser Gln Val Gly Gln Gly Gln
2540                2545                2550

Ser Glu Gly Pro Arg Thr Ser Arg Asn Trp Gly Ser Ser Phe Ser
2555                2560                2565

Gln Asp Ser Asp Ser Gln Gly His Ser Glu Asp Ser Glu Arg Trp
2570                2575                2580

Ser Gly Ser Ala Ser Arg Asn His His Gly Ser Ala Gln Glu Gln
2585                2590                2595

Leu Arg Asp Gly Ser Arg His Pro Arg Ser His Gln Glu Asp Arg
2600                2605                2610

Ala Gly His Gly His Ser Asp Ser Ser Arg Gln Ser Gly Thr
2615                2620                2625

Arg His Thr Gln Thr Ser Ser Gly Gly Gln Ala Ala Ser Ser His
2630                2635                2640

Glu Gln Ala Arg Ser Ser Ala Gly Glu Arg His Gly Ser His His
2645                2650                2655

Gln Gln Ser Ala Asp Ser Ser Arg His Ser Gly Ile Gly His Gly
2660                2665                2670

Gln Ala Ser Ser Ala Val Arg Asp Ser Gly His Arg Gly Tyr Ser
2675                2680                2685

Gly Ser Gln Ala Ser Asp Asn Glu Gly His Ser Glu Asp Ser Asp
2690                2695                2700

Thr Gln Ser Val Ser Ala His Gly Gln Ala Gly Ser His Gln Gln
2705                2710                2715

Ser His Gln Glu Ser Ala Arg Gly Arg Ser Gly Glu Thr Ser Gly
2720                2725                2730

His Ser Gly Ser Phe Leu Tyr Gln Val Ser Thr His Glu Gln Ser
2735                2740                2745

Glu Ser Ser His Gly Trp Thr Gly Pro Ser Thr Arg Gly Arg Gln
2750                2755                2760

Gly Ser Arg His Glu Gln Ala Gln Asp Ser Ser Arg His Ser Ala
2765                2770                2775

Ser Gln Asp Gly Gln Asp Thr Ile Arg Gly His Pro Gly Ser Ser
2780                2785                2790
```

```
Arg Gly Gly Arg Gln Gly Tyr His His Glu His Ser Val Asp Ser
2795                2800                2805

Ser Gly His Ser Gly Ser His His Ser His Thr Thr Ser Gln Gly
2810                2815                2820

Arg Ser Asp Ala Ser Arg Gly Gln Ser Gly Ser Arg Ser Ala Ser
2825                2830                2835

Arg Thr Thr Arg Asn Glu Glu Gln Ser Gly Asp Gly Ser Arg His
2840                2845                2850

Ser Gly Ser Arg His His Glu Ala Ser Thr His Ala Asp Ile Ser
2855                2860                2865

Arg His Ser Gln Ala Val Gln Gly Gln Ser Glu Gly Ser Arg Arg
2870                2875                2880

Ser Arg Arg Gln Gly Ser Ser Val Ser Gln Asp Ser Asp Ser Glu
2885                2890                2895

Gly His Ser Glu Asp Ser Glu Arg Trp Ser Gly Ser Ala Ser Arg
2900                2905                2910

Asn His His Gly Ser Ala Gln Glu Gln Leu Arg Asp Gly Ser Arg
2915                2920                2925

His Pro Arg Ser His Gln Glu Asp Arg Ala Gly His Gly His Ser
2930                2935                2940

Ala Asp Ser Ser Arg Gln Ser Gly Thr Arg His Thr Gln Thr Ser
2945                2950                2955

Ser Gly Gly Gln Ala Ala Ser Ser His Glu Gln Ala Arg Ser Ser
2960                2965                2970

Ala Gly Glu Arg His Gly Ser His His Gln Gln Ser Ala Asp Ser
2975                2980                2985

Ser Arg His Ser Gly Ile Gly His Gly Gln Ala Ser Ser Ala Val
2990                2995                3000

Arg Asp Ser Gly His Arg Gly Tyr Ser Gly Ser Gln Ala Ser Asp
3005                3010                3015

Asn Glu Gly His Ser Glu Asp Ser Asp Thr Gln Ser Val Ser Ala
3020                3025                3030

His Gly Gln Ala Gly Ser His Gln Gln Ser His Gln Glu Ser Ala
3035                3040                3045

Arg Gly Arg Ser Gly Glu Thr Ser Gly His Ser Gly Ser Phe Leu
3050                3055                3060

Tyr Gln Val Ser Thr His Glu Gln Ser Glu Ser Ser His Gly Trp
3065                3070                3075

Thr Gly Pro Ser Thr Arg Gly Arg Gln Gly Ser Arg His Glu Gln
3080                3085                3090

Ala Gln Asp Ser Ser Arg His Ser Ala Ser Gln Tyr Gly Gln Asp
3095                3100                3105

Thr Ile Arg Gly His Pro Gly Ser Ser Arg Gly Gly Arg Gln Gly
3110                3115                3120

Tyr His His Glu His Ser Val Asp Ser Gly His Ser Gly Ser
3125                3130                3135

His His Ser His Thr Thr Ser Gln Gly Arg Ser Asp Ala Ser Arg
3140                3145                3150

Gly Gln Ser Gly Ser Arg Ser Ala Ser Arg Thr Thr Arg Asn Glu
3155                3160                3165

Glu Gln Ser Gly Asp Ser Ser Arg His Ser Val Ser Arg His His
3170                3175                3180

Glu Ala Ser Thr His Ala Asp Ile Ser Arg His Ser Gln Ala Val
```

```
              3185              3190              3195
Gln Gly Gln Ser Glu Gly Ser Arg Arg Ser Arg Gln Gly Ser
        3200              3205              3210
Ser Val Ser Gln Asp Ser Asp Ser Glu Gly His Ser Glu Asp Ser
        3215              3220              3225
Glu Arg Trp Ser Gly Ser Ala Ser Arg Asn His Arg Gly Ser Val
        3230              3235              3240
Gln Glu Gln Ser Arg His Gly Ser Arg His Pro Arg Ser His His
        3245              3250              3255
Glu Asp Arg Ala Gly His Gly His Ser Ala Asp Arg Ser Arg Gln
        3260              3265              3270
Ser Gly Thr Arg His Ala Glu Thr Ser Ser Gly Gly Gln Ala Ala
        3275              3280              3285
Ser Ser His Glu Gln Ala Arg Ser Ser Pro Gly Glu Arg His Gly
        3290              3295              3300
Ser Arg His Gln Gln Ser Ala Asp Ser Ser Arg His Ser Gly Ile
        3305              3310              3315
Pro Arg Gly Gln Ala Ser Ser Ala Val Arg Asp Ser Arg His Trp
        3320              3325              3330
Gly Ser Ser Gly Ser Gln Ala Ser Asp Ser Glu Gly His Ser Glu
        3335              3340              3345
Glu Ser Asp Thr Gln Ser Val Ser Gly His Gly Gln Ala Gly Pro
        3350              3355              3360
His Gln Gln Ser His Gln Glu Ser Ala Arg Asp Arg Ser Gly Gly
        3365              3370              3375
Arg Ser Gly Arg Ser Gly Ser Phe Leu Tyr Gln Val Ser Thr His
        3380              3385              3390
Glu Gln Ser Glu Ser Ala His Gly Arg Thr Arg Thr Ser Thr Gly
        3395              3400              3405
Arg Arg Gln Gly Ser His His Glu Gln Ala Arg Asp Ser Ser Arg
        3410              3415              3420
His Ser Ala Ser Gln Glu Gly Gln Asp Thr Ile Arg Gly His Pro
        3425              3430              3435
Gly Ser Ser Arg Arg Gly Arg Gln Gly Ser His Tyr Glu Gln Ser
        3440              3445              3450
Val Asp Arg Ser Gly His Ser Gly Ser His His Ser His Thr Thr
        3455              3460              3465
Ser Gln Gly Arg Ser Asp Ala Ser Arg Gly Gln Ser Gly Ser Arg
        3470              3475              3480
Ser Ala Ser Arg Gln Thr Arg Asn Asp Glu Gln Ser Gly Asp Gly
        3485              3490              3495
Ser Arg His Ser Trp Ser His His His Glu Ala Ser Thr Gln Ala
        3500              3505              3510
Asp Ser Ser Arg His Ser Gln Ser Gly Gln Gly Gln Ser Ala Gly
        3515              3520              3525
Pro Arg Thr Ser Arg Asn Gln Gly Ser Ser Val Ser Gln Asp Ser
        3530              3535              3540
Asp Ser Gln Gly His Ser Glu Asp Ser Glu Arg Trp Ser Gly Ser
        3545              3550              3555
Ala Ser Arg Asn His Arg Gly Ser Ala Gln Glu Gln Ser Arg Asp
        3560              3565              3570
Gly Ser Arg His Pro Thr Ser His His Glu Asp Arg Ala Gly His
        3575              3580              3585
```

```
Gly His Ser Ala Glu Ser Ser Arg Gln Ser Gly Thr His His Ala
    3590            3595                3600

Glu Asn Ser Ser Gly Gly Gln Ala Ala Ser Ser His Glu Gln Ala
    3605            3610                3615

Arg Ser Ser Ala Gly Glu Arg His Gly Ser His His Gln Gln Ser
    3620            3625                3630

Ala Asp Ser Ser Arg His Ser Gly Ile Gly His Gly Gln Ala Ser
    3635            3640                3645

Ser Ala Val Arg Asp Ser Gly His Arg Gly Ser Ser Gly Ser Gln
    3650            3655                3660

Ala Ser Asp Ser Glu Gly His Ser Glu Asp Ser Asp Thr Gln Ser
    3665            3670                3675

Val Ser Ala His Gly Gln Ala Gly Pro His Gln Gln Ser His Gln
    3680            3685                3690

Glu Ser Thr Arg Gly Arg Ser Ala Gly Arg Ser Gly Arg Ser Gly
    3695            3700                3705

Ser Phe Leu Tyr Gln Val Ser Thr His Glu Gln Ser Glu Ser Ala
    3710            3715                3720

His Gly Arg Ala Gly Pro Ser Thr Gly Gly Arg Gln Gly Ser Arg
    3725            3730                3735

His Glu Gln Ala Arg Asp Ser Ser Arg His Ser Ala Ser Gln Glu
    3740            3745                3750

Gly Gln Asp Thr Ile Arg Gly His Pro Gly Ser Arg Arg Gly Gly
    3755            3760                3765

Arg Gln Gly Ser Tyr His Glu Gln Ser Val Asp Arg Ser Gly His
    3770            3775                3780

Ser Gly Ser His His Ser His Thr Thr Ser Gln Gly Arg Ser Asp
    3785            3790                3795

Ala Ser His Gly Gln Ser Gly Ser Arg Ser Ala Ser Arg Glu Thr
    3800            3805                3810

Arg Asn Glu Glu Gln Ser Gly Asp Gly Ser Arg His Ser Gly Ser
    3815            3820                3825

Arg His His Glu Ala Ser Thr Gln Ala Asp Ser Ser Arg His Ser
    3830            3835                3840

Gln Ser Gly Gln Gly Glu Ser Ala Gly Ser Arg Arg Ser Arg Arg
    3845            3850                3855

Gln Gly Ser Ser Val Ser Gln Asp Ser Asp Ser Glu Ala Tyr Pro
    3860            3865                3870

Glu Asp Ser Glu Arg Arg Ser Glu Ser Ala Ser Arg Asn His His
    3875            3880                3885

Gly Ser Ser Arg Glu Gln Ser Arg Asp Gly Ser Arg His Pro Gly
    3890            3895                3900

Ser Ser His Arg Asp Thr Ala Ser His Val Gln Ser Ser Pro Val
    3905            3910                3915

Gln Ser Asp Ser Ser Thr Ala Lys Glu His Gly His Phe Ser Ser
    3920            3925                3930

Leu Ser Gln Asp Ser Ala Tyr His Ser Gly Ile Gln Ser Arg Gly
    3935            3940                3945

Ser Pro His Ser Ser Ser Ser Tyr His Tyr Gln Ser Glu Gly Thr
    3950            3955                3960

Glu Arg Gln Lys Gly Gln Ser Gly Leu Val Trp Arg His Gly Ser
    3965            3970                3975
```

-continued

Tyr Gly  Ser Ala
    3980